US011512083B2

(12) United States Patent
Crew et al.

(10) Patent No.: US 11,512,083 B2
(45) Date of Patent: *Nov. 29, 2022

(54) COMPOUNDS AND METHODS FOR THE ENHANCED DEGRADATION OF TARGETED PROTEINS

(71) Applicants: Arvinas Operations, Inc., New Haven, CT (US); Yale University, New Haven, CT (US)

(72) Inventors: Andrew P. Crew, Guilford, CT (US); Craig M. Crews, New Haven, CT (US); Xin Chen, Trumbull, CT (US); Hanqing Dong, Madison, CT (US); Caterina Ferraro, Stamford, CT (US); Yimin Qian, Plainsboro, NJ (US); Kam Siu, Milford, CT (US); Jing Wang, Milford, CT (US); Meizhong Jin, East Northport, NY (US); Michael Berlin, Flemington, NJ (US); Kurt Zimmermann, Durham, CT (US)

(73) Assignees: Arvinas Operations, Inc., New Haven, CT (US); Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/905,641

(22) Filed: Jun. 18, 2020

(65) Prior Publication Data
US 2020/0392131 A1    Dec. 17, 2020

Related U.S. Application Data

(63) Continuation of application No. 15/074,820, filed on Mar. 18, 2016, now Pat. No. 10,730,870.
(Continued)

(51) Int. Cl.
| | |
|---|---|
| *C07D 521/00* | (2006.01) |
| *C07D 413/14* | (2006.01) |
| *C07D 471/12* | (2006.01) |
| *C07D 417/14* | (2006.01) |
| *C07D 207/16* | (2006.01) |
| *C07D 207/26* | (2006.01) |
| *C07D 401/06* | (2006.01) |
| *C07D 401/10* | (2006.01) |
| *C07D 403/06* | (2006.01) |
| *C07D 405/06* | (2006.01) |
| *C07D 405/12* | (2006.01) |
| *C07D 413/06* | (2006.01) |
| *C07D 413/12* | (2006.01) |
| *A61K 31/422* | (2006.01) |
| *A61K 31/437* | (2006.01) |
| *A61K 31/4439* | (2006.01) |
| *A61K 31/5377* | (2006.01) |
| *C07D 471/04* | (2006.01) |
| *A61K 45/06* | (2006.01) |
| *C07D 417/12* | (2006.01) |
| *C07D 403/14* | (2006.01) |

(Continued)

(52) U.S. Cl.
CPC ............ *C07D 471/04* (2013.01); *A61K 45/06* (2013.01); *C07D 401/14* (2013.01); *C07D 403/06* (2013.01); *C07D 403/14* (2013.01); *C07D 405/14* (2013.01); *C07D 413/14* (2013.01); *C07D 417/12* (2013.01); *C07D 417/14* (2013.01); *C07D 495/04* (2013.01)

(58) Field of Classification Search
CPC .. C07D 521/00; C07D 413/14; C07D 471/12; C07D 417/14; C07D 207/16; C07D 207/26; C07D 401/06; C07D 401/10; C07D 403/06; C07D 405/06; C07D 405/12; C07D 413/06; C07D 413/12; A61K 31/422; A61K 31/437; A61K 31/4439; A61K 31/5377
See application file for complete search history.

(56) References Cited

U.S. PATENT DOCUMENTS

| | | |
|---|---|---|
| 6,306,663 B1 | 10/2001 | Kenten et al. |
| 6,670,348 B1 | 12/2003 | Rosen et al. |

(Continued)

FOREIGN PATENT DOCUMENTS

| | | |
|---|---|---|
| EP | 2985285 | 2/2016 |
| WO | WO 2000/050445 | 8/2000 |

(Continued)

OTHER PUBLICATIONS

U.S. Appl. No. 15/074,820, filed Mar. 18, 2016, US 2016-0272639 A1.
(Continued)

*Primary Examiner* — Bruck Kifle
(74) *Attorney, Agent, or Firm* — Lathrop GPM LLP; Brian C. Trinque; Nicole Sassu

(57) ABSTRACT

The present invention relates to bifunctional compounds, which find utility as modulators of targeted ubiquitination, especially inhibitors of a variety of polypeptides and other proteins which are degraded and/or otherwise inhibited by bifunctional compounds according to the present invention. In particular, the present invention is directed to compounds, which contain on one end a VHL ligand which binds to the ubiquitin ligase and on the other end a moiety which binds a target protein such that the target protein is placed in proximity to the ubiquitin ligase to effect degradation (and inhibition) of that protein. The present invention exhibits a broad range of pharmacological activities associated with compounds according to the present invention, consistent with the degradation/inhibition of targeted polypeptides.

17 Claims, 1 Drawing Sheet

Related U.S. Application Data

(60) Provisional application No. 62/135,125, filed on Mar. 18, 2015.

(51) Int. Cl.
*C07D 401/14* (2006.01)
*C07D 405/14* (2006.01)
*C07D 495/04* (2006.01)

(56) References Cited

U.S. PATENT DOCUMENTS

| | | |
|---|---|---|
| 7,030,141 B2 | 4/2006 | Bigge et al. |
| 7,041,298 B2 | 5/2006 | Deshaies et al. |
| 7,208,157 B2 | 4/2007 | Sakamoto et al. |
| 9,500,653 B2 | 11/2016 | Crews et al. |
| 9,632,089 B2 | 4/2017 | Crews et al. |
| 2005/0019813 A1 | 1/2005 | Conaway et al. |
| 2008/0214501 A1 | 9/2008 | Zhengying et al. |
| 2010/0286127 A1 | 11/2010 | Miyoshi et al. |
| 2012/0270800 A1 | 10/2012 | Verdine et al. |
| 2014/0088143 A1 | 3/2014 | Jain |
| 2014/0256700 A1 | 9/2014 | Poss |
| 2014/0302523 A1 | 10/2014 | Crews et al. |
| 2014/0356322 A1 | 12/2014 | Crews et al. |
| 2014/0371206 A1 | 12/2014 | Albrecht et al. |
| 2015/0119435 A1 | 4/2015 | Crews et al. |
| 2015/0141470 A1 | 5/2015 | Garraway et al. |
| 2015/0148342 A1 | 5/2015 | Combs et al. |
| 2015/0259288 A1 | 9/2015 | Nam et al. |
| 2015/0291562 A1 | 10/2015 | Crew et al. |
| 2015/0344473 A1 | 10/2015 | Du et al. |
| 2016/0022642 A1 | 1/2016 | Crews et al. |
| 2016/0045607 A1 | 2/2016 | Crew et al. |
| 2016/0058872 A1 | 3/2016 | Arvinas |
| 2016/0136230 A1 | 5/2016 | Campos et al. |
| 2016/0176864 A1 | 6/2016 | Norris et al. |
| 2016/0214972 A1 | 7/2016 | Jin et al. |
| 2016/0272639 A1 | 9/2016 | Crew et al. |
| 2016/0368911 A1 | 12/2016 | Campos et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0281784 A1 | 10/2017 | Wang et al. |
| 2017/0307614 A1 | 10/2017 | Crews et al. |
| 2017/0327469 A1 | 11/2017 | Crew et al. |
| 2018/0072711 A1 | 3/2018 | Crew et al. |

FOREIGN PATENT DOCUMENTS

| | | |
|---|---|---|
| WO | WO 2000/066119 | 11/2000 |
| WO | WO 2002/066512 | 8/2002 |
| WO | WO 2002/100845 | 12/2002 |
| WO | WO 2006/113942 | 10/2006 |
| WO | WO 2007/106670 | 9/2007 |
| WO | WO 2008/011392 | 1/2008 |
| WO | WO 2009/015254 | 1/2009 |
| WO | WO 2010/141805 | 12/2010 |
| WO | WO 2011/143660 | 11/2011 |
| WO | WO 2011/143669 | 11/2011 |
| WO | WO 2012/003281 | 1/2012 |
| WO | WO 2012/040389 A2 | 3/2012 |
| WO | WO 2012/040527 | 3/2012 |
| WO | WO 2012/078559 | 6/2012 |
| WO | WO 2012/090104 | 7/2012 |
| WO | WO 2013/106643 | 7/2013 |
| WO | WO 2013/106646 | 7/2013 |
| WO | WO 2013/170147 | 11/2013 |
| WO | WO 2014/001356 | 1/2014 |
| WO | WO 2014/108452 | 7/2014 |
| WO | WO 2014/123418 | 8/2014 |
| WO | WO 2014/128111 | 8/2014 |
| WO | WO 2015/000868 | 1/2015 |
| WO | WO 2015/011084 | 1/2015 |
| WO | WO 2015/022332 | 2/2015 |
| WO | WO 2015/015318 | 5/2015 |
| WO | WO 2015/067770 | 5/2015 |
| WO | WO 2015/074064 | 5/2015 |
| WO | WO 2015/160845 | 10/2015 |
| WO | WO 2015/195863 | 12/2015 |
| WO | WO 2016/050821 | 4/2016 |
| WO | WO 2016/069578 | 5/2016 |
| WO | WO 2016/105518 | 6/2016 |
| WO | WO 2016/118666 | 7/2016 |
| WO | WO 2016/146985 | 9/2016 |
| WO | WO 2016/172134 | 10/2016 |
| WO | WO 2016/197114 | 12/2016 |
| WO | WO 2017/011590 | 1/2017 |
| WO | WO 2017/030814 | 2/2017 |
| WO | WO 2017/046036 | 3/2017 |
| WO | WO 2017/079267 | 5/2017 |
| WO | WO 2017/185036 | 10/2017 |

OTHER PUBLICATIONS

Ahn, et al., "HIF-1alpha peptide derivatives with modifications at the hydroxyproline residue as activators of HIF-1alpha", Bioorg Med Chem Lett. 19(15), 2009, 4403-4405, May 27, 2009.

Albrecht, B., et al., "Identification of a benzoisoxazoloazepine inhibitor (CPI-0610) of the bromodomain and extra-terminal (BETA) family as a candidate for human clinical trials", Journal Med. Chem. 59, 1330-1339 (2016), Jan. 27, 2016.

Allan, GF, et. al, "Therapeutic androgen receptor ligands", Nuclear Receptor Signaling, 2003, 1, e009 DOI:10.621.01009 9 1-4, Sep. 27, 2003.

Asangani, I.A. et al., "Therapeutic Targeting of BET Bromodomain Proteins in Castration-Resistant Prostate Cancer", Nature, 2014, 510: 278-282, Apr. 23, 2014.

Baratta, M.G. et al., "An in-tumor genetic screen reveals that the Bet bromodomain protein, BRD4, is a potential therapeutic target in ovarian carcinonoma", PNAS, 112: 232-237 (2015) Dec. 22, 2014.

Bargagna-Mohan, et al., "Use of PROTACS as molecular probes of angiogenesis", Bioorg Med Chem Left. 15(11) 2005, 2724-2727, Jun. 2, 2005

Battista, M.J., Fulvestrant for the treatment of endometrial cancer, Expert Opin Investig Drugs 25, 475-483, Feb. 16, 2016.

Belkina, A.C. et al., "BET domain co-regulators in obesity, inflammation and cancer", Nat. Rev. Cancer, 12 (2012) 465-477, Jun. 22, 2012.

Boi, M. et al., "The BET Bromodomain inhibitor OTX015 Affects pathogenetic Pathways in Preclinical B-cell Tumor Models and synergizes with Targeted Drugs", Clin. Cancer Res., (2015) 21(7):1628-1638, Jan. 26, 2015.

Boitano, et al., "Aryl Hydrocarbon Receptor Antagonists Promote the Expansion of Human Hematopoietic Stem Cells", Science10 Sep. 2010: vol. 329, pp. 1345-1348.

Bondeson, et al., "Catalytic in vivo protein knockdown by small-molecule PROTACS", National Chem Biol. 11(8) Aug. 2015, 611-617.

Bradbury, RH, et. al, "Small-molecule androgen receptor downregulators as an approach to treatment of advanced prostate cancer", Bioorganic & Medicinal Chemistry Letters, 2011, 21: 5442-5445, Jul. 2, 2011.

Brough, et al., "4,5-Diarylisoxazole HSP90 Chaperone Inhibitors: Potential Therapeutic Agents for the Treatment of Cancer", J Med Chem. 51(2), Jan. 24, 2008, 196-218.

Buckley, et al., "HaloPROTACS: use of small molecule PROTACS to induce degradation of HaloTag fusion proteins", ACS Chem Biol. 10(8), 2015, 1831-1837, Aug. 21, 2015.

Buckley, et al., "Small-molecule inhibitors of the interaction between the E3 ligase VHL and HIF1a", Angew Chem Int Ed Engl.51(46): Nov. 12, 2012, 11463-11467.

Buckley, et al., "Targeting the von Hippel-Lindau E3 ubiquitin ligase using small molecules to disrupt the VHL/HIF-1α interaction", Journal of the American Chemical Society, Feb. 27, 2012, 134(10): 4465-4468.

(56) References Cited

OTHER PUBLICATIONS

Carmony, KC, et al., "PROTAC-Induced Proteolytic Targeting", Methods Mol. Biol., 2012, vol. 832, pp. 627-638, Dec. 5, 2013.
CAS 155180-53-3 published 1994.
CAS 155255-73-5 published 1995.
CAS Registry No. 1004933-70-3, which entered STN on Feb. 21, 2008.
CAS Registry No. 871986-52-6 entered STN Jan 16, 2006.
Ceribelli, M. et al., "Blockade of oncongenic IKB kinase activity in diffuse large B-cell lymphoma by bromodomain and extraterminal domain protein inhibitors", PNAS, 111 (2014) 11365-11370, Aug. 5, 2014.
Chang, et al., "Structural basis for G9a-like protein lysine methyltransferase inhibition by BIX-01294", Nat Struct Mol Biol. 16(3), Mar. 2009, 312-317.
Chapuy, B. et al., "Discovery and characterization of super-enhancer-associated dependencies in diffuse large B cell lymphoma", Cancer Cell, 24 (2013) 777-790, Dec. 9, 2013.
Chung, et al., "Discovery and Characterization of Small Molecule Inhibitors of the BET Family Bromodomains", J Med Chem. 54(11), Jun. 9, 2011, 3827-3838.
Corson, et al., "Design and applications of bifunctional small molecules: why two heads are better than one", ACS Chemical Biology vol. 3 No. 11, pp. 677-692; Nov. 21, 2008.
Crews, C. M., "Targeting the undruggable proteome: the small molecules of my dreams", *Chem Biol* 17, 551-555, doi:S1074-5521(10)00196-1 [pii] 10.1016/j.chembiol.2010.05.011 (2010), Jun. 25, 2010.
Cyrus, et al., "Jostling for position: optimizing linker location in the design of estrogen receptor-targeting PROTACs", Chem Med Chem. 5(7), Jul. 5, 2010, 979-985.
Cyrus, K. et al, "Impact of Linker Length on the Activity of PROTACs," Mol. Biosyst., 2011, vol. 7, No. 2, pp. 359-364, Feb. 2011.
Cyrus, K. et al, "Two-Headed PROTAC: an Effective New Tool for Targeted Protein Degradation," Chembiochem., 2010, vol. 11, pp. 1531-1534, Jul. 26, 2010.
Dawson, et al., "Inhibition of BET recruitment to chromatin as an effective treatment for MLL-fusion leukemia", Nature 478, Oct. 2, 2011, 529-533.
Delmore, J.E. et al., "BET Bromodomain inhibition as a therapeutic strategy to target c-Myc", Cell, 146 (2011) 904-917 Platform Sep. 1, 2011.
Deroo, B.J., et al., "Estrogen receptors and human disease", Journal of Clinical Investigation, (2006), vol. 116(3), pp. 561-570, Mar. 2006.
Di, J et al. "Reactivation of p53 by inhibiting Mdm2 E3 Ligase: a novel antitumor approach", Current Cancer Drug Targets (2011), 11(8), 987-994, Oct. 2011.
Ding, Q, et al., "Discovery of RG7388, a potent and selective p53-MDM2 inhibitor in clinical development", J Med Chem. Jul. 25, 2013; 56(14):5979-83. doi: 10.1021/jm400487c. Epub Jul. 16, 2013. PubMed PMID: 23808545 (J. Med. Chem. (2013) 56, 5979-5983 Ding, et al).
Dixon, S. J. et al., "Identifying druggable disease-modifying gene products",. *Curr Opin Chem Biol* 13, 549-555, doi:S1367-5931(09)00107-0 [pii] 10.1016/j.cbpa.2009.08.003 (2009), Sep. 7, 2009.
Filippakopoulos, et al., "Selective inhibition of BET bromodomains", Nature 468, Dec. 23, 2010, 1067-1073.
Finnin, et al., "Structures of a histone deacetylase homologue bound to the TSA and SAHA inhibitors", Nature 401, Sep. 9, 1999, 188-193.
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
Gangjee. A. et al., "The contribution of a 2-amino group on receptor tyrosine kinase inhibition and antiangiogenic activity in 4-anilinosubstituted pyrrolo [2,3-d] pyrimidines", Bioorganic & Medicinal Chemistry Letters, 2010, vol. 20, No. 10, pp. 3177-3181, Mar 24, 2010.
Golub, et al., "Molecular classification of cancer: class discovery and class prediction by gene expression monitoring", Science 286, 531-537 (1991), Oct. 15, 1991.
Gosink, M et al., "Redirecting the specificity of ubiquitination by modifying ubiquitin-conjugating enzymes", Pro. Natl. Acad Sci, vol. 92, pp. 9117-9121, 1995, Sep. 26, 1995.
Guo, C., et. al, "Design of oxobenzimidazoles and oxindoles as novel androgen receptor antagonists", Bioorganic & Medicinal Chemistry Letters, 2012, 22:2572-2578, Feb. 7, 2012.
Gustafson, et al., "Small-Molecule-Mediated Degradation of the Androgen Receptor through Hydrophobic Tagging", Agnew Chem Int Ed., 54: 9659-9662 (2015), Jun. 17, 2015.
Hewings, et al., "3,5-Dimethylisoxazoles Act as Acetyllysine-mimetic Bromodomain", J Med Chem. 54(19), Oct. 13, 2011, 6761-6770.
Hines, J., et al., "Posttranslational protein knockdown coupled to receptor tyrosine kinase activation with phosphoPROTACs", Proc Natl Acad Sci USA 110, 8942-8947 (2013), May 14, 2013.
Hoffmann, J. et al. Characterization of New Estrogen Receptor Destabilizing Compounds: Effects on Estrogen-Sensitive and Tamoxifen-Resistant Breast Cancer. JNCI Journal of the National Cancer Institute 96, 210-218 (2004), Feb. 4, 2004.
Hon, et al., "Structural basis for the recognition of hydroxyproline in Hlf-1 alpha by pVHL", Nature 417, Jun. 27, 2002, 975-978.
Huang, et al., (2016) "Drugging the undruggables: exploring the ubiquitin system for drug development." *Cell Res* 26(4):484-498, Apr. 2016.
Ishikawa, T. et al., "Design and synthesis of novel human epidermal growth factor receptor 2 (HER2)/epidermal growth factor receptor (EGFR) dual inhibitors bearing a pyrrolo[3,2-dpyrimidine scaffold", Journal of Medicinal Chemistry 2011, 54 (23), 8030-8050, Oct. 17, 2011.
Ivan, M., et al., "HIFa Targeted for VHL-Mediated Destruction by Proline Hydroxylation: Implications for O2 Sensing", Science, vol. 292, No. 5516, pp. 464-468, 2001, Apr. 20, 2001.
Jang, E.R. et al., "Targeted Degradation of Proteins by PROTACs," Curr. Protoc. Chem. Biol., 2010, vol. 2, No. 2, pp. 71-87, Jun. 1, 2010.
Japanese Office Action dated Jan. 30, 2020, for JP 2018-500278 (with English Translation).
Jung, M. E. et al "Structure-Activity Relationship for Thioydantoin Androgen Receptor Antagonists for Castration-Resistant Prostate Cancer (CRPC)", J. Med. Chem. 2010, 53, 2779-2796, Mar. 10, 2010.
Kim, et al., "Heat shock protein as molecular targets for breast cancer therapeutics", J. Breast Cancer. 14(3), Sep. 2011, 167-174.
Knott, Edward (1955). "Compounds containing sulphur chromophores. Part I. The action of bases on heterocyclic sulphide quarternary salts", Journal of the Chemical Society (resumed). 10.1039/jr9550000916. 949-954) (USPTO summary attached).
Konecny, G.E., et al., "Activity of the Dual Kinase Inhibitor Lapatinib (GW572016) against HER-2-Overexpressing and Trastuzumab-Treated Breast Cancer Cells", Cancer Research 66, 1630-1639 (2006), Feb. 2006.
Kurimchak, A. M. et al., "Resistance to BET Bromodomain Inhibitors is Mediated by Kinome Reprogramming in Ovarian Cancer", Cell Reports 16, 1273-1286 (2016) Aug. 2, 2016.
Lai, A.C., et al., "Modular PROTAC Design for the Degradation of Oncogenic BCR-ABL", Angew Chem Int Ed Engl 55, 807-810 (2016), Jan. 11, 2016.
Lala, et al., "Role of nitric oxide in tumor progression: Lessons from experimental tumors", Cancer and Metastasis Reviews 17:91-106 (1998), Mar. 1998.
Lebraud, H., et al., "Protein Degradation by In-Cell Self-Assembly of Proteolysis Targeting Chimeras", ACS Central Science, 2, 927-934 (2016) Dec. 5, 2016.
Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.

(56) References Cited

OTHER PUBLICATIONS

Lelais, G. et al., "Discovery of (R,E)-N-(7-Chloro-1-(1-[4-(dimethylamino)but-2-enoyl]azepan-3-yl)-1H-benzo[d]imidazol-2-yl)-2-methylisonicotinamide (EGF816), a novel, potent, and WT sparing covalent inhibitor of oncogenic (L858R, ex19del) and resistent (T790M) EGFR mutants for the treatment of EGFR mutant non-small-cell lung cancers", Journal of Medicinal Chemistry 2016, 59(14), 6671-6689, Jul. 2016.
Levine, et al., Targeting the androgen receptor with steroid conjugates, J. Med. Chem., vol. 57., No. 20. pp. 8224-8237, (2014) Sep. 14, 2014.
Li, Yan, et al., "Single polymer-drug conjugate carrying two drugs for fixed-dose co-delivery", Medicinal Chemistry, 2014, vol. 4(10): 676-683, Jan. 2014.
Liu, et al., "Discovery of a 2,4-diamino-7-aminoalkoxyquinazoline as a potent and selective inhibitor of histone lysine methyltransferase G9a", J Med Chem. 52(24), Dec. 24, 2009, 7950-7953.
Llinas-Brunet, et al., "Discovery of a potent and selective noncovalent linear inhibitor of the hepatitis C virus NS3 protease (BI 201335)", J Med Chem. 53(17), Sep. 9, 2010, 6466-6476.
Lountos, et al., "Structural Characterization of Inhibitor Complexes with Checkpoint Kinase 2 (Chk2), a Drug Target for Cancer Therapy", J Struct Biol.176(3), Dec. 2011, 292-301.
Loven, J. et al., "Selective Inhibition of Tumor Oncogenes by Disruption of Super Enhancers", Cell, 153 (2013) 320-334, Apr. 11, 2013.
Lu, et al., "Hijacking the E3 ubiquitin ligase cereblon to efficiently target BRD4", Chem Biol 22(6), 2015, 755-763, Jun. 18, 2015.
Martin-Kohler, A. et al., "Furo [2,3-d] pyrimidines and Oxazolo [5,4-d] pyrimidines as Inhibitors of Receptor Tyrosine Kinases (RTK)", Helvetica Chimica Acta, 2004, vol. 87, No. 4, pp. 956-975 See abstract; and figure 1, Apr. 26, 2004.
Medline Plus Trusted Health Information for You, www.nlm.nih.gov/medlineplus/cancer.html_pp. 1-10, (2007).
Mehellou, Y., De Clercq E., "Twenty-six years of anti-HIV drug discovery: where do we stand and where do we go?", J Med Chem. Jan. 28, 2010, 53(2):521-538. doi: 10.1021/jm900492g. Review. PubMed PMID: 19785437.
Mertz, J.A. et al., "Targeting MYC dependence in cancer by inhibiting BET bromodomains", PNAS, 108 (2011) 16669-16674, Oct. 4, 2011.
Millan,-et al "Design and Synthesis of Inhaled p38 Inhibitors for the Treatment of Chronic Obstructive Pulmonary Disease", J Med Chem.54(22), Nov. 24, 2011, 7797-7814.
Min, Jung-hyun, et al., "Structure of an HIV-1-alpha—pVHL complex: hydroxyproline recognition in signaling", Jun. 7, 2002, 296: 1886-1889.
Mohler, M.L., et al., Androgen receptor antagonists: a patent review (2008-2011), Expert Opinion on Therapeutic Patents, vol. 22, No. 5. pp. 541-565, (2012).
Neklesa, T.K., et al., "Chemical biology: Greasy tags for protein removal", Nature 487, 308-309 (2012), Jul. 18, 2012.
Nicodeme, et al., "Suppression of inflammation by a synthetic histone mimic", Nature 468, Dec. 23, 2010, 1119-1123.
Noel, J. Kay, Abstract C244: "Development of the BET Bromodomain inhibitor OTX015", Mol Cancer Ther 2013; 12(11 Suppl); C244 1-4, Nov. 2013.
Pepe, A. et. al., "Synthesis and structure-activity relationship studies of novel dihydropyridones as androgen receptor modulators", J. Med. Chem. 2013, 56, 8280-8297, Sep. 17, 2013.
Puissant, A. et al., "Targeting MYCN in neuroblastoma by BET bromodomain inhibition", Cancer discovery, 3 (2013) 308-323, Mar. 2013.
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071, Apr. 2008.
Raina, K., et al., "PROTAC-induced BET protein degradation as a therapy for castration-resistant prostate cancer", Proc Natl Acad Sci USA 113, 7124-7129 (2016), Jun. 28, 2016.

Response filed on Aug. 29, 2019, to U.S. Final Office Action dated May 29, 2019, for U.S. Appl. No. 14/371,956.
Richters, A., et al., "Identification and further development of potent TBK1 inhibitors", ACS Chemical Biology, vol. 10, No. 1, Jan. 16, 2015, pp. 289-298 (2015), Dec. 26, 2015.
Robertson, J. F. R. Fulvestrant (Faslodex)—how to make a good drug better. Oncologist 12, 774-784 (2007), Jul. 2007.
Rodriguez-Gonzalez, et al., "Targeting steroid hormone receptors for ubiquitination and degradation in breast and prostate cancer", Oncogene. 27(57), Dec. 4, 2008, 7201-7211 868.
Rotili, D., et al., "Photoactivable peptides for identifying enzyme-substrate and protein-protein interactions", Chem Commun (Carob) 47(5), Feb. 2011, 1488-1490.
Rusch, M., et al., "Identification of Acyl Protein Thioesterases 1 and 2 as the Cellular Targets of the Ras-Signaling Modulators Palmostatin B amd M", Angew. Chem. Int. Ed., 50: 9838-9842. doi:10.1002/anie.201102967 (Angew. Chem. Int. Ed. 2011, 50, 9838-9842) (2011), Oct. 10, 2011.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1-Cullin-F box complex for ubiquitination and degradation", Proc. Natl Acad Sci U S A.98(15), Jul. 17, 2001, 8554-8559.
Scagliotti, G., et al., "Phase III Multinational, Randomized, Double-Blind, Placebo-Controlled Study of Tivantinib (ARQ 197) Plus Erlotinib Versus Erlotinib Alone in Previously Treated Patients with Locally Advanced or Metastatic Nonsquamous Non-Small-Cell Lung Cancer", Journal of Clinical Oncology 33, 2667-2674 (2015), Aug. 20, 2015.
Schenkel, et al., "Discovery of Potent and Highly Selective Thienopyridine Janus Kinase 2 Inhibitors", J Med Chem.54(24), Dec. 22, 2011, 8440-8450.
Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (2008) 5904-5908, Nov. 15, 2008.
Sequist, L.V., et al., "Randomized Phase II Study of Erlotinib Plus Tivantinib Versus Erlotinib Plus Placebo in Previously Treated Non-Small-Cell Lung Cancer", Journal of Clinical Oncology 29, 3307-3315 (2011).
Smith, et al., "Targeted Intracellular Protein Degradation Induced by a Small Molecule: En Route to Chemical Proteomics", Bioorg Med Chem Lett. 18(22), Nov. 15, 2008, 5904-5908.
Stuhlmiller, Timothy J., et al., "Inhibition of Lapatinib-Induced Kinome Reprogramming in ERBB2-Positive Breast Cancer by Targeting BET Family Bromodomains", Cell Reports 11, 390-404 (2015), Apr. 21, 2015.
Toure, et al., (2016) "Small-Molecule PROTACS: New Approaches to Protein Degradation." *Angew Chem Int Ed Engl* 55(6):1966-1973 (Feb. 5, 2016).
U.S. Final Office Action dated May 29, 2019, for U.S. Appl. No. 14/371,956.
Vallee, et al., "Tricyclic Series of Heat Shock Protein 90 (HSP90) Inhibitors Part I: Discovery of Tricyclic Imidazo [4,5-c] Pyridines as Potent Inhibitors of the Hsp90 Molecular Chaperone", J Med Chem. 54(20), Oct. 27, 2011, 7206-7219.
Vamos M., et al., "Expedient synthesis of highly potent antagonists of inhibitor of apoptosis proteins (IAPs) with unique selectivity for ML-IAP", ACS Chem. Biol., 8(4), 725-732 (2013), Jan. 16, 2013.
Van Eis, et al., "2,6-Naphthyridines as potent and selective inhibitors of the novel protein kinase C isozymes", Bioorg Med Chem Lett.21(24), Dec. 15, 2011, 7367-7372.
Van Molle, et al., "Dissecting fragment-based lead discovery at the von Hippel-Lindau protein:hypoxia inducible factor 1a protein-protein interface", Chem Biol. 19(10), Oct. 26, 2012, 1300-1312.
Vassilev, et al., "In vivo activation of the p53 pathway by small-molecule antagonists of MDM2", Science 303, Feb. 6, 2004, 844-848.

(56) References Cited

OTHER PUBLICATIONS

Vu, B. et al. "Discovery of RG7112: a small-molecule MDM2 inhibitor in clinical development", ACS Med. Chem. Lett. (2013) 4, 466-469, Apr. 2, 2013.

Wang, C. et al. Estrogen induces c-myc gene expression via an upstream enhancer activated by the estrogen receptor and the AP-1 transcription factor. Mol. Endocrinol. 25, 1527-1538 (2011), Sep. 2011.

Wang, S., et al. "Small-molecule inhibitors of the MDM2-p53 protein-protein interaction (MDM2 inhibitors) in clinical trials for cancer treatment", J. Med. Chem. (2015) 58, 1038-1052, Feb. 12, 2015.

Wang, S., et al. "Temporal activation of p53 by a specific MDM2 inhibitor is selectively toxic to tumors and leads to complete tumor growth inhabitation", PNAS USA (2008) 105, 3933-3938, Mar. 11, 2008.

Willson, T.M. et al., "3-[4-(1,2-Diphenylbut-1-EnylPhenyl] Acrylic Acid: A non-steroidal estrogen with functional selectivity for bone over uterus in rats", Journal of Medicinal Chemistry, American Chemical Society, US May 25, 1994, vol. 37 No. 11, pp. 1550-1552.

Winter, et al., "Phthalimide Conjugation as a strategy for in vivo target protein degradation", Science, 2015 vol. 348 (6241), pp. 1376-1381 [Pub online: May 21, 2015].

Wright, et al., "Structure-Activity Relationships in Purine-Based Inhibitor Binding to HSP90 Isoforms", Chem Biol. 11 (6), Jun. 2004, 775-785.

Zengerle, et al., "Selective Small Molecule Induced Degradation of the BET Bromodomain Protein BRD4" ACS Chemical Biology, Jun. 2, 2015, vol. 10, pp. 1770-1777.

Zhang B.et al., "Small-molecule MDM2-p53 inhibitors: recent advances", Future Med. Chem. (2015) 7, 631-645.

Zhang, D. et al., "Targeted Degradation of Proteins by Small Molecules: A Novel Tool for Functional Proteomics," comb Chem. High Throughput Screen., 2004, vol. 7, No. 7, pp. 689-697, Nov. 2004.

Zillhardt, M., et al., "Foretinib (GSK1363089), an Orally Available Multikinase Inhibitor of c-Met and VEGFR-2, Blocks Proliferation, Induces Anoikis, and Impairs Ovarian Cancer Metastasis", Clinical Cancer Research 17, 4042-4051 (2011), Jun. 15, 2011.

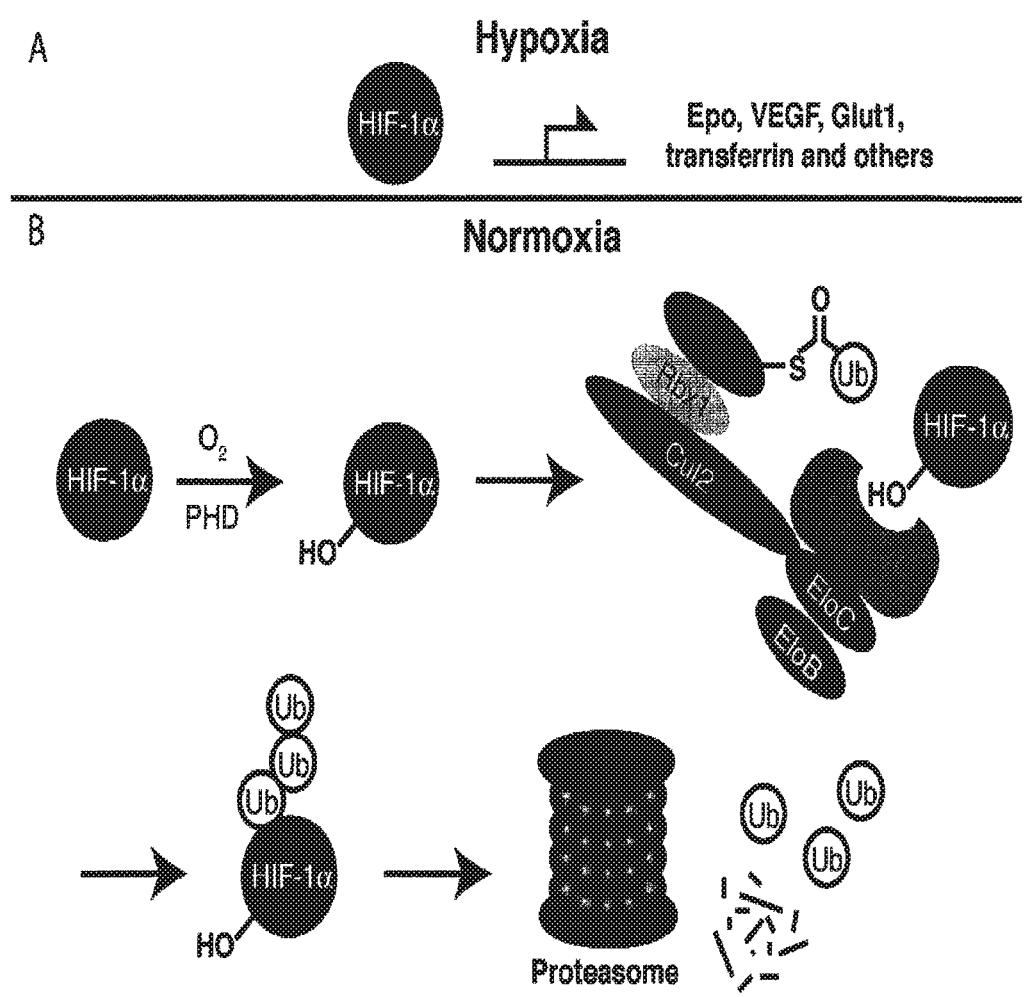

COMPOUNDS AND METHODS FOR THE ENHANCED DEGRADATION OF TARGETED PROTEINS

CROSS-REFERENCE TO RELATED APPLICATIONS

The present disclosure is a continuation of U.S. Non-Provisional patent application Ser. No. 15/074,820, filed on Mar. 18, 2016, titled: COMPOUNDS AND METHODS FOR THE ENHANCED DEGRADATION OF TARGETED PROTEINS, which claims priority to U.S. Provisional Patent Application Ser. No. 62/135,125 filed on Mar. 18, 2015; all of which are incorporated herein by reference in their entirety for all purposes.

STATEMENT REGARDING FEDERALLY FUNDED RESEARCH

This invention was made with government support under grant no. AI084140 of the National Institutes of Health. The government has certain rights in the invention.

BACKGROUND

1. Field of the Discovery

The present invention relates to bifunctional compounds, which find utility as modulators of targeted ubiquitination. In particular, the present invention is directed to compounds, which contain on one end a VHL ligand, which binds to the VHL E3 ubiquitin ligase and on the other end a moiety, which binds a target protein such that degradation of the target protein/polypeptide is effectuated. The present invention exhibits a broad range of pharmacological activities associated with compounds according to the present invention, consistent with the degradation/inhibition of targeted polypeptides.

2. Background Information

E3 ubiquitin ligases (of which over 600 are known in humans) confer substrate specificity for ubiquitination and are more attractive therapeutic targets than general proteasome inhibitors due to their specificity for certain protein substrates. Although the development of ligands of E3 ligase has proven challenging, in part due to the fact that they must disrupt protein-protein interactions recent developments have provided specific ligands which bind to these ligases. Protein-protein interaction interactions are notoriously difficult to target using small molecules due to their large contact surfaces and the shallow grooves or flat interfaces involved. Conversely, most small molecule drugs bind enzymes or receptors in tight and well-defined pockets. Since the discovery of nutlins, the first small molecule E3 ligase inhibitors, additional compounds have been reported that target Inhibitors of Apoptosis Proteins (IAPs), SCFMet30, and SCFCdc4, however, the field remains underdeveloped.

One E3 ligase with exciting therapeutic potential is the von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. While HIF-1α is constitutively expressed, its intracellular levels are kept very low under normoxic conditions via its hydroxylation by prolyl hydroxylase domain (PHD) proteins and subsequent VHL-mediated ubiquitination (FIG. 1).

The crystal structure of VHL with ligands has been obtained, confirming that a small compound can mimic the binding mode of the transcription factor HIF-1α, the major substrate of VHL. Using rational design, the first small molecule ligands of Von Hippel Lindau (VHL) the substrate recognition subunit of the E3 ligase VCB, an important target in cancer, chronic anemia and ischemia were generated.

However, an ongoing need exists in the art for effective small molecule therapeutics across disease indications. The present description provides means to recruit proteins to E3 ligases for ubiquitination and degradation, to the endpoint of providing therapies based upon the degradation of targeted proteins.

SUMMARY

The present disclosure relates to the discovery that an ubiquitin pathway protein ubiquitinates any target protein once the ubiquitin pathway protein and the target protein are placed in proximity by a chimeric construct that binds the ubiquitin pathway protein and the target protein. Accordingly, the present invention provides compositions and associated methods of use that result in the ubiquitination and subsequent degradation of a chosen target protein. The present invention also provides a library of compositions and the use thereof.

In one aspect, the disclosure provides small molecules (i.e., non-peptide based compounds) which function to recruit endogenous proteins to E3 Ubiquitin Ligase for degradation.

In another aspect, the disclosure provides proteolysis targeting chimera compounds or PROTACs that modulate protein degradation in a patient or subject and can be used for treating disease states or conditions which are modulated through the degraded protein.

In another aspect, the disclosure provides pharmaceutical compositions comprising effective amounts of the compounds as described herein, especially including inhibitors for therapeutic treatment of a patient or subject, preferably including a human patient or subject.

In another aspect, the disclosure provides methods for identifying endogenous proteins in a biological system, especially including a human system, which bind to protein binding moieties in compounds according to the present invention.

In another aspect, the disclosure provides methods for identifying the effects of the degradation of proteins of interest in a biological system using compounds according to the present invention.

In another aspect, the disclosure provides methods for treating a disease or disorder in a subject, for example, a patient such as a human, where the degradation of a targeted protein will produce an intended therapeutic effect.

In another aspect, the disclosure provides compounds and compositions which may be used in a first medical application.

Where applicable or not specifically disclaimed, any one of the aspects or embodiments described herein are contemplated to be able to combine with any other one or more embodiments, even though the embodiments are described under different aspects of the invention.

The preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention. The publications and other materials used herein to illuminate the background of the invention, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which:

FIG. 1 shows (A) HIF-1α accumulation leads to the transcriptional upregulation of genes involved in the hypoxic response, such as erythropoietin and VEGF. (B) Under normoxic conditions HIF-1 α is hydroxylated, recognized by VHL, ubiquitinated and degraded by the proteasome, preventing transcriptional upregulation.

DETAILED DESCRIPTION

The following is a detailed description provided to aid those skilled in the art in practicing the present invention. Those of ordinary skill in the art may make modifications and variations in the embodiments described herein without departing from the spirit or scope of the present disclosure. All publications, patent applications, patents, figures and other references mentioned herein are expressly incorporated by reference in their entirety, including WO 2013/106643 and US 2014-0356322.

Presently described are compositions that bind an E3 ubiquitin ligase protein complex. In particular, compositions are described that bind to Von Hippel-Lindau (VHL), the substrate recognition subunit of the E3 ligase complex VCB. In addition, the description provides bifunctional compounds including the same and associates methods of use for effectuating the ubiquitination and/or degradation of a chosen target protein. The description also provides a library of compounds as described herein.

The following terms are used to describe the present invention.

Unless otherwise defined, all technical and scientific terms used herein have the same meaning as commonly understood by one of ordinary skill in the art to which this invention belongs applying that term in context to its use in describing the present invention. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond ⫽ is shown, both a double bond and single bond are represented within the context of the compound shown.

The term "patient" or "subject" is used throughout the specification to describe an animal, preferably a human or a domesticated animal, to whom treatment, including prophylactic treatment, with the compositions according to the present invention is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present invention, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

The term "VCB E3 Ubiquitin Ligase," "Von Hippel-Lindau (or VHL) E3 Ubiquitin Ligase," "VHL," or "Ubiquitin Ligase," which are generally used interchangeably unless the context indicates otherwise, is used to describe a target enzyme(s) binding site of ubiquitin ligase moieties as described herein, e.g., in the bifunctional (chimeric) compounds as described herein. VCB E3 is a protein that in combination with an E2 ubiquitin-conjugating enzyme causes the attachment of ubiquitin to a lysine on a target protein; the E3 ubiquitin ligase targets specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

As used herein, a moiety that binds the E3 ubiquitin ligase or component thereof, e.g., VHL, is referred to as ubiquitin ligase binding moiety or "ULM."

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of these and other types of small molecule target proteins. By coupling the ULM to a protein target binding moiety ("PTM"), the target protein is ubiquitinated and/or degraded by the proteasome (see FIG. 1).

As indicated above, the description relates to the surprising and unexpected discovery that an E3 ubiquitin ligase protein ubiquitinates a target protein once it and the target protein are placed in proximity by a bifunctional PROTAC compound that binds the E3 ubiquitin ligase protein or component thereof and the target protein. Accordingly, the description provides such compounds that bind to such E3 ubiquitin ligase proteins, as well as bifunctional PROTAC compounds comprising the same.

Compounds and Compositions.

Presently described are compounds useful for regulating protein activity. The compounds comprise a ubiquitin pathway protein binding moiety (preferably for an E3 ubiquitin ligase, alone or in complex with an E2 ubiquitin conjugating enzyme which is responsible for the transfer of ubiquitin to targeted proteins) as described herein. Preferably the E3 ubiquitin ligase binding moiety is a small molecule (i.e., not peptide based). In certain aspects and embodiments, the ubiquitin pathway protein binding moiety is chemically linked, via a bond or through a chemical linker, to a protein targeting moiety, wherein the ubiquitin ligase binding moiety recognizes an ubiquitin ligase and the targeting moiety recognizes a target protein, and wherein the ubiquitin ligase protein binding moiety is coupled to the targeting moiety.

In one aspect, the description provides ubiquitin ligase binding compounds (ULMs) capable of binding an E3 ubiquitin ligase, e.g., VHL, as described further below. In certain embodiments, the ULM binds VHL.

In an additional aspect, the present invention is directed to a compound according to the structure: L-ULM, where L is a linker group and ULM is a ubiquitin ligase binding moiety. In certain embodiments, the ULM is coupled directly or via a chemical linker to a PTM.

In another aspect, the description provides compounds that comprise a PTM group according to the general structure: ULM-L-PTM, where ULM is an E3 ubiquitin ligase, e.g., VHL, binding moiety, PTM is a chemical moiety (protein targeting Moiety), which binds to a target protein or polypeptide, which is ubiquitinated by an ubiquitin ligase and is chemically linked directly to the ULM group or through a linker moiety L, which can be a bond or a chemical linker. In certain embodiments, PTM is alternatively a ULM' group which is also an E3 ubiquitin ligase binding moiety, which may be the same or different than the ULM group and is linked directly to the ULM group directly or through a linker moiety or a pharmaceutically acceptable salt, enantiomer, stereoisomer, solvate or polymorph thereof. In certain embodiments, at least one of the ULM and ULM' (when present) are coupled to a PTM, PTM' or combination thereof directly (a bond) or via a chemical linker.

In certain aspects of the invention, where PTM is a ULM' group, the compound resembles a dimeric compound where both ends of the compound comprise an ubiquitin ligase binding moiety as otherwise described herein.

Although ULM group and PTM group may be covalently linked to the linker group through any group which is appropriate and stable to the chemistry of the linker, in certain embodiments, and as detailed further below, the linker may be independently covalently bonded to the ULM group and the PTM group through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain aspects, the linker may be linked to an optionally substituted alkyl, alkylene, alkene or alkyne group, an aryl group or a heterocyclic group on the ULM and/or PTM groups.

In an additional aspect, the description provides a library of compounds. The library comprises more than one compound wherein each composition is a ULM as described herein.

In an additional aspect, the description provides a library of compounds of formula of A-B, wherein A is a ubiquitin pathway protein binding moiety or ULM (preferably, an E3 ubiquitin ligase moiety as otherwise disclosed herein), and B is a protein binding member of a molecular library or PTM, wherein A is coupled (preferably, through a linker moiety) to B, and wherein the ubiquitin pathway protein binding moiety recognizes an ubiquitin pathway protein, in particular, an E3 ubiquitin ligase. In a particular embodiment, the library contains a specific ubiquitination recognition moiety for VHL for an E3 ubiquitin ligase (ubiquitin pathway protein binding moiety as otherwise disclosed herein) with random target protein binding elements (e.g., a chemical compound library). As such, the target protein is not determined in advance and the method can be used to determine the activity of a putative protein binding element and its pharmacological value as a target upon degradation by ubiquitin ligase.

In any of the aspects or embodiments described herein, the ULM and where present, ULM', are each independently a group according to the chemical structure:

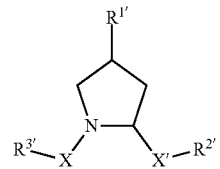

where $R^{1'}$ is an optionally substituted $C_1$-$C_6$ alkyl group, an optionally substituted —$(CH_2)_n$OH, an optionally substituted —$(CH_2)_n$SH, an optionally substituted $(CH_2)_n$—O—$(C_1$-$C_6)$alkyl group, an optionally substituted $(CH_2)_n$—WCOCW—$(C_0$-$C_6)$alkyl group containing an epoxide moiety WCOCW where each W is independently H or a $C_1$-$C_3$ alkyl group, an optionally substituted —$(CH_2)_n$COOH, an optionally substituted —$(CH_2)_n$C(O)—$(C_1$-$C_6$ alkyl), an optionally substituted —$(CH_2)_n$NHC(O)—$R_1$, an optionally substituted —$(CH_2)_n$C(O)—$NR_1R_2$, an optionally substituted —$(CH_2)_n$OC(O)—$NR_1R_2$, —$(CH_2O)_n$H, an optionally substituted —$(CH_2)_n$OC(O)—$(C_1$-$C_6$ alkyl), an optionally substituted —$(CH_2)_n$C(O)—O—$(C_1$-$C_6$ alkyl), an optionally substituted —$(CH_2O)_n$COOH, an optionally substituted —$(OCH_2)_n$O—$(C_1$-$C_6$ alkyl), an optionally substituted —$(CH_2O)_n$C(O)—$(C_1$-$C_6$ alkyl), an optionally substituted —$(OCH_2)_n$NHC(O)—$R_1$, an optionally substituted —$(CH_2O)_n$C(O)—$NR_1R_2$, —$(CH_2CH_2O)_n$H, an optionally substituted —$(CH_2CH_2O)_n$COOH, an optionally substituted —$(OCH_2CH_2)_n$O—$(C_1$-$C_6$ alkyl), an optionally substituted —$(CH_2CH_2O)_n$C(O)—$(C_1$-$C_6$ alkyl), an optionally substituted —$(OCH_2CH_2)_n$NHC(O)—$R_1$, an optionally substituted —$(CH_2CH_2O)_n$C(O)—$NR_1R_2$, an optionally substituted —$SO_2R_S$, an optionally substituted $S(O)R_S$, $NO_2$, CN or halogen (F, Cl, Br, I, preferably F or Cl);

$R_1$ and $R_2$ are each independently H or a $C_1$-$C_6$ alkyl group which may be optionally substituted with one or two hydroxyl groups or up to three halogen groups (preferably fluorine);

$R_S$ is a $C_1$-$C_6$ alkyl group, an optionally substituted aryl, heteroaryl or heterocycle group or a —$(CH_2)_m$$NR_1R_2$ group, X and X' are each independently C=O, C=S, —S(O), S(O)$_2$, (preferably X and X' are both C=O);

R$^{2'}$ is an optionally substituted —(CH$_2$)$_n$—(C=O)$_u$(NR$_1$)$_v$(SO$_2$)$_w$alkyl group, an optionally substituted —(CH$_2$)$_n$—(C=O)$_u$(NR$_1$)$_v$(SO$_2$)$_w$NR$_{1N}$R$_{2N}$ group, an optionally substituted —(CH$_2$)$_n$—(C=O)$_u$(NR$_1$)$_v$(SO$_2$)$_w$-Aryl, an optionally substituted —(CH$_2$)$_n$—(C=O)$_u$(NR$_1$)$_v$(SO$_2$)$_w$-Heteroaryl, an optionally substituted —(CH$_2$)$_n$—(C=O)$_v$NR$_1$(SO$_2$)$_w$-Heterocycle, an optionally substituted —NR$^1$—(CH$_2$)$_n$—C(O)$_u$(NR$_1$)$_v$(SO$_2$)$_w$-alkyl, an optionally substituted —NR$^1$—(CH$_2$)$_n$—C(O)$_u$(NR$_1$)$_v$(SO$_2$)$_w$—NR$_{1N}$R$_{2N}$, an optionally substituted —NR$^1$—(CH$_2$)$_n$—C(O)$_u$(NR$_1$)$_v$(SO$_2$)$_w$—NR$_1$—C(O)R$_{1N}$, an optionally substituted —NR$^1$—(CH$_2$)$_n$—(C=O)$_u$(NR$_1$)$_v$(SO$_2$)$_w$-Aryl, an optionally substituted —NR$^1$—(CH$_2$)$_n$—(C=O)$_u$(NR$_1$)$_v$(SO$_2$)$_w$-Heteroaryl or an optionally substituted —NR$^1$—(CH$_2$)$_n$—(C=O)$_v$NR$_1$(SO$_2$)$_w$-Heterocycle, an optionally substituted —X$^{R2'}$-alkyl group; an optionally substituted —X$^{R2'}$-Aryl group; an optionally substituted —X$^{R2'}$-Heteroaryl group; an optionally substituted —X$^{R2'}$-Heterocycle group; an optionally substituted;

R$^{3'}$ is an optionally substituted alkyl, an optionally substituted —(CH$_2$)$_n$—(O)$_u$(NR$_1$)$_v$(SO$_2$)$_w$-alkyl, an optionally substituted —(CH$_2$)$_n$—C(O)$_u$(NR$_1$)$_v$(SO$_2$)$_w$—NR$_{1N}$R$_{2N}$, an optionally substituted —(CH$_2$)$_n$—C(O)$_u$(NR$_1$)$_v$(SO$_2$)$_w$—NR$_1$C(O)R$_{1N}$, an optionally substituted —(CH$_2$)$_n$—C(O)$_u$(NR$_1$)$_v$(SO$_2$)$_w$—C(O)NR$_1$R$_2$, an optionally substituted —(CH$_2$)$_n$—C(O)$_u$(NR$_1$)$_v$(SO$_2$)$_w$-Aryl, an optionally substituted —(CH$_2$)$_n$—C(O)$_u$(NR$_1$)$_v$(SO$_2$)$_w$-Heteroaryl, an optionally substituted —(CH$_2$)$_n$—C(O)$_u$(NR$_1$)$_v$(SO$_2$)$_w$-Heterocycle, an optionally substituted —NR$^1$—(CH$_2$)$_n$—C(O)$_u$(NR$_1$)$_v$(SO$_2$)$_w$-alkyl, an optionally substituted —NR$^1$—(CH$_2$)$_n$—C(O)$_u$(NR$_1$)$_v$(SO$_2$)$_w$—NR$_{1N}$R$_{2N}$, an optionally substituted —NR$^1$—(CH$_2$)$_n$—C(O)$_u$(NR$_1$)$_v$(SO$_2$)$_w$—NR$_1$C(O)R$_{1N}$, an optionally substituted —NR$^1$—(CH$_2$)$_n$—C(O)$_u$(NR$_1$)$_v$(SO$_2$)$_w$-Aryl, an optionally substituted —NR$^1$—(CH$_2$)$_n$—C(O)$_u$(NR$_1$)$_v$(SO$_2$)$_w$-Heteroaryl, an optionally substituted —NR$^1$—(CH$_2$)$_n$—C(O)$_u$(NR$_1$)$_v$(SO$_2$)$_w$-Heterocycle, an optionally substituted —O—(CH$_2$)$_n$—(C=O)$_u$(NR$_1$)$_v$(SO$_2$)$_w$-alkyl, an optionally substituted —O—(CH$_2$)n-(C=O)$_u$(NR$_1$)$_v$(SO$_2$)$_w$—NR$_{1N}$R$_{2N}$, an optionally substituted —O—(CH$_2$)n-(C=O)$_u$(NR$_1$)$_v$(SO$_2$)$_w$—NR$_1$C(O)R$_{1N}$, an optionally substituted —O—(CH$_2$)$_n$—(C=O)$_u$(NR$_1$)$_v$(SO$_2$)$_w$-Aryl, an optionally substituted —O—(CH$_2$)$_n$—(C=O)$_u$(NR$_1$)$_v$(SO$_2$)$_w$-Heteroaryl or an optionally substituted —O—(CH$_2$)$_n$—(C=O)$_u$(NR$_1$)$_v$(SO$_2$)$_w$-Heterocycle; —(CH$_2$)$_n$—(V)$_{n'}$—(CH$_2$)$_n$—(V)$_{n'}$-alkyl group, an optionally substituted —(CH$_2$)$_n$—(V)$_{n'}$—(CH$_2$)$_n$—(V)$_{n'}$-Aryl group, an optionally substituted —(CH$_2$)$_n$—(V)$_{n'}$—(CH$_2$)$_n$—(V)$_{n'}$-Heteroaryl group, an optionally substituted —(CH$_2$)$_n$—(V)$_{n'}$—(CH$_2$)$_n$—(V)$_{n'}$-Heterocycle group, an optionally substituted —(CH$_2$)$_n$—N(R$_{1'}$)(C=O)$_{m'}$—(V)$_{n'}$-alkyl group, an optionally substituted —(CH$_2$)$_n$—N(R$_{1'}$)(C=O)$_{m'}$—(V)$_{n'}$-Aryl group, an optionally substituted —(CH$_2$)$_n$—N(R$_{1'}$)(C=O)$_{m'}$—(V)$_{n'}$-Heteroaryl group, an optionally substituted —(CH$_2$)$_n$—N(R$_{1'}$)(C=O)$_{m'}$—(V)$_{n'}$-Heterocycle group, an optionally substituted —X$^{R3'}$-alkyl group; an optionally substituted —X$^{R3'}$-Aryl group; an optionally substituted —X$^{R3'}$-Heteroaryl group; an optionally substituted —X$^{R3'}$-Heterocycle group; an optionally substituted;

where R$_{1N}$ and R$_{2N}$ are each independently H, C$_1$-C$_6$ alkyl which is optionally substituted with one or two hydroxyl groups and up to three halogen groups or an optionally substituted —(CH$_2$)$_n$-Aryl, —(CH$_2$)$_n$-Heteroaryl or —(CH$_2$)$_n$-Heterocycle group;

V is O, S or NR$_1$;

R$_1$ is the same as above;

R$^1$ and R$_{1'}$ are each independently H or a C$_1$-C$_3$ alkyl group;

X$^{R2'}$ and X$^{R3'}$ are each independently an optionally substituted —CH$_2$)$_n$—, —CH$_2$)$_n$—CH(X$_v$)=CH(X$_v$)— (cis or trans), —CH$_2$)$_n$—CH=CH—, —(CH$_2$CH$_2$O)$_n$— or a C$_3$-C$_6$ cycloalkyl group, where X$_v$ is H, a halo or a C$_1$-C$_3$ alkyl group which is optionally substituted;

each m is independently 0, 1, 2, 3, 4, 5, 6;
each m' is independently 0 or 1;
each n is independently 0, 1, 2, 3, 4, 5, 6;
each n' is independently 0 or 1;
each u is independently 0 or 1;
each v is independently 0 or 1;
each w is independently 0 or 1; and wherein any one or more of R$^{1'}$, R$^{2'}$, R$^{3'}$, X and X' of ULM is optionally modified to be covalently bonded to the PTM group through a linker group when PTM is not ULM', or when PTM is ULM', any one or more of R$^{1'}$, R$^{2'}$, R$^{3'}$, X and X' of each of ULM and ULM' are optionally modified to be covalently bonded to each other directly or through a linker group, or a pharmaceutically acceptable salt, stereoisomer, solvate or polymorph thereof.

In any of the aspects or embodiments described herein, the ULM and when present, ULM', are each independently a group according to the chemical structure:

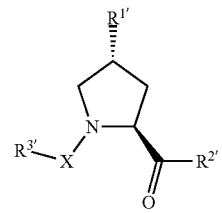

wherein each of R$^{1'}$, R$^{2'}$ and R$^{3'}$ are the same as above and X is C=O, C=S, —S(O) group or a S(O)$_2$ group, more preferably a C=O group, and wherein any one or more of R$^{1'}$, R$^{2'}$ and R$^{3'}$ are optionally modified to bind a linker group to which is further covalently bonded to the PTM group when PTM is not ULM', or when PTM is ULM', any one or more of R$^{1'}$, R$^{2'}$, R$^{3'}$ of each of ULM and ULM' are optionally modified to be covalently bonded to each other directly or through a linker group, or a pharmaceutically acceptable salt, enantiomer, diastereomer, solvate or polymorph thereof.

In any of the aspects or embodiments described herein, the ULM, and when present, ULM', are each independently according to the chemical structure:

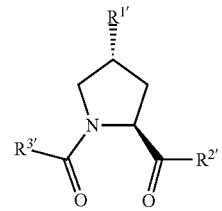

wherein any one or more of R$^{1'}$, R$^{2'}$ and R$^{3'}$ are optionally modified to bind a linker group to which is further covalently bonded to the PTM group when PTM is not ULM', or when PTM is ULM', any one or more of R$^{1'}$, R$^{2'}$, R$^{3'}$ of each of ULM and ULM' are optionally modified to be covalently bonded to each other directly or through a linker group, or a pharmaceutically acceptable salt, enantiomer, diastereomer, solvate or polymorph thereof.

In further preferred aspects of the invention, $R^{1'}$ is preferably a hydroxyl group or a group which may be metabolized to a hydroxyl or carboxylic group, such that the compound represents a prodrug form of an active compound. Exemplary preferred $R^{1'}$ groups include, for example, —$(CH_2)_n$OH, $(CH_2)_n$—O—$(C_1$-$C_6)$alkyl group, —$(CH_2)_n$COOH, —$(CH_2O)_n$H, an optionally substituted —$(CH_2)_n$OC(O)—$(C_1$-$C_6$ alkyl), or an optionally substituted —$(CH_2)_n$C(O)—O—$(C_1$-$C_6$ alkyl), wherein n is 0 or 1. Where $R^{1'}$ is or contains a carboxylic acid group, a hydroxyl group or an amine group, the hydroxyl group, carboxylic acid group or amine (each of which may be optionally substituted), may be further chemically modified to provide a covalent link to a linker group to which the PTM group (including a ULM' group) is bonded;

X and X', where present, are preferably a C=O, C=S, —S(O) group or a S(O)$_2$ group, more preferably a C=O group;

$R^{2'}$ is preferably an optionally substituted —$NR^1$-T-Aryl, an optionally substituted —$NR^1$-T-Heteroaryl group or an optionally substituted —$NR^1$-T-Heterocycle, where $R^1$ is H or $CH_3$, preferably H and T is an optionally substituted —$(CH_2)_n$— group, wherein each one of the methylene groups may be optionally substituted with one or two substituents, preferably selected from halogen, an amino acid sidechain as otherwise described herein or a $C_1$-$C_3$ alkyl group, preferably one or two methyl groups, which may be optionally substituted; and n is 0 to 6, often 0, 1, 2 or 3, preferably 0 or 1. Alternatively, T may also be a —$(CH_2O)_n$— group, a —$(OCH_2)_n$— group, a —$(CH_2CH_2O)_n$— group, a —$(OCH_2CH_2)_n$— group, all of which groups are optionally substituted.

Preferred Aryl groups for $R^{2'}$ include optionally substituted phenyl or naphthyl groups, preferably phenyl groups, wherein the phenyl group is optionally substituted with a linker group to which is attached a PTM group (including a ULM' group), a halogen (preferably F or Cl), an amine, monoalkyl- or dialkyl amine (preferably, dimethylamine), F, Cl, OH, COOH, $C_1$-$C_6$ alkyl, preferably $CH_3$, $CF_3$, OMe, OCF$_3$, NO$_2$, or CN group (each of which may be substituted in ortho-, meta- and/or para-positions of the phenyl ring, preferably para-), an optionally substituted phenyl group (the phenyl group itself is optionally substituted with a linker group attached to a PTM group, including a ULM' group), and/or at least one of F, Cl, OH, COOH, $CH_3$, $CF_3$, OMe, OCF$_3$, NO$_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

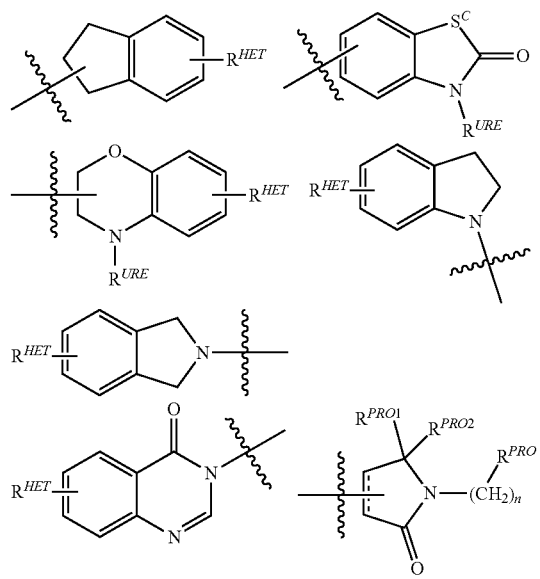

where S is $CHR^{SS}$, $NR^{URE}$, or O;

$R^{HET}$ is H, CN, NO$_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, NO$_2$, halo (preferably F or Cl), optionally substituted $C_1$-$C_6$ alkyl (preferably substituted with one or two hydroxyl groups or up to three halo groups), optionally substituted O—$(C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocycle, preferably for example piperidine, morpholine, pyrrolidine, tetrahydrofuran);

$R^{PRO}$ is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ are each independently H, an optionally substituted $C_1$-$C_3$ alkyl group or together form a keto group; and each n is independently 0, 1, 2, 3, 4, 5, or 6 (preferably 0 or 1), or an optionally substituted heterocycle, preferably tetrahydrofuran, tetrahydrothiene, piperidine, piperazine or morpholine (each of which groups when substituted, are preferably substituted with a methyl or halo (F, Br, Cl), each of which groups may be optionally substituted with a linker group to which is attached a PTM group (including a ULM' group).

In certain preferred aspects,

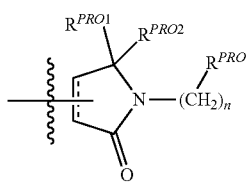

is a

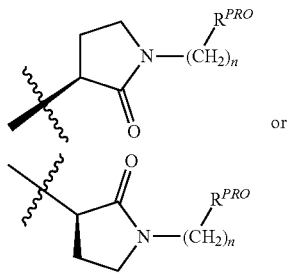

group, where $R^{PRO}$ and n are the same as above.

Preferred heteroaryl groups for $R^2$ include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

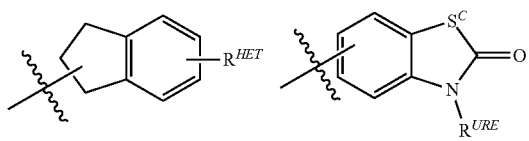

-continued

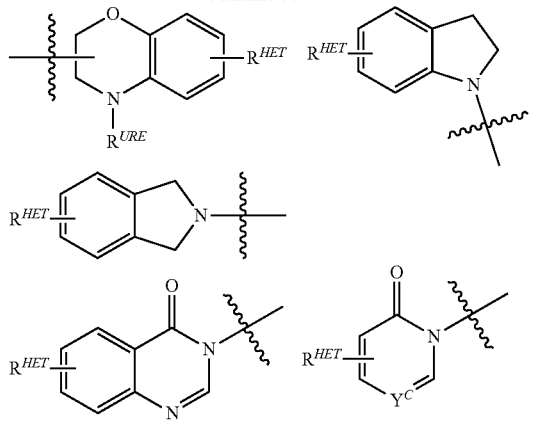

where $S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $—C{\equiv}C—R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted $O—(C_1$-$C_6$ alkyl) (preferably substituted with one or two hydroxyl groups or up to three halo groups) or an optionally substituted $—C(O)(C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a $—C(O)(C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or $C—R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $—C{\equiv}C—R_a$ where $R_a$ is H or a $C_1$-$C_6$ alkyl group (preferably $C_1$-$C_3$ alkyl), each of which groups may be optionally substituted with a linker group to which is attached a PTM group (including a ULM' group).

Preferred heterocycle groups for $R^{2'}$ include tetrahydrofuran, tetrahydrothiene, tetrahydroquinoline, piperidine, piperazine, pyrrollidine, morpholine, oxane or thiane, each of which groups may be optionally substituted, or a group according to the chemical structure:

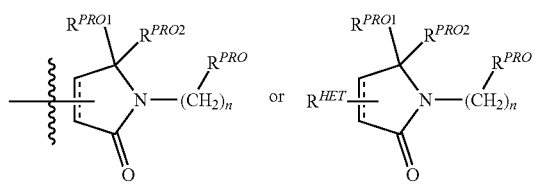

preferably, a

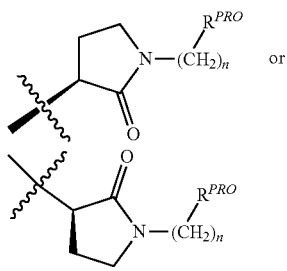

group, where $R^{PRO}$ is H, optionally substituted $C_1$-$C_6$ alkyl or an optionally substituted aryl, heteroaryl or heterocyclic group; $R^{PRO1}$ and $R^{PRO2}$ are each independently H, an optionally substituted $C_1$-$C_3$ alkyl group or together form a keto group and each n is independently 0, 1, 2, 3, 4, 5, or 6 (often 0 or 1), each of which groups may be optionally substituted with a linker group to which is attached a PTM group (including a ULM' group).

Preferred $R^{2'}$ substituents for use in the present invention also include specifically (and without limitation to the specific compound disclosed) the $R^{2'}$ substituents which are found in the identified compounds disclosed herein (which includes the specific compounds which are disclosed in the present specification, and the figures which are attached hereto). Each of these $R^{2'}$ substituents may be used in conjunction with any number of $R^{3'}$ substituents which are also disclosed herein.

$R^3$ is preferably an optionally substituted-T-Aryl, an optionally substituted
-T-Heteroaryl, an optionally substituted-T-Heterocycle, an optionally substituted
—$NR^1$-T-Aryl, an optionally substituted —$NR^1$-T-Heteroaryl or an optionally substituted
—$NR^1$-T-Heterocycle, where $R^1$ is H or a $C_1$-$C_3$ alkyl group, preferably H or $CH_3$, T is an optionally substituted —$(CH_2)_n$— group, wherein each one of the methylene groups may be optionally substituted with one or two substituents, preferably selected from halogen, a $C_1$-$C_3$ alkyl group or the sidechain of an amino acid as otherwise described herein, preferably methyl, which may be optionally substituted; and n is 0 to 6, often 0, 1, 2, or 3 preferably 0 or 1. Alternatively, T may also be a —$(CH_2O)_n$— group, a —$(OCH_2)_n$— group, a —$(CH_2CH_2O)_n$— group, a —$(OCH_2CH_2)_n$— group, each of which groups is optionally substituted.

Preferred aryl groups for $R^{3'}$ include optionally substituted phenyl or naphthyl groups, preferably phenyl groups, wherein the phenyl or naphthyl group is optionally substituted with a linker group to which is attached a PTM group (including a ULM' group) and/or a halogen (preferably F or Cl), an amine, monoalkyl- or dialkyl amine (preferably, dimethylamine), an amido group (preferably a —$(CH_2)_m$—$NR_1C(O)R_2$ group where m, $R_1$ and $R_2$ are the same as above), a halo (often F or Cl), OH, $CH_3$, $CF_3$, OMe, $OCF_3$, $NO_2$, CN or a $S(O)_2R_S$ group ($R_S$ is a $C_1$-$C_6$ alkyl group, an optionally substituted aryl, heteroaryl or heterocycle group or a —$(CH_2)_mNR_1R_2$ group), each of which may be substituted in ortho-, meta- and/or para-positions of the phenyl ring, preferably para-), or an Aryl (preferably phenyl), Heteroaryl or Heterocycle. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, CN or a linker group to which is attached a PTM group (including a ULM' group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methyl-substituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo- (preferably, F) or methylsubstitutedpyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally substituted with a linker group to which is attached a PTM group (including a ULM' group).

Preferred Heteroaryl groups for $R^{3'}$ include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—$OC_1$-$C_6$ alkyl group), an optionally substituted pyridine (2-, 3, or 4-pyridine) or a group according to the chemical structure:

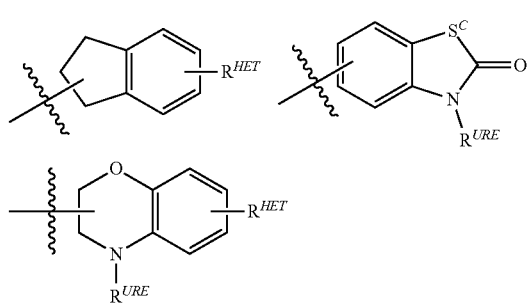

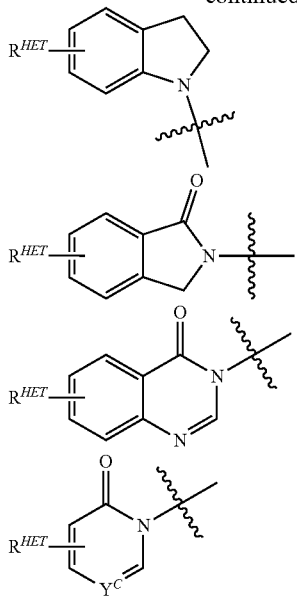

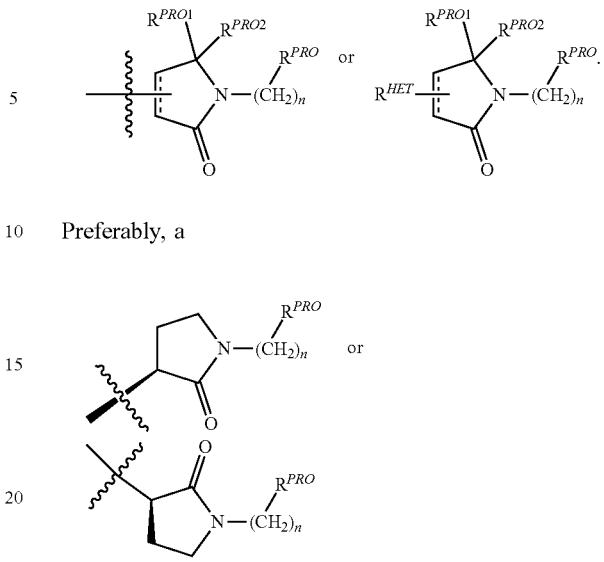

Preferably, a group;

where S$^c$ is CHR$^{SS}$, NR$^{URE}$, or O;

R$^{HET}$ is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

R$^{SS}$ is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

R$^{URE}$ is H, a C$_1$-C$_6$ alkyl (preferably H or C$_1$-C$_3$ alkyl) or a —C(O)(C$_1$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and Y$^C$ is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl). Each of said heteroaryl groups may be optionally substituted with a linker group to which is attached a PTM group (including a ULM' group).

Preferred heterocycle groups for R$^{3'}$ include tetrahydroquinoline, piperidine, piperazine, pyrrolidine, morpholine, tetrahydrofuran, tetrahydrothiophene, oxane and thiane, each of which groups may be optionally substituted or a group according to the chemical structure:

where R$^{PRO}$ is H, optionally substituted C$_1$-C$_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a C$_1$-C$_3$ alkyl group, preferably methyl or a halo group, preferably F or Cl), benzofuran, indole, indolizine, azaindolizine;

R$^{PRO1}$ and R$^{PRO2}$ are each independently H, an optionally substituted C$_1$-C$_3$ alkyl group or together form a keto group, and each n is 0, 1, 2, 3, 4, 5, or 6 (preferably 0 or 1), wherein each of said Heterocycle groups may be optionally substituted with a linker group to which is attached a PTM group (including a ULM' group).

Preferred R$^{3'}$ substituents for use in the present invention also include specifically (and without limitation to the specific compound disclosed) the R$^{3'}$ substituents which are found in the identified compounds disclosed herein (which includes the specific compounds which are disclosed in the present specification, and the figures which are attached hereto). Each of these R$^{3'}$ substituents may be used in conjunction with any number of R$^{2'}$ substituents, which are also disclosed herein.

In certain alternative preferred embodiments, R$^{2'}$ is an optionally substituted —NR$_1$—X$^{R2'}$-alkyl group, —NR$_1$—X$^{R2'}$-Aryl group; an optionally substituted —NR$_1$—X$^{R2'}$-HET, an optionally substituted —NR$_1$—X$^{R2'}$-Aryl-HET or an optionally substituted —NR$_1$—X$^{R2'}$-HET-Aryl;

where R$_1$ is H or a C$_1$-C$_3$ alkyl group (preferably H);

X$^{R2'}$ is an optionally substituted —CH$_2$)$_n$—, —CH$_2$)$_n$—CH(X$_v$)=CH(X$_v$)— (cis or trans),
—CH$_2$)$_u$—CH≡CH—, —(CH$_2$CH$_2$O)$_n$— or a C$_3$-C$_6$ cycloalkyl group;

where X$_v$ is H, a halo or a C$_1$-C$_3$ alkyl group which is optionally substituted with one or two hydroxyl groups or up to three halogen groups;

Alkyl is an optionally substituted C1-C$_{10}$ alkyl (preferably a C$_1$-C$_6$ alkyl) group (in certain preferred embodiments, the alkyl group is end-capped with a halo group, often a Cl or Br);

Aryl is an optionally substituted phenyl or naphthyl group (preferably, a phenyl group); and HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl) or a group according to the chemical structure:

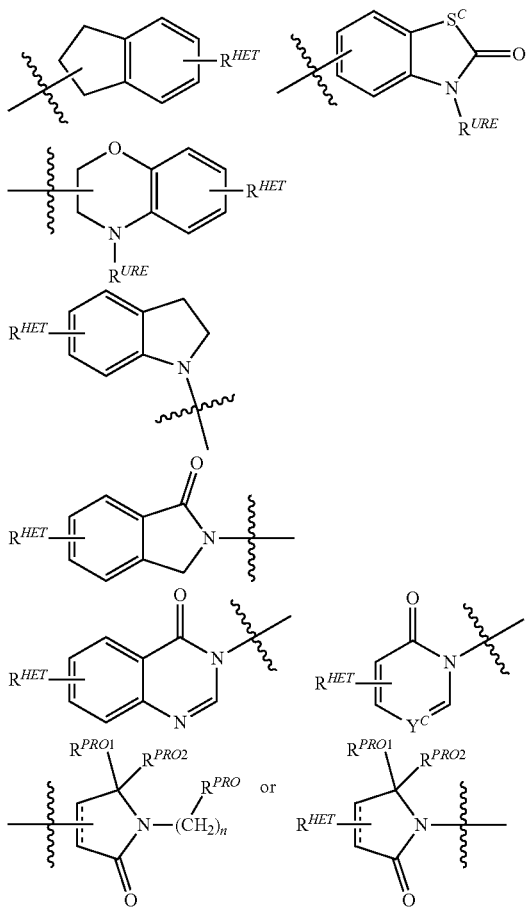

where S is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ are each independently H, an optionally substituted $C_1$-$C_3$ alkyl group or together form a keto group, and each n is independently 0, 1, 2, 3, 4, 5, or 6 (preferably 0 or 1). Each of said groups may be optionally substituted with a linker group to which is attached a PTM group (including a ULM' group).

In certain alternative preferred embodiments of the present invention, $R^{3'}$ is an optionally substituted —$(CH_2)_n$—$(V)_{n'}$—$(CH_2)_n$—$(V)_{n'}$—$R^{S3'}$ group, an optionally substituted —$(CH_2)_n$—$N(R_1)(C═O)_{m'}$—$(V)_{n'}$—$R^{S3'}$ group, an optionally substituted —$X^{R3'}$-alkyl group, an optionally substituted —$X^{R3'}$-Aryl group; an optionally substituted —$X^{R3'}$-HET group, an optionally substituted —$X^{R3'}$-Aryl-HET group or an optionally substituted —$X^{R3'}$-HET-Aryl group;

where $R^{S3'}$ is an optionally substituted alkyl group ($C_1$-$C_{10}$, preferably $C_1$-$C_6$ alkyl), an optionally substituted Aryl group or a HET group;

$R_1$, is H or a $C_1$-$C_3$ alkyl group (preferably H);

V is O, S or $NR_1$;

$X^{R3'}$ is —$(CH_2)_n$—, —$(CH_2CH_2O)_n$—, —$CH_2)_n$—CH$(X_v)$═CH$(X_v)$— (cis or trans), —$CH_2)_n$—CH≡CH—, or a $C_3$-$C_6$ cycloalkyl group, all optionally substituted;

where $X_v$ is H, a halo or a $C_1$-$C_3$ alkyl group which is optionally substituted with one or two hydroxyl groups or up to three halogen groups;

Alkyl is an optionally substituted $C_1$-$C_{10}$ alkyl (preferably a $C_1$-$C_6$ alkyl) group (in certain preferred embodiments, the alkyl group is end-capped with a halo group, often a Cl or Br);

Aryl is an optionally substituted phenyl or napthyl group (preferably, a phenyl group); and HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl), or a group according to the chemical structure:

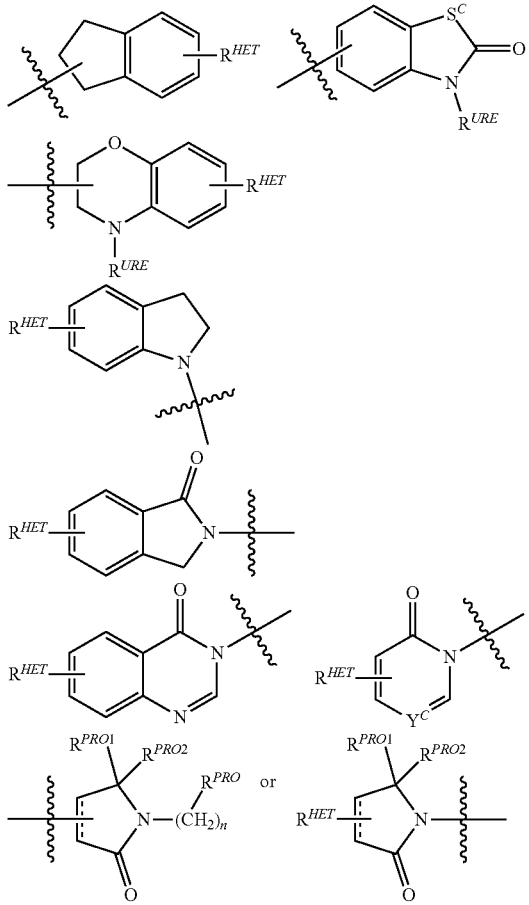

where S is CHR$^{SS}$, NR$^{URE}$, or O;

R$^{HET}$ is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

R$^{SS}$ is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

R$^{URE}$ is H, a C$_1$-C$_6$ alkyl (preferably H or C$_1$-C$_3$ alkyl) or a —C(O)(C$_0$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

Y$^C$ is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

R$^{PRO}$ is H, optionally substituted C$_1$-C$_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a C$_1$-C$_3$ alkyl group, preferably methyl or a halo group, preferably F or Cl), benzofuran, indole, indolizine, azaindolizine;

R$^{PRO1}$ and R$^{PRO2}$ are each independently H, an optionally substituted C$_1$-C$_3$ alkyl group or together form a keto group;

each n is independently 0, 1, 2, 3, 4, 5, or 6 (preferably 0 or 1);

each m' is 0 or 1; and each n' is 0 or 1;

wherein each of said compounds, preferably on the alkyl, Aryl or Het groups, is optionally substituted with a linker group to which is attached a PTM group (including a ULM' group).

In alternative embodiments, R$^{3'}$ is —(CH$_2$)$_n$-Aryl, —(CH$_2$CH$_2$O)$_n$-Aryl, —(CH$_2$)$_n$-HET or —(CH$_2$CH$_2$O)$_n$-HET;

where Aryl is phenyl which is optionally substituted with one or two substitutents, wherein said substituent(s) is preferably selected from —(CH$_2$)$_n$OH, C$_1$-C$_6$ alkyl which itself is further optionally substituted with CN, halo (up to three halo groups), OH, —(CH$_2$)$_n$O(C$_1$-C$_6$)alkyl, amine, mono- or di-(C$_1$-C$_6$ alkyl) amine wherein the alkyl group on the amine is optionally substituted with 1 or 2 hydroxyl groups or up to three halo (preferably F, Cl) groups, or said Aryl group is substituted with —(CH$_2$)$_n$OH, —(CH$_2$)$_n$—O—(C$_1$-C$_6$)alkyl, —(CH$_2$)$_n$—O—(CH$_2$)$_n$—(C$_1$-C$_6$)alkyl, —(CH$_2$)$_n$—C(O)(C$_0$-C$_6$) alkyl, —(CH$_2$)$_n$—C(O)O(C$_0$-C$_6$)alkyl, —(CH$_2$)$_n$—OC(O)(C$_0$-C$_6$)alkyl, amine, mono- or di-(C$_1$-C$_6$ alkyl) amine wherein the alkyl group on the amine is optionally substituted with 1 or 2 hydroxyl groups or up to three halo (preferably F, Cl) groups, CN, NO$_2$, an optionally substituted —(CH$_2$)$_n$—(V)$_{m'}$—CH$_2$)$_n$—(V)$_{m'}$—(C$_1$-C$_6$)alkyl group, a —(V)$_{m'}$—(CH$_2$CH$_2$O)$_n$—R$^{PEG}$ group where V is O, S or NR$_{1'}$, R$_{1'}$ is H or a C$_1$-C$_3$ alkyl group (preferably H) and R$^{PEG}$ is H or a C$_1$-C$_6$ alkyl group which is optionally substituted (including being optionally substituted with a carboxyl group), or said Aryl group is optionally substituted with a heterocycle, including a heteroaryl, selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, (when substituted each preferably substituted with a C$_1$-C$_3$ alkyl group, preferably methyl or a halo group, preferably F or Cl), or a group according to the chemical structure:

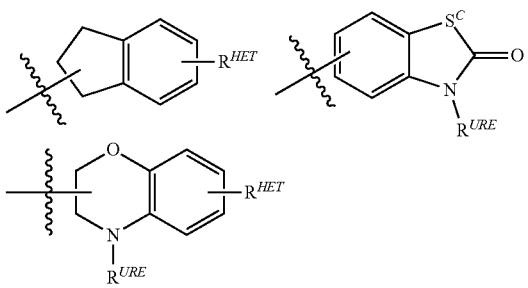

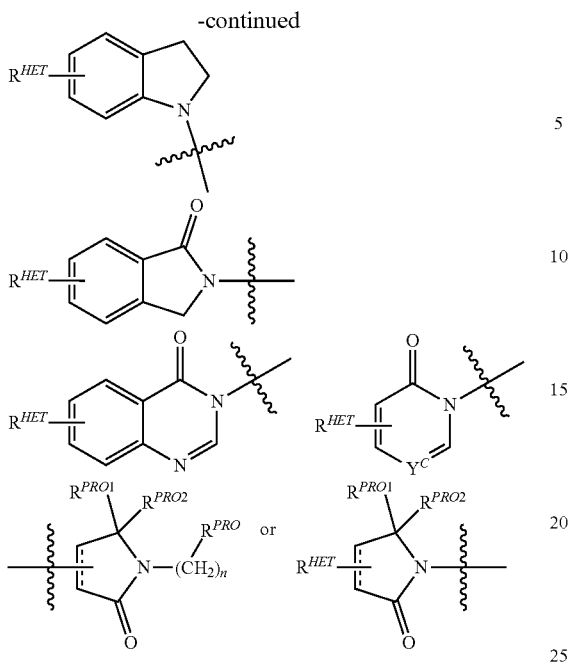

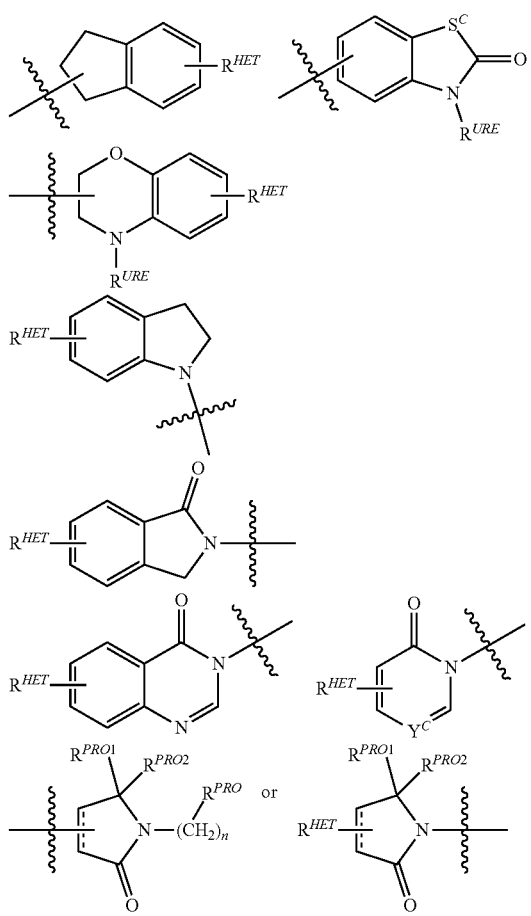

where $S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ are each independently H, an optionally substituted $C_1$-$C_3$ alkyl group or together form a keto group;

HET is preferably oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine, or a group according to the chemical structure:

where $S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ is H, optionally substituted $C_1$-$C_6$ alkyl or an optionally substituted aryl, heteroaryl or heterocyclic group;

$R^{PRO1}$ and $R^{PRO2}$ are each independently H, an optionally substituted $C_1$-$C_3$ alkyl group or together form a keto group;

each m' is independently 0 or 1; and each n is independently 0, 1, 2, 3, 4, 5, or 6 (preferably 0 or 1), wherein each of said compounds, preferably on said Aryl or HET groups, is optionally substituted with a linker group to which is attached a PTM group (including a ULM' group).

In still additional embodiments, preferred compounds include those according to the chemical structure:

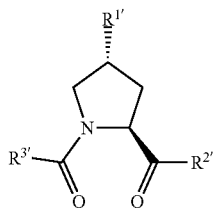

where $R^{1'}$ is OH or a group which is metabolized in a patient or subject to OH;

$R^{2'}$ is a —NH—$CH_2$-Aryl-HET (preferably, a phenyl linked directly to a methyl substituted thiazole);

$R^{3'}$ is a —$CHR^{CR3'}$—NH—C(O)—$R^{3P1}$ group or a —$CHR^{CR3'}$—$R^{3P2}$ group;

where $R^{CR3'}$ is a $C_1$-$C_4$ alkyl group, preferably methyl, isopropyl or tert-butyl;

$R^{3P1}$ is $C_1$-$C_3$ alkyl (preferably methyl), an optionally substituted oxetane group (preferably methyl substituted, a —$(CH_2)_n OCH_3$ group where n is 1 or 2 (preferably 2), or a

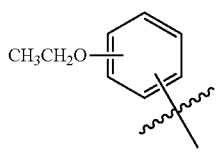

group (the ethyl ether group is preferably meta-substituted on the phenyl moiety), a morpholino group (linked to the carbonyl at the 2- or 3-position;

$R^{3P2}$ is a

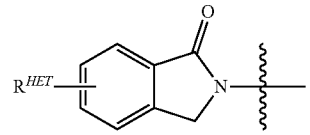

group;
Aryl is phenyl;
HET is an optionally substituted thiazole or isothiazole; and
$R^{HET}$ is H or a halo group (preferably H);
or a pharmaceutically acceptable salt, stereoisomer, solvate or polymorph thereof, wherein each of said compounds is optionally substituted with a linker group to which is attached a PTM group (including a ULM' group).

In certain aspects, bifunctional compounds comprising a ubiquitin E3 ligase binding moiety (ULM), wherein ULM is a group according to the chemical structure:

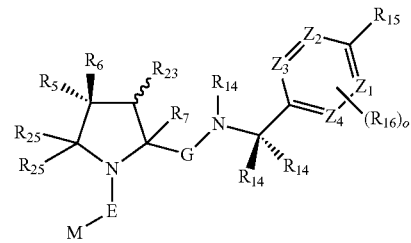

wherein, each $R_5$ and $R_6$ is independently OH, SH, or optionally substituted alkyl or $R_5$, $R_6$, and the carbon atom to which they are attached form a carbonyl;

$R_7$ is H or optionally substituted alkyl;

E is a bond, C=O, or C=S;

G is a bond, optionally substituted alkyl, —COOH or C=J;

J is O or N—$R_8$;

$R_8$ is H, CN, optionally substituted alkyl or optionally substituted alkoxy;

M is optionally substituted aryl, optionally substituted heteroaryl, optionally substituted heterocyclic or

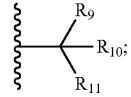

each $R_9$ and $R_{10}$ is independently H; optionally substituted alkyl, optionally substituted cycloalkyl, optionally substituted hydroxyalkyl, optionally substituted thioalkyl, a disulphide linked ULM, optionally substituted heteroaryl, or haloalkyl; or $R_9$, $R_{10}$, and the carbon atom to which they are attached form an optionally substituted cycloalkyl;

$R_{11}$ is optionally substituted heterocyclic, optionally substituted alkoxy, optionally substituted heteroaryl, optionally substituted aryl, or

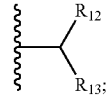

$R_{12}$ is H or optionally substituted alkyl;

$R_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate, each $R_{14}$ is independently H, haloalkyl, optionally substituted cycloalkyl, optionally substituted alkyl or optionally substituted heterocycloalkyl;

$R_{15}$ is H, optionally substituted heteroaryl, haloalkyl, optionally substituted aryl, optionally substituted alkoxy, or optionally substituted heterocyclyl;

each $R_{16}$ is independently halo, optionally substituted alkyl, optionally substituted haloalkyl, CN, or optionally substituted haloalkoxy;

each $R_{25}$ is independently H or optionally substituted alkyl; or both $R_{25}$ groups can be taken together to form an oxo or optionally substituted cycloalkyl group;

$R_{23}$ is H or OH;

$Z_1$, $Z_2$, $Z_3$, and $Z_4$ are independently C or N; and o is 0, 1, 2, 3, or 4, or a pharmaceutically acceptable salt, stereoisomer, solvate or polymorph thereof.

In certain embodiments, the ULM is coupled to a protein targeting moiety (PTM) directly via a bond or through a chemical linker (L).

In certain embodiments, G is C=J, J is O, $R_7$ is H, each $R_{14}$ is H, and o is 0.

In certain embodiments, G is C=J, J is O, $R_7$ is H, each $R_{14}$ is H, $R_{15}$ is optionally substituted heteroaryl, and o is 0. In other instances, E is C=O and M is

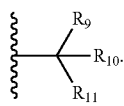

In certain embodiments, E is C=O, $R_{11}$ is optionally substituted heterocyclic or

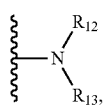

and M is

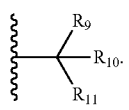

In certain embodiments, E is C=O, M is

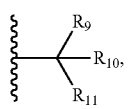

and $R_{11}$ is

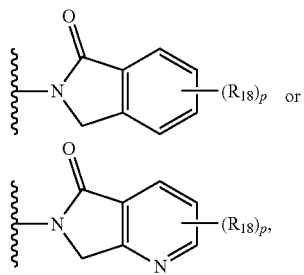

each $R_{18}$ is independently halo, optionally substituted alkoxy, cyano, optionally substituted alkyl, haloalkyl, or haloalkoxy; and p is 0, 1, 2, 3, or 4.

In certain embodiments, ULM and where present, ULM', are each independently a group according to the chemical structure:

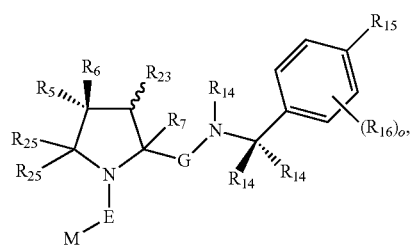

wherein G is C=J, J is O, $R_7$ is H, each $R_{14}$ is H, o is 0, $R_{15}$ is

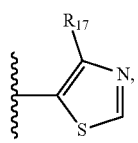

and $R_{17}$ is H, halo, optionally substituted cycloalkyl, optionally substituted alkyl, optionally substituted alkenyl, and haloalkyl. In other instances, $R_{17}$ is alkyl (e.g., methyl) or cycloalkyl (e.g., cyclopropyl). In certain embodiments, the ULM is coupled to a PTM directly via a bond or by a chemical linker.

In other embodiments, ULM and where present, ULM', are each independently a group according to the chemical structure:

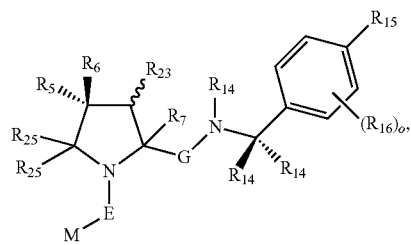

wherein G is C=J, J is O, $R_7$ is H, each $R_{14}$ is H, o is 0, and $R_{15}$ is selected from the group consisting of:

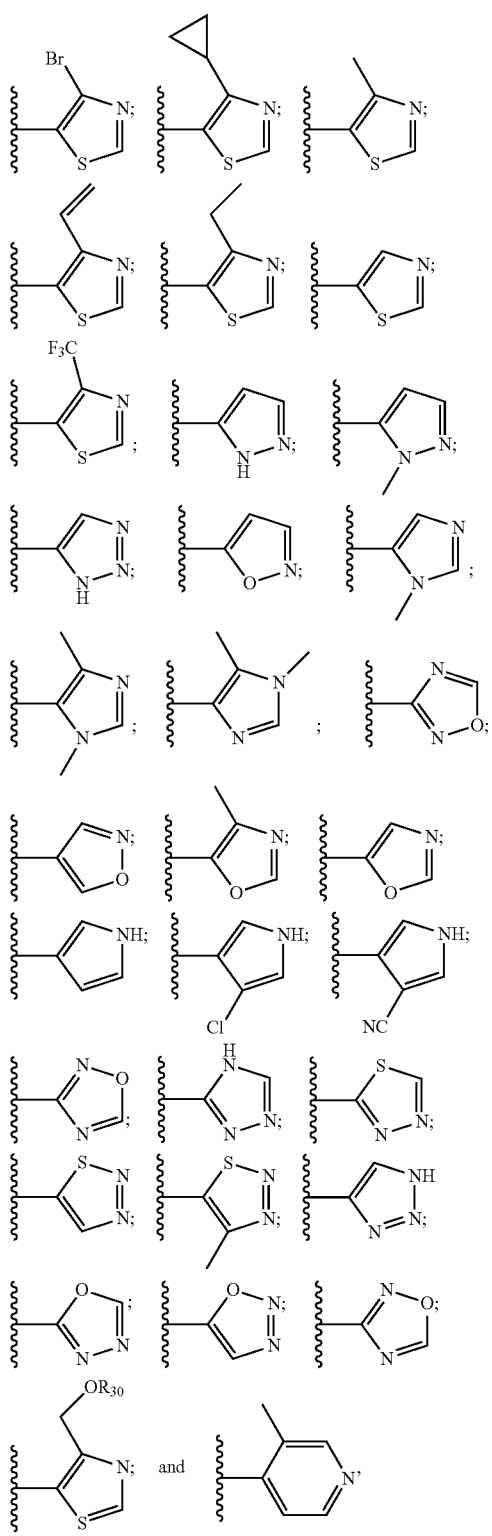
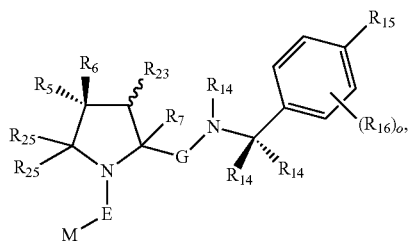
wherein E is C=O, M is
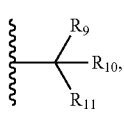
$R_{11}$ is selected from the group consisting of:
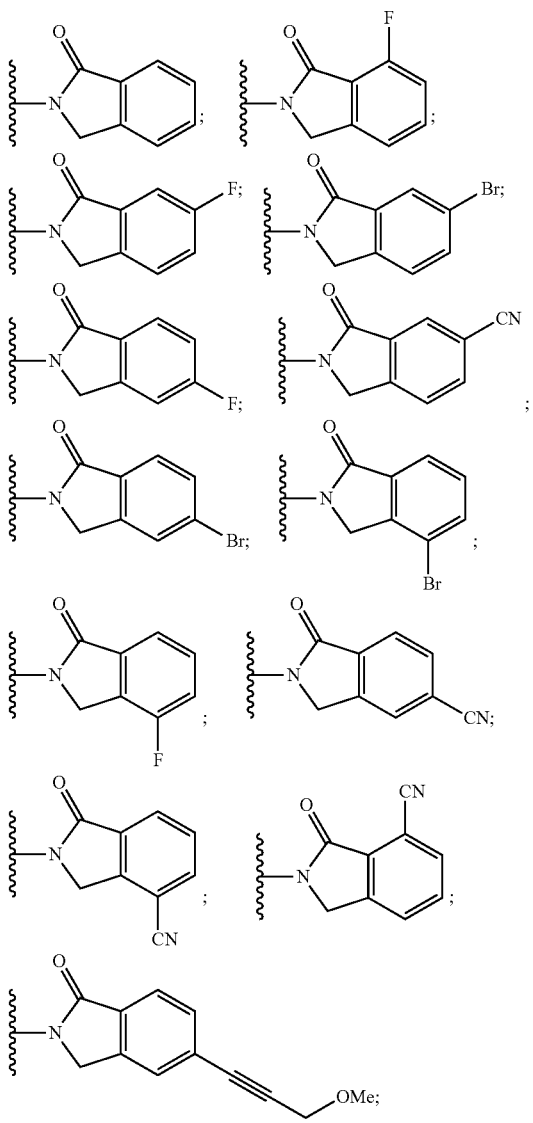
wherein $R_{30}$ is H or an optionally substituted alkyl. In certain embodiments, the ULM is coupled to a PTM directly via a bond or by a chemical linker.
In other embodiments, ULM and where present, ULM', are each independently a group according to the chemical structure:

-continued

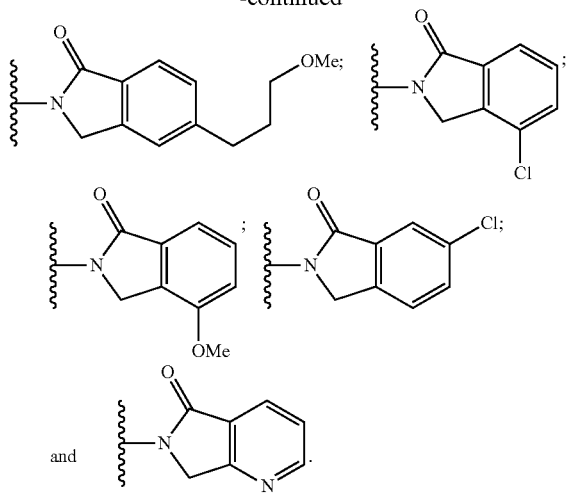

In certain embodiments, the ULM is coupled to a PTM directly via a bond or by a chemical linker.

In still other embodiments, a compound of the chemical structure,

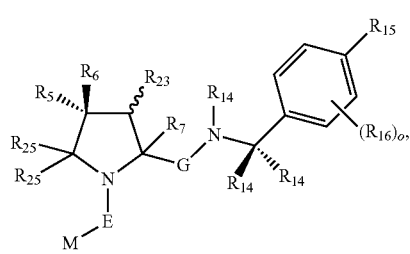

wherein E is C=O, $R_{11}$ is

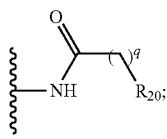

and M is

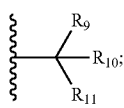

wherein q is 1 or 2;

$R_{20}$ is H, optionally substituted alkyl, optionally substituted cycloalkyl, optionally substituted aryl, or

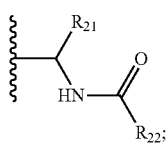

$R_{21}$ is H or optionally substituted alkyl; and $R_{22}$ is H, optionally substituted alkyl, optionally substituted alkoxy, or haloalkyl. In certain embodiments, the ULM is coupled to a PTM directly via a bond or by a chemical linker.

In any of the above embodiments, $R_{11}$ is selected from the group consisting of:

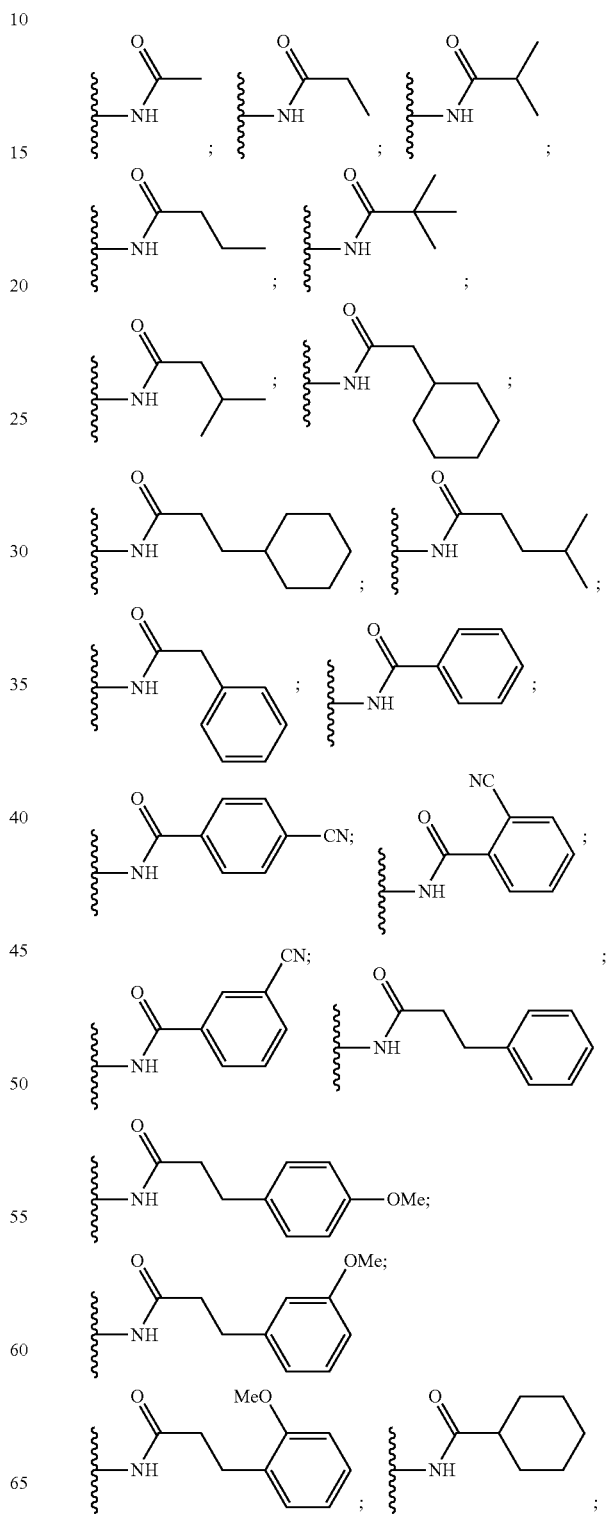

33 34
-continued -continued
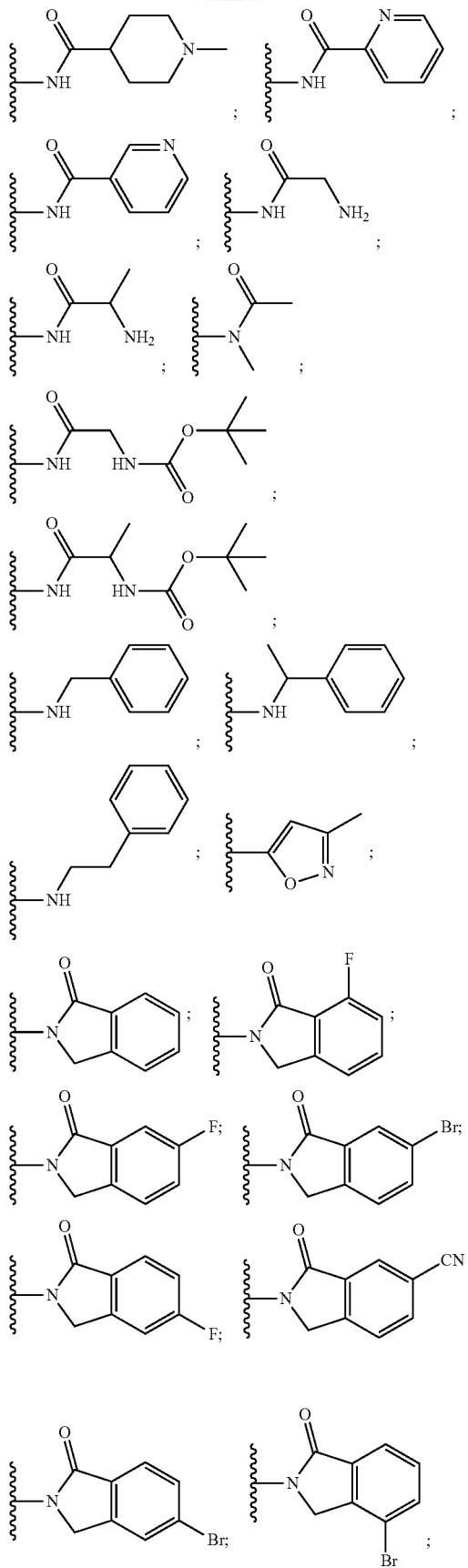
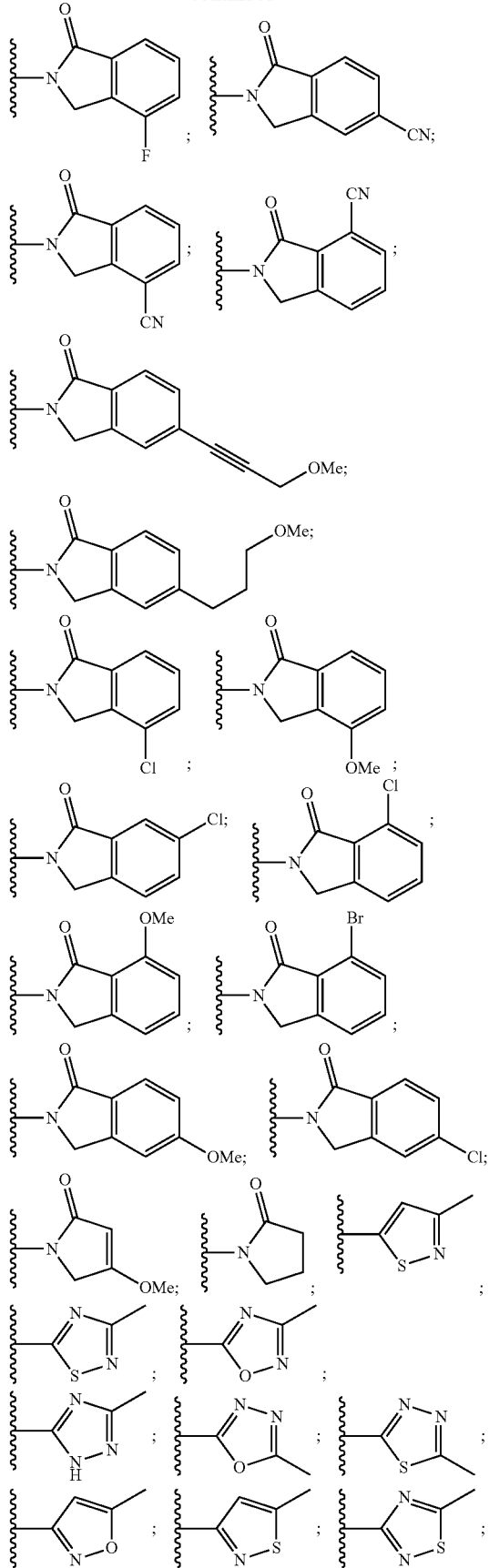

-continued
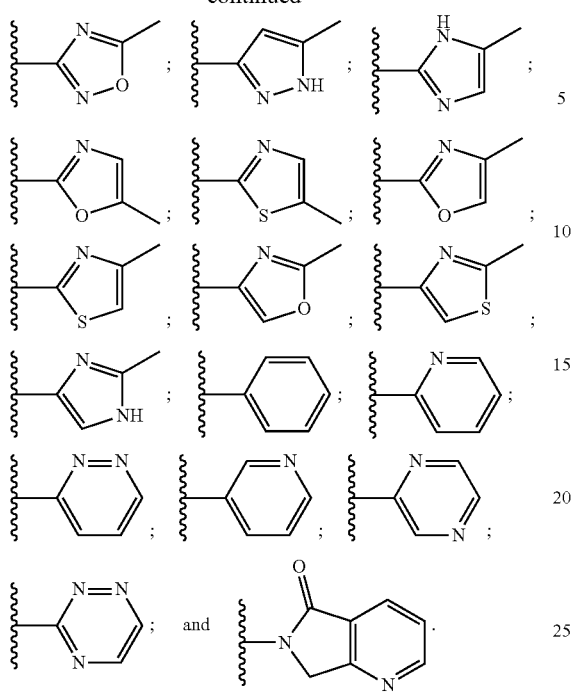
In certain embodiments, $R_{11}$ is selected from the group consisting of:
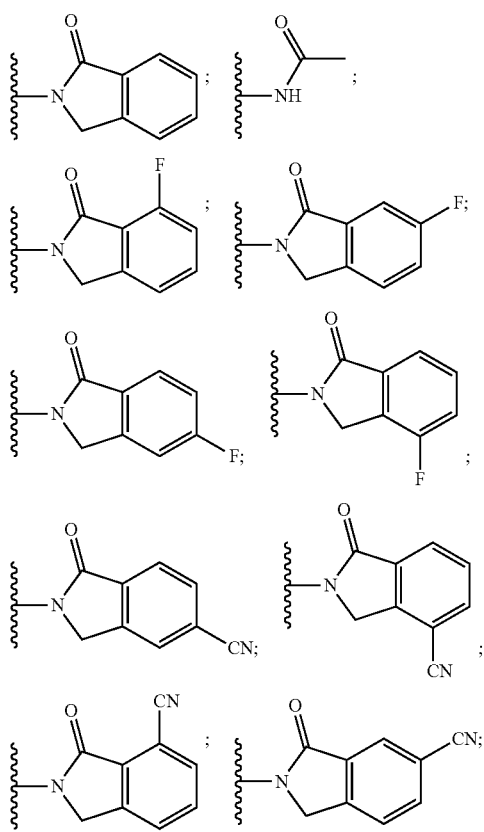
-continued
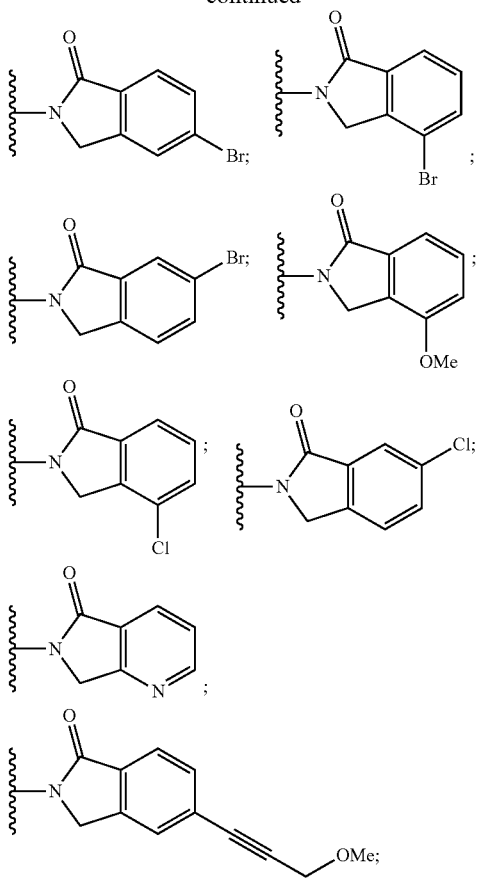
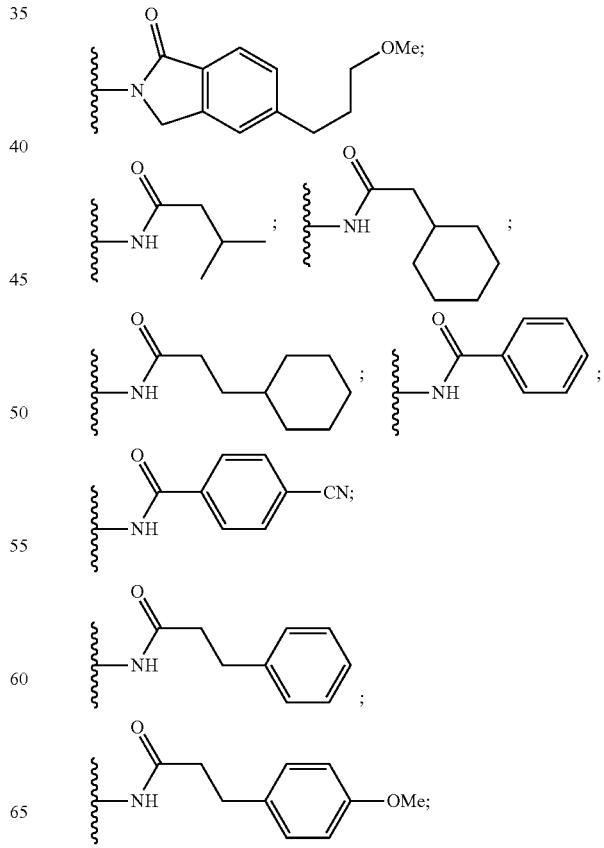

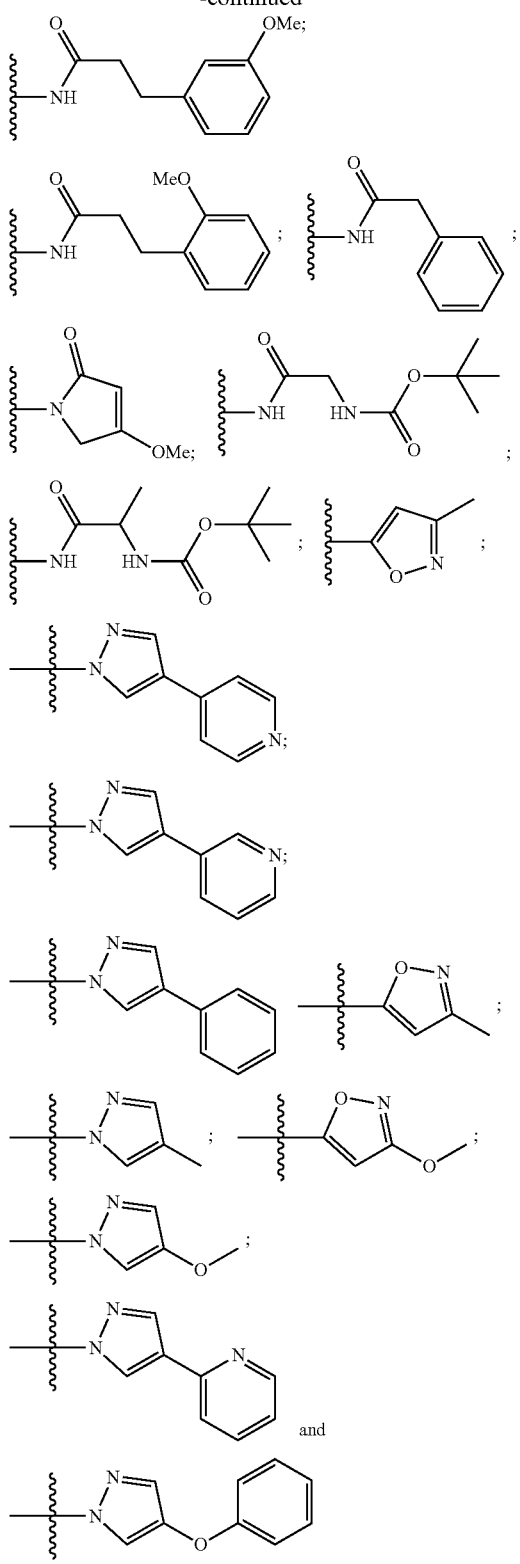

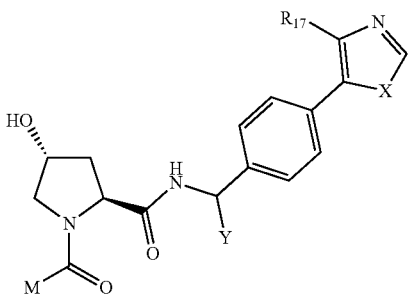

wherein X is O or S
Y is H, methyl or ethyl
$R_{17}$ is H, methyl, ethyl, hydoxymethyl or cyclopropyl;
M is optionally substituted heteroaryl, optionally substituted aryl, $R_9$ is H;
$R_{10}$ is H, optionally substituted alkyl, optionally substituted haloalkyl, optionally substituted heteroaryl, optionally substituted aryl, optionally substituted hydroxyalkyl, optionally substituted thioalkyl or cycloalkyl.
R11 is optionally substituted heteroaromatic, optionally substituted heterocyclic, optionally substituted aryl or

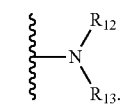

and $R_{12}$ is H or optionally substituted alkyl;
$R_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate.

In some embodiments, ULM and where present, ULM', are each independently a group according to the chemical structure:

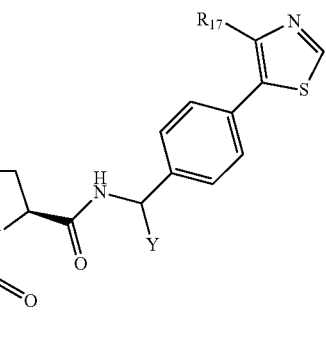

wherein Y is H, methyol or ethyl
R9 is H;
$R_{10}$ is isopropyl, tert-butyl, sec-butyl, cyclopentyl, or cyclohexyl;
R11 is optionally substituted amide, optionally substituted isoindolinone, optionally substituted isooxazole, optionally substituted heterocycles.

In other preferred embodiments of the invention, ULM and where present, ULM', are each independently a group according to the chemical structure:

In certain embodiments, ULM (or when present ULM') is a group according to the chemical structure:

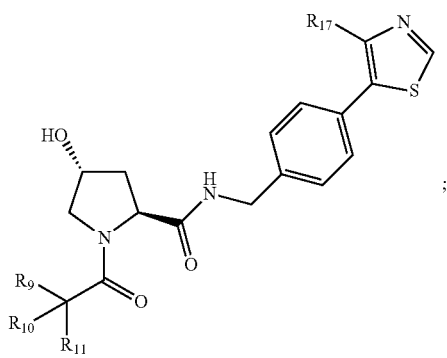

wherein $R_{17}$ is methyl, ethyl, or cyclopropyl; and $R_9$, $R_{10}$, and $R_{11}$ are as defined above. In other instances, $R_9$ is H; and $R_{10}$ is H, alkyl, or cycloalkyl (preferably, isopropyl, tert-butyl, sec-butyl, cyclopentyl, or cyclohexyl).

In any of the aspects or embodiments described herein, the ULM (or when present, ULM') as described herein may be a pharmaceutically acceptable salt, enantiomer, diastereomer, solvate or polymorph thereof. In addition, in any of the aspects or embodiments described herein, the ULM (or when present, ULM') as described herein may be coupled to a PTM directly via a bond or by a chemical linker.

In certain aspects of the invention, the ULM moiety is selected from the group consisting of:

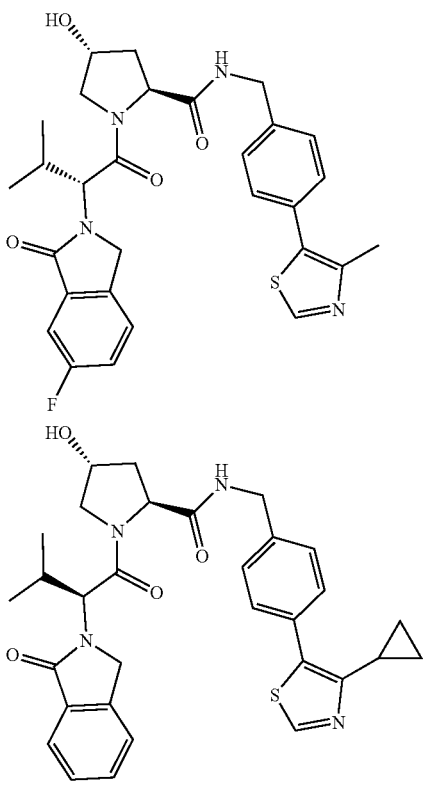

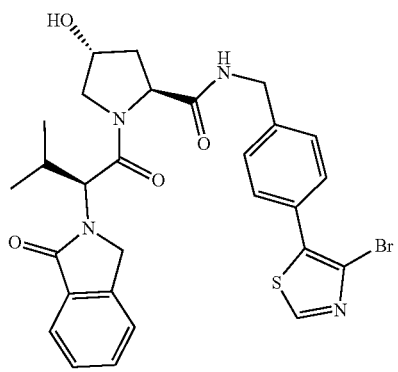

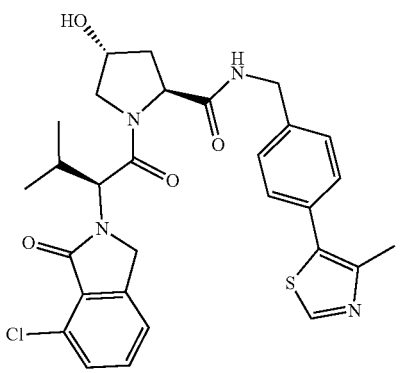

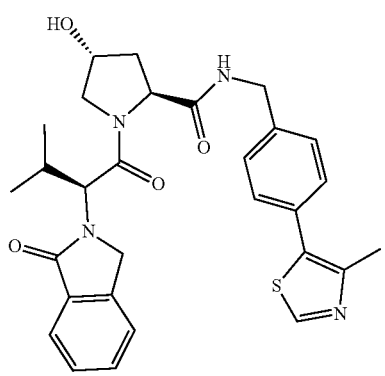

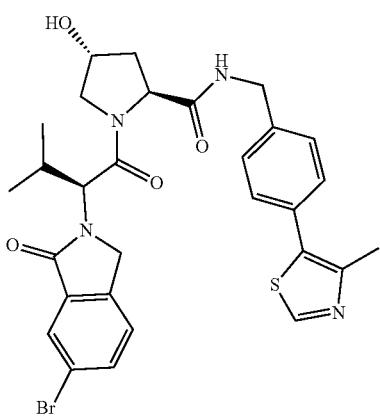

41
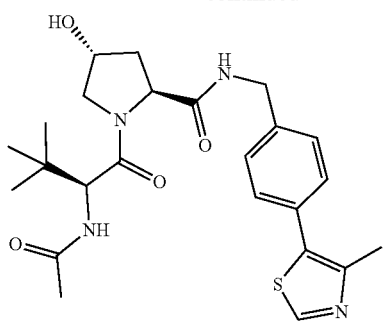
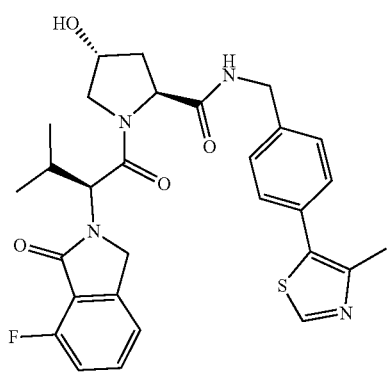
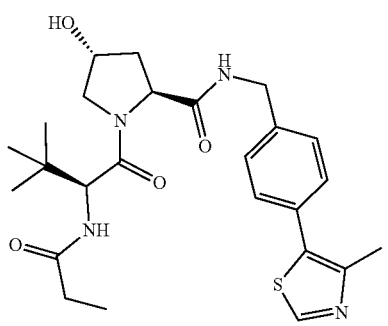
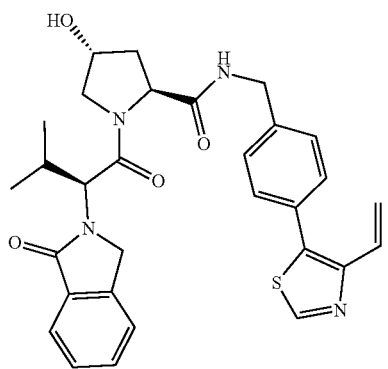
42
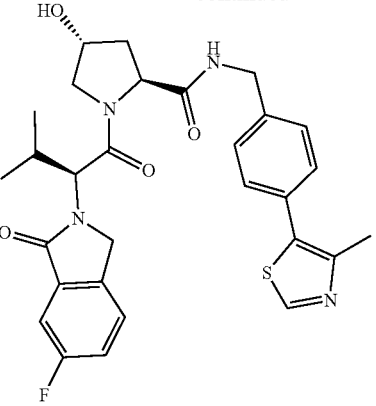
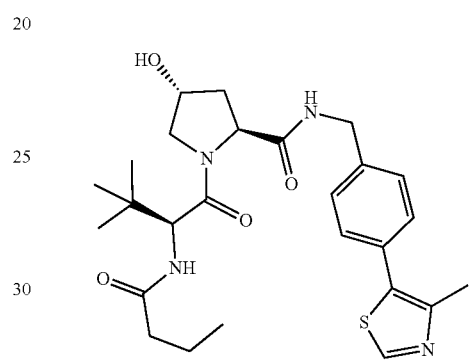
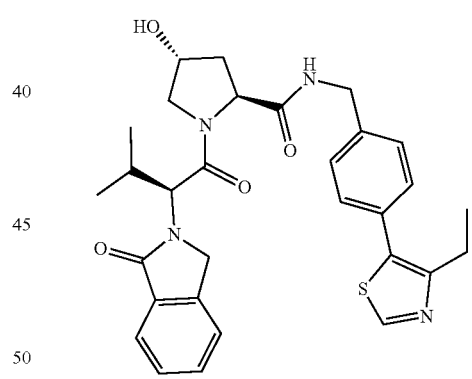
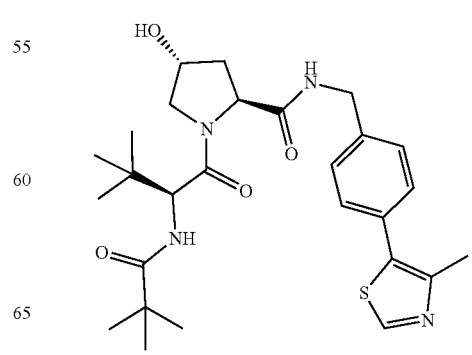

43
-continued
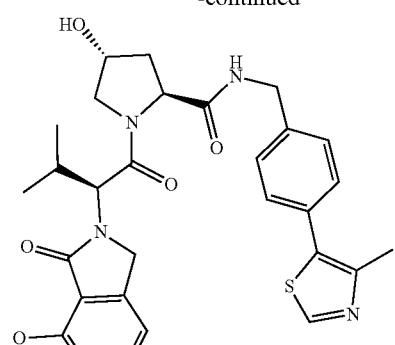
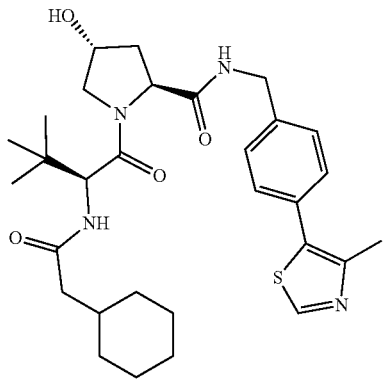
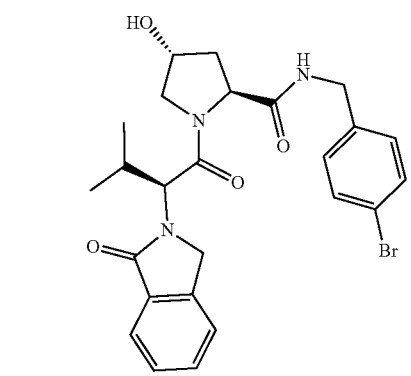
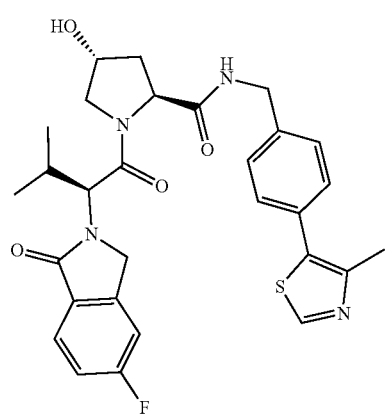
44
-continued
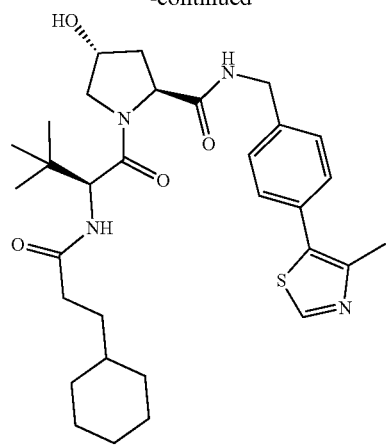
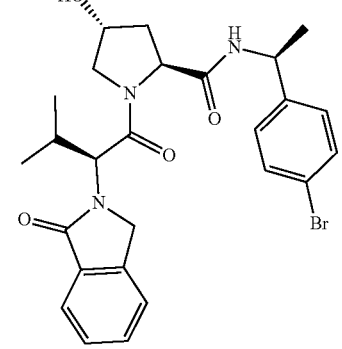
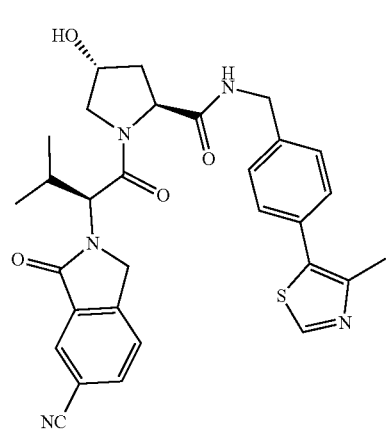
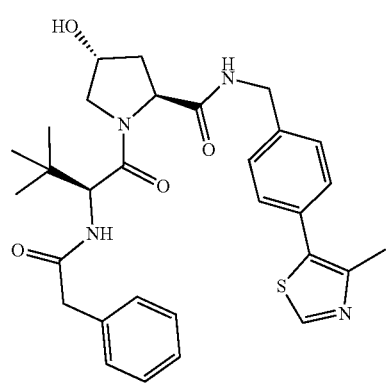

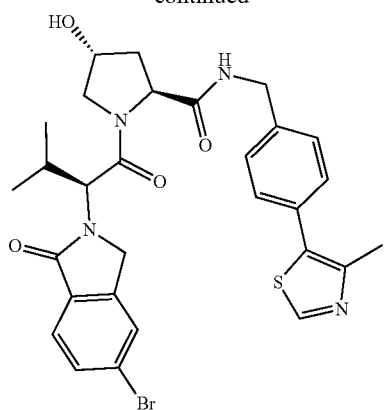
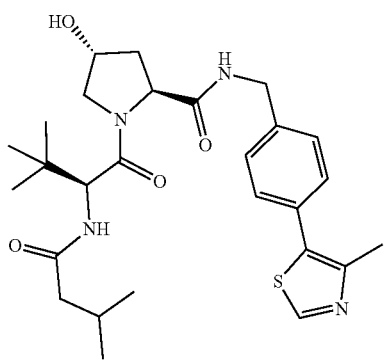
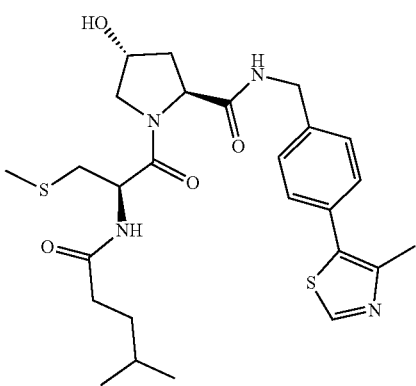
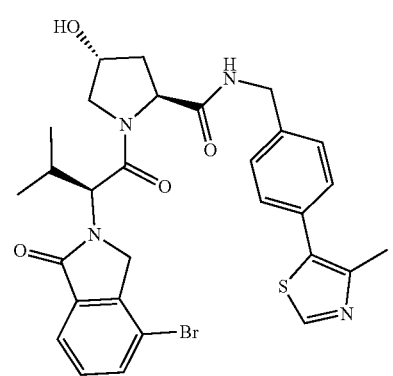
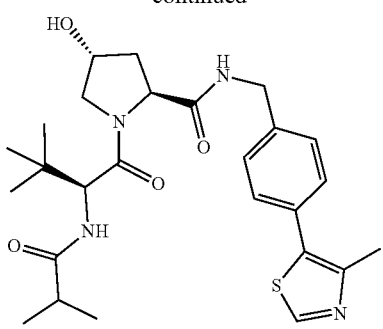
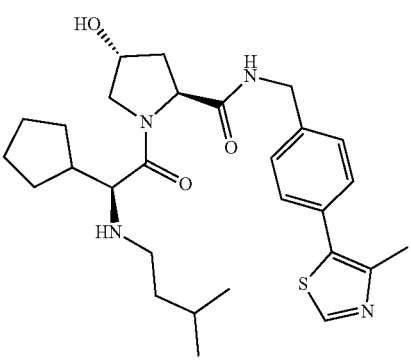
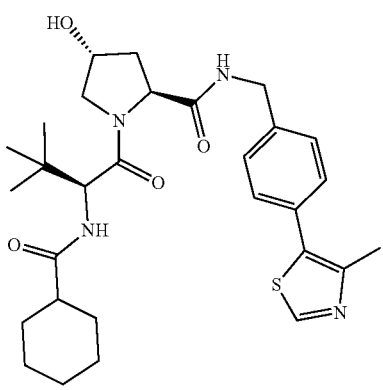
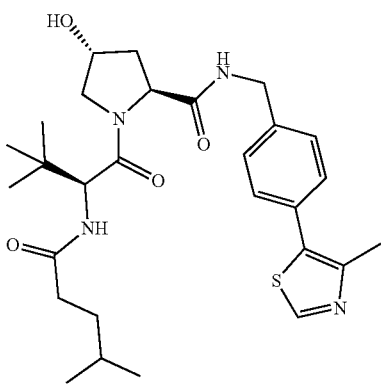

47
-continued
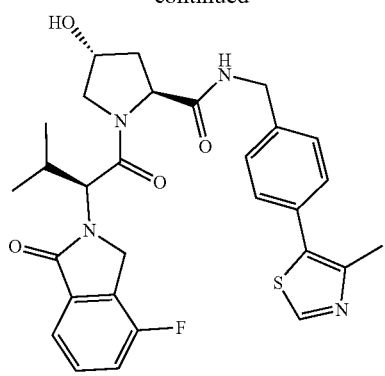
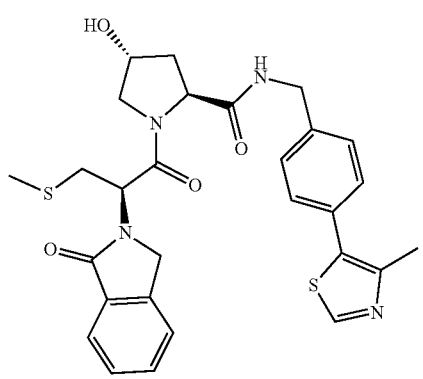
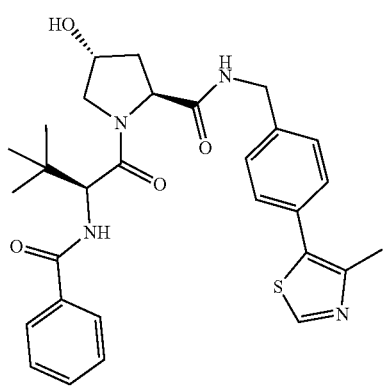
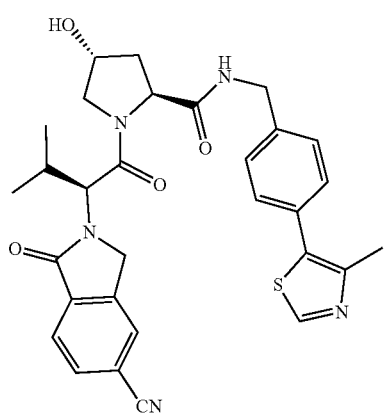
48
-continued
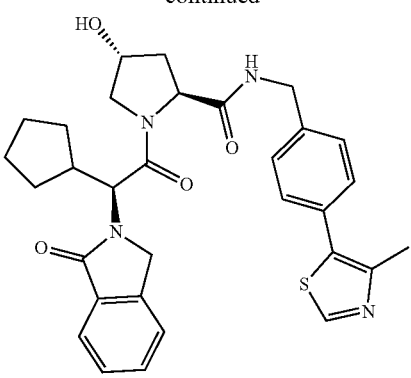
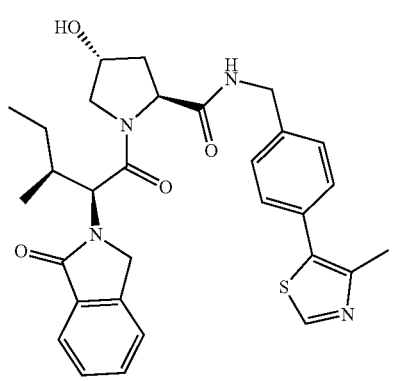
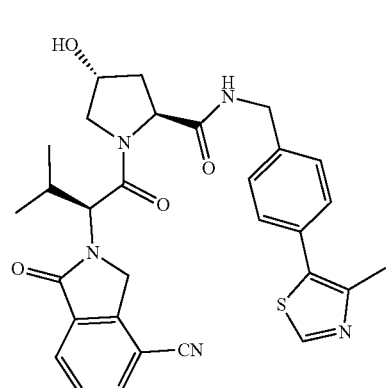
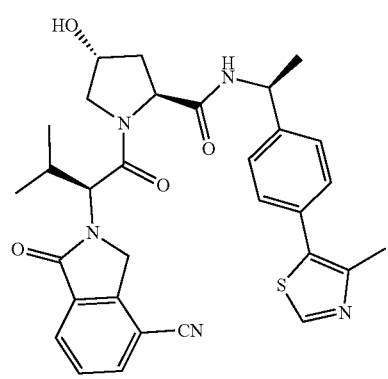

49
-continued
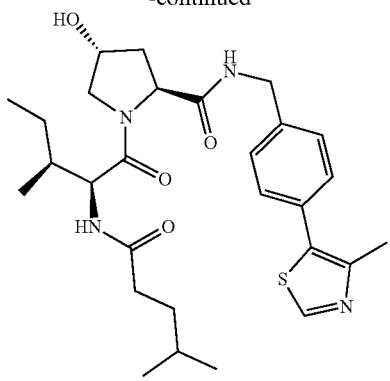
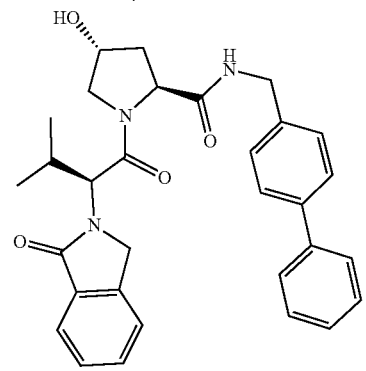
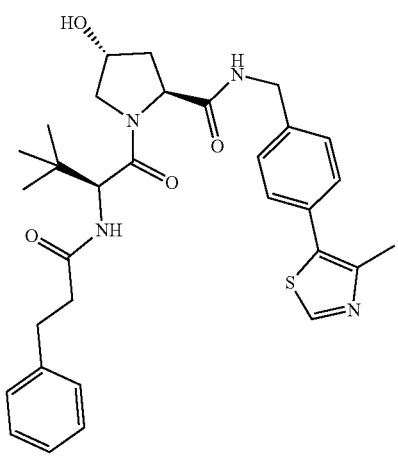
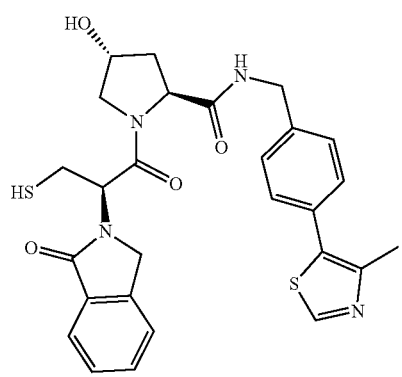
50
-continued
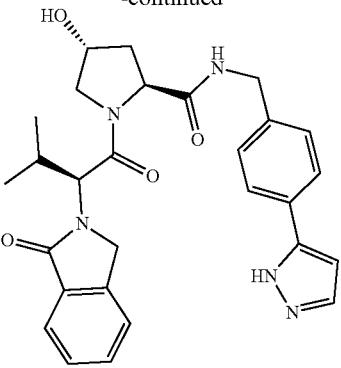
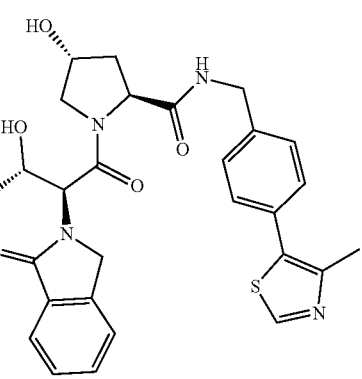
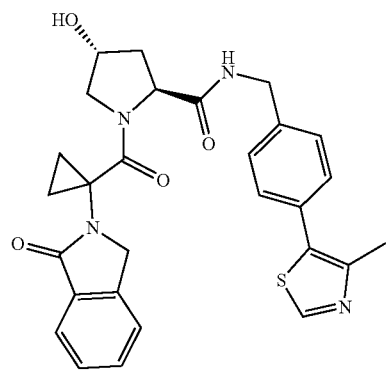
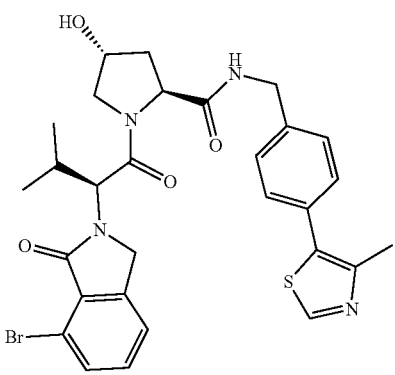

51
-continued
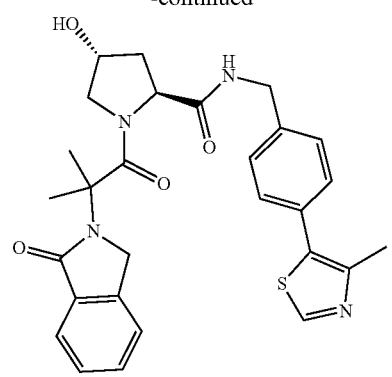
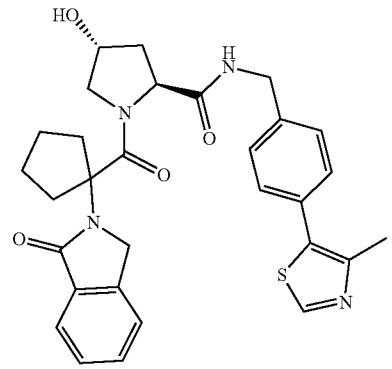
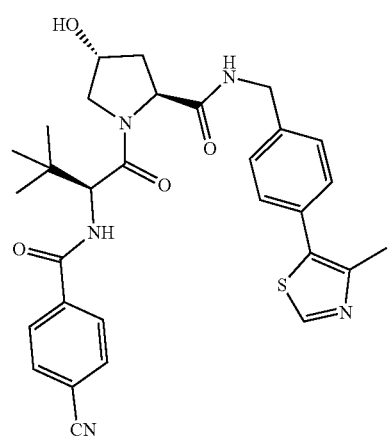
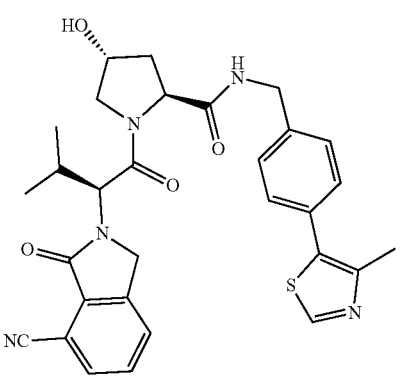
52
-continued
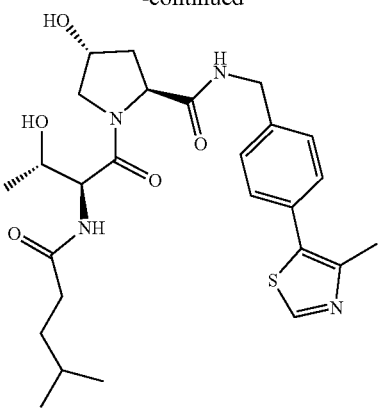
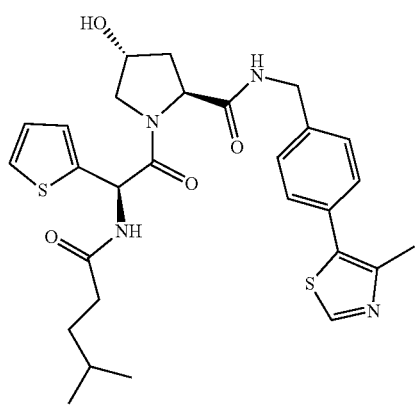
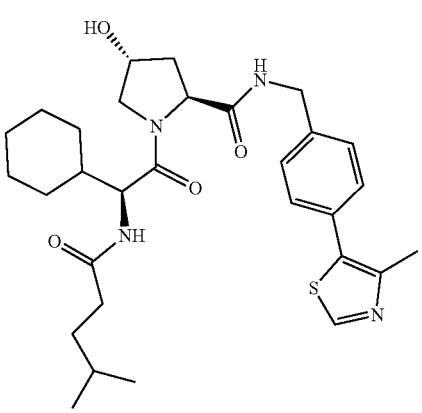
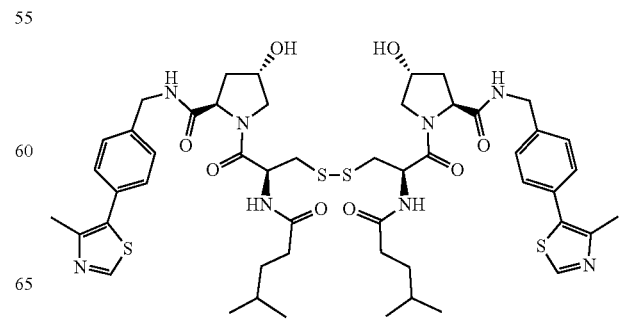

53
-continued
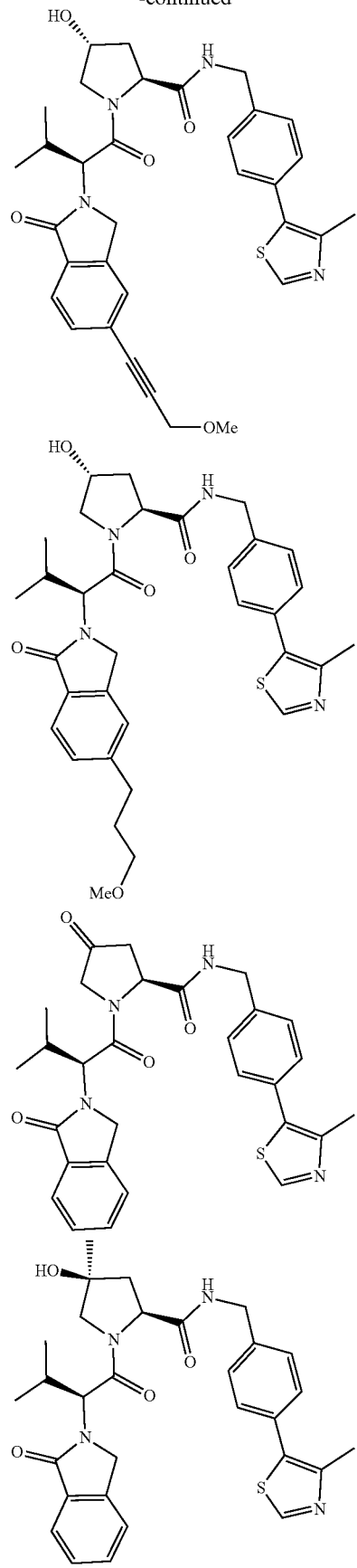
54
-continued
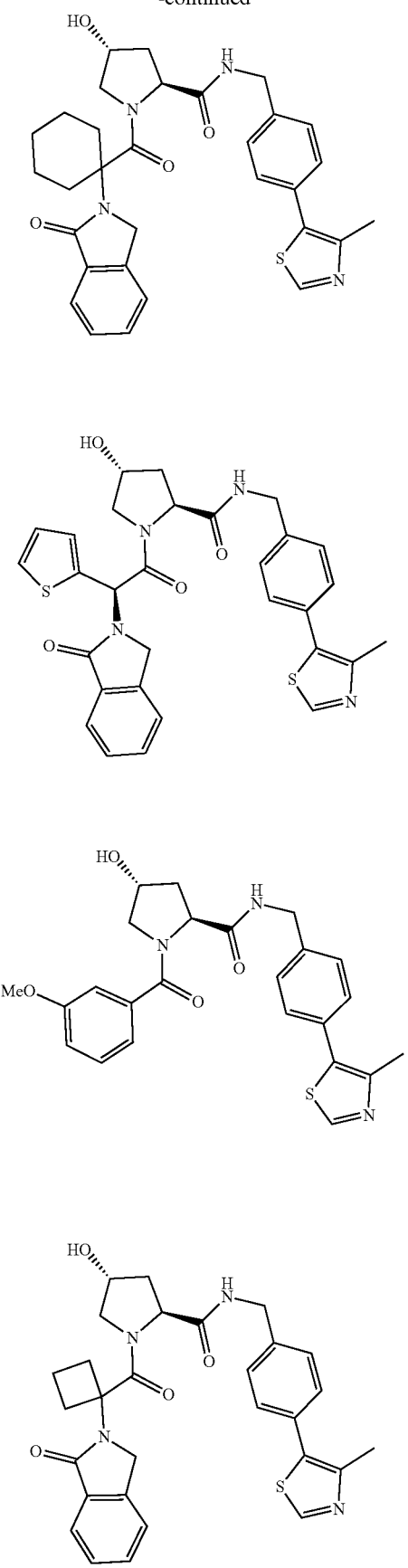

-continued
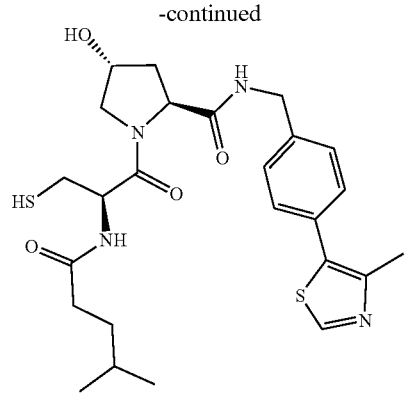
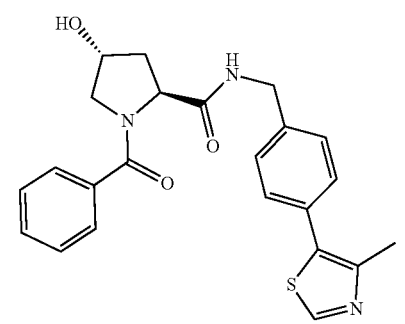
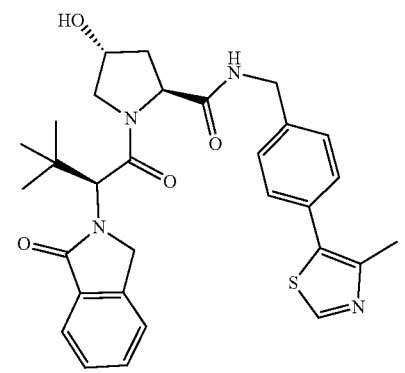
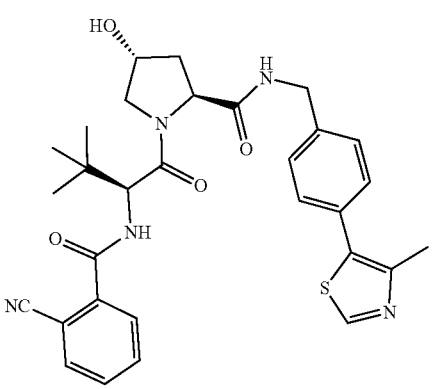
-continued
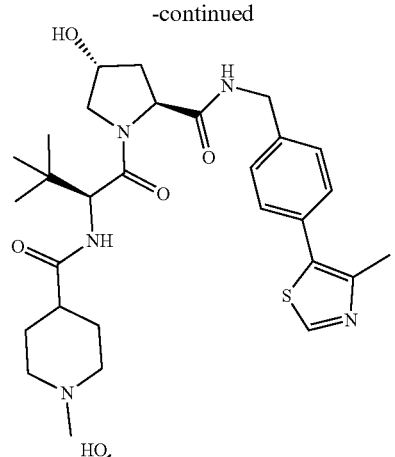
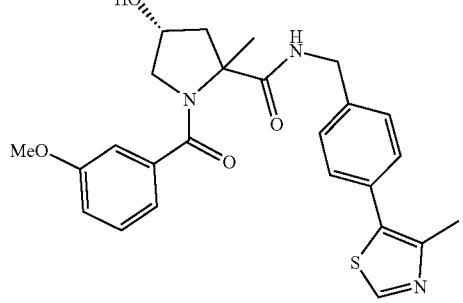
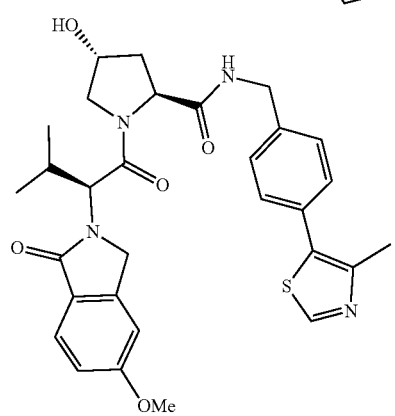
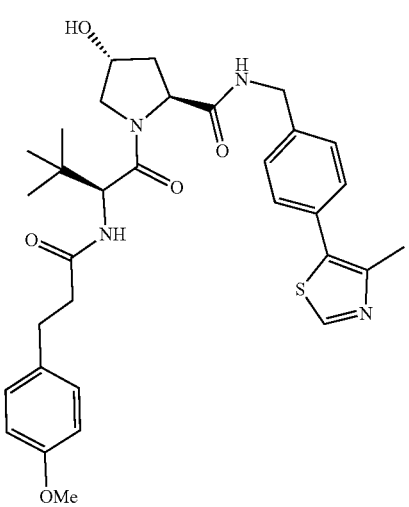

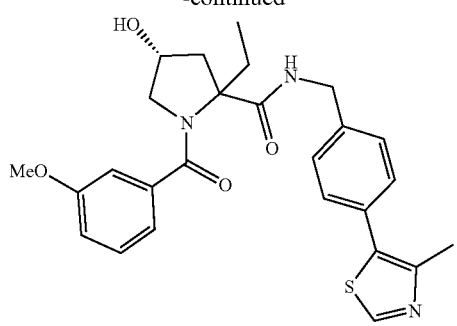
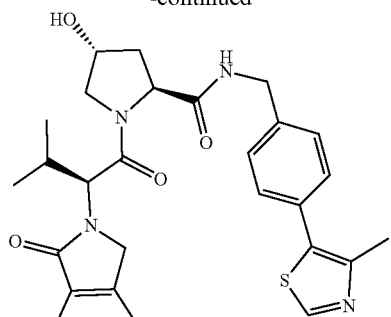
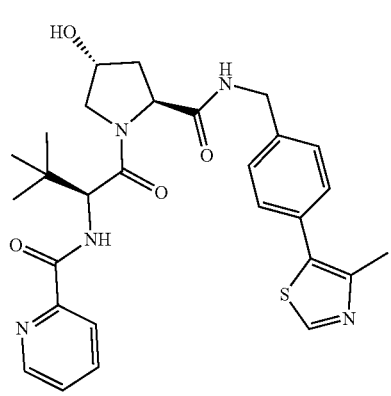
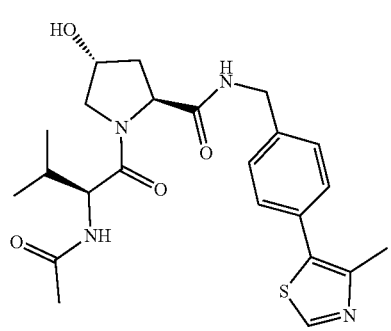
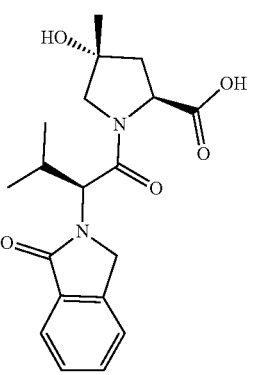

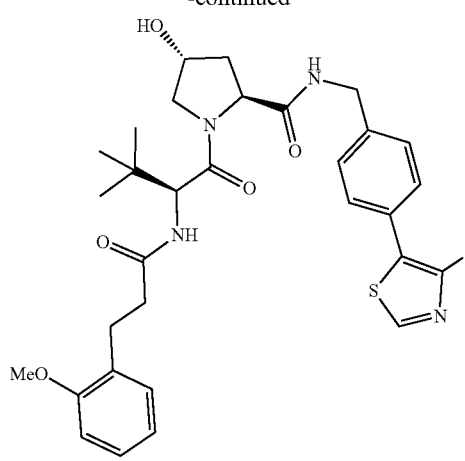
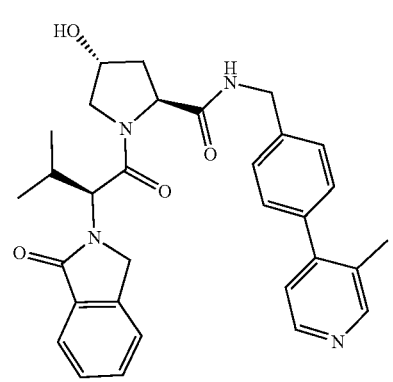
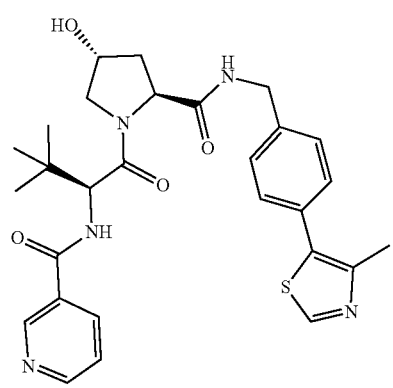
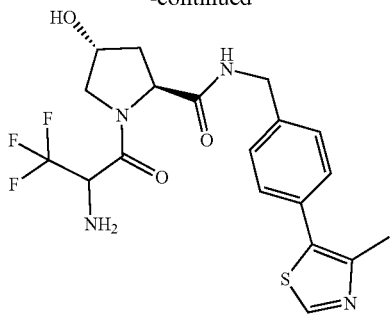
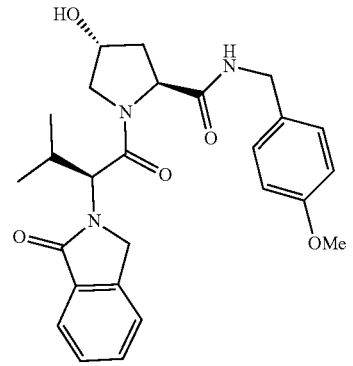
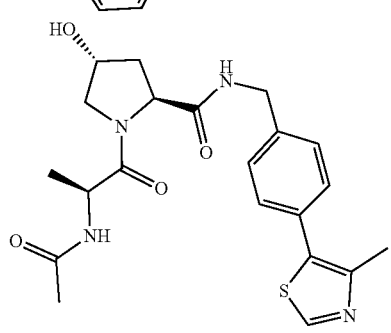
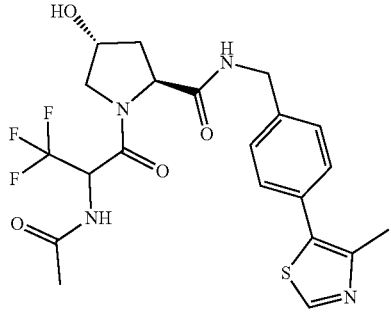

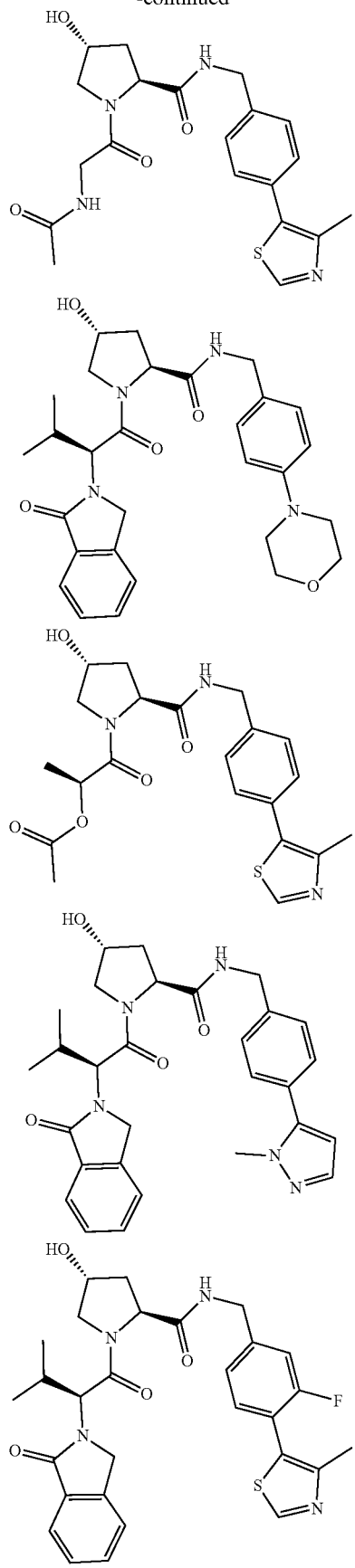
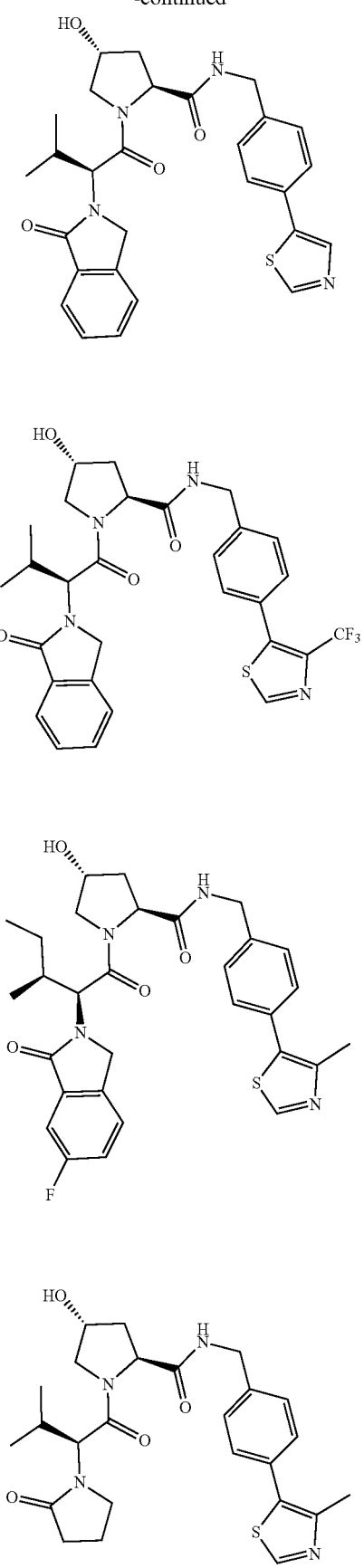

63
-continued
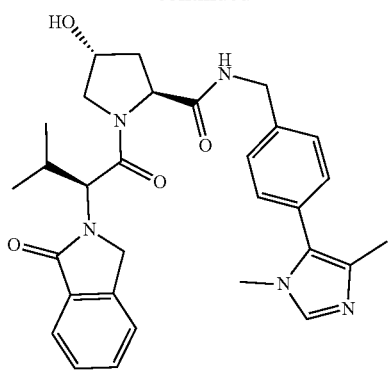
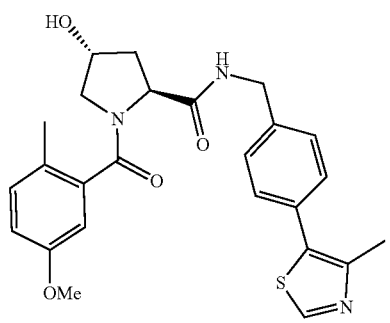
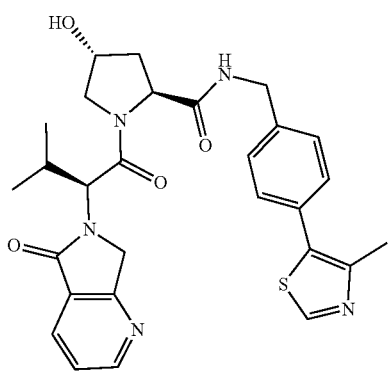
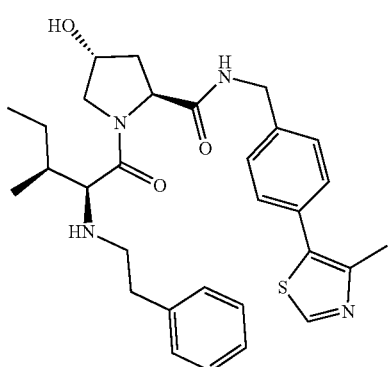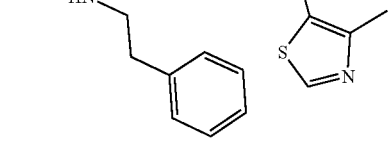
64
-continued
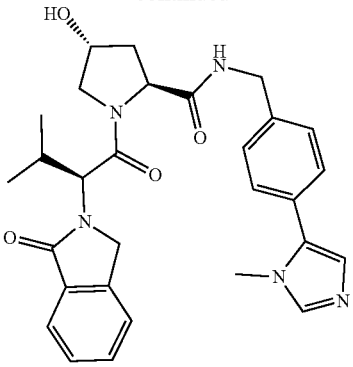
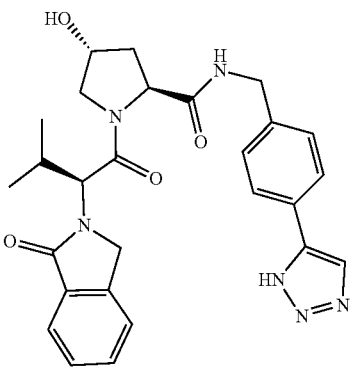
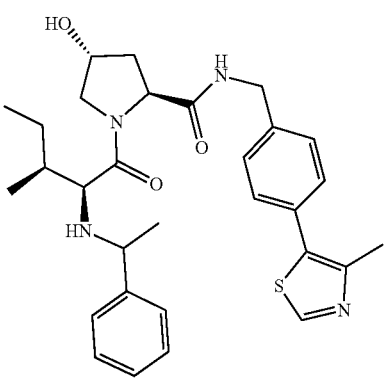
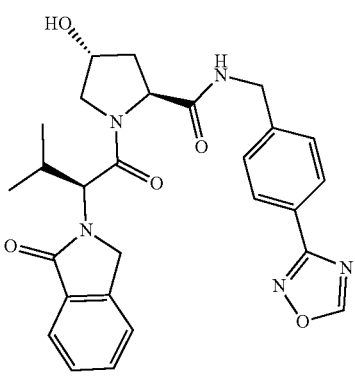

65
-continued
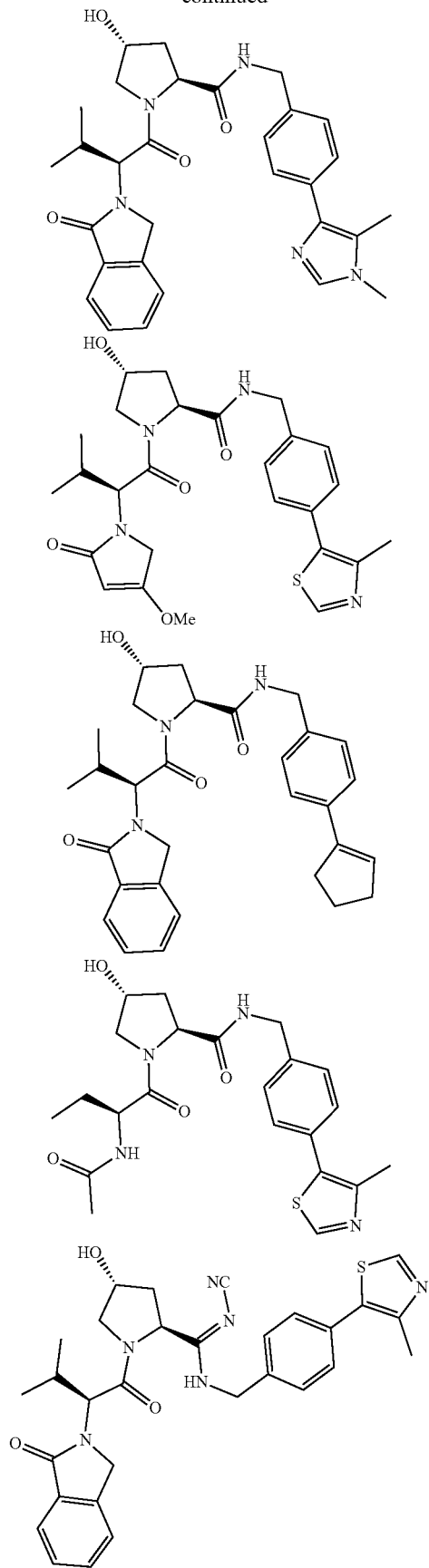
66
-continued
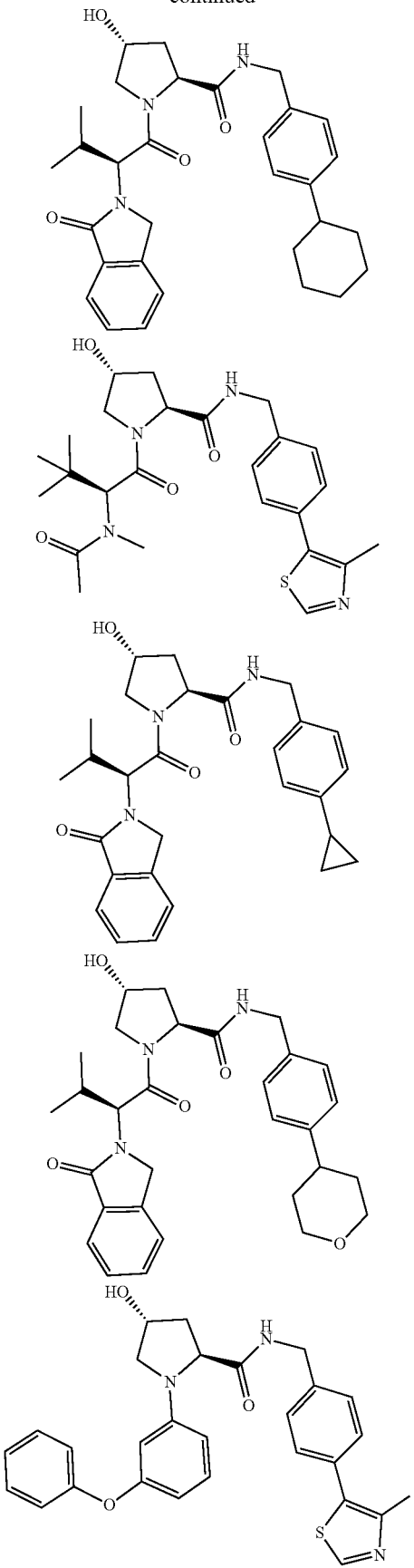

67
-continued
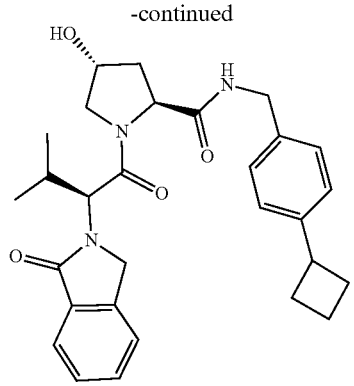
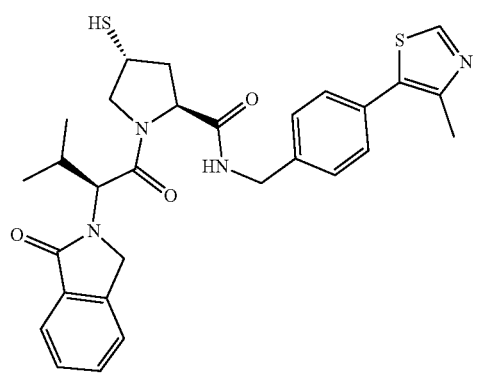
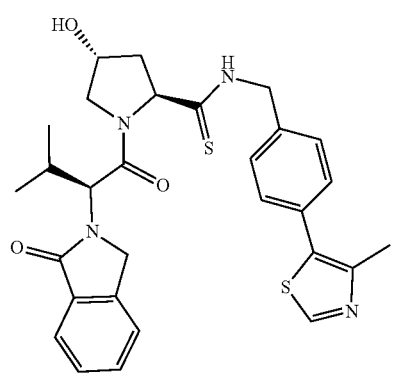
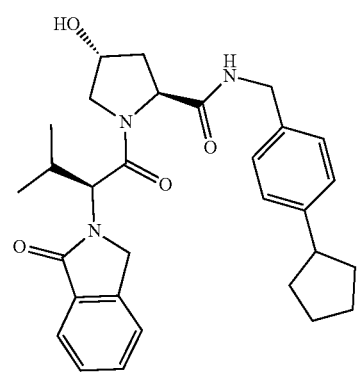
68
-continued
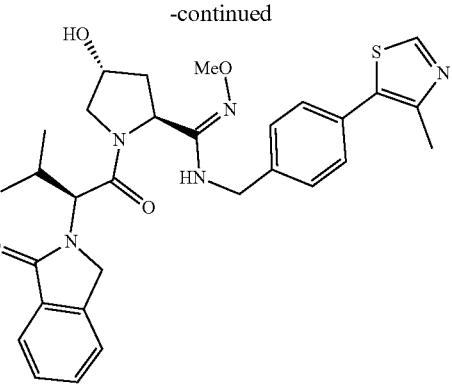
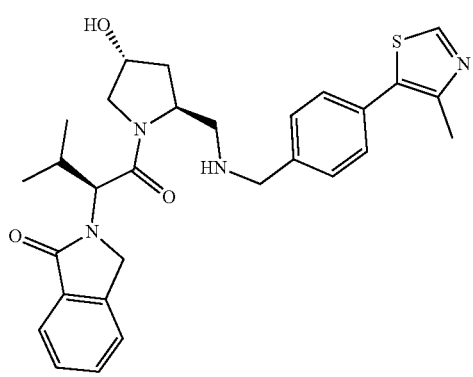
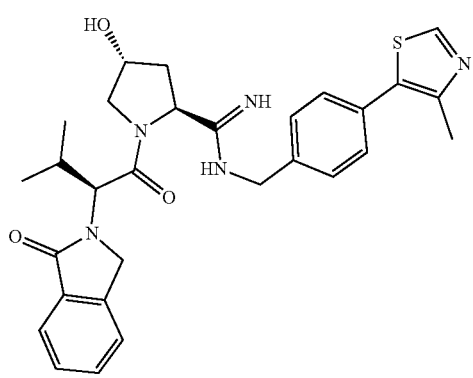
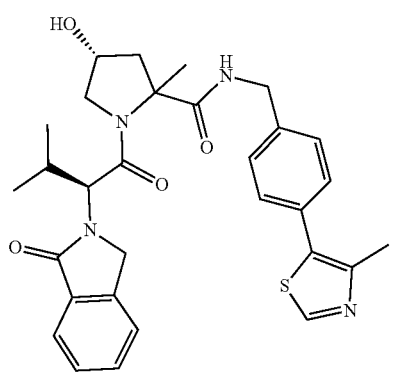

69
-continued
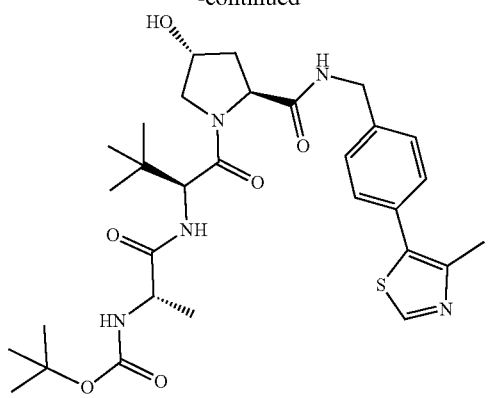
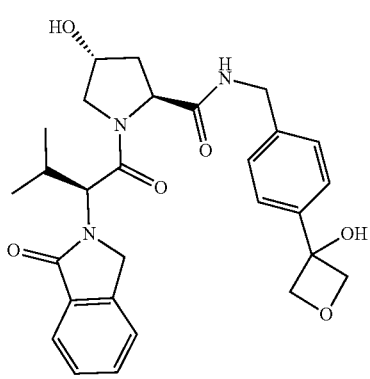
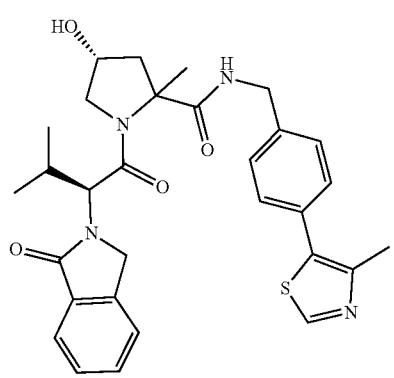
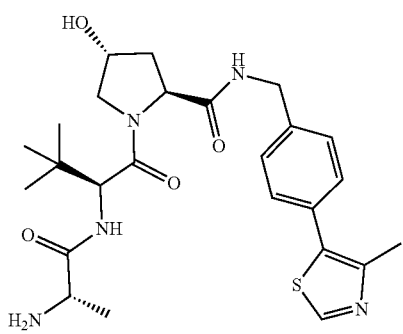
70
-continued
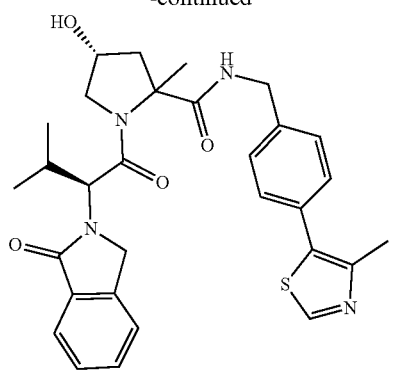
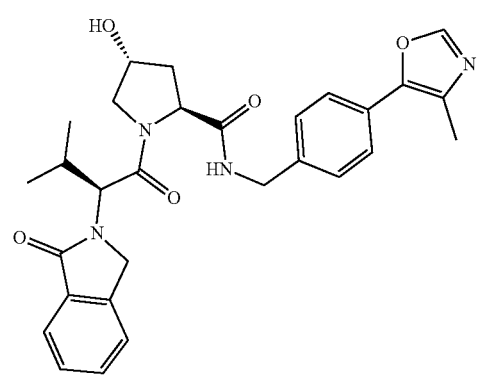
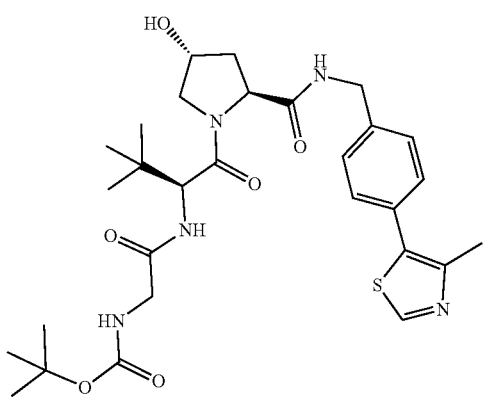
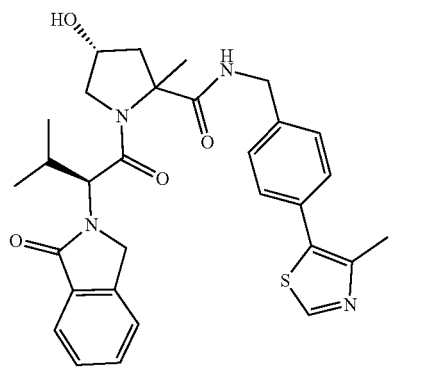

71
-continued
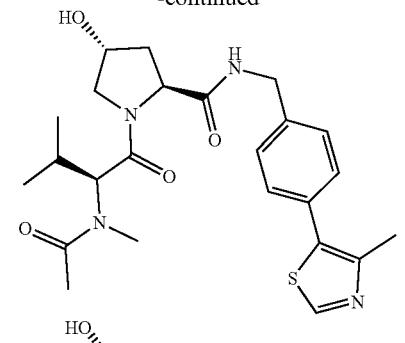
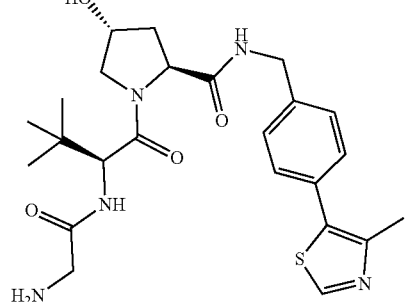
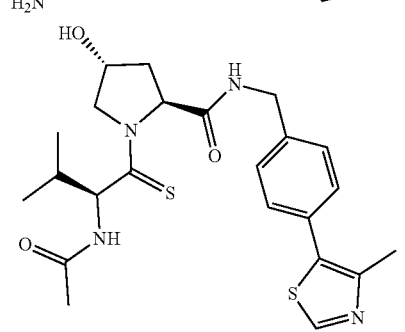
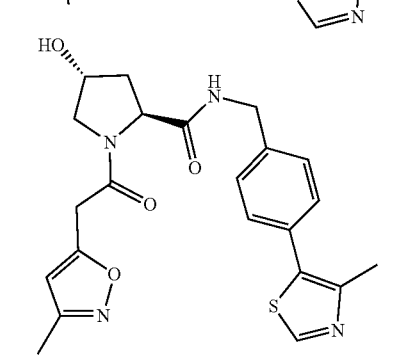
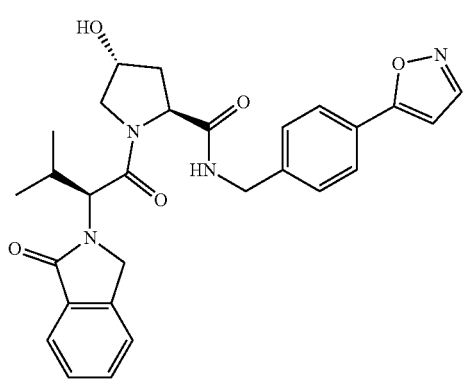
72
-continued
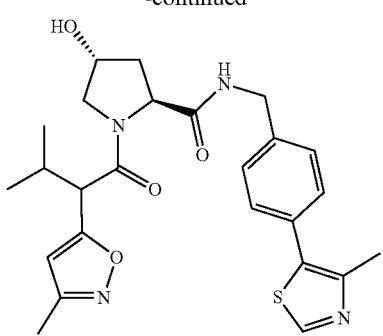
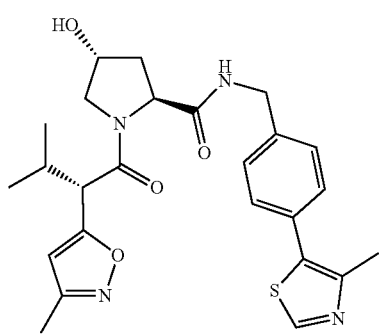
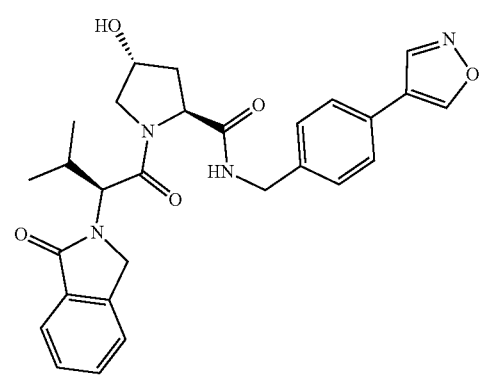
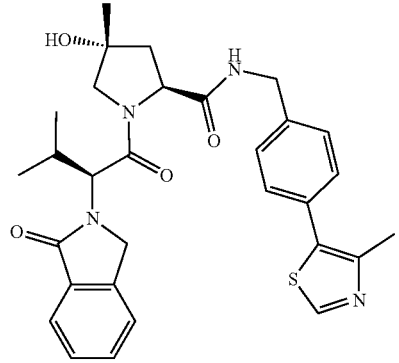

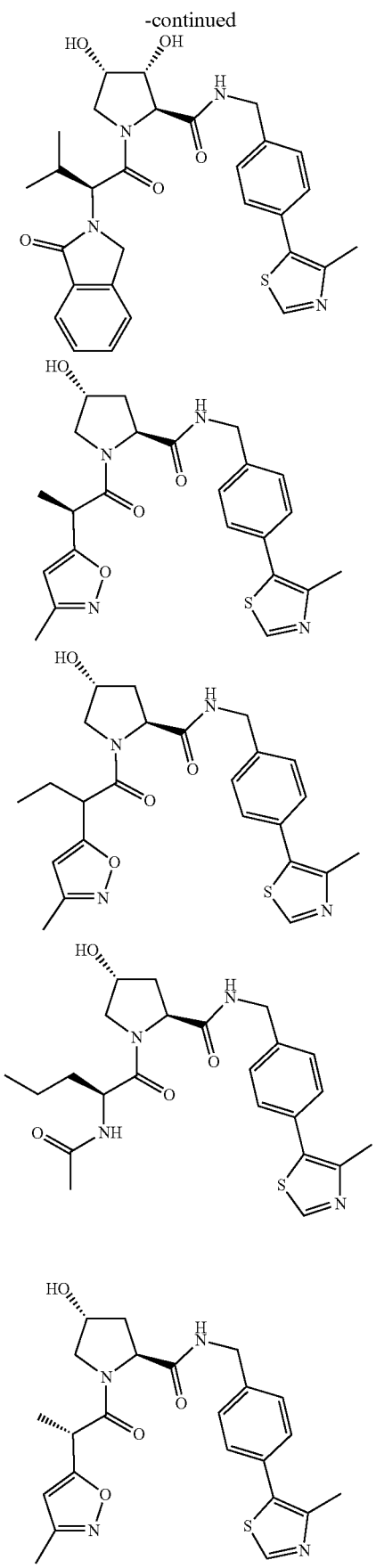
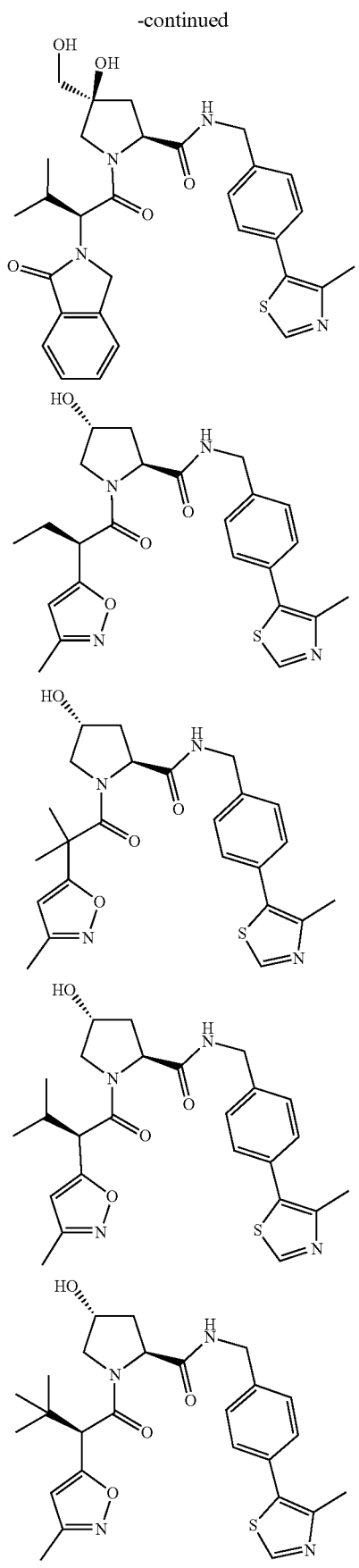

75
-continued
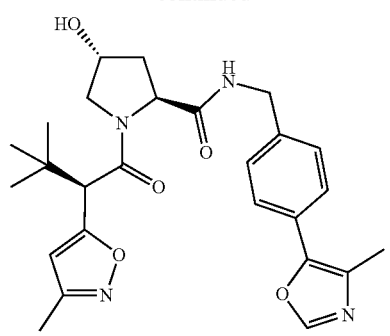
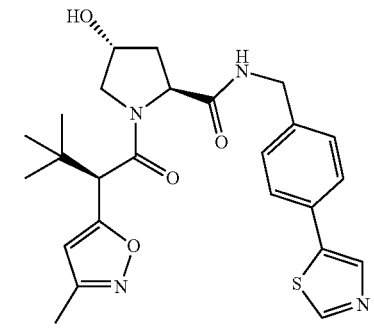
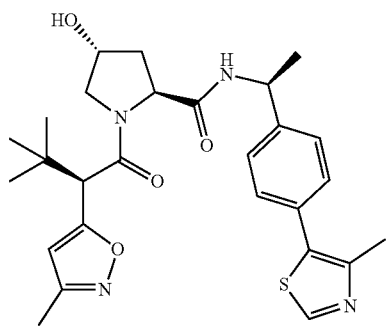
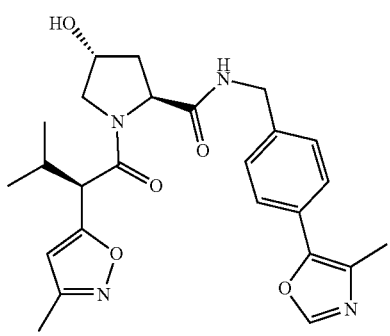
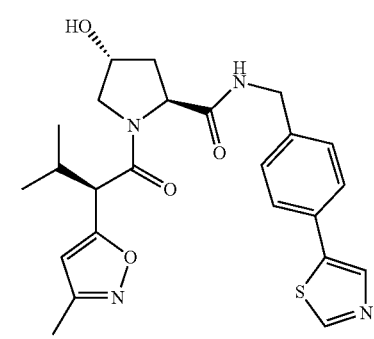
76
-continued
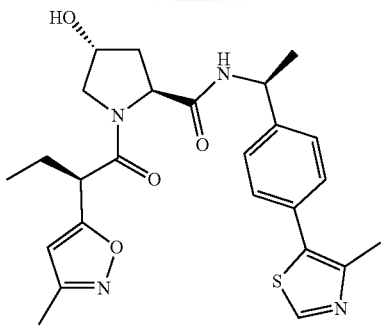
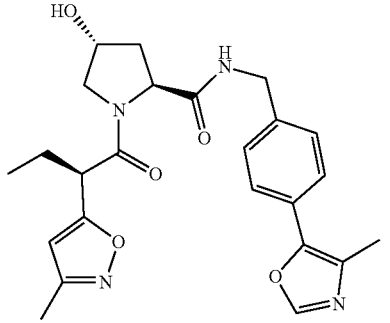
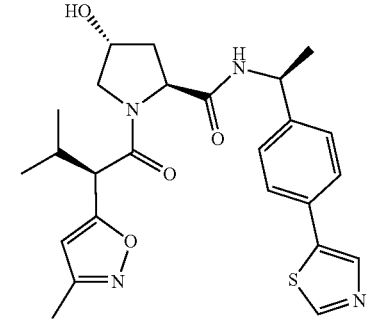
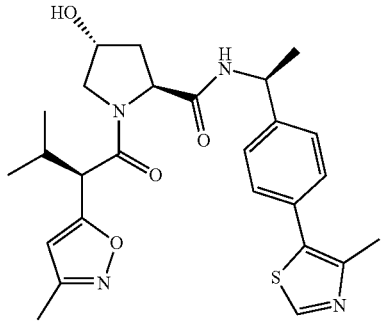
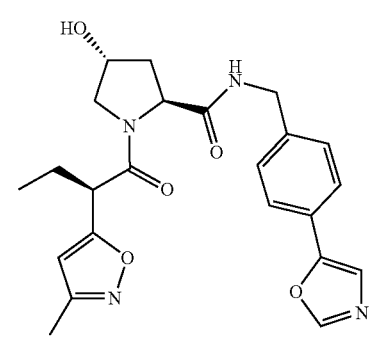

77
-continued
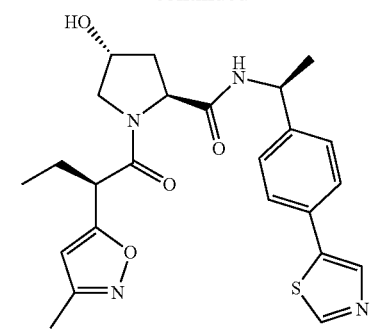
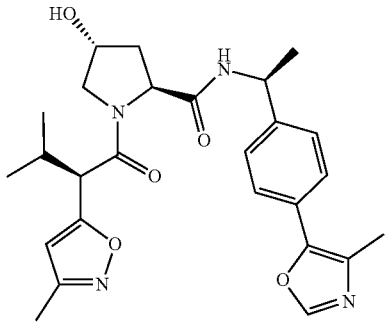
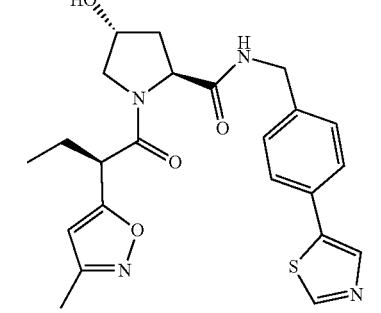
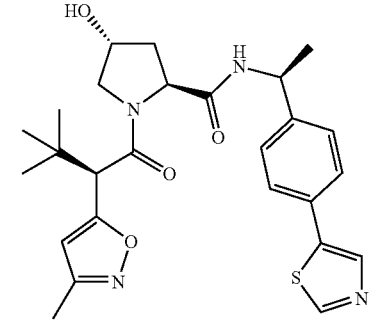
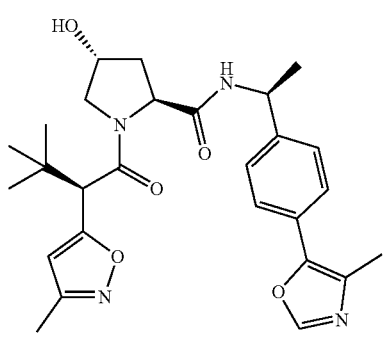
78
-continued
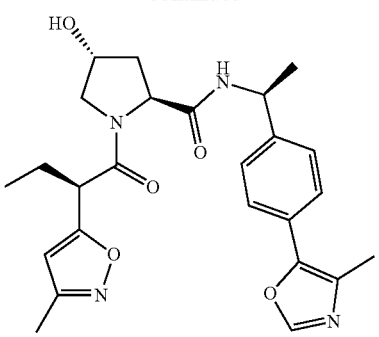
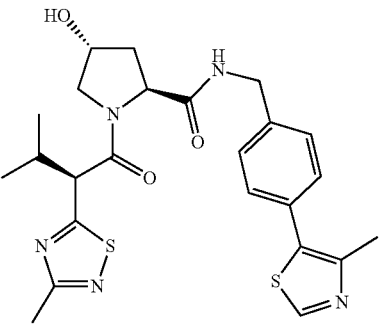
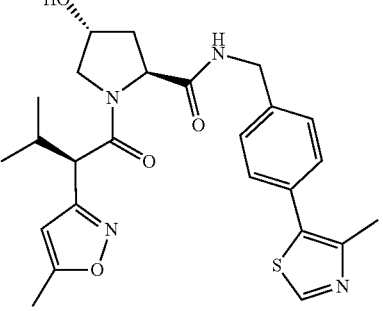
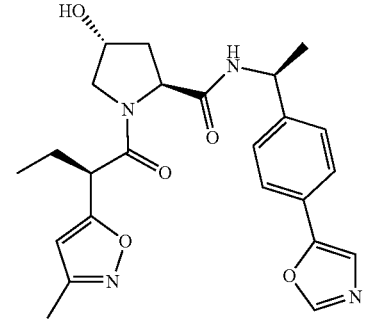
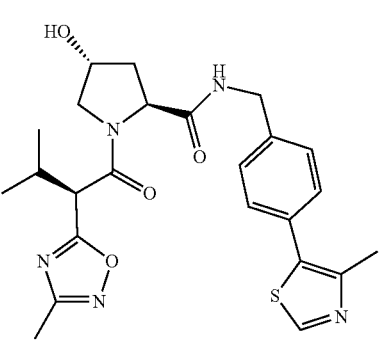

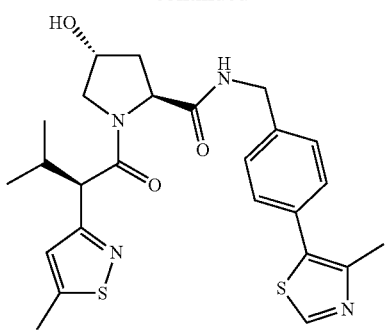
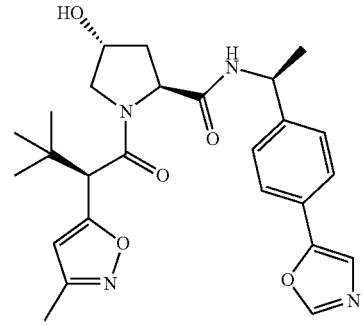
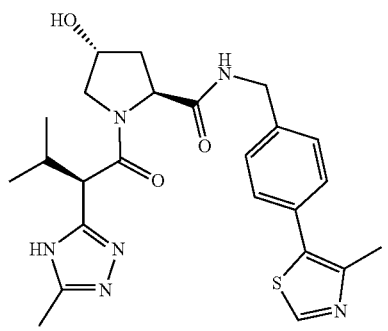
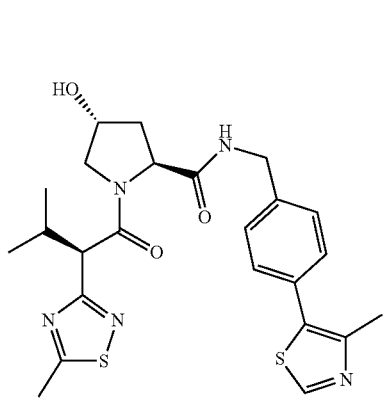
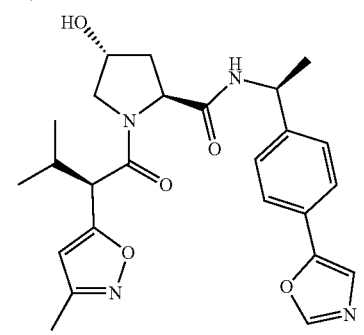
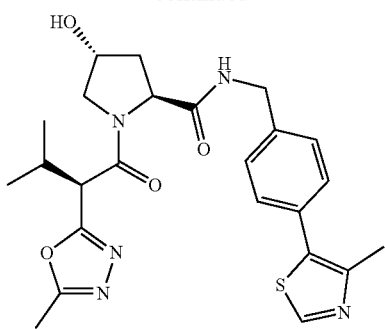
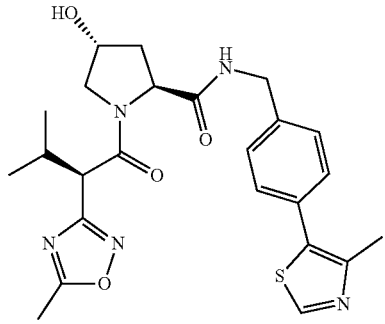
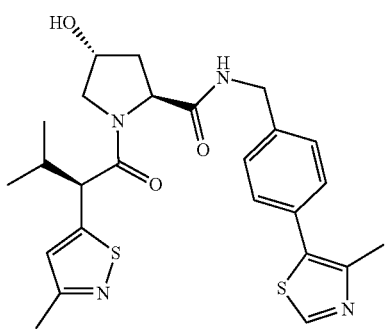
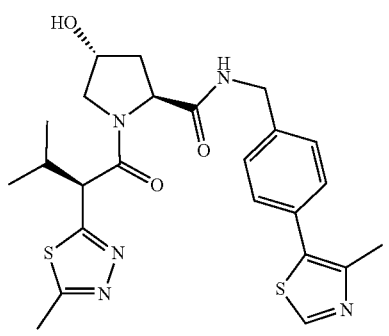
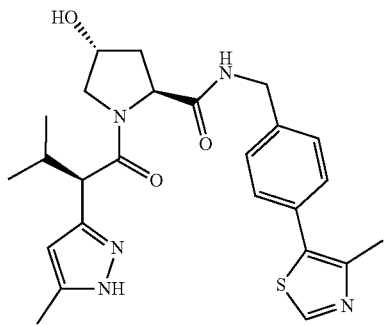

81
-continued
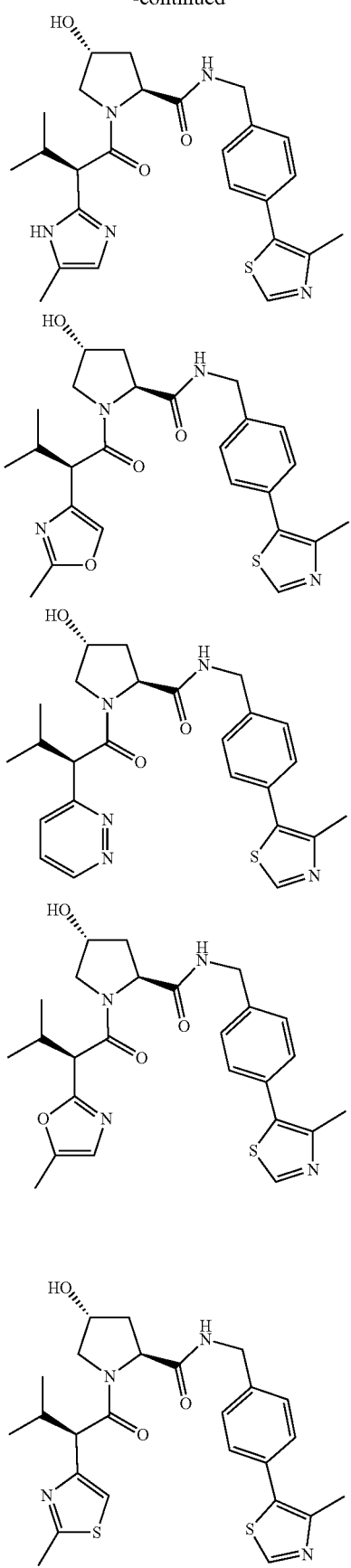
82
-continued
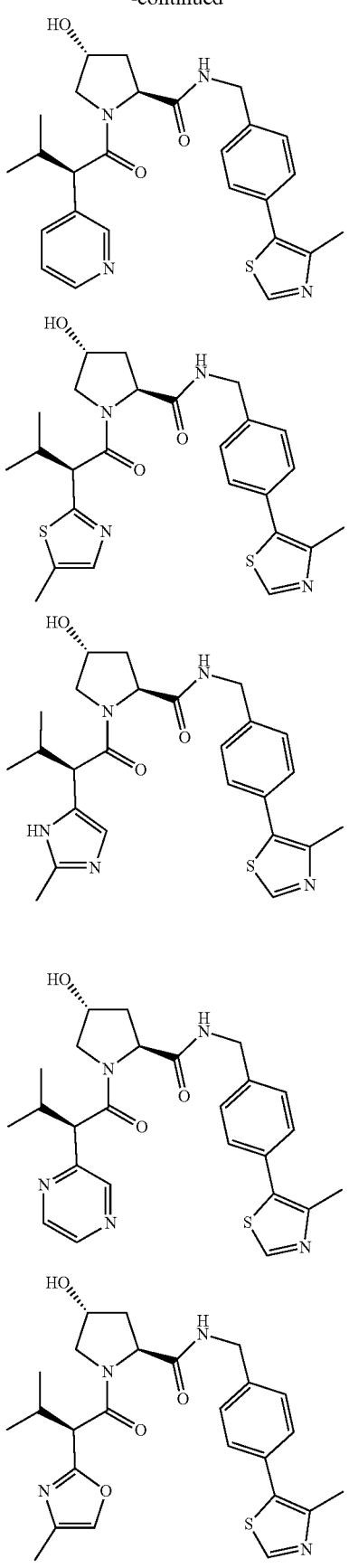

83
-continued
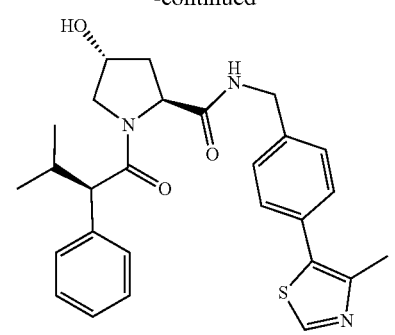
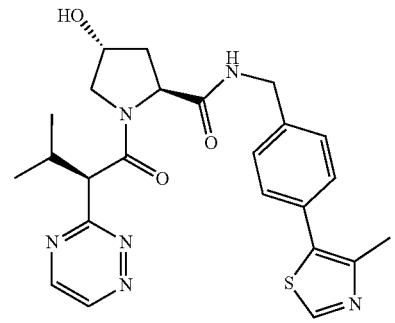
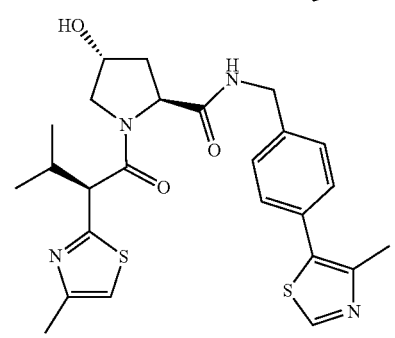
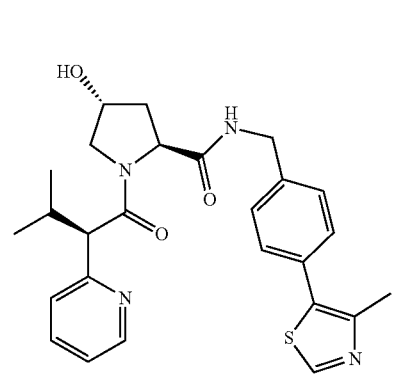
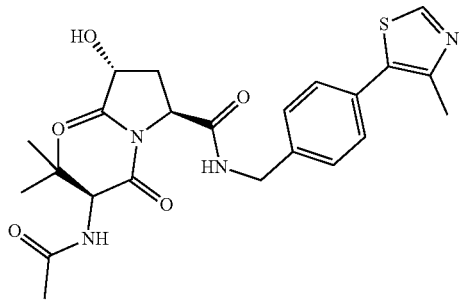
84
-continued
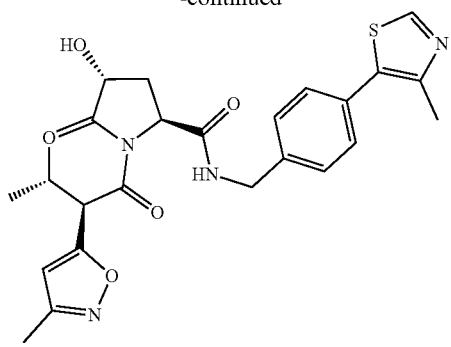
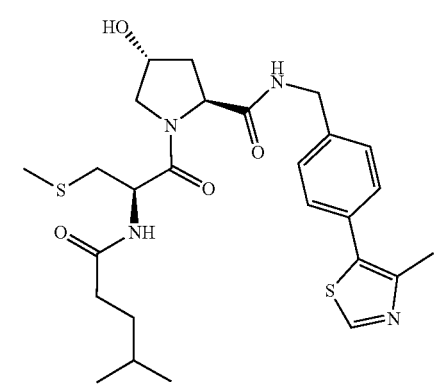
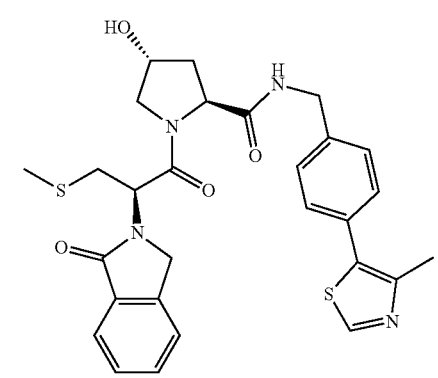
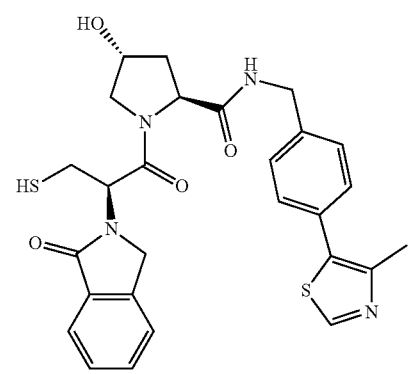

85
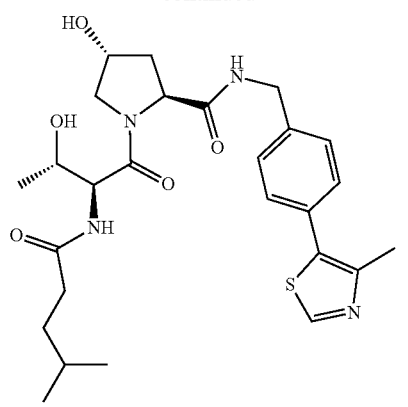
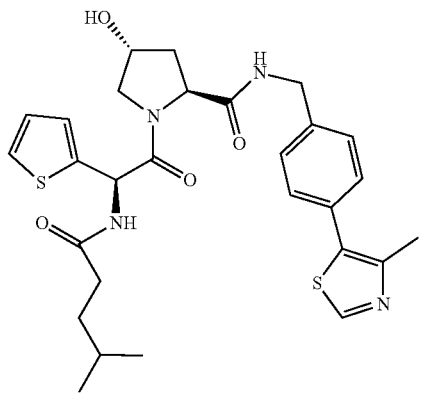
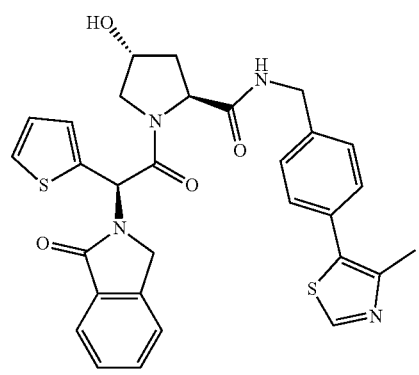
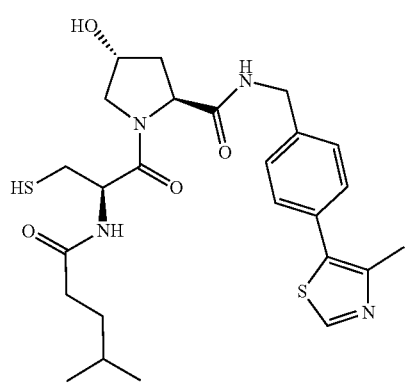
86
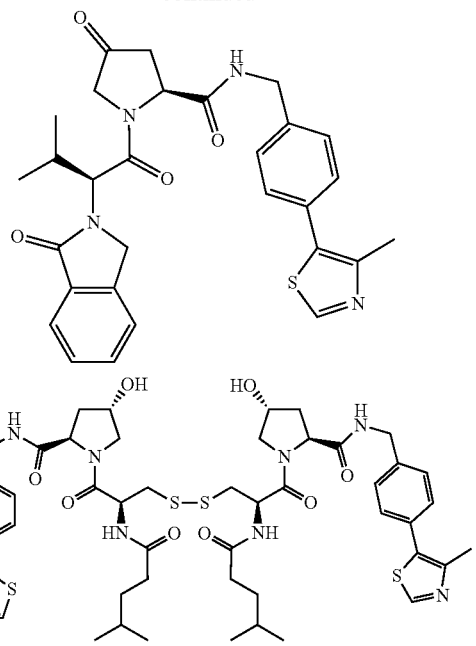
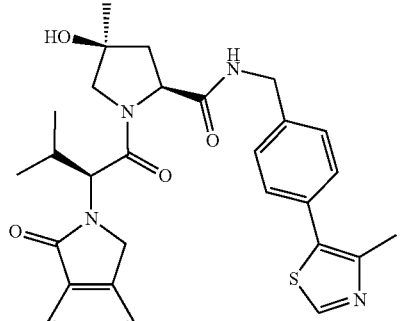
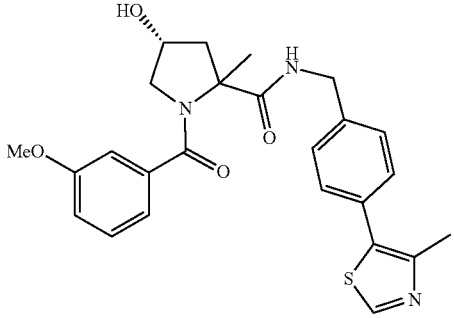
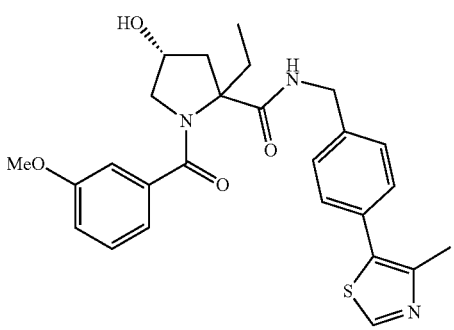

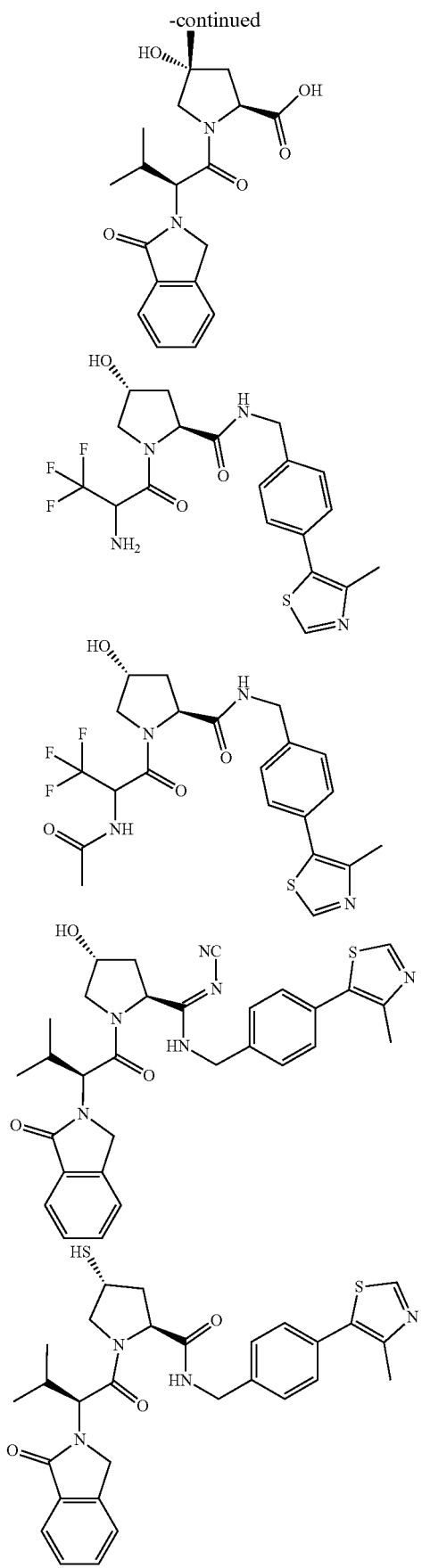
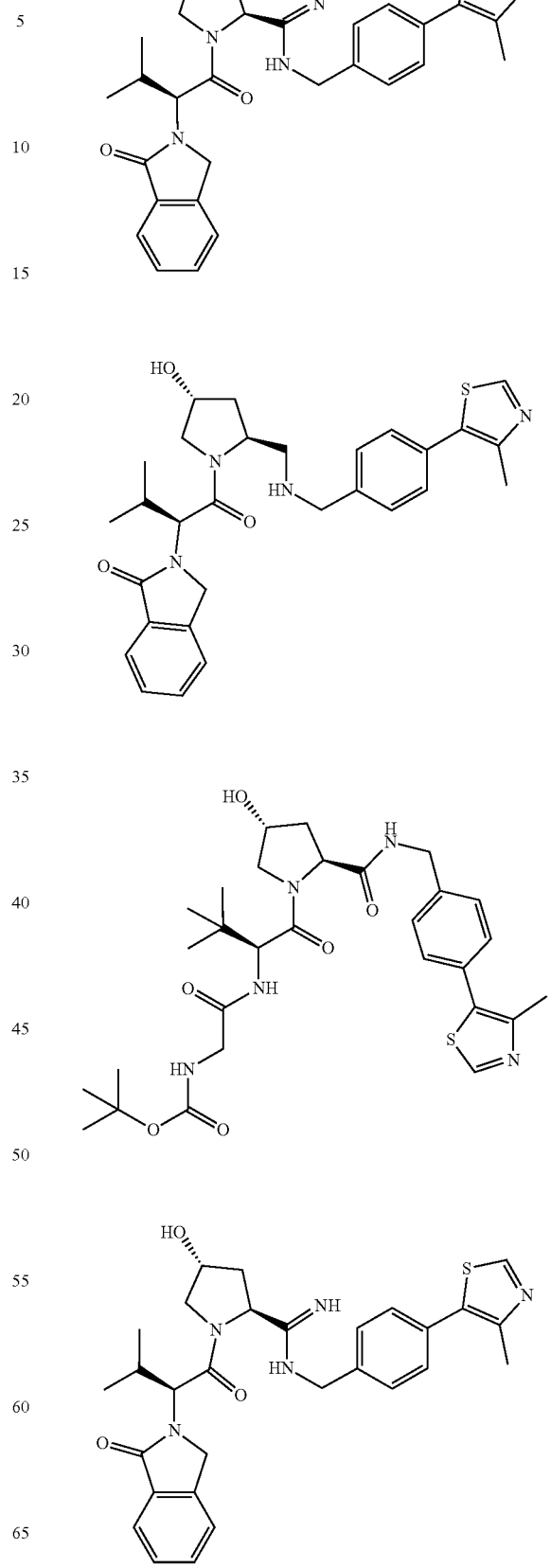

89
-continued
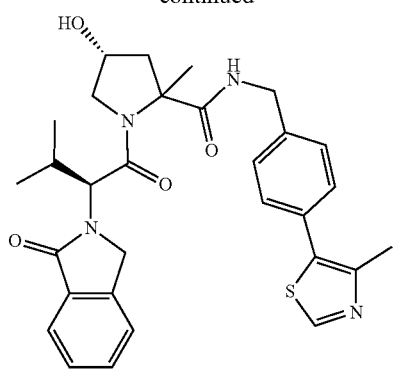
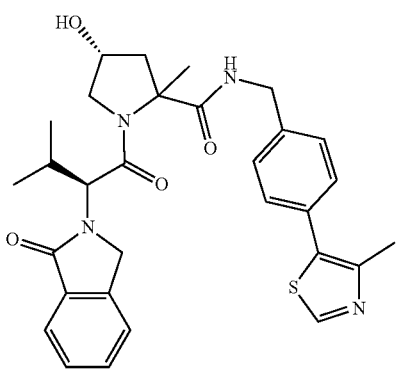
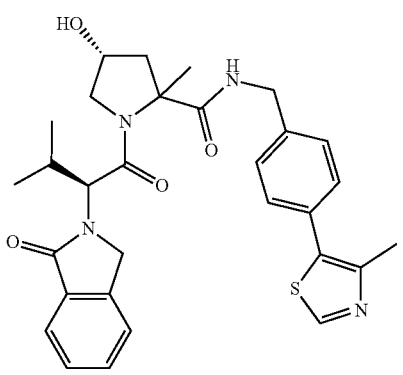
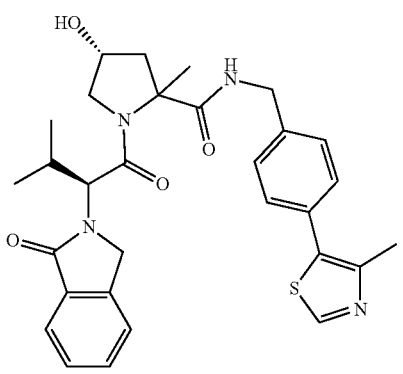
90
-continued
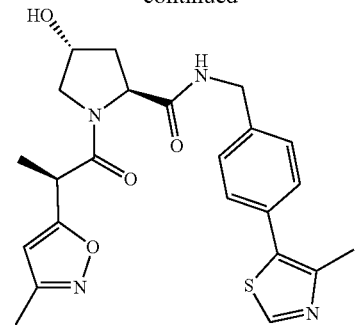
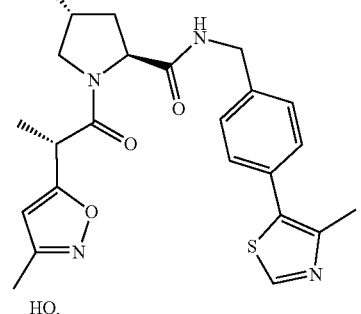
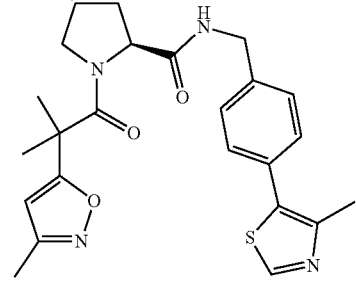
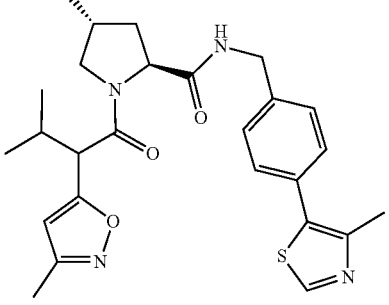
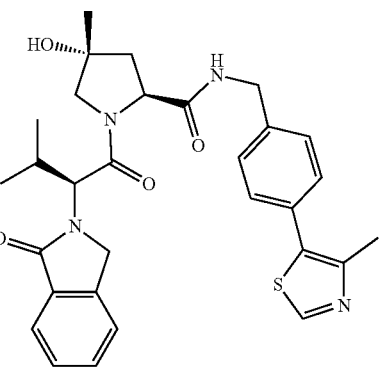

91
-continued
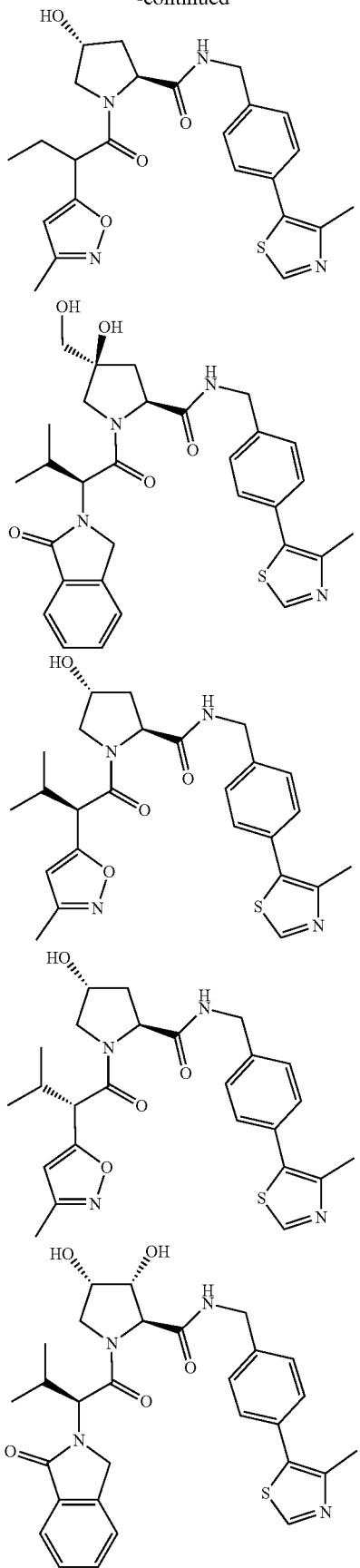
92
-continued
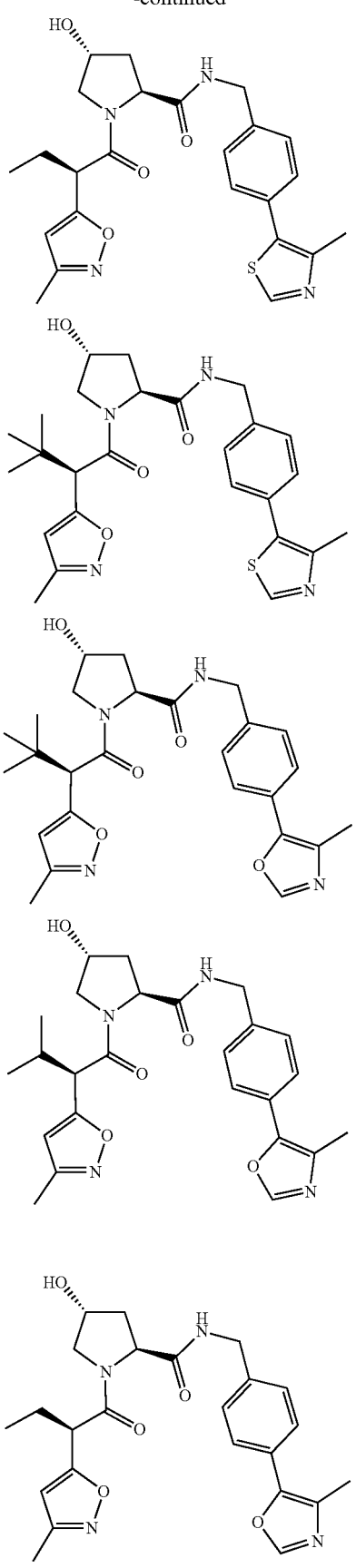

93
-continued
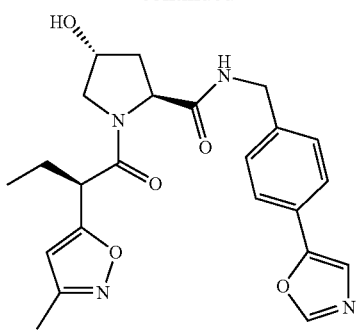
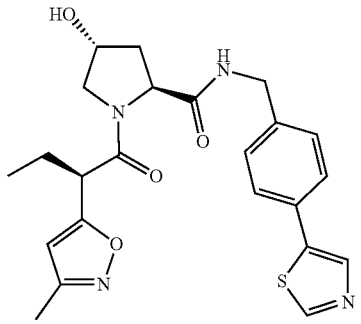
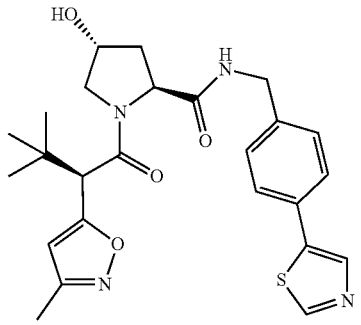
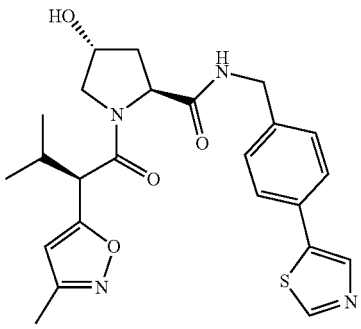
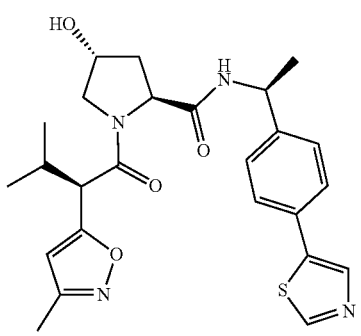
94
-continued
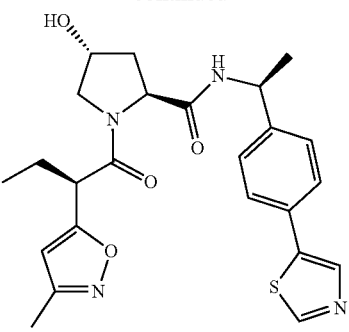
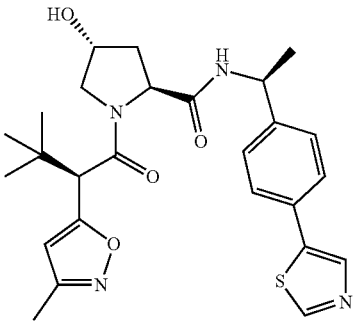
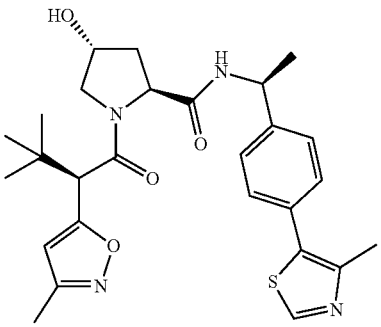
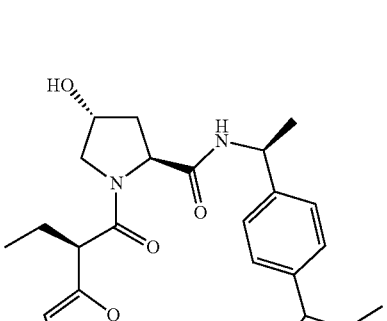
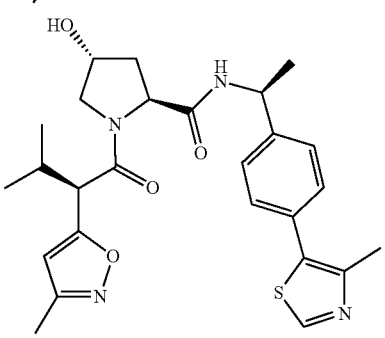

95
-continued
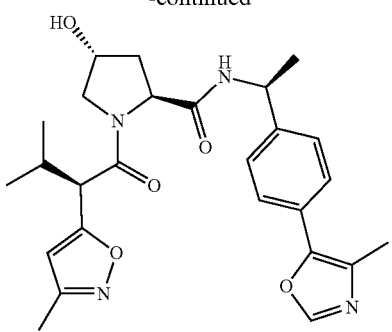
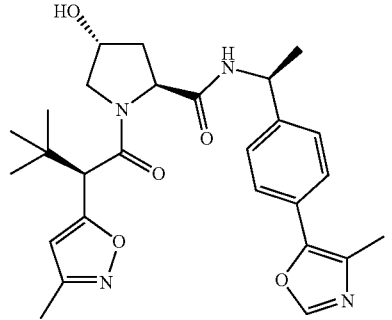
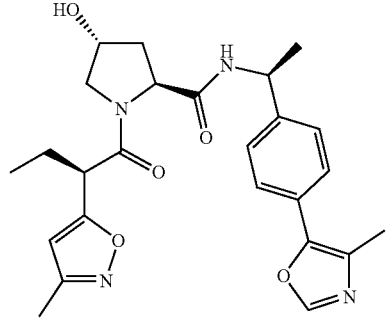
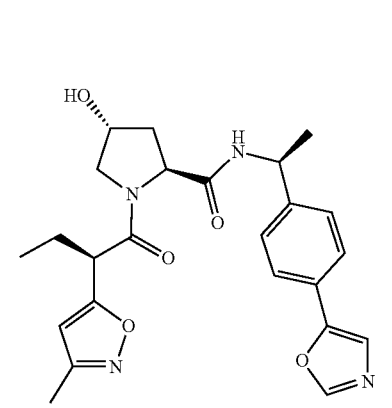
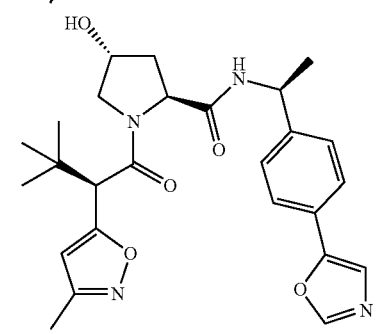
96
-continued
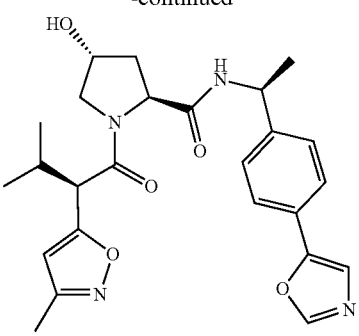
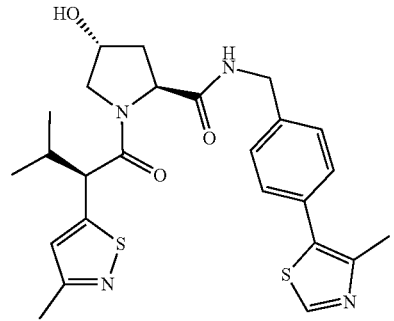
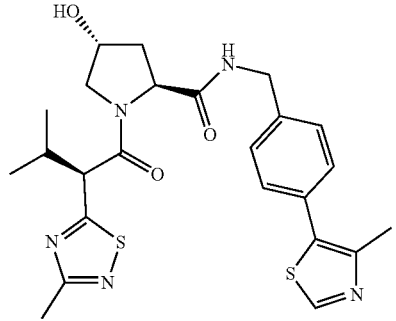
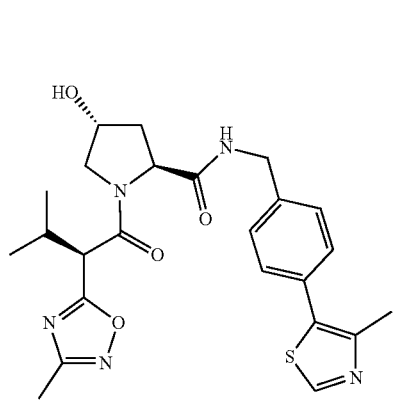
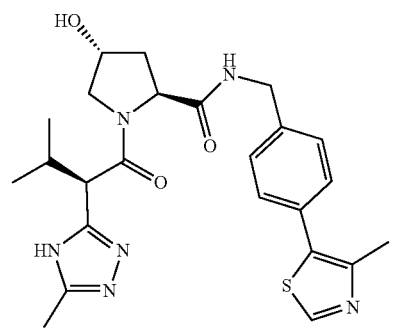

97
-continued
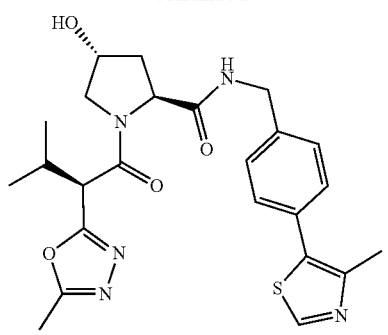
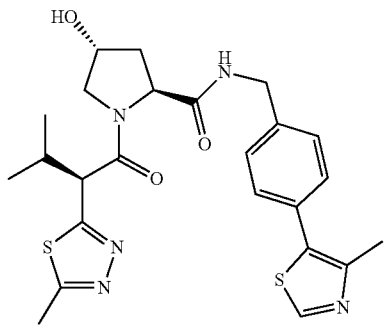
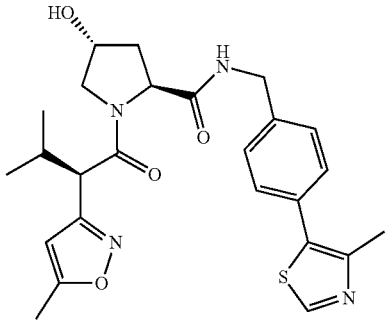
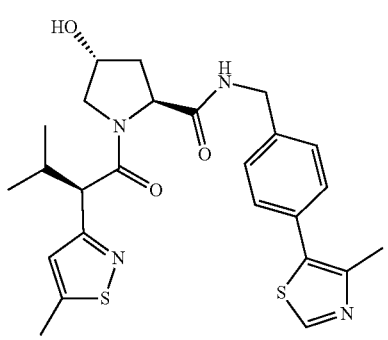
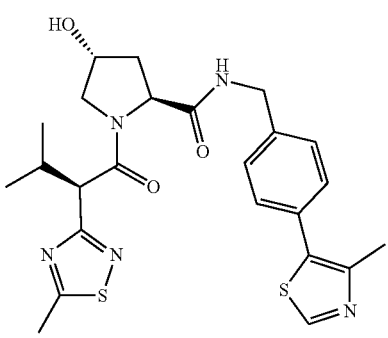
98
-continued
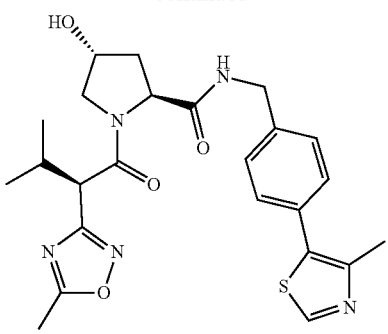
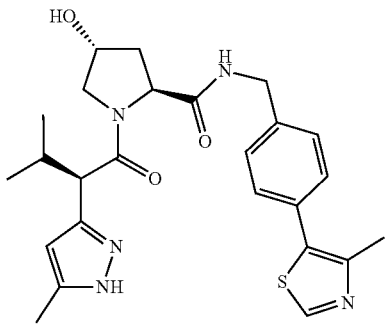
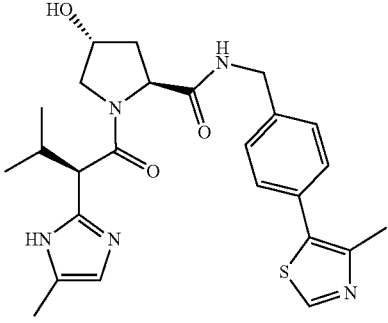
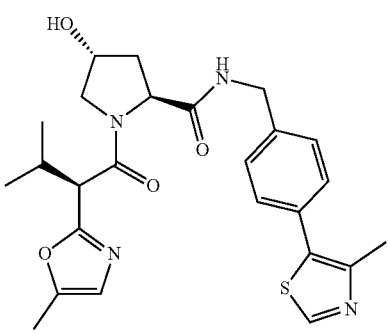
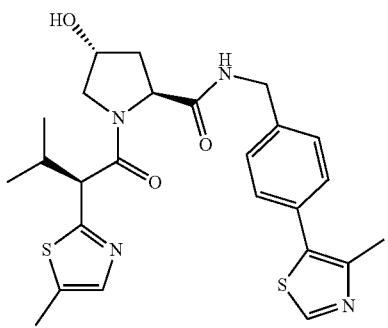

99
-continued
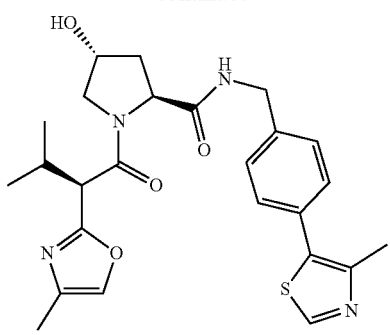
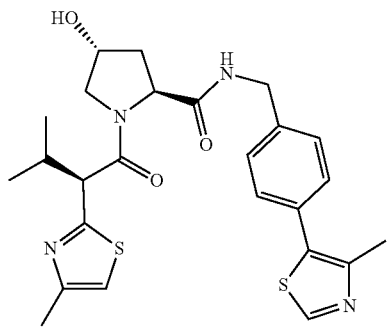
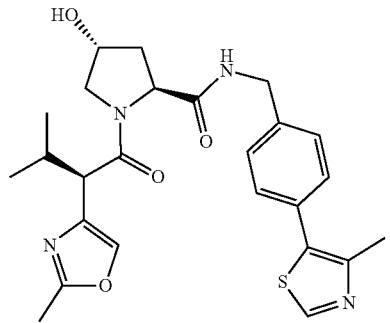
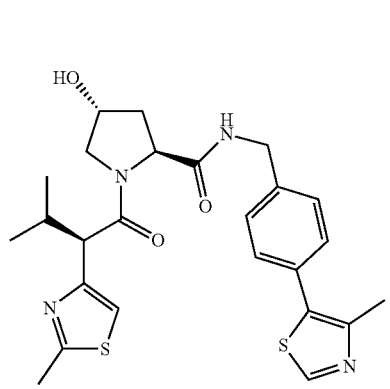
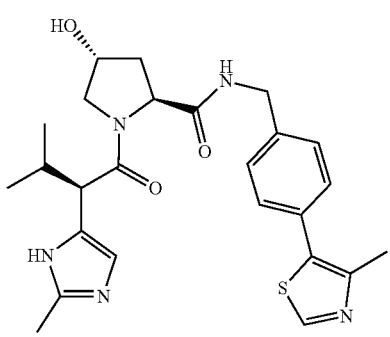
100
-continued
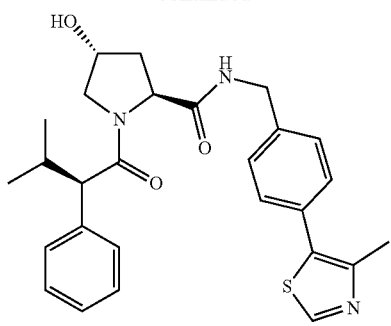
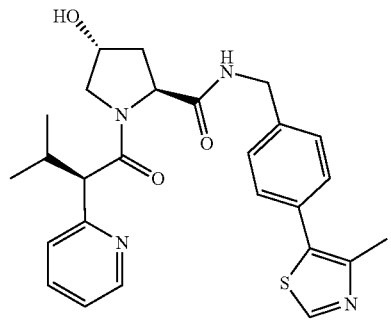
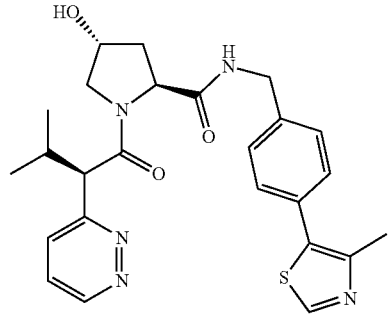
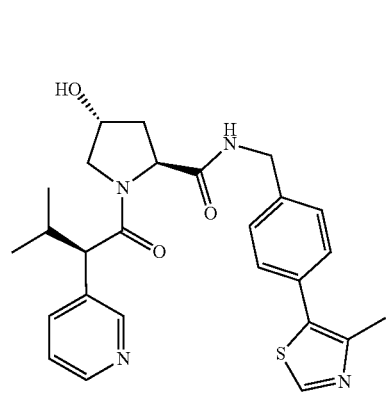
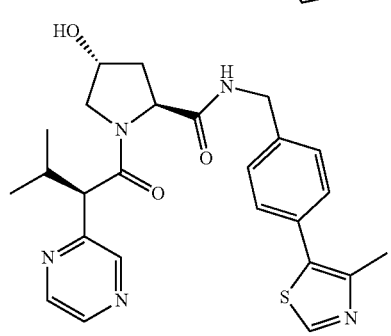

-continued
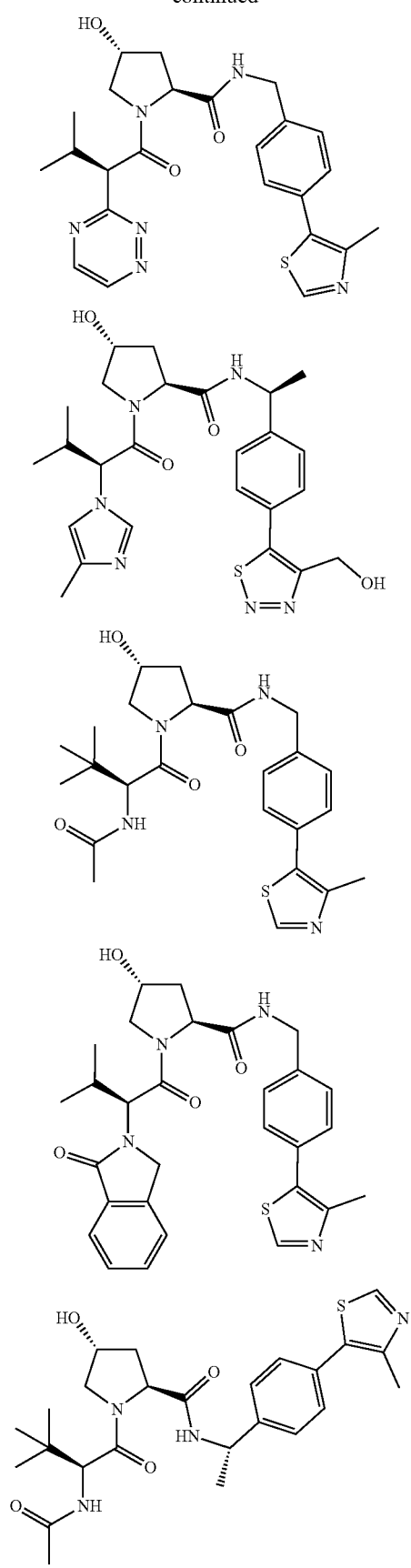
-continued
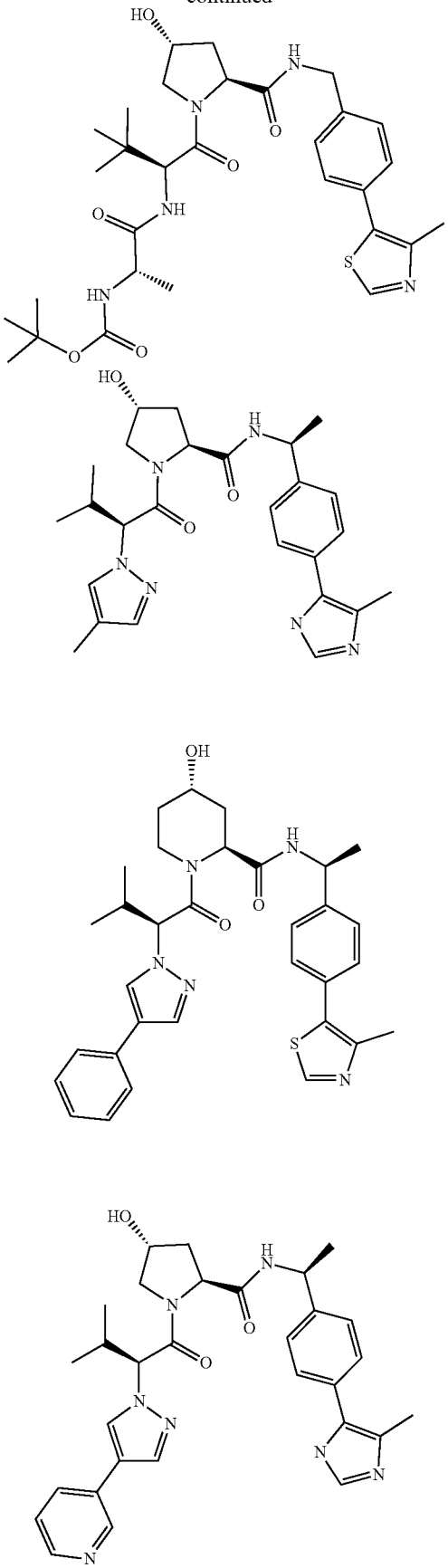

-continued

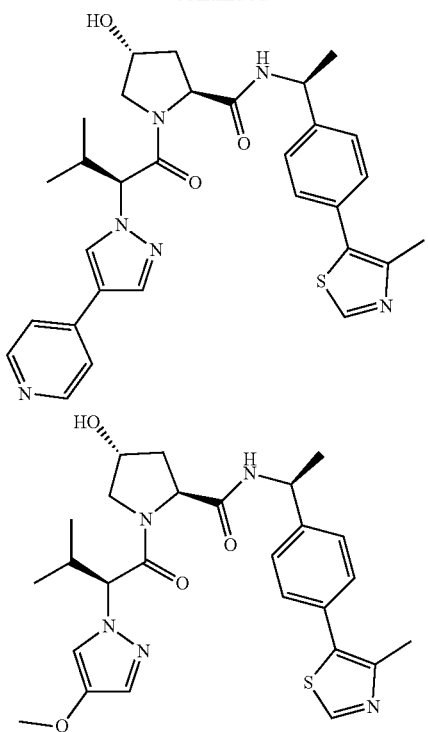

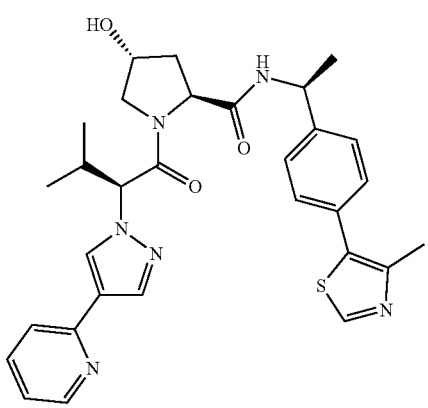

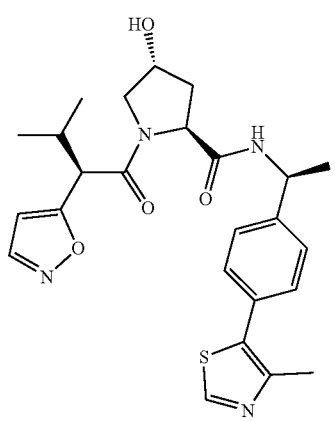

-continued

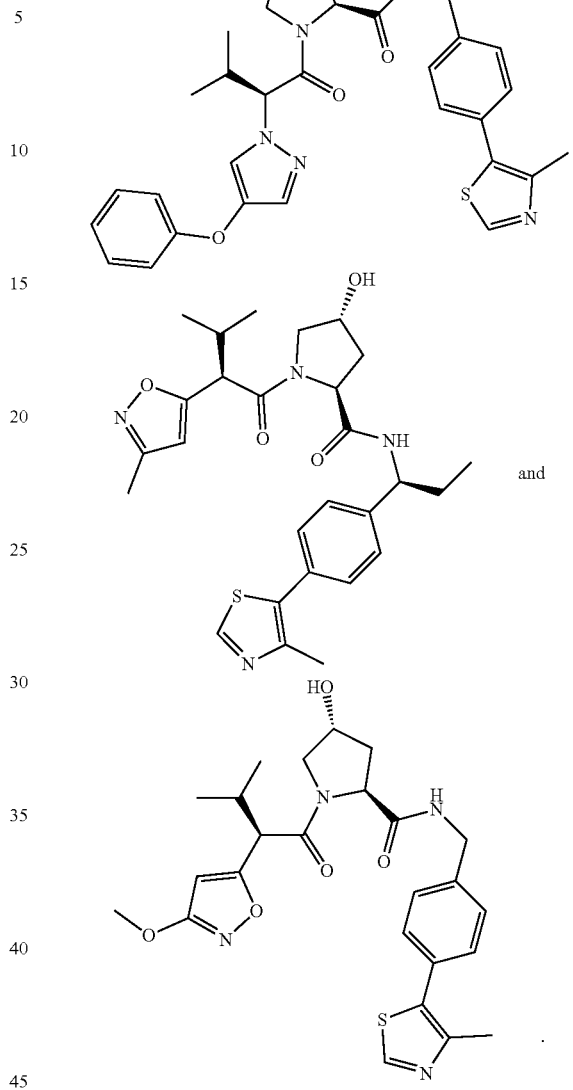

and

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, the alkyl group is end-capped with a halogen group (At, Br, Cl, F, or I). In certain preferred embodiments, compounds according to the present invention which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "Alkenyl" refers to linear, branch-chained or cyclic $C_2$-$C_{10}$ (preferably $C_2$-$C_6$) hydrocarbon radicals containing at least one C=C bond.

The term "Alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a —(CH$_2$)$_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present invention and may include substituents which themselves may be further substituted) at a carbon (or nitrogen) position anywhere on a molecule within context, and includes as substituents hydroxyl, thiol, carboxyl, cyano (C≡N), nitro (NO$_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present invention may include, for example —SiR$_1$R$_2$R$_3$ groups where each of R$_1$ and R$_2$ is as otherwise described herein and R$_3$ is H or a $C_1$-$C_6$ alkyl group, preferably R$_1$, R$_2$, R$_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteroaryl moiety) through an optionally substituted —(CH$_2$)$_m$ or alternatively an optionally substituted —(OCH$_2$)$_m$—, —(OCH$_2$CH$_2$)$_m$— or —(CH$_2$CH$_2$O)$_m$— group, which may be substituted with any one or more of the above-described substituents. Alkylene groups —(CH$_2$)$_m$— or —(CH$_2$)$_n$— groups or other chains such as ethylene glycol chains, as identified above, may be substituted anywhere on the chain. Preferred substitutents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sidechain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present invention, a moiety in a molecule may be optionally substituted with up to five substituents, preferably up to three substituents. Most often, in the present invention moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—NR$_1$R$_2$ or —N(R)—C(O)—O—R$_1$, nitro, cyano and amine (especially including a $C_1$-$C_6$ alkylene-NR$_1$R$_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —(CH$_2$)$_m$— (here, m and n are in context, 1, 2, 3, 4, 5 or 6), —S—, —S(O)—, SO$_2$— or —NH—C(O)—NH—, —(CH$_2$)$_n$OH, —(CH$_2$)$_n$SH, —(CH$_2$)$_n$COOH, $C_1$-$C_6$ alkyl, —(CH$_2$)$_n$O—($C_1$-$C_6$ alkyl), —(CH$_2$)$_n$C(O)—($C_1$-$C_6$ alkyl), —(CH$_2$)$_n$OC(O)—($C_1$-$C_6$ alkyl), —(CH$_2$)$_n$C(O)O—($C_1$-$C_6$ alkyl), —(CH$_2$)$_n$NHC(O)—R$_1$, —(CH$_2$)$_n$C(O)—NR$_1$R$_2$, —(OCH$_2$)$_n$OH, —(CH$_2$O)$_n$COOH, $C_1$-$C_6$ alkyl, —(OCH$_2$)$_n$O—($C_1$-$C_6$ alkyl), —(CH$_2$O)$_n$C(O)—($C_1$-$C_6$ alkyl), —(OCH$_2$)$_n$NHC(O)—R$_1$, —(CH$_2$O)$_n$C(O)—NR$_1$R$_2$, —S(O)$_2$—R$_S$, —S(O)—R$_S$ (R$_S$ is $C_1$-$C_6$ alkyl or a —(CH$_2$)$_m$—NR$_1$R$_2$ group), NO$_2$, CN or halogen (F, Cl, Br, I, preferably F or Cl), depending on the context of the use of the substituent. R$_1$ and R$_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present invention at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (monocyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —$(CH_2)_n$ OH, —$(CH_2)_n$—O—($C_1$-$C_6$)alkyl, —$(CH_2)_n$—O—$(CH_2)_n$—($C_1$-$C_6$)alkyl, —$(CH_2)_n$—C(O)($C_0$-$C_6$) alkyl, —$(CH_2)_n$—C(O)O($C_0$-$C_6$) alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably substituted with a linker group attached to a PTM group, including a ULM group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine)

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described above.

Exemplary heterocyclics include: azetidinyl, benzimidazolyl, 1.4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO— heteroaryl, —SO2-alkyl, —SO2-substituted alkyl, —SO2-aryl, oxo (=O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxynitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

Exemplary Linkers.

-$A_1$- . . . -Aq-, wherein $A_1$ is a group which links a moiety selected from the group consisting of ULM, PTM, and a combination thereof, to the linker Aq or directly to a moiety selected from the group consisting of ULM, PTM, and a combination thereof In certain embodiments, the compounds as described herein include one or more PTM chemically linked or coupled to one or more ULMs or ULM's via a chemical linker (L). In certain embodiments, the linker group L is a group comprises one or more covalently connected structural units of A (e.g. -$A_1$ . . . $A_q$-), wherein $A_1$ is a group coupled to at least one of a ULM, a PTM or a combination thereof. In certain embodiments, q is an integer greater than or equal to 0. In certain embodiments, q is an integer greater than or equal to 1.

In certain embodiments, e. g., where q is greater than 2, $A_q$ is a group which is connected to a ULM or ULM' moiety, and $A_1$ and $A_q$ are connected via structural units of A (number of such structural units of A: q-2).

In certain embodiments, e. g., where q is 2, $A_q$ is a group which is connected to $A_1$ and to a ULM or ULM' moiety.

In certain embodiments, e. g., where q is 1, the structure of the linker group L is -$A_1$-, and $A_1$ is a group which is connected to a ULM or ULM' moiety and a PTM moiety.

In additional embodiments, q is an integer from 1 to 100, 1 to 90, 1 to 80, 1 to 70, 1 to 60, 1 to 50, 1 to 40, 1 to 30, 1 to 20, or 1 to 10.

In certain embodiments, $A_1$ to $A_q$ are, each independently, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$=$CR^{L2}$, C≡C, $SiR^{L1}R^{L2}$, $P(O)R^{L1}$, $P(O)OR^{L1}$, $NR^{L3}C$(=NCN)$NR^{L4}$, $NR^{L3}C$(=NCN), $NR^{L3}C$(=$CNO_2$)$NR^{L4}$, $C_{3-11}$cycloalkyl optionally substituted with 0-6 $R^{L1}$ and/or $R^{L2}$ groups, $C_{3-11}$heteocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, wherein $R^{L1}$ or $R^{L2}$, each independently, can be linked to other A groups to form cycloalkyl and/or heterocyclyl moeity which can be further substituted with 0-4 $R^{L5}$ groups;

wherein $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}$cycloalkyl$)_2$, $N(C_{1-8}$cycloalkyl)($C_{1-8}$alkyl), OH, $NH_2$, SH, $SO_2C_{1-8}$alkyl, $P(O)(OC_{1-8}$alkyl)($C_{1-8}$alkyl), $P(O)(OC_{1-8}$alkyl$)_2$, CC—$C_{1-8}$-alkyl, CCH, CH=CH($C_{1-8}$alkyl), C($C_{1-8}$alkyl)=CH($C_{1-8}$alkyl), C($C_{1-8}$alkyl)=C($C_{1-8}$alkyl$)_2$, $Si(OH)_3$, $Si(C_{1-8}$alkyl$)_3$, $Si(OH)(C_{1-8}$alkyl$)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}$alkyl$)_2$, $SONHC_{1-8}$alkyl, $SON(C_{1-8}$alkyl$)_2$, $CONHC_{1-8}$alkyl, $CON(C_{1-8}$alkyl$)_2$, $N(C_{1-8}$alkyl)$CONH(C_{1-8}$alkyl), $N(C_{1-8}$alkyl)$CON(C_{1-8}$alkyl$)_2$, $NHCONH(C_{1-8}$alkyl), $NHCON(C_{1-8}$alkyl$)_2$, $NHCONH_2$, $N(C_{1-8}$alkyl)$SO_2NH(C_{1-8}$alkyl), $N(C_{1-8}$alkyl) $SO_2N(C_{1-8}$alkyl$)_2$, NH $SO_2NH(C_{1-8}$alkyl), NH $SO_2N(C_{1-8}$alkyl$)_2$, NH $SO_2NH_2$.

In certain embodiments, A is independently selected from a bond (i.e., absent), —$(CH_2)_i$—O, —$(CHR)_i$—O, $(CR_2)_i$—O, —$(CH_2)_i$—S, —$(CH_2)$—N—R, —S, —S(O), —$S(O)_2$, —OP(O)OR, —$SiR_2$, a

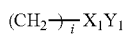

group wherein $X_1Y_1$ forms an amide group, or a urethane group, ester or thioester group, or a

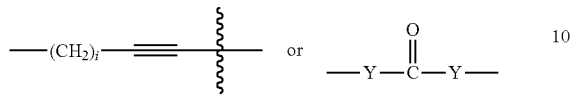

group;

each R is independently H, or a $C_1$-$C_3$ alkyl, an alkanol group or a heterocycle (including a water soluble heterocycle, preferably, a morpholino, piperidine or piperazine group to promote water solubility of the linker group);

each Y is independently a bond, O, S or N—R; and each i is independently 0 to 100, 1 to 75, 1 to 60, 1 to 55, 1 to 50, 1 to 45, 1 to 40, 2 to 35, 3 to 30, 1 to 15, 1 to 10, 1 to 8, 1 to 6; 1, 2, 3, 4 or 5.

In preferred aspects A is a

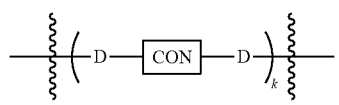

group where each D is independently a bond (absent),

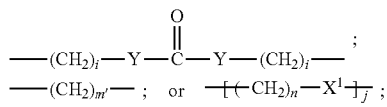

j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

k is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; preferably k is 1, 2, 3, 4, or 5;

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

$X^1$ is O, S or N—R, preferably O;

Y is the same as above; and CON is a connector group (which may be a bond) which connects $A_1$ to $A_q$, when present in the linker group.

In preferred aspects, CON is a bond (absent), a heterocycle including a water soluble heterocycle such as a piperazinyl or other group or a group, wherein $X^2$ is independently O, S, $NR_4$, OP(O)OR, $SiR_2$, —CC, cycloalkyl, heterocyclyl, S(O), $S(O)_2$, —$S(O)_2O$, —$OS(O)_2$, or $OS(O)_2O$;

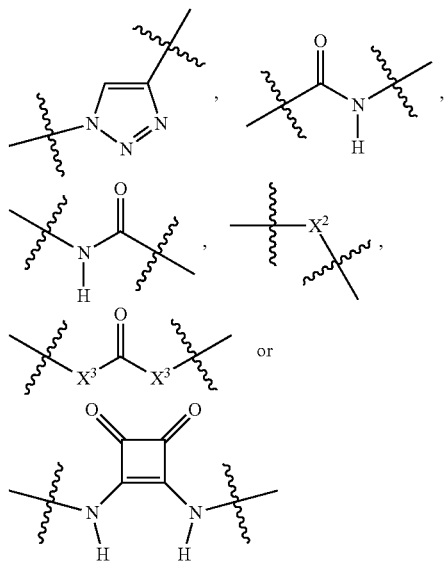

$X^3$ is O, S, $CHR_4$, $NR_4$; and $R^4$ is H or a $C_1$-$C_3$ alkyl group optionally substituted with one or two hydroxyl groups, or a pharmaceutically acceptable salt, enantiomer or stereoisomer thereof.

In alternative preferred aspects, CON is a group or an amide group.

In another aspect, the linker can be asymmetric or symmetrical.

In alternative preferred aspects, CON is a

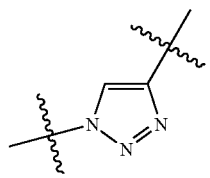 [SMILES: *c1cn(*)nn1]

group or an amide group.

In alternative preferred aspects, the linker group is an optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units. In certain embodiments, the linker is optionally substituted; i.e., comprises chemical groups interdispersed within or on the PEG linker. In certain additional embodiment, the PEG linker is substituted with an alkyl, alkylene, aromatic group, or aryl group, e.g., phenyl, benzyl or heterocyclyl group, or amino acid side chain and is optionally interdispersed with optionally substituted, O, N, S, P or Si atoms.

In certain embodiments, the linker (L) is selected from the group consisting of:

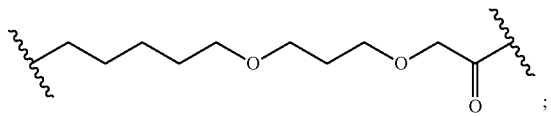

113
-continued
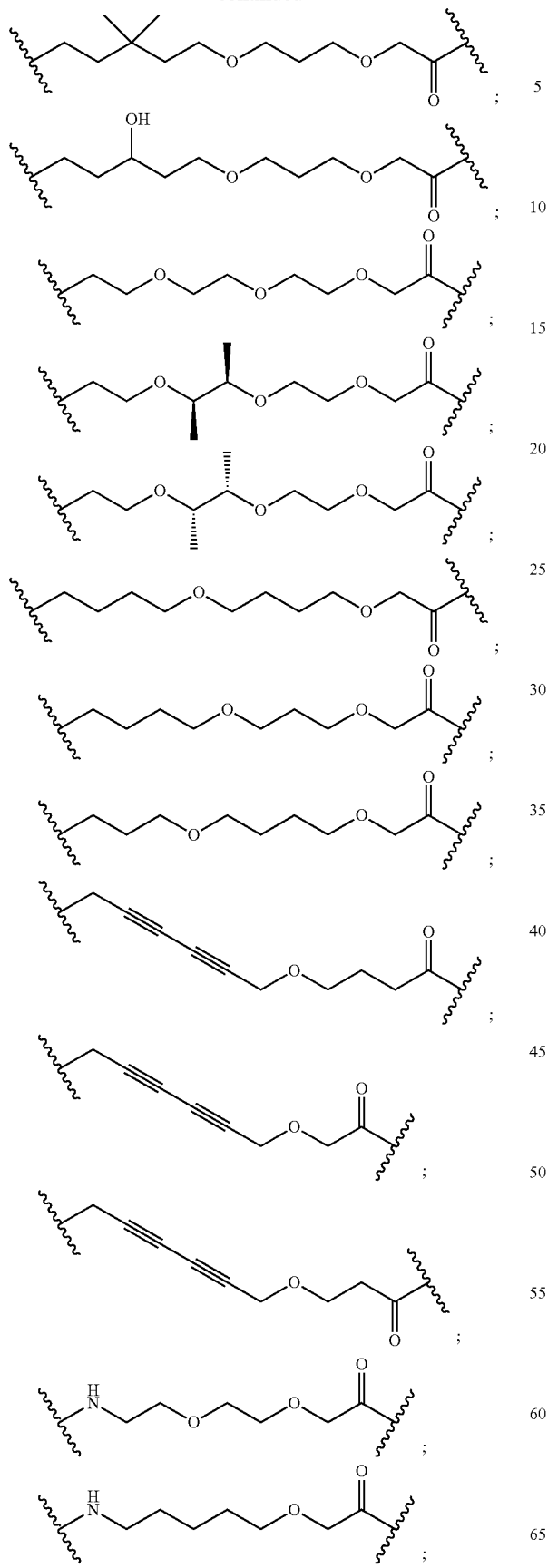
114
-continued
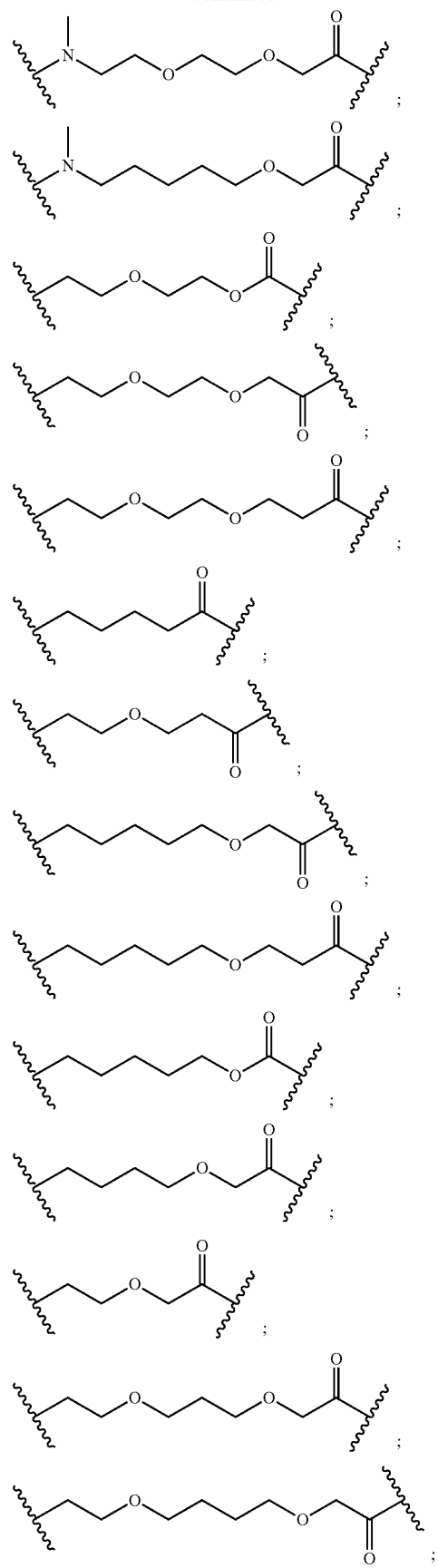

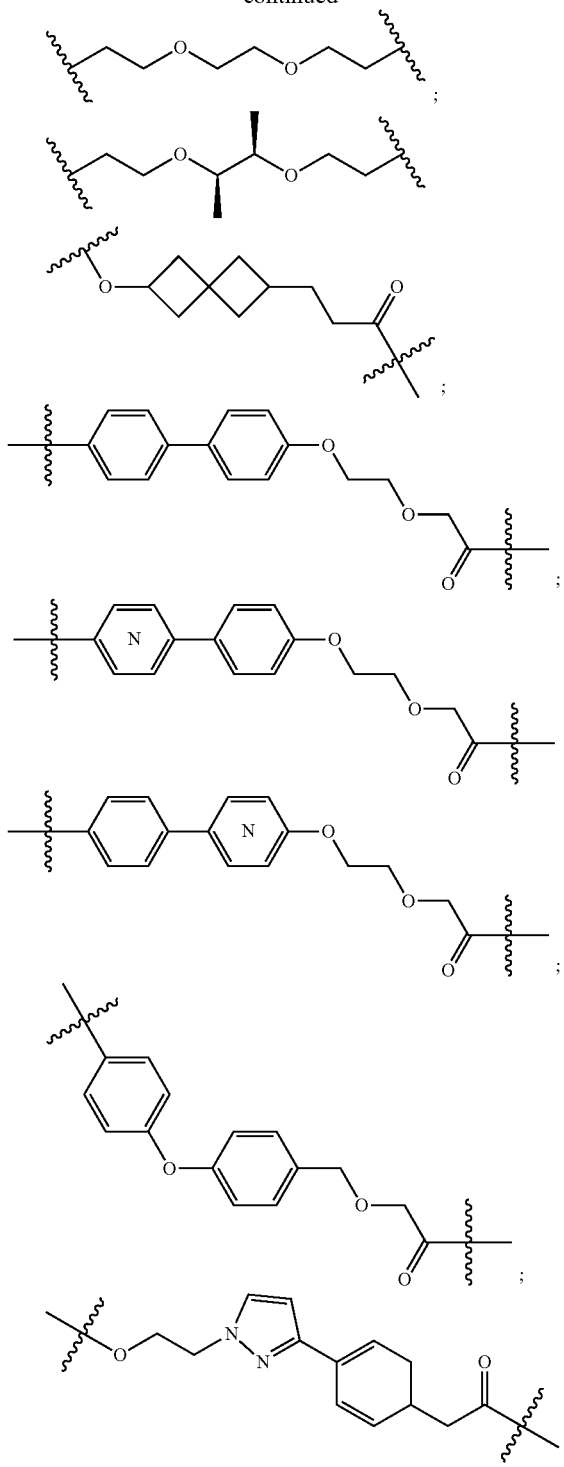

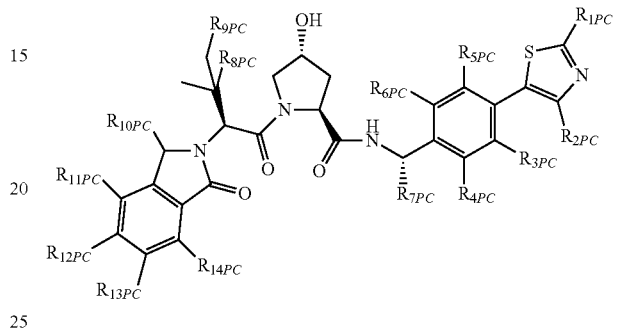

In an additional embodiment, particularly preferred compounds according to the present invention may be identified according to any one or more of the chemical structures as set forth in FIG. 19 hereof:

Wherein any one or more of $R_{1PC}$, $R_{2PC}$, $R_{3PC}$, $R_{4PC}$, $R_{5PC}$, $R_{6PC}$, $R_{7PC}$, $R_{8PC}$, $R_{9PC}$, $R_{10PC}$, $R_{11PC}$, $R_{12PC}$, $R_{13PC}$ and $R_{14PC}$ is a

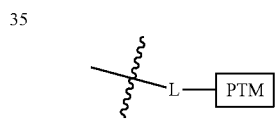

group,
where L is a linker group and

is a protein targeting moiety, or
A pharmaceutically acceptable salt, stereoisomer, solvate or polymorph thereof.

In preferred embodiments, no more than two of $R_{1PC}$, $R_{2PC}$, $R_{3PC}$, $R_{4PC}$, $R_{5PC}$, $R_{6PC}$, $R_{7PC}$, $R_{8PC}$, $R_{9PC}$, $R_{10PC}$, $R_{11PC}$, $R_{12PC}$, $R_{13PC}$ and $R_{14PC}$ is a

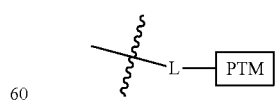

group and the other of groups $R_{1PC}$, $R_{2PC}$, $R_{3PC}$, $R_{4PC}$, $R_{5PC}$, $R_{6PC}$, $R_{7PC}$, $R_{8PC}$, $R_{9PC}$, $R_{10PC}$, $R_{11PC}$, $R_{12PC}$, $R_{13PC}$ and $R_{14PC}$ are independently H or a $CH_3$ group, often H.

Certain preferred embodiments are directed to ULM compounds according to the chemical structure:

Although the ULM group and PTM group (including a ULM' group) may be covalently linked to the linker group through any group which is appropriate and stable to the chemistry of the linker, in preferred aspects of the present invention, the linker is independently covalently bonded to the ULM group and the PTM group (including a ULM' group) preferably through an amide, ester, thioester, keto group, carbamate (urethane) or ether, each of which groups may be inserted anywhere on the ULM group and PTM group (including a ULM' group) to provide maximum binding of the ULM group on the ubiquitin ligase and the PTM group on the target protein to be degraded. (It is noted that in certain aspects where the PTM group is a ULM' group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

Exemplary Structures with Sites for Linkers.

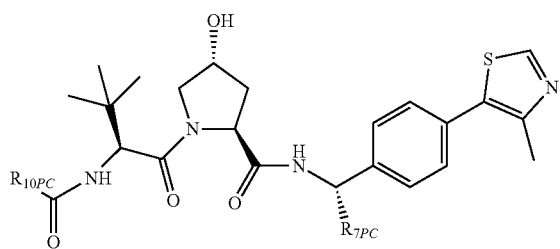

wherein $R_{7PC}$ and $R_{10PC}$ are each independently a -[L-PTM] group or H; or a pharmaceutically acceptable salt, stereoisomer, solvate or polymorph thereof. Preferably, either of $R_{7PC}$ or $R_{10PC}$ is a -[L-PTM] group and the other $R_{7PC}$ or $R_{10PC}$ is H.

In still other preferred embodiments, the compound has the chemical structure:

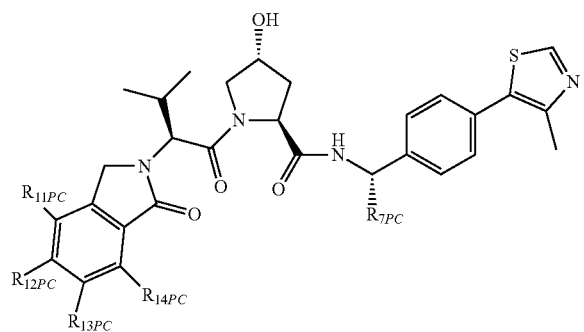

wherein $R_{7PC}$, $R_{11PC}$ $R_{12PC}$, $R_{13PC}$ and $R_{14PC}$ are each independently a -[L-PTM]group or H; or a pharmaceutically acceptable salt, stereoisomer, solvate or polymorph thereof. Preferably, one of $R_{7PC}$, $R_{11PC}$, $R_{12PC}$, $R_{13PC}$ and $R_{14PC}$ is a -[L-PTM] group and the other groups are H, or a pharmaceutically acceptable salt, stereoisomer, solvate or polymorph thereof.

In still other preferred embodiments, the compound has the chemical structure:

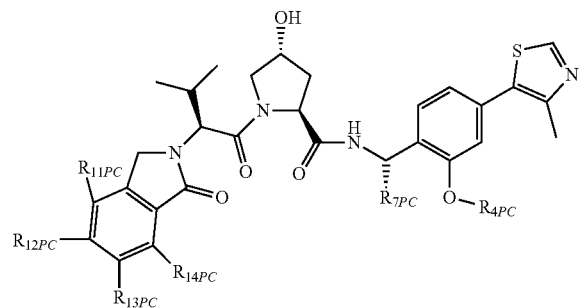

wherein $R_{4PC}$, $R_{7PC}$, $R_{11PC}$ $R_{12PC}$, $R_{13PC}$ and $R_{14PC}$ are each independently a -[L-PTM] group or H; or a pharmaceutically acceptable salt, stereoisomer, solvate or polymorph thereof. Preferably, either of $R_{4PC}$, $R_{7PC}$ or one of $R_{11PC}$, $R_{12PC}$, $R_{13PC}$ and $R_{14PC}$ is a -[L-PTM] group and the other groups are H; or a pharmaceutically acceptable salt, stereoisomer, solvate or polymorph thereof.

In still other embodiments, the ULM compound has the chemical structure:

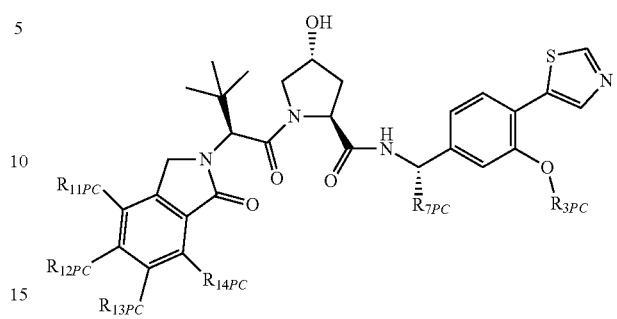

wherein $R_{3PC}$, $R_{7PC}$, $R_{11PC}$ $R_{12PC}$, $R_{13PC}$ and $R_{14PC}$ are each independently a-[L-PTM] group or H; or a pharmaceutically acceptable salt, stereoisomer, solvate or polymorph thereof. Preferably, one of $R_{3PC}$, $R_{7PC}$, $R_{11PC}$, $R_{12PC}$, $R_{13PC}$ and $R_{14PC}$ is a -[L-PTM] group and the other groups are H; or a pharmaceutically acceptable salt, stereoisomer, solvate or polymorph thereof.

In still other preferred embodiments, the compound has the chemical structure:

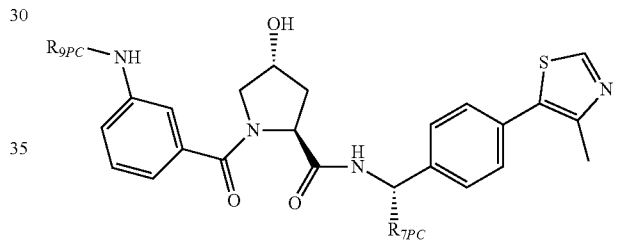

wherein $R_{7PC}$ and $R_{9PC}$ are each independently a -[L-PTM] group or H; or a pharmaceutically acceptable salt, stereoisomer, solvate or polymorph thereof. Preferably, one of $R_{7PC}$ and $R_{9PC}$ is a -[L-PTM] group and the other group is H; or a pharmaceutically acceptable salt, stereoisomer, solvate or polymorph thereof.

In the above embodiments, the linker group may be any linker group as described hereinabove, below is preferably a polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycole units.

Exemplary PTMs.

In other aspects of the invention, the PTM group is a group that binds to target proteins. Targets of the PTM group are numerous in kind and are selected from proteins that are expressed in a cell such that at least a portion of the sequences is found in the cell and may bind to a PTM group. The term "protein" includes oligopeptides and polypeptide sequences of sufficient length that they can bind to a PTM group according to the present invention. Any protein in a eukaryotic system or a microbial system, including a virus, bacteria or fungus, as otherwise described herein, are targets for ubiquitination mediated by the compounds according to the present invention. Preferably, the target protein is a eukaryotic protein. In certain aspects, the protein binding moiety is a haloalkane (preferably a C1-C10 alkyl group which is substituted with at least one halo group, preferably a halo group at the distil end of the alkyl group (i.e., away from the linker or ULM group), which may covalently bind to a dehalogenase enzyme in a patient or subject or in a diagnostic assay.

PTM groups according to the present invention include, for example, include any moiety which binds to a protein specifically (binds to a target protein) and includes the following non-limiting examples of small molecule target protein moieties: Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of these nine types of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

Any protein, which can bind to a protein target moiety or PTM group and acted on or degraded by an ubiquitin ligase is a target protein according to the present invention. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catrabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes including humans as targets for drug therapy, other animals, including domesticated animals, microbials for the determination of targets for antibiotics and other antimicrobials and plants, and even viruses, among numerous others.

In still other embodiments, the PTM group is a haloalkyl group, wherein said alkyl group generally ranges in size from about 1 or 2 carbons to about 12 carbons in length, often about 2 to 10 carbons in length, often about 3 carbons to about 8 carbons in length, more often about 4 carbons to about 6 carbons in length. The haloalkyl groups are generally linear alkyl groups (although branched-chain alkyl groups may also be used) and are end-capped with at least one halogen group, preferably a single halogen group, often a single chloride group. Haloalkyl PTM groups for use in the present invention are preferably represented by the chemical structure —(CH$_2$)$_v$-Halo where v is any integer from 2 to about 12, often about 3 to about 8, more often about 4 to about 6. Halo may be any halogen, but is preferably Cl or Br, more often Cl.

In still other embodiments, the PTM group is a

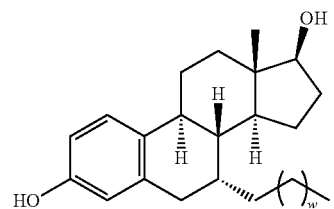

group, where w is 0 to 3, preferably 1 or 2. This group binds selectively to estrogen receptors and is useful for treating diseases which are modulated through estrogen receptors, and in particular cancers, such as breast cancer, endometrial cancer, ovarian cancer and uterine cancer, among others.

The present invention may be used to treat a number of disease states and/or conditions, including any disease state and/or condition in which proteins are dysregulated and where a patient would benefit from the degradation of proteins.

In another aspect, the present invention relates to pharmaceutical compositions comprising an effective amount of a compound as set forth hereinabove, in combination with a pharmaceutically acceptable carrier, additive or excipient, and optionally an additional bioactive agent.

In alternative aspects, the present invention relates to a method for treating a disease state by degrading a protein or polypeptide through which a disease state or condition is modulated comprising administering to said patient or subject an effective amount of at least one compound as described hereinabove, optionally in combination with an additional bioactive agent. The method according to the present invention may be used to treat a large number of disease states or conditions including cancer, by virtue of the administration of effective amounts of at least one compound described herein.

Protein target moieties according to the present invention include, for example, Haloalkane halogenase inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR). The compositions described below exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited hereinbelow are incorporated by reference herein in their entirety.

Heat Shock Protein 90 (HSP90) Inhibitors:

HSP90 inhibitors as used herein include, but are not limited to:

The HSP90 inhibitors identified in Vallee, et al., "Tricyclic Series of Heat Shock Protein 90 (HSP90) Inhibitors Part I: Discovery of Tricyclic Imidazo[4,5-C]Pyridines as Potent Inhibitors of the HSP90 Molecular Chaperone (2011) *J. Med. Chem.* 54: 7206, including

YKB N-[4-(3H-IMIDAZO[4,5-C]PYRIDIN-2-YL)-9H-FLUOREN-9-YL]-SUCCINAMIDE

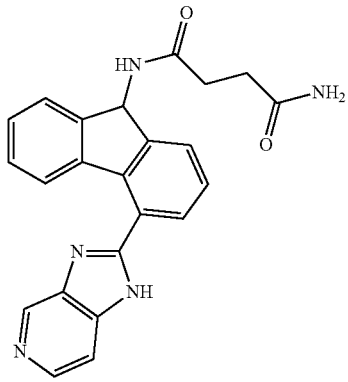 [SMILES: NC(=O)CCC(=O)NC1c2ccccc2-c2c(-c3nc4cnccc4[nH]3)cccc21]

Derivatized where a linker group L or a

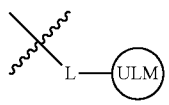

group is attached via the terminal amide group;

2. The HSP90 inhibitor p54 (modified):

p54 8-[(2,4-dimethylphenyl)sulfanyl]-3-pent-4-yn-1-yl-3H-purin-6-amine

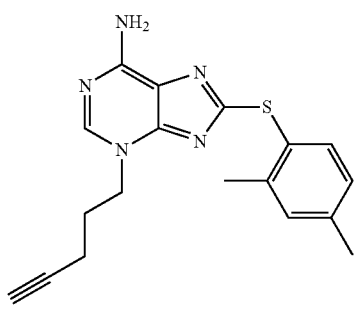 [SMILES: C#CCCCn1cnc(N)c2nc(Sc3ccc(C)cc3C)nc1-2]

Where a linker group L or a

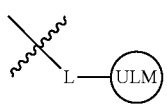

group is attached via the terminal acetylene group;

3. The HSP90 inhibitors (modified) identified in Brough, et al., "4,5-Diarylisoxazole HSP90 Chaperone Inhibitors: Potential Therapeutic Agents for the Treatment of Cancer", *J. MED. CHEM.* vol: 51, pag:196 (2008), including the compound 2GJ (5-[2,4-DIHYDROXY-5-(1-METHYL-ETHYL)PHENYL]-N-ETHYL-4-[4-(MORPHOLIN-4-YL-METHYL)PHENYL]ISOXAZOLE-3-CARBOXAMIDE) having the structure:

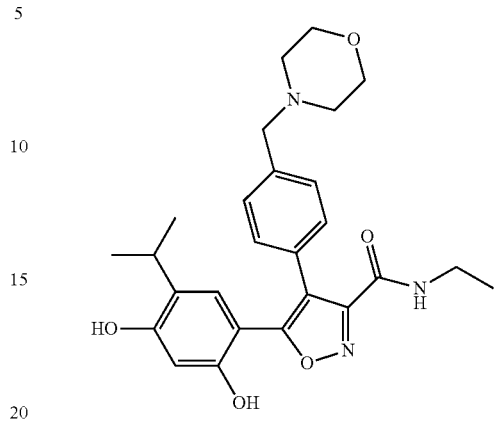

Derivatized, where a linker group L or a

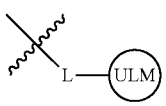

group is attached via the amide group (at the amine or at the alkyl group on the amine;

4. The HSP90 inhibitors (modified) identified in Wright, et al., Structure-Activity Relationships in Purine-Based Inhibitor Binding to HSP90 Isoforms, *Chem Biol.* 2004 June; 11(6):775-85, including the HSP90 inhibitor PU3 having the structure:

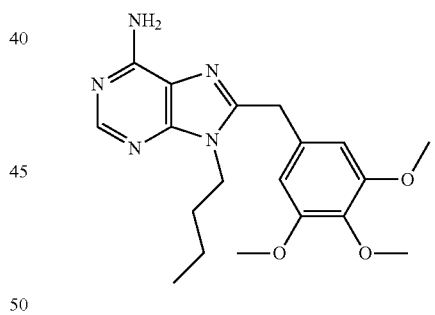

Where a linker group L or

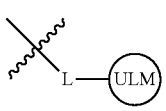

is attached via the butyl group; and

5. The HSP90 inhibitor Geldanamycin ((4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1] (derivatized) or any of its derivatives (e.g. 17-alkylamino-17-desmethoxygeldanamycin ("17-AAG") or 17-(2-dimethylaminoethyl)amino-17-desmethoxygeldanamycin ("17-DMAG")) (derivatized, where a linker group L or a

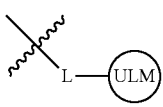

group is attached via the amide group).

II. Kinase and Phosphatase Inhibitors:

Kinase inhibitors as used herein include, but are not limited to:

Erlotinib Derivative Tyrosine Kinase Inhibitor

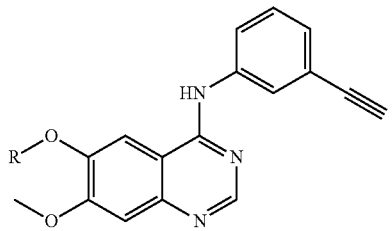

Where R is a linker group L or a

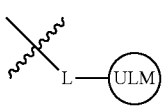

group attached via the ether group;

2. The kinase inhibitor Sunitanib (derivatized):

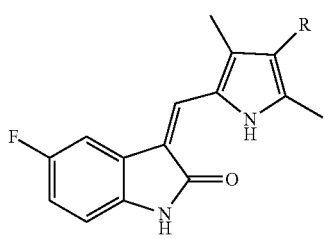

(Derivatized where R is a linker group L or a

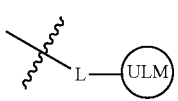

group attached to the pyrrole moiety);

3. Kinase Inhibitor Sorafenib (derivatized)

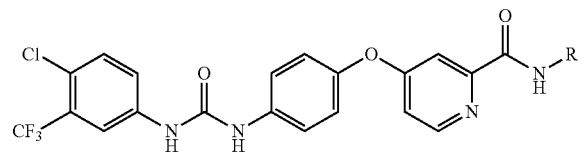

(Derivatized where R is a linker group L or a

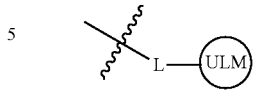

group attached to the phenyl moiety);

4. The kinase inhibitor Desatinib (derivatized)

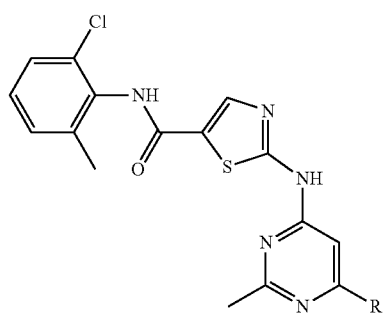

(Derivatized where R is a linker group L or a

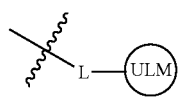

attached to the pyrimidine);

The kinase inhibitor Lapatinib (derivatized)

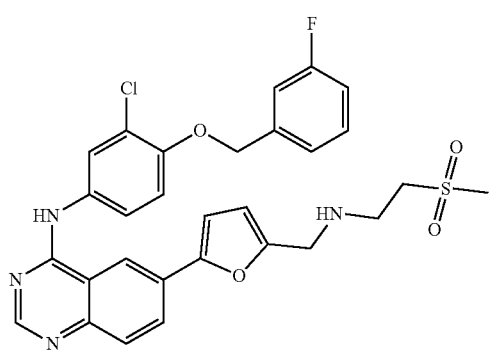 [SMILES: CS(=O)(=O)CCNCc1ccc(-c2ccc3ncnc(Nc4ccc(OCc5cccc(F)c5)c(Cl)c4)c3c2)o1]

Derivatized where a linker group L or a

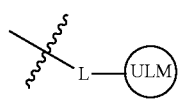

group is attached via the terminal methyl of the sulfonyl methyl group;

The kinase inhibitor U09-CX-5279 (Derivatized)

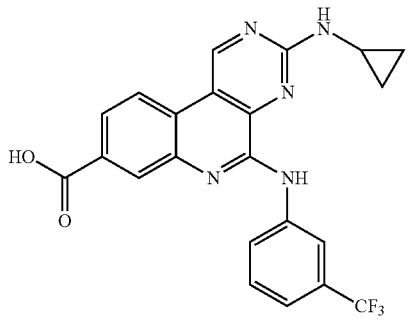 [SMILES: O=C(O)c1ccc2c(c1)nc(Nc1cccc(C(F)(F)F)c1)c1nc(NC3CC3)ncc12]

Derivatized where a linker group L or a

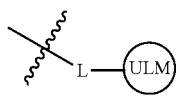

group is attached via the amine (aniline), carboxylic acid or amine alpha to cyclopropyl group, or cyclopropyl group;

7. The kinase inhibitors identified in Millan, et al., Design and Synthesis of Inhaled P38 Inhibitors for the Treatment of Chronic Obstructive Pulmonary Disease, *J. MED. CHEM.* vol:54, pag:7797 (2011), including the kinase inhibitors Y1W and Y1X (Derivatized) having the structures:

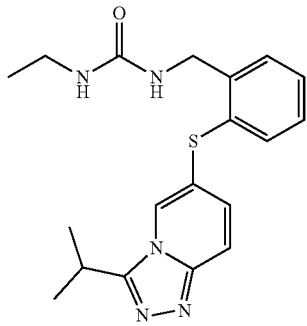 [SMILES: CCNC(=O)NCc1ccccc1Sc1ccc2nnc(C(C)C)n2c1]

YIX 1-ethyl-3-(2-{[3-(1-methylethyl)[1,2,4]triazolo[4,3-a]pyridin-6-yl]sulfanyl}benzyl)urea Derivatized where a linker group L or a

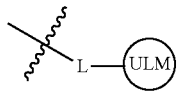

group is attached preferably via the propyl group;

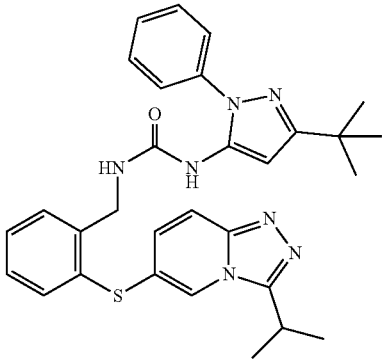 [SMILES: CC(C)c1nnc2ccc(Sc3ccccc3CNC(=O)Nc3cc(C(C)(C)C)nn3-c3ccccc3)cn12]

YIW 1-(3-tert-butyl-1-phenyl-1H-pyrazol-5-yl)-3-(2-{[3-(1-methylethyl)[1,2,4]triazolo[4,3-a]pyridin-6-yl]sulfanyl}benzyl)urea Derivatized where a linker group L or a

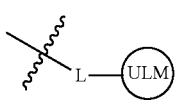

group is attached preferably via either the propyl group or the butyl group;

8. The kinase inhibitors identified in Schenkel, et al., Discovery of Potent and Highly Selective Thienopyridine Janus Kinase 2 Inhibitors *J. Med. Chem.*, 2011, 54 (24), pp 8440-8450, including the compounds 6TP and 0TP (Derivatized) having the structures:

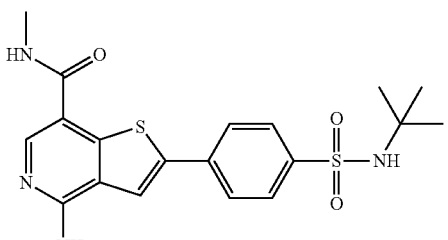

6TP 4-amino-2-[4-(tert-butylsulfamoyl)phenyl]-N-methylthieno[3,2-c]pyridine-7-carboxamide Thienopyridine 19

Derivatized where a linker group L or a

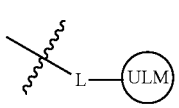

group is attached preferably via the terminal methyl group bound to amide moiety;

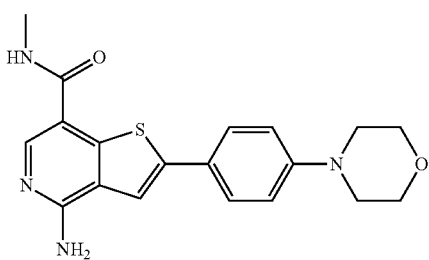 [SMILES: CNC(=O)c1cnc(N)c2cc(-c3ccc(N4CCOCC4)cc3)sc12]

OTP 4-amino-N-methyl-2-[4-(morpholin-4-yl)phenyl]thieno[3,2-c]pyridine-7-carboxamide Thienopyridine 8

Derivatized where a linker group L or a

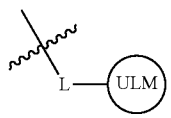

group is attached preferably via the terminal methyl group bound to the amide moiety;

9. The kinase inhibitors identified in Van Eis, et al., "2,6-Naphthyridines as potent and selective inhibitors of the novel protein kinase C isozymes", *Biorg. Med. Chem. Lett.* 2011 Dec. 15; 21(24):7367-72, including the kinase inhibitor 07U having the structure:

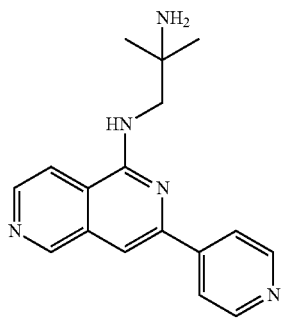 [SMILES: CC(C)(N)CNc1nc(-c2ccncc2)cc2cnccc12]

07U 2-methyl-N~1~-[3-(pyridin-4-yl)-2,6-naphthyridin-1-yl]propane-1,2-diamine

Derivatized where a linker group L or a

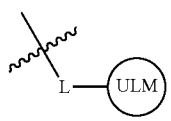

group is attached preferably via the secondary amine or terminal amino group;

10. The kinase inhibitors identified in Lountos, et al., "Structural Characterization of Inhibitor Complexes with Checkpoint Kinase 2 (Chk2), a Drug Target for Cancer Therapy", *J. STRUCT. BIOL.* vol:176, pag:292 (2011), including the kinase inhibitor YCF having the structure:

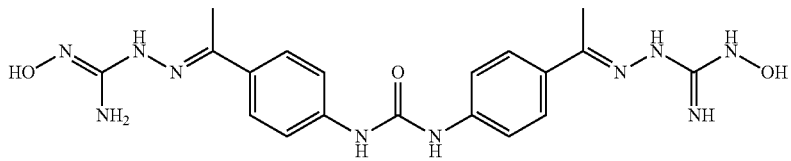 [SMILES: C/C(=N\NC(=N)NO)c1ccc(NC(=O)Nc2ccc(/C(C)=N/N/C(N)=N/O)cc2)cc1]

Derivatized where a linker group L or a

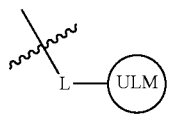

group is attached preferably via either of the terminal hydroxyl groups;

11. The kinase inhibitors identified in Lountos, et al., "Structural Characterization of Inhibitor Complexes with Checkpoint Kinase 2 (Chk2), a Drug Target for Cancer Therapy", *J. STRUCT. BIOL.* vol:176, pag:292 (2011), including the kinase inhibitors XK9 and NXP (derivatized) having the structures:

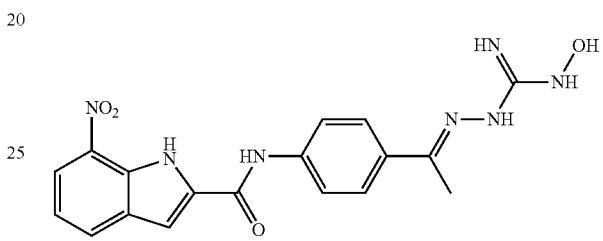

XK9 N-{4-[(1E)-N—(N-hydroxycarbamimidoyl)ethanehydrazonoyl]phenyl}-7-nitro-1H-indole-2-carboxamide

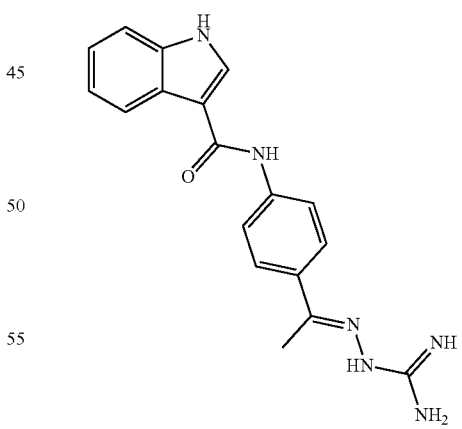

NXP N-{4-[(1E)-N-CARBAMIMIDOYLETHANE-HYDRAZONOYL]PHENYL}-1H-INDOLE-3-CARBOXAMIDE

Derivatized where a linker group L or a

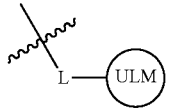

group is attached preferably via the terminal hydroxyl group (XK9) or the hydrazone group (NXP);

12. The kinase inhibitor Afatinib (derivatized) (N-[4-[(3-Chloro-4-fluorophenyl)amino]-7-[[(3S)-tetrahydro-3-furanyl]oxy]-6-quinazolinyl]-4(dimethylamino)-2-butenamide) (Derivatized where a linker group L or a

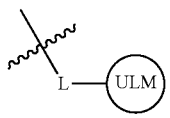

group is attached preferably via the aliphatic amine group);

13. The kinase inhibitor Fostamatinib (derivatized) ([6-({5-fluoro-2-[(3,4,5-trimethoxyphenyl)amino]pyrimidin-4-yl}amino)-2,2-dimethyl-3-oxo-2,3-dihydro-4H-pyrido[3,2-b]-1,4-oxazin-4-yl]methyl disodium phosphate hexahydrate) (Derivatized where a linker group L or a

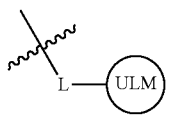

group is attached preferably via a methoxy group);

14. The kinase inhibitor Gefitinib (derivatized) (N-(3-chloro-4-fluoro-phenyl)-7-methoxy-6-(3-morpholin-4-yl-propoxy)quinazolin-4-amine) (Derivatized where a linker group L or a

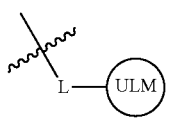

group is attached preferably via a methoxy or ether group);

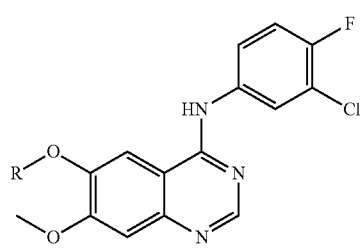

15. The kinase inhibitor Lenvatinib (derivatized) (4-[3-chloro-4-(cyclopropylcarbamoylamino)phenoxy]-7-methoxy-quinoline-6-carboxamide) (Derivatized where a linker group L or a

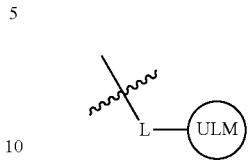

group is attached preferably via the cyclopropyl group);

16. The kinase inhibitor Vandetanib (derivatized) (N-(4-bromo-2-fluorophenyl)-6-methoxy-7-[(1-methylpiperidin-4-yl)methoxy]quinazolin-4-amine) (derivatized where a linker group L or a

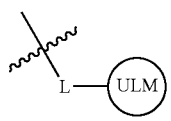

group is attached preferably via the methoxy or hydroxyl group); and

17. The kinase inhibitor Vemurafenib (derivatized) (propane-1-sulfonic acid {3-[5-(4-chlorophenyl)-1H-pyrrolo[2,3-b]pyridine-3-carbonyl]-2,4-difluoro-phenyl}-amide) (Derivatized where a linker group L or a

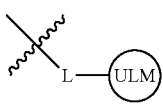

group is attached preferably via the sulfonyl propyl group);

18. The kinase inhibitor Gleevec (derivatized):

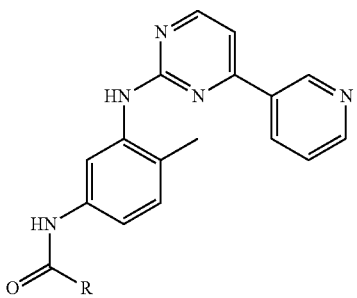

(Derivatized where R as a linker group L or a

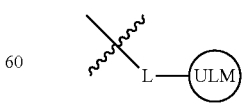

group is attached preferably via the amide group or via the aniline amine group);

The kinase inhibitor Pazopanib (derivatized) (VEGFR3 inhibitor):

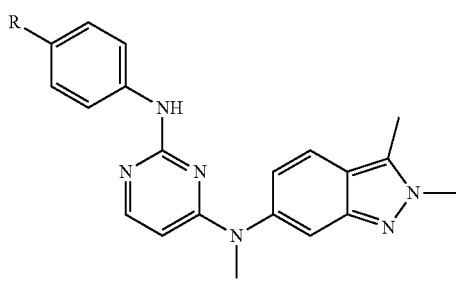

(Derivatized where R is a linker group L or a

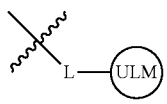

group preferably attached to the phenyl moiety or via the aniline amine group);

The kinase inhibitor AT-9283 (Derivatized) Aurora Kinase Inhibitor

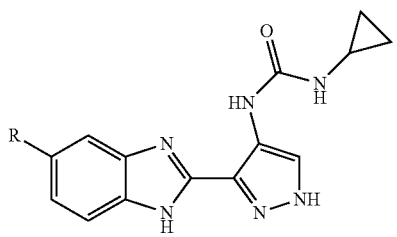

(where R is a linker group L or a

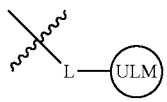

group attached preferably to the phenyl moiety);

The kinase inhibitor TAE684 (derivatized) ALK inhibitor

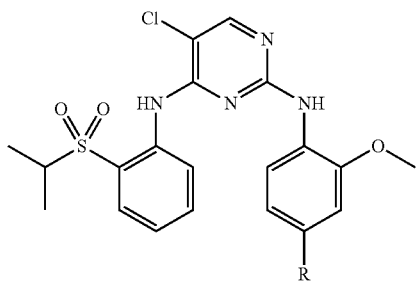

(where R is a linker group L or a

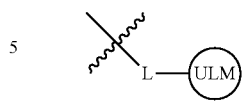

group attached preferably to the phenyl moiety);

The kinase inhibitor Nilotanib (derivatized) Abl inhibitor:

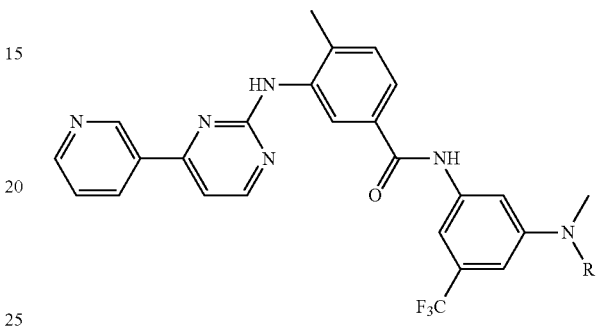

(Derivatized where R is a linker group L or a

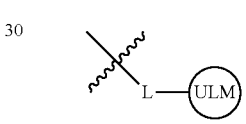

group attached preferably to the phenyl moiety or the aniline amine group);

27. Kinase Inhibitor NVP-BSK805 (derivatized) JAK2 Inhibitor

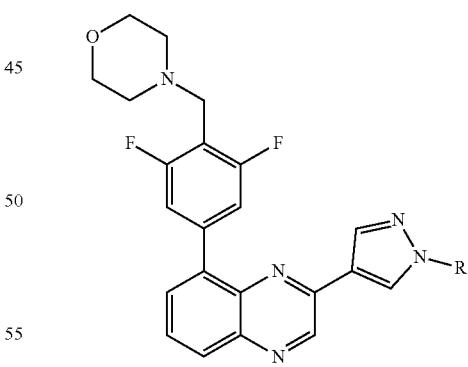

(Derivatized where R is a linker group L or a

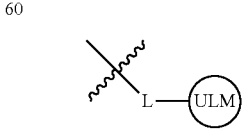

group attached to the phenyl moiety or the diazole group);

28. Kinase Inhibitor Crizotinib Derivatized Alk Inhibitor

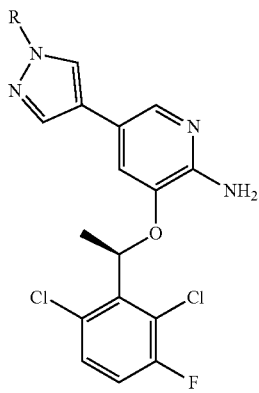

(Derivatized where R is a linker group L or a

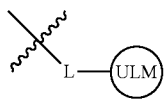

group attached to the phenyl moiety or the diazole group);

29. Kinase Inhibitor JNJ FMS (derivatized) Inhibitor

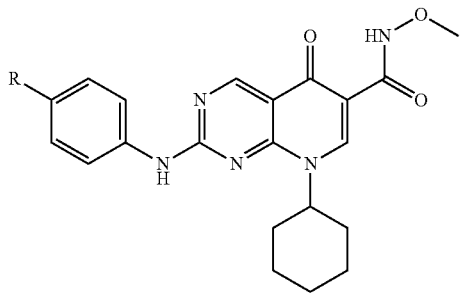

(Derivatized where R is a linker group L or a

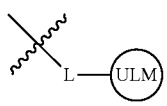

group attached preferably to the phenyl moiety);

The kinase inhibitor Foretinib (derivatized) Met Inhibitor

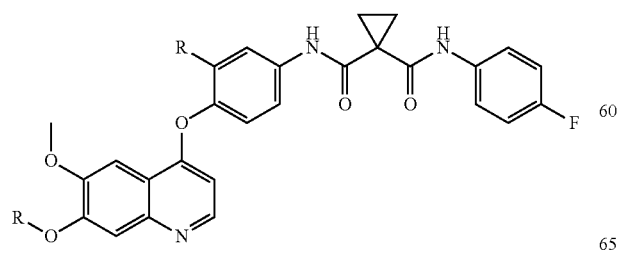

(Derivatized where R is a linker group L or a

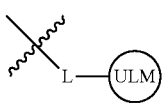

group attached to the phenyl moiety or a hydroxyl or ether group on the quinoline moiety);

31. The allosteric Protein Tyrosine Phosphatase Inhibitor PTP1B (derivatized):

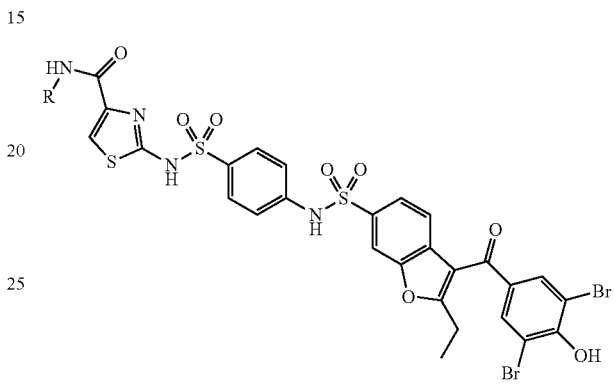

Derivatized where a linker group L or a

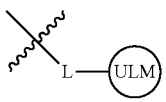

group is preferably attached at R, as indicated.

The inhibitor of SHP-2 Domain of Tyrosine Phosphatase (derivatized):

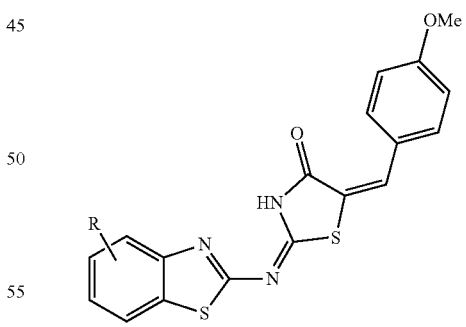

Derivatized where a linker group L or a

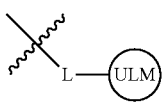

group is attached preferably at R.

The inhibitor (derivatized) of BRAF (BRAF$^{V600E}$)/MEK:

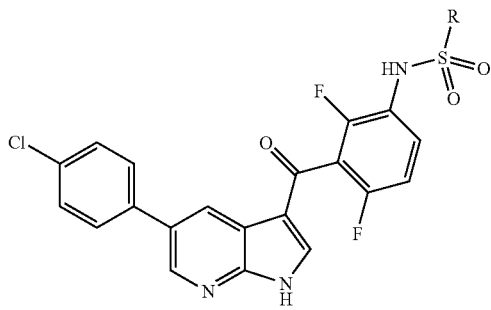

Derivatized where a linker group L or a

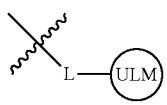

group is attached preferably at R.

34. Inhibitor (derivatized) of Tyrosine Kinase ABL

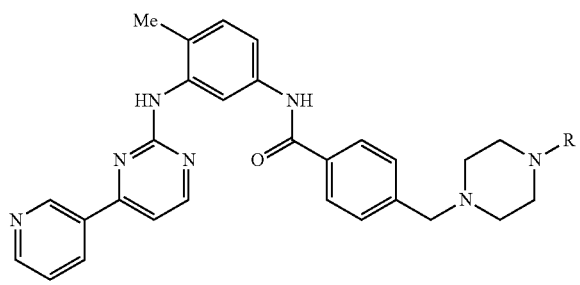

(Derivatized where "R" designates a site for attachment of a linker group L or a

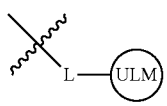

group on the piperazine moiety).

III. MDM2 Inhibitors:

MDM2 inhibitors as used herein include, but are not limited to:

1. The MDM2 inhibitors identified in Vassilev, et al., In vivo activation of the p53 pathway by small-molecule antagonists of MDM2, *SCIENCE* vol:303, pag:844-848 (2004), and Schneekloth, et al., Targeted intracellular protein degradation induced by a small molecule: En route to chemical proteomics, *Bioorg. Med. Chen. Lett.* 18 (2008) 5904-5908, including (or additionally) the compounds nutlin-3, nutlin-2, and nutlin-1 (derivatized) as described below, as well as all derivatives and analogs thereof:

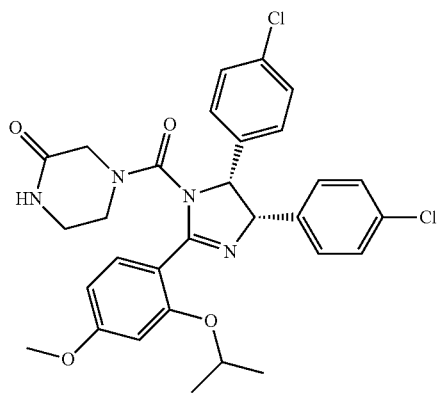 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(Derivatized where a linker group L or a

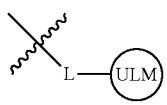

group is attached preferably at the methoxy group or as a hydroxyl group)

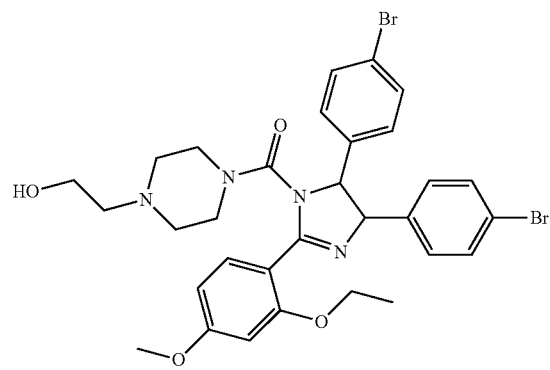 [SMILES: CCOc1cc(OC)ccc1C1=NC(c2ccc(Br)cc2)C(c2ccc(Br)cc2)N1C(=O)N1CCN(CCO)CC1]

(Derivatized where a linker group L or a

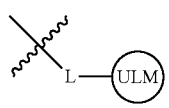

group is attached preferably at the methoxy group or hydroxyl group);

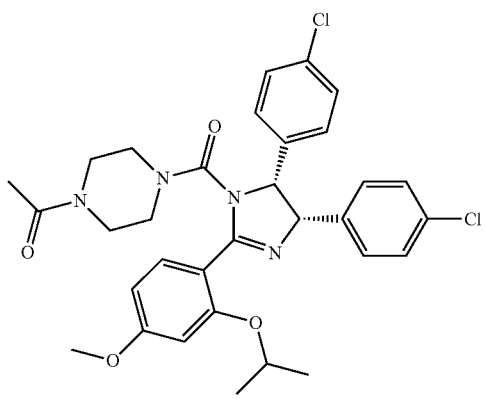 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1]

(Derivatized where a linker group L or a

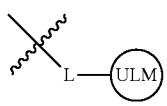

group is attached via the methoxy group or as a hydroxyl group); and

Trans-4-Iodo-4'-Boranyl-Chalcone

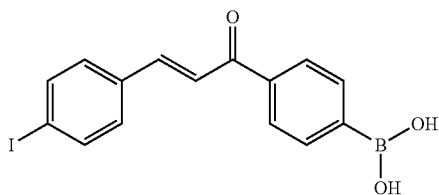 [SMILES: O=C(/C=C/c1ccc(I)cc1)c1ccc(B(O)O)cc1]

(Derivatized where a linker group L or a linker group L or a

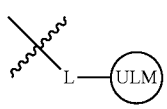

group is attached a linker group L or a

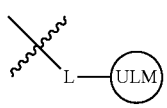

group is attached group is attached via a hydroxy group);

IV. Compounds Targeting Human BET Bromodomain-containing proteins:

Compounds targeting Human BET Bromodomain-containing proteins include, but are not limited to the compounds associated with the targets as described below, where "R" designates a site for linker group L or a

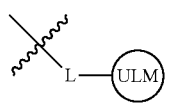

group attachment for example:

1.

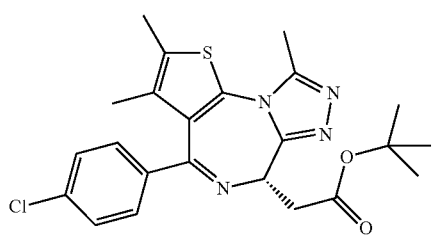

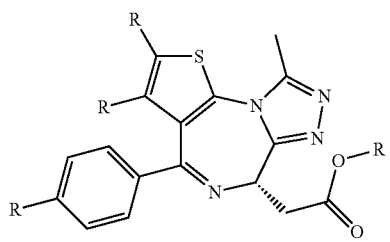

JQ1, Filippakopoulos et al. Selective inhibition of BET bromodomains. Nature (2010)

2.

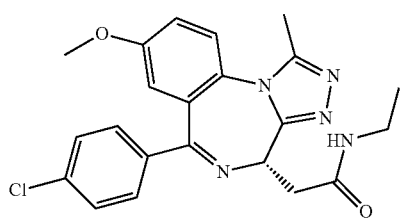

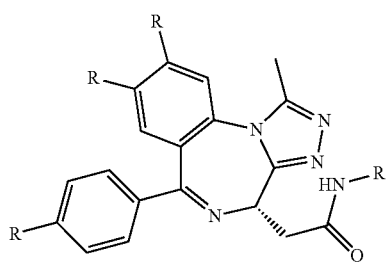

I-BET, Nicodeme et al. Supression of Inflammation by a Synthetic Histone Mimic. Nature (2010). Chung et al. Discovery and Characterization of Small Molecule Inhibitors of the BET Family Bromodomains. J. Med Chem. (2011).

3.

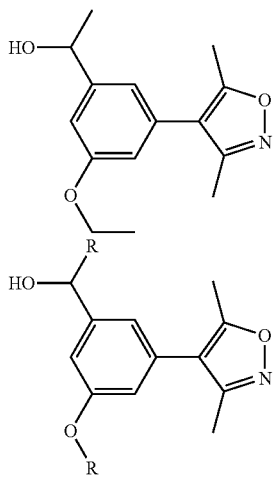

Hewings et al. 3,5-Dimethylisoxazoles Act as Acetyl-lysine Bromodomain Ligands. J. Med. Chem. (2011) 54 6761.

4.

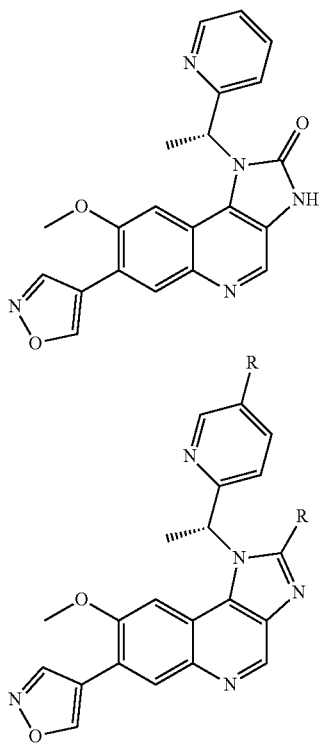

I-BET151, Dawson et al. Inhibition of BET Recruitment to Chromatin as an Effective Treatment for MLL-fusion Leukemia. Nature (2011).

(Where R, in each instance, designates a site for attachment, for example, of a linker group L or a -(L-ULM) group).

V. HDAC Inhibitors:

HDAC Inhibitors (derivatized) include, but are not limited to:

1.

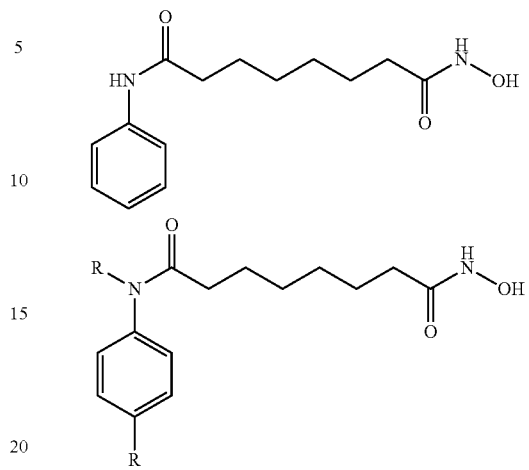

Finnin, M. S. et al. Structures of a histone deacetylase homologue bound to the TSA and SAHA inhibitors. Nature 401, 188-193 (1999).

(Derivatized where "R" designates a site for attachment of a linker group L or a

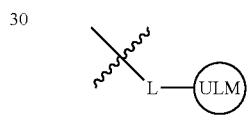

group); and

2. Compounds as defined by formula (I) of PCT WO0222577 ("DEACETYLASE INHIBITORS") (Derivatized where a linker group L or a

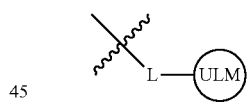

group is attached via the hydroxyl group);

VI. Human Lysine Methyltransferase Inhibitors:

Human Lysine Methyltransferase inhibitors include, but are not limited to:

1.

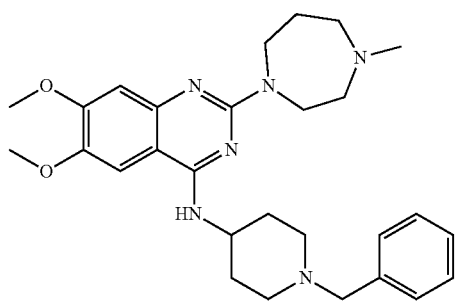

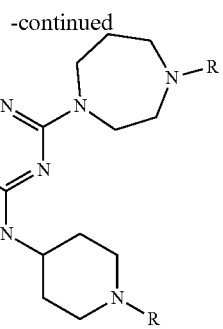

Chang et al. Structural basis for G9a-like protein lysine methyltransferase inhibition by BIX-01294. Nat Struct Mol Biol (2009) vol. 16 (3) pp. 312-7

(Derivatized where "R" designates a site for attachment of a linker group L or a

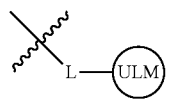

group);

2.

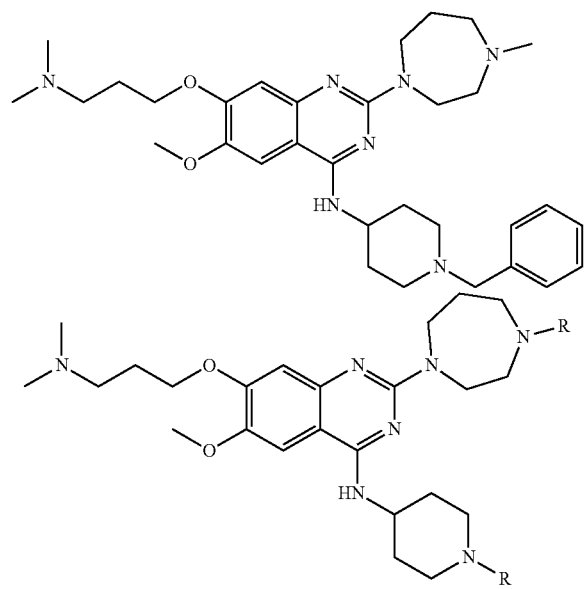

Liu F, Chen X, Allali-Hassani A, et al. Discovery of a 2,4-diamino-7-aminoalkoxyquinazoline as a potent and selective inhibitor of histone lysine methyltransferase G9a. J Med Chem 2009; 52(24):7950-3

(Derivatized where "R" designates a potential site for attachment of a linker group L or a

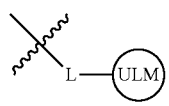

group);

3. Azacitidine (derivatized) (4-amino-1-β-D-ribofuranosyl-1,3,5-triazin-2(1H)-one) (Derivatized where a linker group L or a

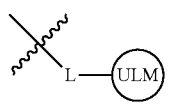

group is attached via the hydroxy or amino groups); and

4. Decitabine (derivatized) (4-amino-1-(2-deoxy-b-D-erythro-pentofuranosyl)-1, 3, 5-triazin-2(1H)-one) (Derivatized where a linker group L or a

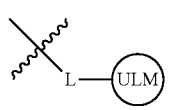

group is attached via either of the hydroxy groups or at the amino group).

VII. Angiogenesis Inhibitors:

Angiogenesis inhibitors include, but are not limited to:

1. GA-1 (derivatized) and derivatives and analogs thereof, having the structure(s) and binding to linkers as described in Sakamoto, et al., Development of Protacs to target cancer-promoting proteins for ubiquitination and degradation, *Mol Cell Proteonics* 2003 December; 2(12):1350-8;

2. Estradiol (derivatized), which may be bound to a linker group L or a

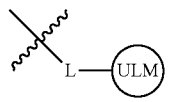

group as is generally described in Rodriguez-Gonzalez, et al., Targeting steroid hormone receptors for ubiquitination and degradation in breast and prostate cancer, *Oncogene* (2008) 27, 7201-7211;

3. Estradiol, testosterone (derivatized) and related derivatives, including but not limited to DHT and derivatives and analogs thereof, having the structure(s) and binding to a linker group L or a

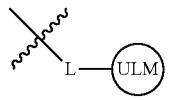

group as generally described in Sakamoto, et al., Development of Protacs to target cancer-promoting proteins for ubiquitination and degradation, *Mol Cell Proteomics* 2003 December; 2(12):1350-8; and 4. Ovalicin, fumagillin (derivatized), and derivatives and analogs thereof, having the structure(s) and binding to a linker group L or a

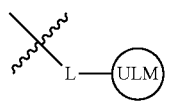

group as is generally described in Sakamoto, et al., Protacs: chimeric molecules that target proteins to the Skp1-Cullin-F box complex for ubiquitination and degradation *Proc Natl Acad Sci USA.* 2001 Jul. 17; 98(15):8554-9 and U.S. Pat. No. 7,208,157.

VIII. Immunosuppressive Compounds:

Immunosuppressive compounds include, but are not limited to:

1. AP21998 (derivatized), having the structure(s) and binding to a linker group L or a

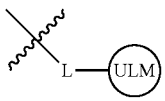

group as is generally described in Schneekloth, et al., Chemical Genetic Control of Protein Levels: Selective in Vivo Targeted Degradation, *J. AM. CHEM. SOC.* 2004, 126, 3748-3754;

2. Glucocorticoids (e.g., hydrocortisone, prednisone, prednisolone, and methylprednisolone) (Derivatized where a linker group L or a

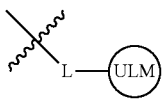

group is to bound, e.g. to any of the hydroxyls) and beclometasone dipropionate (Derivatized where a linker group or a

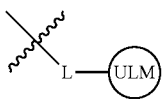

is bound, e.g. to a proprionate);

3. Methotrexate (Derivatized where a linker group or a group can be bound, e.g. to either of the terminal hydroxyls);

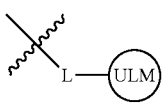

4. Ciclosporin (Derivatized where a linker group or a

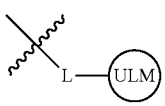

group can be bound, e.g. at any of the butyl groups);

5. Tacrolimus (FK-506) and rapamycin (Derivatized where a linker group L or a

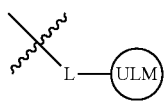

group can be bound, e.g. at one of the methoxy groups); and

6. Actinomycins (Derivatized where a linker group L or a

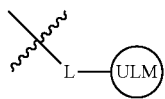

group can be bound, e.g. at one of the isopropyl groups).

IX. Compounds Targeting the Aryl Hydrocarbon Receptor (AHR):

Compounds targeting the aryl hydrocarbon receptor (AHR) include, but are not limited to:

1. Apigenin (Derivatized in a way which binds to a linker group L or a

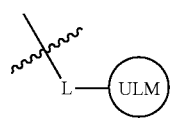

group as is generally illustrated in Lee, et al., Targeted Degradation of the Aryl Hydrocarbon Receptor by the PROTAC Approach: A Useful Chemical Genetic Tool, ChemBioChem Volume 8, Issue 17, pages 2058-2062, Nov. 23, 2007); and 2. SR1 and LGC006 (derivatized such that a linker group L or a

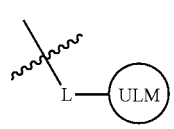

is bound), as described in Boitano, et al., Aryl Hydrocarbon Receptor Antagonists Promote the Expansion of Human Hematopoietic Stem Cells, *Science* 10 Sep. 2010: Vol. 329 no. 5997 pp. 1345-1348.

X. Compounds targeting RAF Receptor (Kinase):

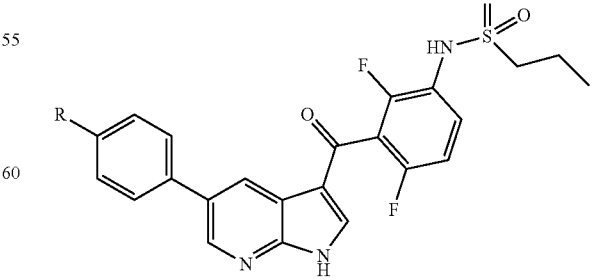

PLX4032

(Derivatized where "R" designates a site for linker group L or

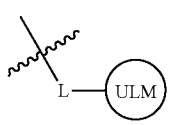

group attachment).

XI. Compounds Targeting FKBP

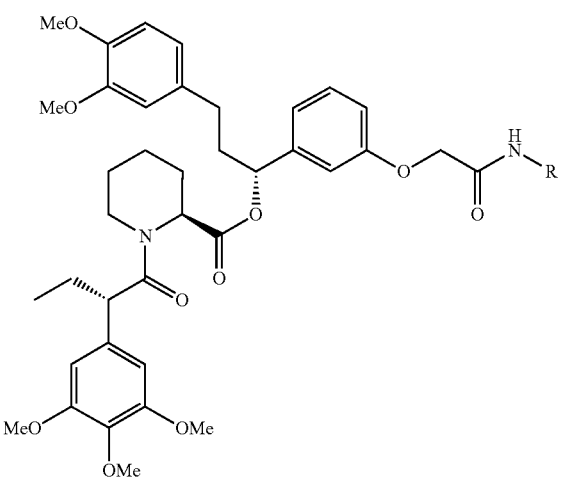

(Derivatized where "R" designates a site for a linker group L or a

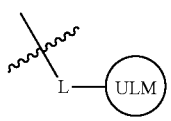

group attachment).

XII. Compounds Targeting Androgen Receptor (AR)
1. RU59063 Ligand (derivatized) of Androgen Receptor

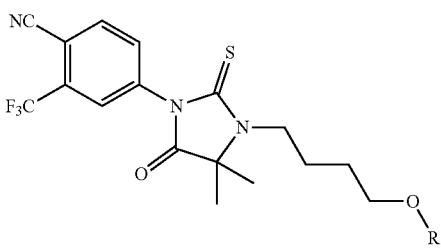

(Derivatized where "R" designates a site for a linker group L or a

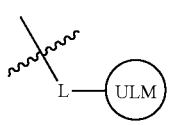

group attachment).

2. SARM Ligand (derivatized) of Androgen Receptor

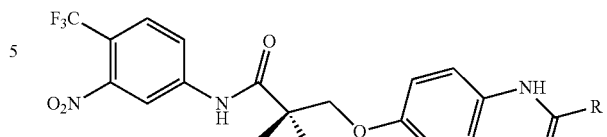

(Derivatized where "R" designates a site for a linker group L or

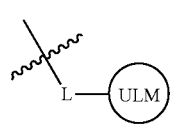

group attachment).
3. Androgen Receptor Ligand DHT (derivatized)

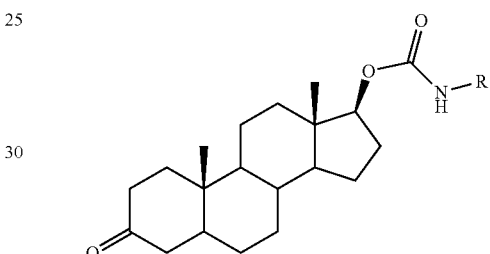

(Derivatized where "R" designates a site for a linker group L or

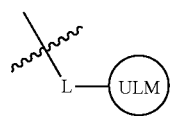

group attachment).
MDV3100-like Ligand (derivatized)

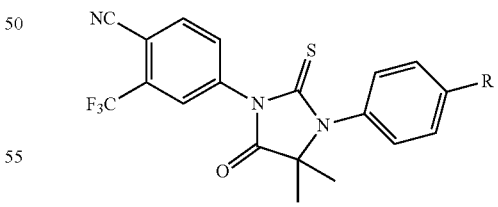

where R designates a linker group L or a

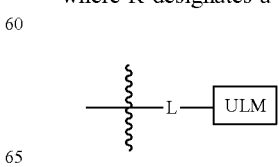

group;

147

ARN-509-like Ligand (derivatized)

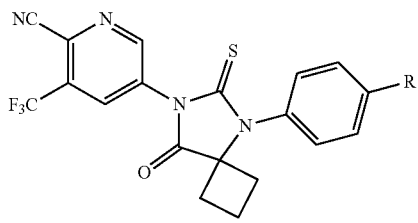

where R designates a linker group L or a

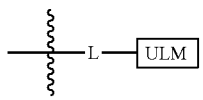

group;

Hexahydrobenzisoxazoles

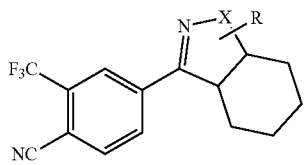

where R designates a linker group L or a

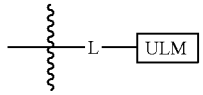

group;

Tetramethylcyclobutanes

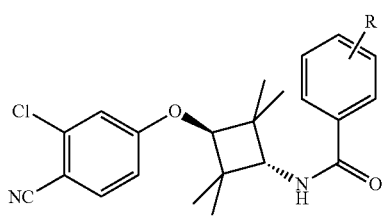

where R designates a linker group L or a

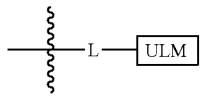

group;

148

XIII. Compounds Targeting Estrogen Receptor (ER) ICI-182780
1. Estrogen Receptor Ligand

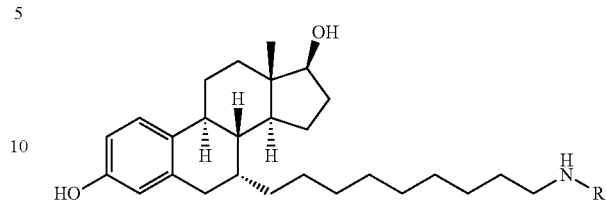

(Derivatized where "R" designates a site for linker group L or

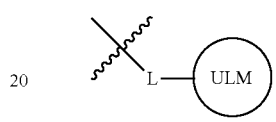

group attachment).

Compounds Targeting Thyroid Hormone Receptor (TR)
Thyroid Hormone Receptor Ligand (derivatized)

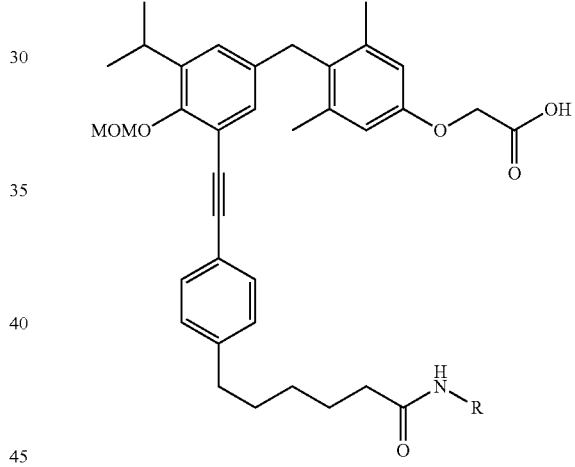

(Derivatized where "R" designates a site for linker group L or

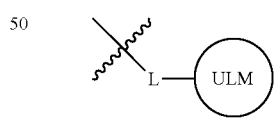

group attachment and MOMO indicates a methoxymethoxy group).

XV. Compounds Targeting HIV Protease
Inhibitor of HIV Protease (derivatized)

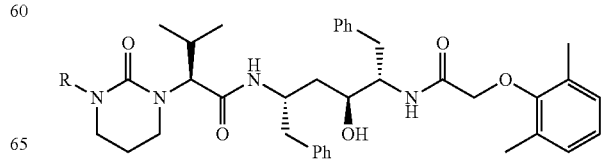

(Derivatized where "R" designates a site for linker group L or

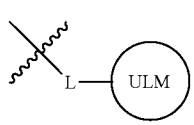

group attachment). See, *J. Med. Chem.* 2010, 53, 521-538.

Inhibitor of HIV Protease

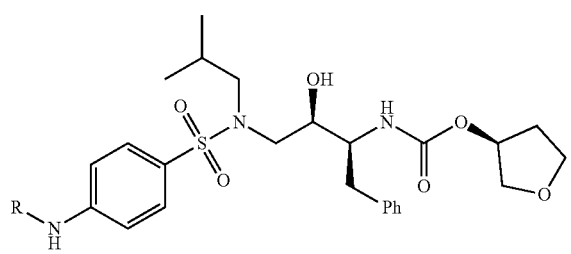

(Derivatized where "R" designates a potential site for linker group L or

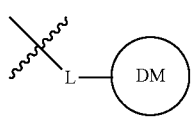

group attachment). See, *J. Med. Chem.* 2010, 53, 521-538.

XVI. Compounds Targeting HIV Integrase

Inhibitor of HIV Integrase (derivatized)

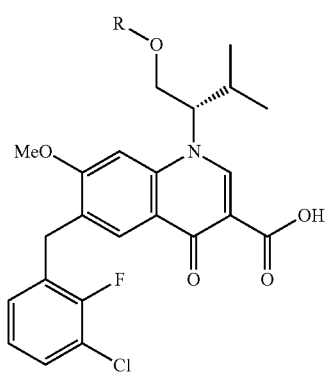

(Derivatized where "R" designates a site for linker group L or

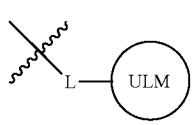

group attachment). See, *J. Med. Chem.* 2010, 53, 6466.

2. Inhibitor of HIV Integrase (derivatized)

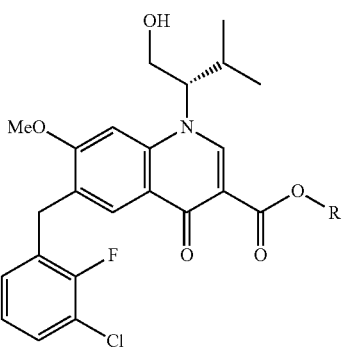

(Derivatized where "R" designates a site for linker group L or

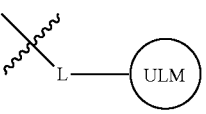

group attachment). See, *J. Med. Chem.* 2010, 53, 6466.

XVII. Compounds Targeting HCV Protease

Inhibitors of HCV Protease (derivatized)

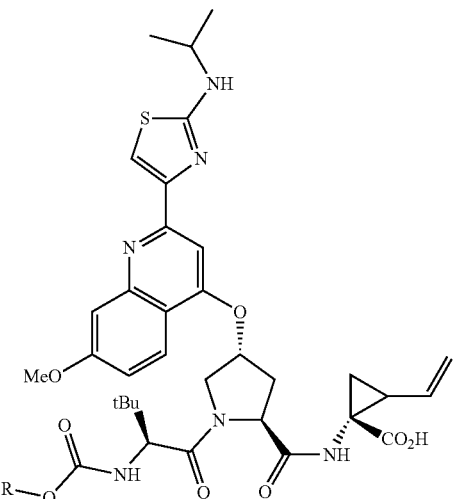

(Derivatized where "R" designates a site for linker group L or

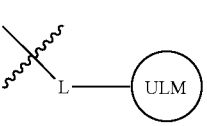

group attachment).

XVIII. Compounds Targeting Acyl-Protein Thioesterase-1 and -2 (APT1 and APT2)

Inhibitor of APT1 and APT2 (derivatized)

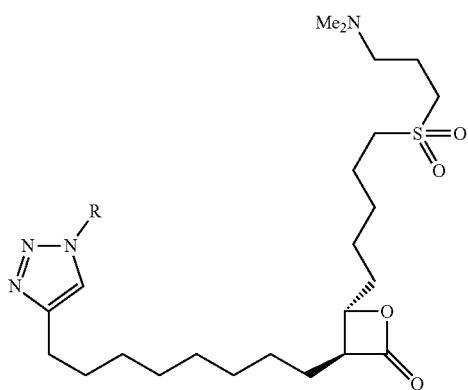

(Derivatized where "R" designates a site for linker group L or

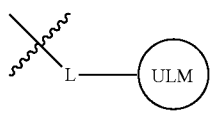

group attachment). See, *Angew. Chem. Int. Ed.* 2011, 50, 9838-9842, where

L is a linker group as otherwise described herein and said ULM group is as otherwise described herein such that

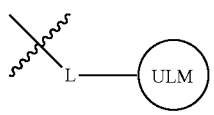

binds the ULM group to a PTM group as otherwise described herein.

The term "target protein" is used to describe a protein or polypeptide, which is a target for binding to a compound according to the present invention and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to ULM groups through linker groups L.

Pharmaceutical Compositions.

In an additional aspect, the description provides therapeutic or pharmaceutical compositions comprising an effective amount of at least one of the compounds as described herein, including, e.g., at least one ULM, at least one PROTAC, and combinations thereof. Pharmaceutical compositions comprising an effective amount of at least one bifunctional compound according to the present invention, and optionally one or more of the compounds otherwise described herein, all in effective amounts, in combination with a pharmaceutically effective amount of a carrier, additive or excipient, represents a further aspect of the disclosure.

In certain embodiments, the compositions comprise pharmaceutically acceptable salts, in particular, acid or base addition salts of compounds as described herein. The acids which are used to prepare the pharmaceutically acceptable acid addition salts of the aforementioned base compounds include those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may in certain embodiments be administered in single or divided unit doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present invention as sprays, mists, or aerosols for intra-nasal, intra-tracheal or pulmonary administration may also be used. The present invention therefore also is directed to pharmaceutical compositions comprising an effective amount of compound according to the present invention, optionally in combination with a pharmaceutically acceptable carrier, additive or excipient. Compounds according to the present invention may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. In certain preferred aspects of the invention, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present invention.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the present invention can be treated by administering to the patient (subject) an effective amount of the compound according to the present invention including pharmaceutically acceptable salts, solvates or polymorphs, thereof optionally in a pharmaceutically acceptable carrier or diluent, either alone, or in combination with other known erythropoiesis stimulating agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as erythropoietin stimulating agents, including EPO and darbapoietin alfa, among others. In certain preferred aspects of the invention, one or more compounds according to the present invention are coadministered with another bioactive agent, such as an erythropoietin stimulating agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present invention.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

Therapeutic Methods.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present invention, are set forth hereinabove.

In still another aspect, the description provides a method of identifying a target protein associated with a predetermined function of a cell. The method comprises incubating a cell with a composition from the library of the present invention; monitoring the predetermined function of the cell; identifying a composition that changes the predetermined function of the cell; identifying a target protein that binds to the identified composition, wherein the target protein is associated with the predetermined function of the cell.

In still another aspect, the description provides a method of identifying a target protein associated with a predetermined function of a cell. The method comprises incubating a cell with a pool of entities from the library of the present invention; monitoring the predetermined function of the cell; identifying a pool of entities that change the predetermined function of the cell; incubating the cell with a composition from the identified pool of entities; monitoring the predetermined function of the cell; identifying a composition that changes the predetermined function of the cell; and identifying a target protein that binds to the identified composition, wherein the target protein is associated with the predetermined function of the cell.

In still another aspect, the description provides a method of ubiquitinating/degrading a target protein in a cell. The method comprises administering a bifunctional composition comprising an ubiquitin pathway protein binding moiety and a targeting moiety, preferably linked through a linker moiety, as otherwise described herein, wherein the ubiquitin pathway protein binding moiety is coupled to the targeting moiety and wherein the ubiquitin pathway protein binding moiety recognizes a ubiquitin pathway protein (e.g., an ubiquitin ligase, preferably an E3 ubiquitin ligase) and the targeting moiety recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present invention provides treatment of a disease state or condition, which is modulated through the target protein by lowering the level of that protein in the cells of a patient.

In still another aspect, the description provides a method of treating or preventing in a patient in need thereof a disease state or condition modulated through a protein where the degradation of that protein will produce a therapeutic effect in that patient, the method comprising administering to a patient in need an effective amount of a compound according to the present invention, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

Target proteins which may be bound to the protein target moiety and degraded by the ligase to which the ubiquitin ligase binding moiety is bound include structural proteins, receptors, enzymes, cell surface proteins, proteins pertinent to the integrated function of a cell, including proteins involved in catalytic activity, aromatase activity, motor activity, helicase activity, metabolic processes (anabolism and catrabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes, including microbes, viruses, fungi and parasites, including humans, microbes, viruses, fungi and parasites, among numerous others, as targets for drug therapy, other animals, including domesticated animals, microbials for the determination of targets for antibiotics and other antimicrobials and plants, and even viruses, among numerous others More specifically, a number of drug targets for human therapeutics represent protein targets to which protein target moiety may be bound and incorporated into compounds according to the present invention. These include proteins which may be used to restore function in numerous polygenic diseases, including for example B7.1 and B7, TINFR1m, TNFR2, NADPH oxidase, BclIBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, RaslRaflMEWERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-1), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvylshikimate-phosphate synthase.

Haloalkane dehalogenase enzymes are another target of specific compounds according to the present invention. Compounds according to the present invention which contain chloroalkane peptide binding moieties ($C_1$-$C_{12}$ often about $C_2$-$C_{10}$ alkyl halo groups) may be used to inhibit and/or degrade haloalkane dehalogenase enzymes which are used in fusion proteins or related diagnostic proteins as described in PCT/US 2012/063401 filed Dec. 6, 2011 and published as WO 2012/078559 on Jun. 14, 2012, the contents of which is incorporated by reference herein.

These various protein targets may be used in screens that identify compound moieties which bind to the protein and by incorporation of the moiety into compounds according to the present invention, the level of activity of the protein may be altered for therapeutic end result.

The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

Further disease states or conditions which may be treated by compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barré syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present invention include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis, Alström syndrome, Alexander disease, Amelogenesis imperfecta, ALA dehydratase deficiency, Anderson-Fabry disease, androgen insensitivity syndrome, Anemia, Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome #arthrochalasia type), ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dubé syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegacpiphyscal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria, Erythroid 5-aminolevulinate synthetase deficiency, Erythropoietic porphyria, erythropoietic protoporphyria, erythropoietic uroporphyria, Friedreich's ataxia, familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysylhydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, betathalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alström syndrome), Vrolik disease, Waardenburg syndrome, Warburg Sjo Fledelius Syndrome, Weissenbacher-Zweymüller syndrome, Wolf-Hirschhorn syndrome, Wolff Periodic disease, Weissenbacher-Zweymüller syndrome and Xeroderma pigmentosum, among others.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML, The term "coadministration" or "combination therapy" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time.

In an additional aspect, the description provides combination therapies comprising an effective amount of a compound as described herein in combination with an additional bioactive agent. The term "bioactive agent" is used to describe an agent, other than a compound as described herein, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc. In certain embodiments, the compound as described herein, the additional bioactive agent or both are present in an effective amount or, in certain embodiments, a synergistically effective amount.

The term "additional anti-cancer agent" is used to describe an anti-cancer agent, which may be combined with compounds according to the present invention to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-1-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, scliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH 2 acetate $[C_{59}H_{84}N_{18}O_{14}$—$(C_2H_4O_2)x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-I 1, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "anti-HIV agent" or "additional anti-HIV agent" includes, for example, nucleoside reverse transcriptase inhibitors (NRTI), other non-nucleoside reverse transcriptase inhibitors (i.e., those which are not representative of the present invention), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present invention include, for example, other NNRTI's (i.e., other than the NNRTI's according to the present invention) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis (methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), 5C13PhS-2Indo1CONH2 (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-Cyano-2-indoyly)carbonyl]-4-[3-(iso-propylamino)-2-pyridinyl]piperazine (piperazine1 pyridine 4 indolyl derivative), 1-[5-[[N-(methyl)methylsulfonylamino]-2-indolylcarbonyl-4-[3-(isopropylamino)-2-pyridinyl]piperazine (piperazine 1pyridine 5 indolyl derivative), 1-[3-(Ethylamino)-2-[pyridinyl]-4-[(5-hydroxy-2-indolyl)carbonyl]piperazine, 1-[(6-Formyl-2-indoyly)carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione (2-Pyridinone 3pyrid 3MeNH Derivative), R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

General Synthetic Approaches

Generic scheme for the synthesis of ULM derivatives is described here. Briefly, the compounds according to the present invention are synthesized pursuant to the general solution phase synthetic scheme (presented hereinbelow) and/or general scheme I, which is directed to solution phase synthesis of compounds according to the present invention. Initially a hydroxyl-protected carboxy substituted (and protected) pyrrolidine compound is reacted with a carboxylic acid containing reagent, which introduces a carbonyl group at the amine of the pyrollidine ring to form an amide group. Alternatively, the pyrrolidine amine may be protected and the carboxylic acid moiety may be condensed with a nucleophilic group on a right hand fragment to provide an amide on the right hand portion of the pyrrolidine moiety. The left and right hand fragments to be condensed onto, respectively, the amine and carboxylic acid group of the pyrrolidine moiety are preferably prepared prior to condensing onto the pyrrolidine group, but other approaches may be taken to introduce groups onto the pyrrolidine group. The individual components which are combined to produce a ULM group can be prepared using blocking groups at preferred functional groups on the ULM group which can be removed so as to react with and covalently link a linker group which is prepared to accommodate a PTM moiety to which is already bound a protein binding moiety or PTM group or may be further reacted to form a covalent bound with a PTM group, which may also may comprise a ULM' group as otherwise described herein. Thus, a carboxylic acid containing left hand fragment may be condensed onto the amine group of the pyrroline, thus forming an amide group with an $R^1$ left hand fragment as depicted below. Onto the carboxyl group, any number of nucleophilic (preferably, amine containing) right hand fragments (pre-synthesized) may be condensed onto the carboxyl group to provide an amide group with an $R^2$ right fragment as depicted below. Formation of the pre-synthesized groups to condense onto the amine and/or the carboxyl moiety of the pyrrolidine proceeds in a facile manner. A solid phase synthetic method can also be used and employs similar methods used in the solution phase synthesis, the major difference being that the hydroxyl group may be bound to a solid support as the other steps of the synthesis occur. The general synthetic methods are applicable to virtually all of the compounds of the present invention with facile modifications being made consistent with the state of chemical synthetic art as used directly or adapted from the specific teachings of the examples which follow.

Scheme 1
Solution Phase Synthesis of UML
Derivatives According to the Present Invention

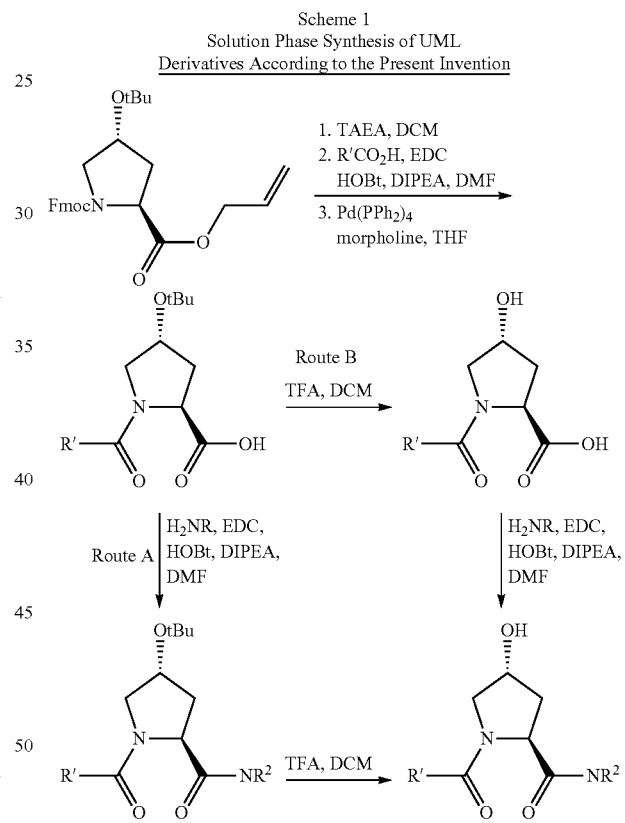

Solution Phase Methods

Solution phase chemistry is favored by many for library construction due to the wider range of organic reactions available for solution-phase synthesis, the technology used traditionally by most synthetic organic chemists, and products in solution can be more easily identified in standard drug target assays and characterized. A problem for solution-phase synthesis of one molecule at a time is the final purification that can be both expensive and slow. Chromatography is commonly a first resort since it usually works. In addition, the problems associated with solution chemistry are compounded when attempting to make tens of thousands of compounds to generate a library or a 'book' for a library.

In the generation of libraries of compounds numerous methods have been devised resulting in the wide spread use of large libraries of chemicals to readily allow the discovery of potential drug candidates. The generation of chemical libraries that are free in solution is typically the goal of most of the pharmaceutical industry. This aim is due to the nature of many of the drug targets and the associated assays. Also the construction and utility of chemical libraries is typically facilitated but the generation of master plates of compounds in solution to form the basis of the chemical library. Thus the general advantages of the solid phase synthesis methods are typically not fully realized in the context of the current drug discovery efforts. The main reason for this is the interest not in binding of the compound to the drug target but to demonstrate that the activity of the drug target is altered, which typically requires compound free in solution. Further concerns with libraries of compounds on a solid phase arise from concerns of the potential influence of the linker and steric effects on the compounds bound to the solid phase.

Thus methods for the discovery of compounds, which bind to target molecules is known in the art. Also, the optimization of the initially discovered compound is well known in the art where the affinity is improved by generation of a pool of related compound via a more selective combinatorial chemistry approach.

The present invention provides a mechanism to overcome these problems in drug and small molecule discovery.

Addition of the Ubiquitin Ligase Binding Moiety (ULM)

At this point in the compound discovery path for the subject invention, the target protein-binding element of the compounds of the invention has been identified. These optimal binding molecules are then subjected to further chemistry to add the ubiquitin ligase binding moiety (ULM), pursuant to the disclosure of the present application.

Protein Level Control

This invention also relates to a method for the control of protein levels with a cell. This is based on the use of compounds of the invention, which are known to interact with a specific target protein such that degradation of a target protein in vivo will result in the control of the amount of protein in a biological system, preferably to a particular therapeutic benefit.

The following examples are used to assist in describing the present invention, but should not be seen as limiting the present invention in any way.

General Methods for Chemical Synthesis

The following general chemical synthetic methods are provided for synthesizing numerous compounds according to the present invention which are set forth in Table 2 Affinity Table above. Each method is presented with reference to a specific compound, the synthetic details of which are presented hereinabove. All of the compounds numbered may be synthesized relatively easily using the straightforward methods which are set forth hereinbelow. In certain instances, more synthetic details are provided for certain preferred embodiments in order to present that information such that it may serve as a template for synthesizing a number of other compounds as otherwise disclosed herein.

All reactions were performed in oven-dried or flame-dried glassware fitted with rubber septa under a positive pressure of nitrogen, unless otherwise noted. Air- and moisture-sensitive liquids were transferred via syringe or cannula. THE was distilled from sodium/benzophenone. Dichloromethane was distilled from calcium hydride. Analytical thin layer chromatography (TLC) was performed using glass plates precoated with silica gel (0.25 mm). TLC plates were visualized by exposure to UV light (UV) or $KMnO_4$. Flash column chromatography was performed using silica gel 60 (230-400 mesh, Merck) with the indicated solvents.

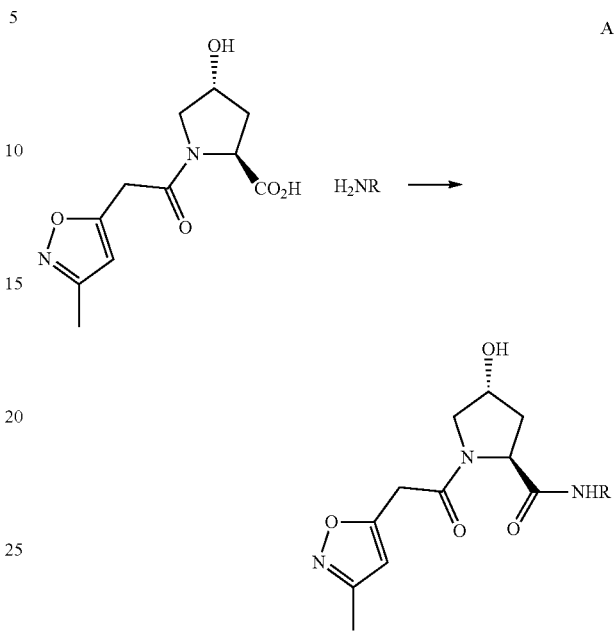

As an example, see the synthesis below for compound VL133:

Synthesis of VL133

(2S,4R)-4-hydroxy-1-(2-(3-methylisoxazol-5-yl)acetyl)pyrrolidine-2-carboxylic acid

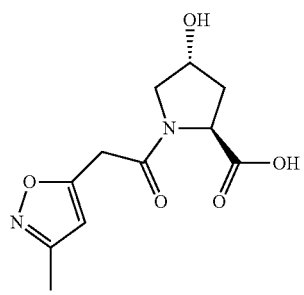 [SMILES: Cc1cc(CC(=O)N2C[C@H](O)C[C@H]2C(=O)O)on1]

(2S,4R)-4-(tert-butoxy)-1-(2-(3-methylisoxazol-5-yl)acetyl)pyrrolidine-2-carboxylic acid (124.9 mg, 0.4 mmol, 1 eq) was dissolved in DCM (18 mL) at room temperature. TFA (2 mL, 10%) was added, and the solution was stirred for 12 hours. It was then concentrated under reduced pressure and purified by column chromatography (4 to 20% MeOH/DCM) to give a yellow oil (99.7 mg, 0.39 mmol, 98%). $^1$H NMR (500 MHz, MeOD) δ 6.24 (s, 1H), 4.55-4.46 (m, 2H), 3.89 (d, J=28.3 Hz, 2H), 3.77 (dd, J=10.9, 4.3 Hz, 1H), 3.62 (d, J=11.0 Hz, 1H), 2.36-2.22 (m, 4H), 2.10 (ddd, J=13.1, 8.0, 4.8 Hz, 1H). $^{13}$C NMR (126 MHz, $CDC_3$) δ 175.33, 168.51, 167.61, 161.61, 105.28, 70.86, 59.33, 56.60, 38.78, 33.85, 11.20. MS (ESI) 255.1 (M+H).

(2S,4R)—N-(4-(1H-pyrrol-3-yl)benzyl)-4-hydroxy-1-(2-(3-methylisoxazol-5-yl)acetyl)pyrrolidine-2-carboxamide (VL133)

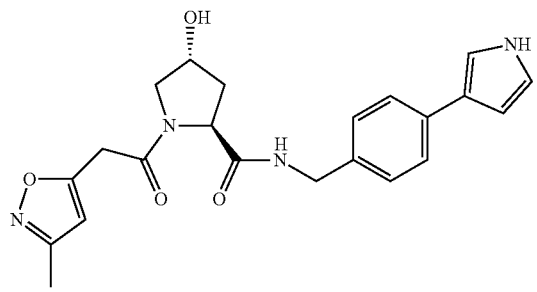

(2S,4R)-4-hydroxy-1-(2-(3-methylisoxazol-5-yl)acetyl)pyrrolidine-2-carboxylic acid (52.6 mg, 0.207 mmol, 1.3 eq), (4-(1H-pyrrol-3-yl)phenyl)methanamine (27.3 mg, 0.159 mmol, 1 eq), EDC (39.7 mg, 0.207 mmol, 1.3 eq) and HOBt (28 mg, 0.207 mmol, 1.3 eq) were dissolved in DMF (4.1 mL) and cooled to 4° C. DIPEA (0.083 mL, 0.477 mmol, 3 eq) was added and the solution was allowed to slowly warm to room temperature. After 16 hours, the mixture was poured into half saturated sodium chloride (aqueous) and extracted 3 times with EtOAc. The organic layer was dried over sodium sulfate, filtered and concentrated under reduced pressure. Purification by column chromatography (1 to 10% 0.5N NH₃ (MeOH/DCM) gave an off white solid (41.5 mg, 0.102 mmol, 64%). $^1$H NMR (400 MHz, DMSO) δ 8.40 (d, J=6.0 Hz, 1H), 7.52-7.39 (m, 2H), 7.22-7.12 (m, 3H), 6.82-6.72 (m, 1H), 6.41 (d, J=1.7 Hz, 1H), 6.24 (s, 1H), 5.17 (d, J=3.9 Hz, 1H), 4.31 (ddd, J=17.1, 13.7, 6.4 Hz, 4H), 3.88 (s, 2H), 3.75-3.65 (m, 1H), 3.52-3.41 (m, 1H), 2.18 (d, J=18.0 Hz, 3H), 2.12-1.99 (m, 1H), 1.94-1.85 (m, 1H). $^{13}$C NMR (101 MHz, DMSO) δ 171.36, 166.69, 165.54, 159.38, 135.66, 134.68, 127.20, 124.21, 123.00, 118.86, 114.71, 105.22, 103.99, 68.61, 58.76, 55.18, 41.63, 38.27, 32.78, 11.00. MS (ESI) 431.5 (M+Na).

For further reference see the following articles and the references cited therein:

Buckley D L et al. J. Am. Chem. Soc 2012, 134, 4465-4468.

Van Molle I et al. A Chemistry & Biology 2012, 19, 1300-1312

Buckley, D *Angew. Chem. Int. Ed.,* 2012, 51, 11463-11467

Buckley, D. L et al. *Angew. Chem.* 2012, 124, 11630-11634.

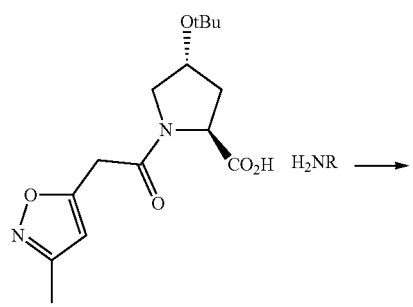

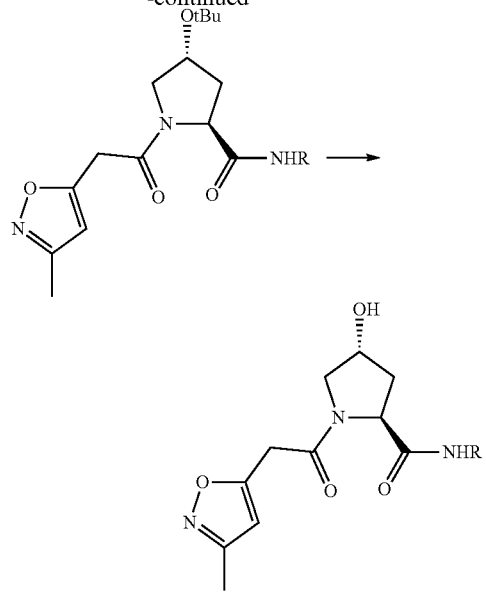

As an example, see the synthesis below for compound VL116:

Synthesis of VL116

(2S,4R)-4-(tert-butoxy)-1-(2-(3-methylisoxazol-5-yl)acetyl)-N-(4-(4-methylthiazol-5-yl)benzyl)pyrrolidine-2-carboxamide

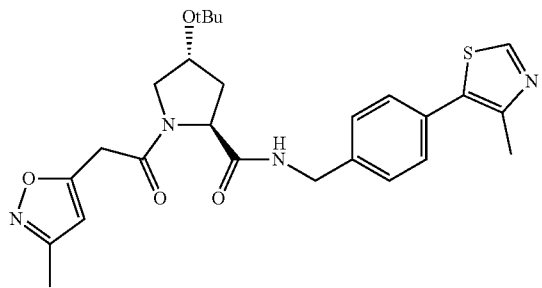

(2S,4R)-4-(tert-butoxy)-1-(2-(3-methylisoxazol-5-yl)acetyl)pyrrolidine-2-carboxylic acid (53.7 mg, 0.173 mmol, 1.3 eq), (4-(4-methylthiazol-5-yl)phenyl)methanamine (27.2 mg, 0.133 mmol, 1 eq), EDC (33.2 mg, 0.173 mmol, 1.3 eq), and HOBt (23.4 mg, 0.173 mmol, 1.3 eq) were dissolved in DMF (3.5 mL) at 4° C. DIPEA (0.07 mL, 0.4 mmol, 3 eq) was added, and the solution was allowed to slowly warm to room temperature. After 19 hours, the mixture was poured into brine and extracted four times with EtOAc. The organic layer was dried with sodium sulfate, filtered and concentrated under reduced pressure. Purification by column chromatography (1 to 5% MeOH/DCM) gave a colorless oil (58.1 mg, 0.117 mmol, 88%). $^1$H NMR (400 MHz, CDCl₃) δ 8.67 (s, 1H), 7.42-7.27 (m, 5H), 6.06 (s, 1H), 4.69 (dd, J=8.4, 2.6 Hz, 1H), 4.59-4.35 (m, 3H), 3.82-3.71 (m, 3H), 3.34 (dd, J=9.9, 6.3 Hz, 1H), 2.59-2.46 (m, 4H), 2.25 (s, 3H), 1.91 (dd, J=8.2, 4.4 Hz, 1H), 1.25-1.14 (m, 9H). $^{13}$C NMR (101 MHz, CDCl₃) δ 170.70, 167.35, 165.30, 160.24, 150.42, 148.59, 138.09, 131.74, 131.05, 129.66, 127.85, 104.19, 74.48, 70.02, 59.12, 54.20, 43.25, 35.59, 33.49, 28.38, 16.19, 11.57. MS (ESI) 497.4 (M+H).

(2S,4R)-4-hydroxy-1-(2-(3-methylisoxazol-5-yl)acetyl)-N-(4-(4-methylthiazol-5-yl)benzyl)pyrrolidine-2-carboxamide (VL116)

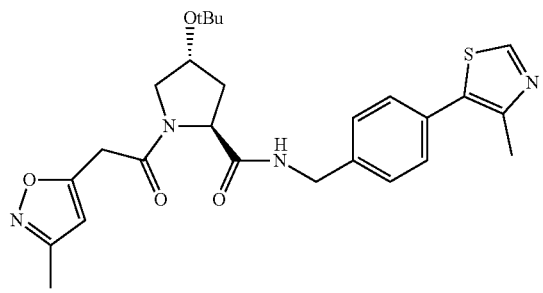

(2S,4R)-4-(tert-butoxy)-1-(2-(3-methylisoxazol-5-yl)acetyl)-N-(4-(4-methylthiazol-5-yl)benzyl)pyrrolidine-2-carboxamide (58.1 mg, 0.117 mmol) was dissolved in DCM (8 mL). TFA (2 mL, 20% vol/vol) was added and the solution was stirred for 12 hours at room temperature, after which it was concentrated under reduced pressure. Purification by column chromatography (1 to 10% 0.5N NH$_3$ (MeOH)/DCM) gave a colorless oil (28.4 mg, 0.065 mmol, 56%). $^1$H NMR (400 MHz, MeOH) δ 8.87 (d, J=2.1 Hz, 1H), 7.50-7.34 (m, 4H), 6.23 (s, 1H), 4.57 (t, J=8.0 Hz, 1H), 4.54-4.38 (m, 3H), 3.93 (d, J=2.4 Hz, 2H), 3.81 (dd, J=10.9, 4.3 Hz, 1H), 3.63 (dd, J=7.2, 5.5 Hz, 1H), 2.46 (d, J=8.8 Hz, 3H), 2.33-2.20 (m, 4H), 2.10 (ddd, J=13.1, 8.2, 4.7 Hz, 1H). $^{13}$C NMR (101 MHz, MeOH) δ 174.43, 168.71, 167.66, 161.58, 152.83, 149.04, 140.14, 133.39, 131.56, 130.43, 128.88, 105.39, 70.86, 60.78, 57.00, 43.65, 39.36, 33.96, 15.81, 11.22. MS (ESI) 441.3 (M+H).

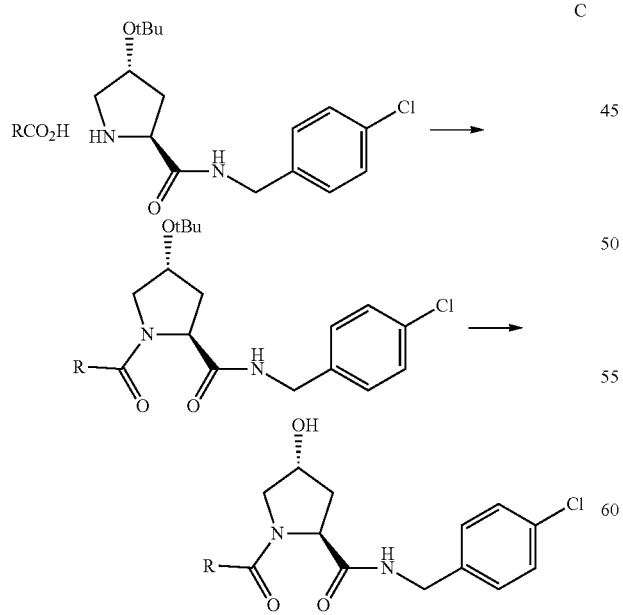

As an example, see the synthesis below for compound VL156:

Synthesis of VL156

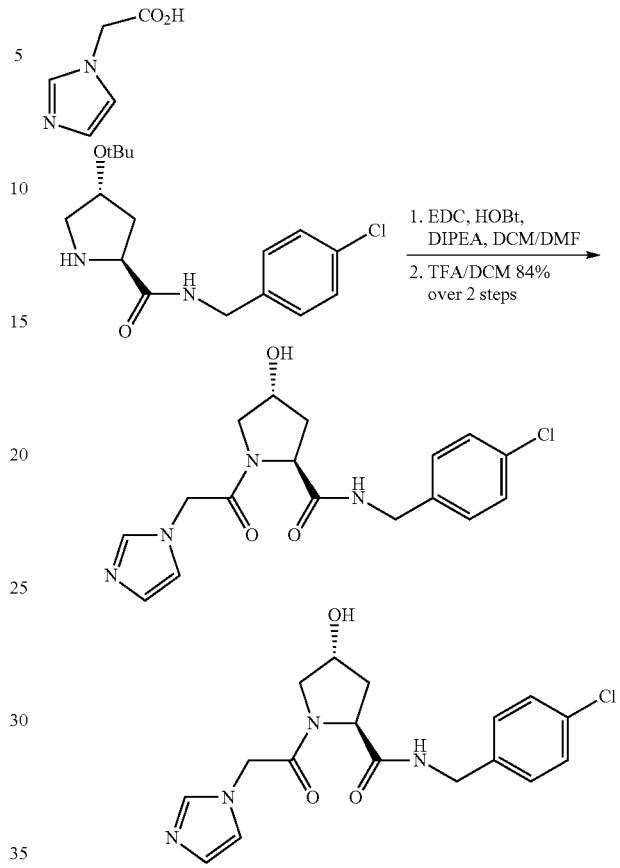

1H-Imidazol-1-ylacetic acid (20.6 mg, 0.163 mmol, 1.3 eq), EDC (31.2 mg, 0.163 mmol, 1.3 eq) and HOBt (22 mg, 0.163 mmol, 1.3 eq) were dissolved in DCM (2.5 mL) and DMF (0.4 mL) at room temperature in a 1 dram vial. After stirring for 15 minutes, DIPEA (0.055 mL, 0.313 mmol, 2.5 eq) was added, followed by (2S,4R)-4-(tert-butoxy)-N-(4-chlorobenzyl)pyrrolidine-2-carboxamide (38.9 mg, 0.125 mmol, 1 eq) after an additional 30 minutes. The mixture was stirred for 14 hours, then diluted with EtOAc and washed with brine. The organic layer was dried over sodium sulfate, filtered and condensed. Purification by column chromatography (1 to 10% MeOH/DCM) gave a white solid, which was used directly in the following step. $^1$H NMR (400 MHz, CD$_3$OD) δ 7.65 (s, 1H), 7.28 (td, J=10.9, 8.4 Hz, 4H), 7.06 (d, J=43.6 Hz, 2H), 4.99 (dd, J=38.1, 17.1 Hz, 2H), 4.51 (t, J=6.6 Hz, 2H), 4.35 (q, J=15.4 Hz, 2H), 3.86 (dd, J=10.2, 5.6 Hz, 1H), 3.45 (dd, J=10.3, 4.1 Hz, 1H), 2.22-2.02 (m, 2H), 1.21 (d, J=13.8 Hz, 9H). MS (ESI) 419.7 (M+H).

The white solid was dissolved in DCM (9 mL) at room temperature. TFA (1 mL) was added and the mixture was stirred for 12 hours and condensed. Purification by column chromatography (1 to 20% 0.5 N methanolic ammonia/DCM) gave a white solid (39.8 mg, 0.11 mmol, 88% over 2 steps). $^1$H NMR (400 MHz, CD$_3$OD) δ 8.73 (s, 1H), 7.47 (d, J=16.9 Hz, 2H), 7.26 (s, 4H), 5.25 (dd, J=37.5, 16.9 Hz, 2H), 4.56 (t, J=7.9 Hz, 2H), 4.44-4.27 (m, 2H), 3.82 (dd, J=10.8, 4.1 Hz, 1H), 3.63 (d, J=10.8 Hz, 1H), 2.36-2.22 (m, 1H), 2.07 (ddd, J=13.1, 8.3, 4.6 Hz, 1H). $^{13}$C NMR (126 MHz, CD$_3$OD) δ 174.14, 166.34, 138.56, 138.20, 133.87, 129.97, 129.49, 124.55, 121.47, 70.94, 61.00, 55.75, 51.33, 43.35, 39.21. MS (ESI) 364.8 (M+H).

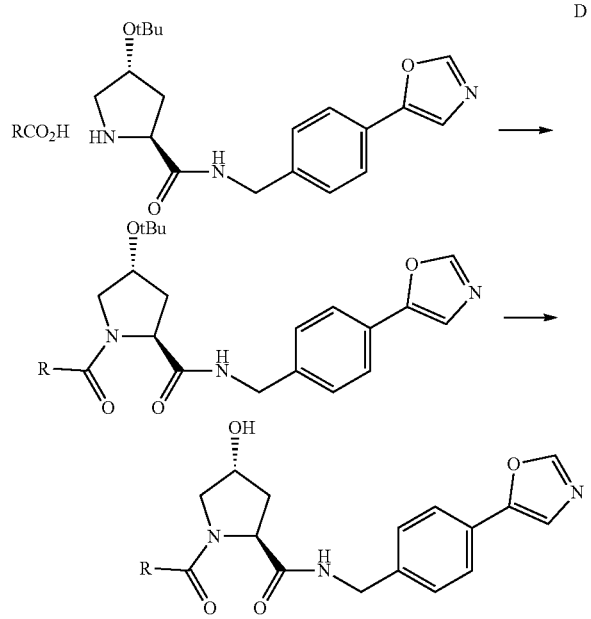

D

As an example, see the synthesis below for compound VL217:

Synthesis of VL217

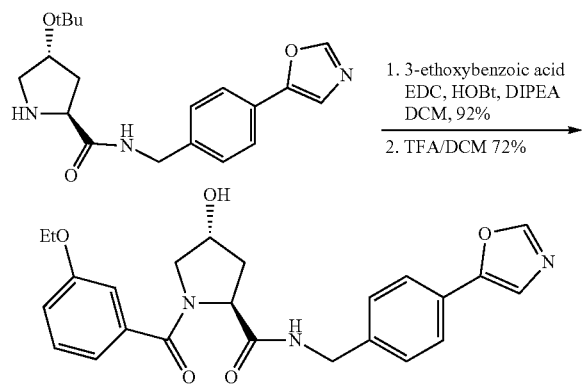

1. 3-ethoxybenzoic acid EDC, HOBt, DIPEA DCM, 92%
2. TFA/DCM 72%

(2S,4R)-4-(tert-butoxy)-1-(3-ethoxybenzoyl)-N-(4-(oxazol-5-yl)benzyl)pyrrolidine-2-carboxamide

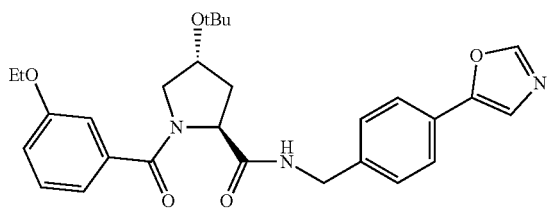 [SMILES: CCOc1cccc(C(=O)N2C[C@H](OC(C)(C)C)C[C@H]2C(=O)NCc2ccc(-c3cnco3)cc2)c1]

3-Ethoxybenzoic acid (13.3 mg, 0.08 mmol, 1 eq), EDC (16.9 mg, 0.088 mmol, 1.1 eq) and HOBt (11.9 mg, 0.88 mmol, 1.1 eq) were dissolved in DCM (0.8 mL) at room temperature. DIPEA (0.0279 mL, 0.16 mmol, 2 eq) was added, followed by (2S,4R)-4-(tert-butoxy)-N-(4-(oxazol-5-yl)benzyl)pyrrolidine-2-carboxamide (33.0 mg, 0.096 mmol, 1.2 eq). The solution was stirred for 21 hours then diluted with EtOAc and washed with 10% citric acid, saturated sodium bicarbonate and brine. The organic layer was dried over sodium sulfate, filtered and condensed. Purification by column chromatography (1 to 5% MeOH/DCM) gave a colorless oil (36.1 mg, 0.073 mmol, 92%). ¹H NMR (400 MHz, CDCl₃) δ 7.90 (s, 1H), 7.61 (dd, J=16.6, 6.9 Hz, 3H), 7.38-7.27 (m, 4H), 6.98 (dd, J=16.0, 6.4 Hz, 3H), 4.92 (dd, J=8.3, 4.7 Hz, 1H), 4.48 (d, J=6.0 Hz, 2H), 4.43-4.31 (m, 1H), 4.03 (q, J=7.0 Hz, 2H), 3.61 (dd, J=10.9, 5.7 Hz, 1H), 3.31 (dd, J=10.9, 4.4 Hz, 1H), 2.73-2.55 (m, 1H), 2.05-1.92 (m, 1H), 1.40 (t, J=7.0 Hz, 3H), 1.13 (s, 9H). MS (ESI) 492.4 (M+H).

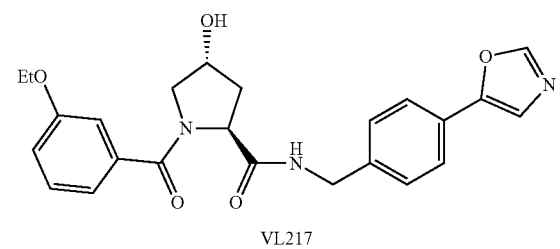 [SMILES: CCOc1cccc(C(=O)N2C[C@H](O)C[C@H]2C(=O)NCc2ccc(-c3cnco3)cc2)c1]

VL217

(2S,4R)-4-(tert-butoxy)-1-(3-ethoxybenzoyl)-N-(4-(oxazol-5-yl)benzyl)pyrrolidine-2-carboxamide (36.1 mg, 0.073 mmol, 1 eq) was dissolved in DCM (9 mL) at room temperature. TFA (1 mL) was added and the solution was stirred for 13 hours, then condensed. Purification by column chromatography (1 to 10% MeOH/DCM) gave a colorless oil (22.9 mg, 0.053 mmol, 72%). ¹H NMR (400 MHz, CD3OD) δ 8.24 (d, J=12.0 Hz, 1H), 7.65 (dd, J=28.0, 8.3 Hz, 2H), 7.47 (dd, J=18.8, 10.6 Hz, 3H), 7.23 (ddd, J=9.4, 4.6, 4.1 Hz, 3H), 7.09-6.87 (m, 2H), 4.75 (dd, J=9.6, 7.7 Hz, 1H), 4.48 (dd, J=49.7, 15.5 Hz, 3H), 4.06 (q, J=7.0 Hz, 2H), 3.84 (dd, J=11.5, 3.5 Hz, 11H), 3.44 (d, J=11.5 Hz, 1H), 2.42-2.29 (m, 1H), 2.21-2.05 (m, 1H), 1.36 (dt, J=24.0, 7.0 Hz, 3H). ¹³C NMR (101 MHz, CD₃OD) δ 174.78, 172.66, 160.35, 153.14, 152.74, 140.85, 138.38, 130.66, 129.00, 127.71, 125.62, 121.77, 120.50, 118.08, 114.30, 71.02, 64.71, 60.85, 59.82, 43.72, 39.32.

E

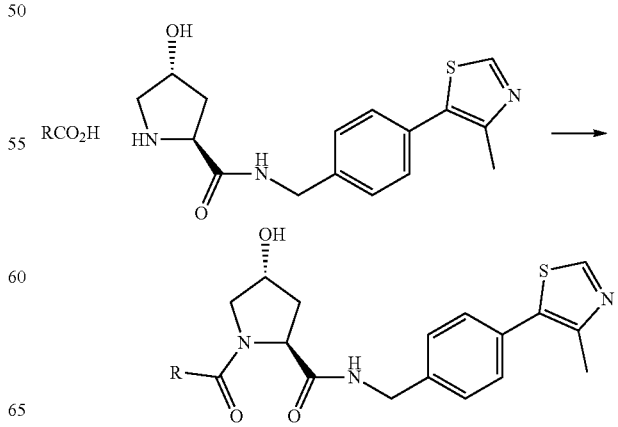

As an example, see the synthesis below for compound VL 219:

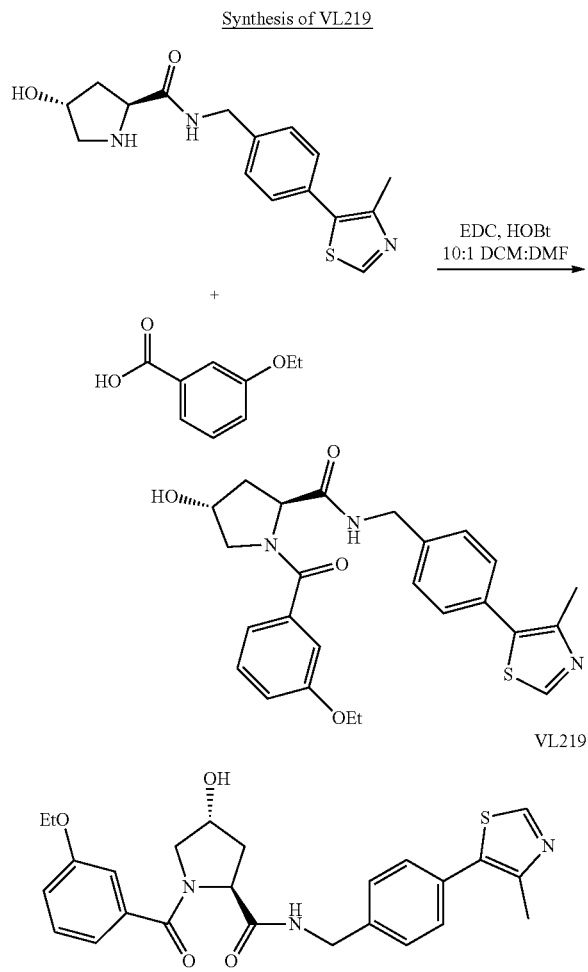

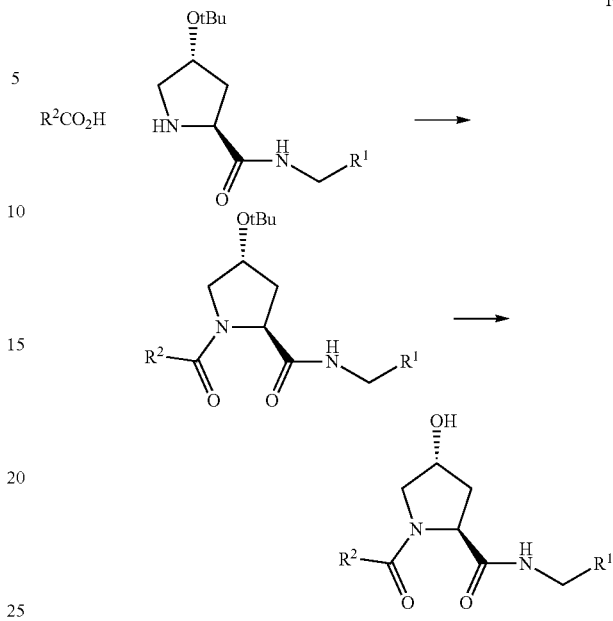

3-ethoxybenzoic acid (17 mg, 0.1 mmol, 1 equiv.) was dissolved in 1 mL 10:1 DCM:DMF and charged with EDC (25 mg, 0.13 mmol 1.3 equiv), and HOBt (21 mg, 0.13 mmol, 1.3 equiv). After 5 minutes of stirring (2S,4R)-4-hydroxy-N-(4-(4-methylthiazol-5-yl)benzyl)pyrrolidine-2-carboxamide (31 mg, 0.095 mmol, 1 equiv) was added. Upon stirring for 18 h the reaction was diluted with 15 mL EtOAc and washed with 25 mL 10% aqueous citric acid and 25 mL saturated $NaHCO_3$. The organic layer was dried with $Na_2SO_4$ and concentrated by vacuum. The resultant oil was purified by silica gel chromatography (DCM to 9% MeOH (0.5 N $NH_3$) in DCM) to yield 25 mg (56% yield) of the product as a white solid. $^1$H NMR (501 MHz, $CD_3OD$) δ 8.87 (s, 1H), 7.51-7.42 (m, 4H), 7.37 (t, J=8.1, 1H), 7.23-7.14 (m, 2H), 7.05 (dd, J=2.2, 8.4, 1H), 4.79 (dd, J=7.7, 9.5, 1H), 4.63-4.40 (m, 3H), 4.08 (q, J=7.0, 2H), 3.86 (dt, J=3.8, 7.6, 1H), 3.47 (d, J=11.5, 1H), 2.47 (s, 3H) 2.36 (dd, J=7.6, 13.2, 1H), 2.14 (ddd, J=5.3, 10.2, 16.4, 1H), 1.41 (t, J=7.0, 3H); $^{13}$C NMR (126 MHz, $CD_3OD$) δ 174.74, 172.64, 160.34, 152.78, 149.05, 140.21, 138.40, 133.39, 131.55, 130.65, 130.44, 128.83, 120.49, 118.07, 114.32, 71.02, 64.71, 60.83, 59.81, 43.67, 39.30, 15.79, 15.06; TLC: (9:1 DCM:MeOH (0.5 N $NH_3$)) $R_f$=0.25; LRMS (ESI) 466.1 $(M+H)^+$.

Method F subsumes methods C, D and E and is a general method which proceeds through commercially available amines.

The following procedures were used to synthesize and/or characterize compounds according to the present invention:

Compound Characterization and Purification:

$^1$HNMR (300 or 400 MHz) and $^{13}$CNMR (100.6 MHz) spectra were recorded on Bruker spectrometers at rt with TMS or the residual solvent peak as the internal standard. The line positions or multiples are given in (δ) and the coupling constants (J) are given as absolute values in Hertz (Hz). The multiplicities in $^1$HNMR spectra are abbreviated as follows: s (singlet), d (doublet), t (triplet), q (quartet), m (multiplet), br or broad (broadened).

Analytical LC-MS data was collected on a Shimadzu LCMS-2020 with a mobile phase of 0.05% TFA in Acetonitrile (A) and 0.05% TFA in HPLC grade water (B); 0.1% FA in Acetonitrile (A) and 0.1% FA in HPLC grade water (B); Acetonitrile (A) and 5 mM ammonium bicarbonate in HPLC grade water (B).

Shimadzu LCMS-2020 equipped with LC-20AD or 30AD pumps, SPD-M20A PDA and Alltech 3300 ELSD. The system uses the following conditions for 2.0 min, 2.6 min, 3 min, 3.6 min, 5 min or 5.6 min run time.

2.0 minute run: Kinetex XB-C 18 100A column, 2.6 μm, 3.0× 50 mm. The flow rate is 1.5 mL/min, the run time is 2.0 min, and the gradient profiles are 0.01 min 10% A, 1.10 min 100% A, 1.60 min 100% A, 1.70 min 10% A, 2.00 min 10% A.

2.6 minute run: Shim-pack VP-ODS column, 2.2 μm, 3.0×50 mm. The flow rate is 1.5 mL/min, the run time is 2.6 min, and the gradient profiles are 0.01 min 5% A, 1.20 min 100% A, 2.20 min 100% A, 2.30 min 5% A, 2.60 min 5% A.

3.0 minute run: ACE UltraCore Super C18 column, 2.5 m, 3.0× 50 mm. The flow rate is 1.5 mL/min, the run time is 3.0 min, and the gradient profiles are 0.01 min 10% A, 2.00 min 95% A, 2.60 min 95% A, 2.70 min 10% A, 3.00 min 10% A.

3.6 minute run: Shim-pack VP-ODS column, 2.2 μm, 3.0× 50 mm. The flow rate is 1.5 mL/min, the run time is 3.6 min, and the gradient profiles are 0.01 min 5% A, 2.20 min 100% A, 3.20 min 100% A, 3.30 min 5% A, 3.60 min 5% A.

5.0 minute run: ACE UltraCore Super C18 column, 2.5 m, 3.0× 50 mm. The flow rate is 1.5 mL/min, the run time is 5.0 min, and the gradient profiles are 0.01 min 10% A, 4.00 min 60% A, 4.70 min 60% A, 4.80 min 10% A, 5.00 min 10% A.

5.6 minute run: Shim-pack VP-ODS column, 2.2 µm, 3.0× 50 mm. The flow rate is 1.5 mL/min, the run time is 5.6 min, and the gradient profiles are 0.01 min 5% A, 3.00 min 50% A, 5.00 min 50% A, 5.20 min 5% A, 5.60 min 5% A.

LCMS data were also collected on an Agilent infinity 1260 LC; Agilent 6230 TOF mass spectrometer The analyses were conducted on a Poroshell 120 EC C18 column (50 mm×3.0 mm internal diameter 2.7 m packing diameter) at 45° C.

The eluents employed were:
A=0.1% v/v solution of formic acid in water.
B=0.1% v/v solution of formic acid in acetonitrile.
The gradient employed was:

| Time (minutes) | Flow Rate (mL/min) | % A | % B |
|---|---|---|---|
| 0 | 1 | 95 | 5 |
| 0.5 | 1 | 95 | 5 |
| 3.0 | 1 | 1 | 99 |
| 4.0 | 1 | 1 | 99 |
| 4.1 | 1 | 95 | 5 |
| 4.5 | 1 | 95 | 5 |

The UV detection is an averaged signal from wavelength of 210 nm to 350 nm and mass spectra were recorded on the mass spectrometer using positive mode electrospray ionization.

Unless otherwise noted, all LC-MS data reported were results based on instrumentation and methods described above. Unless otherwise noted, all compounds were prepared with LC-MS purity >95%.

The following illustrates the mobile phases and gradients used when compounds underwent purification by mass-directed autopreparative HPLC.

Mass-Directed Autopreparative HPLC (Formic Acid Modifier)

The HPLC analysis was conducted on a Sunfire C18 column (150 mm×30 mm internal diameter, 5 µm packing diameter) at ambient temperature.

The solvents employed were:
A=0.1% v/v solution of formic acid in water.
B=0.1% v/v solution of formic acid in acetonitrile.

Mass-Directed Autopreparative HPLC (Trifluoroacetic Acid Modifier)

The HPLC analysis was conducted on a Sunfire C18 column (150 mm×30 mm internal diameter, 5 µm packing diameter) at ambient temperature.

The solvents employed were:
A=0.1% v/v solution of trifluoroacetic acid in water.
B=0.1% v/v solution of trifluoroacetic acid in acetonitrile.

Mass-Directed Autopreparative HPLC (Ammonium Bicarbonate Modifier)

The HPLC analysis was conducted on an XBridge C18 column (150 mm×30 mm internal diameter, 5 µm packing diameter) at ambient temperature.

The solvents employed were:
A=10 mM ammonium bicarbonate in water adjusted to pH 10 with ammonia solution.
B=acetonitrile.

For each of the mass-directed autopreparative purifications, irrespective of the modifier used, the gradient employed was dependent upon the retention time of the particular compound undergoing purification as recorded in the analytical LCMS, and was as follows:

For compounds with an analytical LCMS retention time below 0.6 minutes the following gradient was used:

| Time (minutes) | Flow Rate (mL/min) | % A | % B |
|---|---|---|---|
| 0 | 40 | 99 | 1 |
| 1 | 40 | 99 | 1 |
| 10 | 40 | 70 | 30 |
| 11 | 40 | 1 | 99 |
| 15 | 40 | 1 | 99 |

For compounds with an analytical LCMS retention time between 0.6 and 0.9 minutes the following gradient was used:

| Time (minutes) | Flow Rate (mL/min) | % A | % B |
|---|---|---|---|
| 0 | 40 | 85 | 15 |
| 1 | 40 | 85 | 15 |
| 10 | 40 | 45 | 55 |
| 11 | 40 | 1 | 99 |
| 15 | 40 | 1 | 99 |

For compounds with an analytical LCMS retention time between 0.9 and 1.2 minutes the following gradient was used:

| Time (minutes) | Flow Rate (mL/min) | % A | % B |
|---|---|---|---|
| 0 | 40 | 70 | 30 |
| 1 | 40 | 70 | 30 |
| 10 | 40 | 15 | 85 |
| 11 | 40 | 1 | 99 |
| 15 | 40 | 1 | 99 |

For compounds with an analytical LCMS retention time between 1.2 and 1.4 minutes the following gradient was used:

| Time (minutes) | Flow Rate (mL/min) | % A | % B |
|---|---|---|---|
| 0 | 40 | 50 | 50 |
| 1 | 40 | 50 | 50 |
| 10 | 40 | 1 | 99 |
| 11 | 40 | 1 | 99 |
| 15 | 40 | 1 | 99 |

The UV detection was an averaged signal from wavelength of 210 nm to 350 nm and mass spectra were recorded on a mass spectrometer using alternate-scan positive and negative mode electrospray ionization.

Preparative HPLC purifications were also performed on a Waters® UV-Directed Purification System equipped with 2545 Binary Gradient Module, 2767 Sample Manager and 2489 UV/Visible Detector, controlled by MassLynx V4.1 software. All purification work was completed using the following columns: Atlantis Prep T3 OBD Column, SunFire Prep C18 OBD Column and XBridge Prep Phenyl OBD Column. The mobile phases were water (with 0.1% TFA or 0.01% NH$_4$HCO$_3$) and acetonitrile; all reagents used were of HPLC grade. The flow rate was 30 ml/min. After the columns, a 1:1000 LC packings flow splitter allowed transfer of a small portion of the eluent into the UV detector. The electrospray source was set at 3.0 kV capillary voltage, 30 V conevoltage, 110° C. source temperature, 350° C. desolvation temperature, 600 L/h desolvation gas flow, and 60 L/h cone gas flow. For the analyzer, the multiplier was set at 550 for preparative tune method.

Following the general synthetic methods set forth above and as previously described, the following compounds are synthesized by analogy.

Example 1

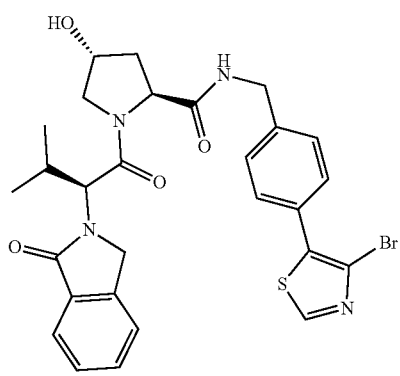 [SMILES: CC(C)[C@@H](C(=O)N1C[C@H](O)C[C@H]1C(=O)NCc1ccc(-c2scnc2Br)cc1)N1Cc2ccccc2C1=O]

(2S,4R)—N-(4-(4-bromothiazol-5-yl)benzyl)-4-hydroxy-1-((S)-3-methyl-2-(1-oxoisoindolin-2-yl)butanoyl)pyrrolidine-2-carboxamide Example 2

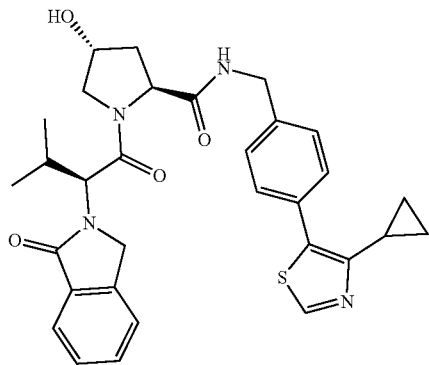 [SMILES: CC(C)[C@@H](C(=O)N1C[C@H](O)C[C@H]1C(=O)NCc1ccc(-c2scnc2C2CC2)cc1)N1Cc2ccccc2C1=O]

(2S,4R)—N-(4-(4-cyclopropylthiazol-5-yl)benzyl)-4-hydroxy-1-((S)-3-methyl-2-(1-oxoisoindolin-2-yl)butanoyl)pyrrolidine-2-carboxamide Example 3

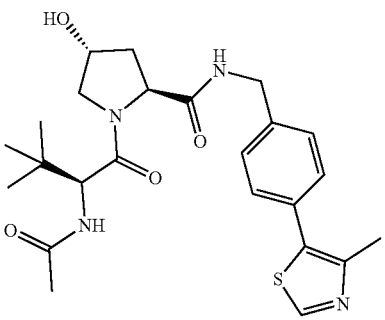 [SMILES: CC(=O)N[C@H](C(=O)N1C[C@H](O)C[C@H]1C(=O)NCc1ccc(-c2scnc2C)cc1)C(C)(C)C]

(2S,4R)-1-((S)-2-acetamido-3,3-dimethylbutanoyl)-4-hydroxy-N-(4-(4-methylthiazol-5-yl)benzyl)pyrrolidine-2-carboxamide Example 4

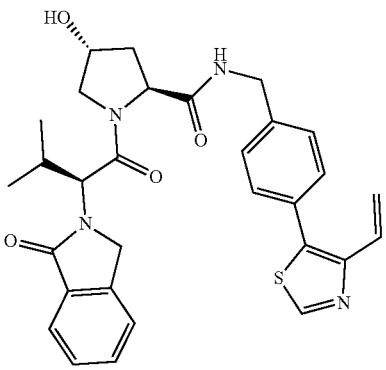 [SMILES: C=Cc1ncsc1-c1ccc(CNC(=O)[C@@H]2C[C@@H](O)CN2C(=O)[C@H](C(C)C)N2Cc3ccccc3C2=O)cc1]

(2S,4R)-4-hydroxy-1-((S)-3-methyl-2-(1-oxoisoindolin-2-yl)butanoyl)-N-(4-(4-vinylthiazol-5-yl)benzyl)pyrrolidine-2-carboxamide Example 5

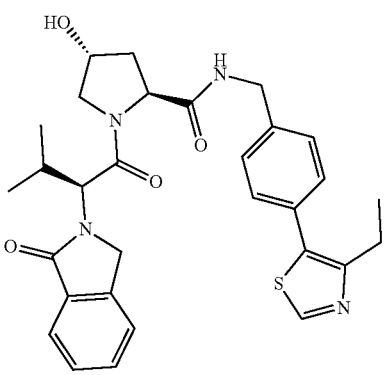 [SMILES: CCc1ncsc1-c1ccc(CNC(=O)[C@@H]2C[C@@H](O)CN2C(=O)[C@H](C(C)C)N2Cc3ccccc3C2=O)cc1]

181

(2S,4R)—N-(4-(4-ethylthiazol-5-yl)benzyl)-4-hydroxy-1-((S)-3-methyl-2-(1-oxoisoindolin-2-yl)butanoyl)pyrrolidine-2-carboxamide Example 6

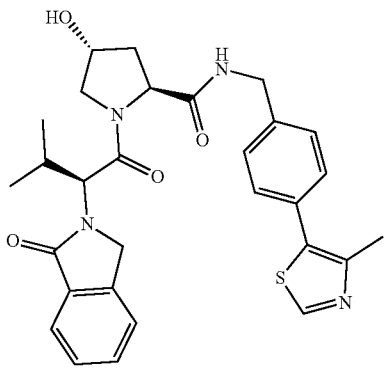 [SMILES: Cc1ncsc1-c1ccc(CNC(=O)[C@@H]2C[C@@H](O)CN2C(=O)[C@H](C(C)C)N2Cc3ccccc3C2=O)cc1]

(2S,4R)-4-hydroxy-1-((S)-3-methyl-2-(1-oxoisoindolin-2-yl)butanoyl)-N-(4-(4-methylthiazol-5-yl)benzyl)pyrrolidine-2-carboxamide Example 7

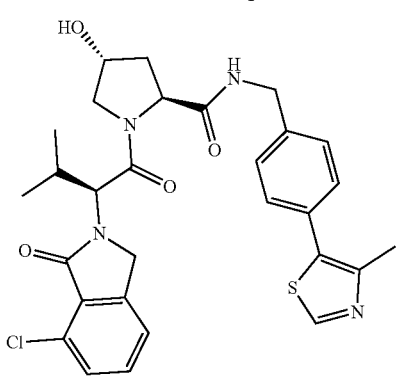

(2S,4R)-1-((S)-2-(7-chloro-1-oxoisoindolin-2-yl)-3-methylbutanoyl)-4-hydroxy-N-(4-(4-methylthiazol-5-yl)benzyl)pyrrolidine-2-carboxamide Example 8

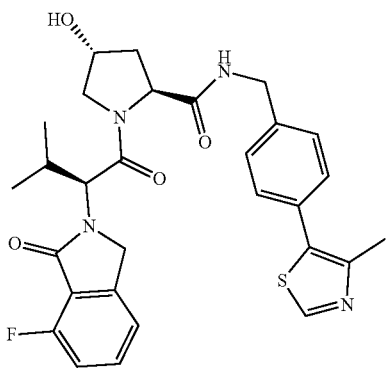

182

(2S,4R)-1-((S)-2-(7-fluoro-1-oxoisoindolin-2-yl)-3-methylbutanoyl)-4-hydroxy-N-(4-(4-methylthiazol-5-yl)benzyl)pyrrolidine-2-carboxamide Example 9

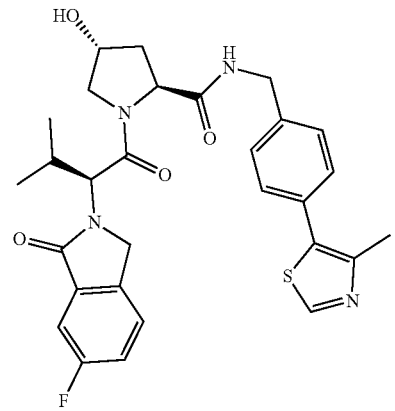 [SMILES: Cc1ncsc1-c1ccc(CNC(=O)[C@@H]2C[C@@H](O)CN2C(=O)[C@H](C(C)C)N2Cc3ccc(F)cc3C2=O)cc1]

((2S,4R)-1-((S)-2-(6-fluoro-1-oxoisoindolin-2-yl)-3-methylbutanoyl)-4-hydroxy-N-(4-(4-methylthiazol-5-yl)benzyl)pyrrolidine-2-carboxamide Example 10

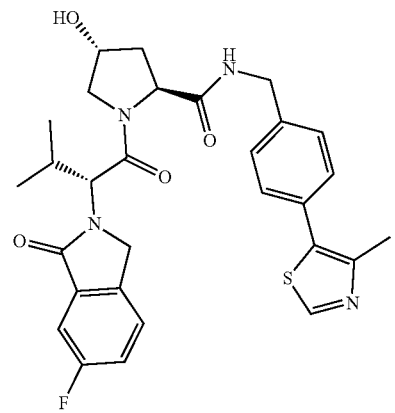 [SMILES: Cc1ncsc1-c1ccc(CNC(=O)[C@@H]2C[C@@H](O)CN2C(=O)[C@@H](C(C)C)N2Cc3ccc(F)cc3C2=O)cc1]

(2S,4R)-1-((R)-2-(6-fluoro-1-oxoisoindolin-2-yl)-3-methylbutanoyl)-4-hydroxy-N-(4-(4-methylthiazol-5-yl)benzyl)pyrrolidine-2-carboxamide Example 11

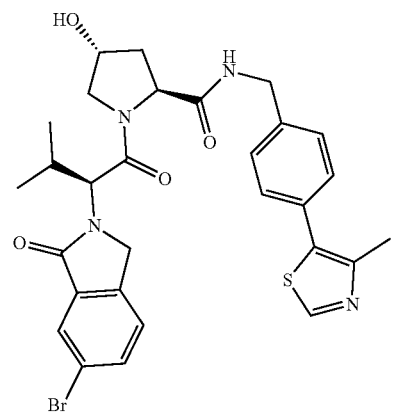 [SMILES: Cc1ncsc1-c1ccc(CNC(=O)[C@@H]2C[C@@H](O)CN2C(=O)[C@H](C(C)C)N2Cc3ccc(Br)cc3C2=O)cc1]

(2S,4R)-1-((S)-2-(6-bromo-1-oxoisoindolin-2-yl)-3-methylbutanoyl)-4-hydroxy-N-(4-(4-methylthiazol-5-yl)benzyl)pyrrolidine-2-carboxamide Example 12

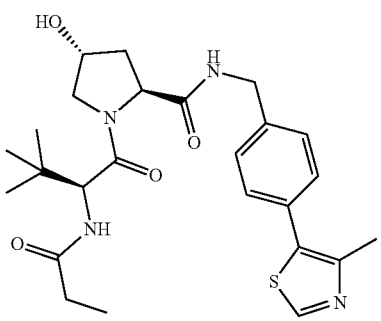 [SMILES: CCC(=O)N[C@H](C(=O)N1C[C@H](O)C[C@H]1C(=O)NCc1ccc(-c2scnc2C)cc1)C(C)(C)C]

(2S,4R)-1-((S)-3,3-dimethyl-2-propionamidobutanoyl)-4-hydroxy-N-(4-(4-methylthiazol-5-yl)benzyl)pyrrolidine-2-carboxamide Example 13

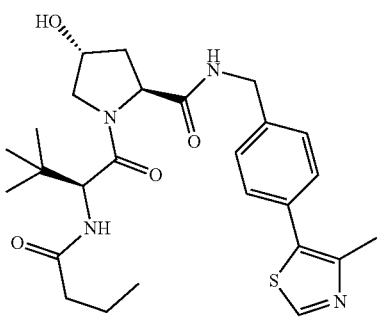 [SMILES: CCCC(=O)N[C@H](C(=O)N1C[C@H](O)C[C@H]1C(=O)NCc1ccc(-c2scnc2C)cc1)C(C)(C)C]

(2S,4R)-1-((S)-2-butyramido-3,3-dimethylbutanoyl)-4-hydroxy-N-(4-(4-methylthiazol-5-yl)benzyl)pyrrolidine-2-carboxamide Example 14

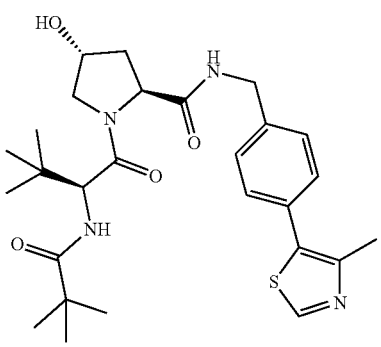 [SMILES: Cc1ncsc1-c1ccc(CNC(=O)[C@@H]2C[C@@H](O)CN2C(=O)[C@@H](NC(=O)C(C)(C)C)C(C)(C)C)cc1]

(2S,4R)-1-((S)-3,3-dimethyl-2-pivalamidobutanoyl)-4-hydroxy-N-(4-(4-methylthiazol-5-yl)benzyl)pyrrolidine-2-carboxamide Example 15

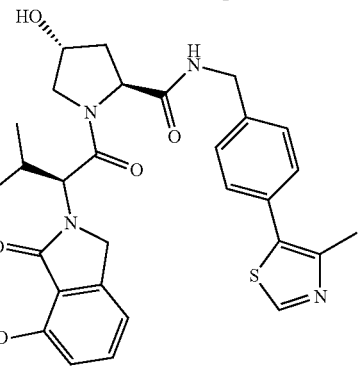

(2S,4R)-4-hydroxy-1-((S)-2-(7-methoxy-1-oxoisoindolin-2-yl)-3-methylbutanoyl)-N-(4-(4-methylthiazol-5-yl)benzyl)pyrrolidine-2-carboxamide Example 16

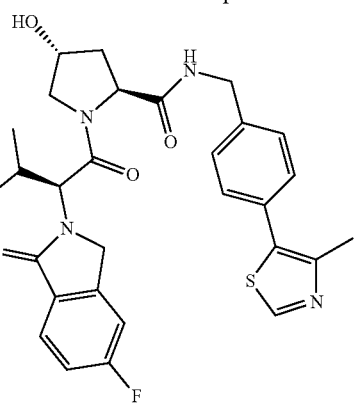

(2S,4R)-1-((S)-2-(5-fluoro-1-oxoisoindolin-2-yl)-3-methylbutanoyl)-4-hydroxy-N-(4-(4-methylthiazol-5-yl)benzyl)pyrrolidine-2-carboxamide Example 17

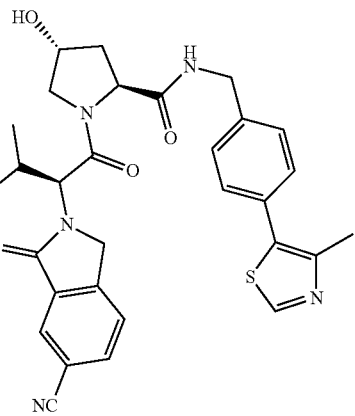

(2S,4R)-1-((S)-2-(6-cyano-1-oxoisoindolin-2-yl)-3-methylbutanoyl)-4-hydroxy-N-(4-(4-methylthiazol-5-yl)benzyl)pyrrolidine-2-carboxamide Example 18

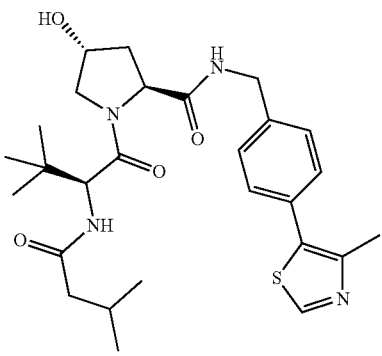 [SMILES: Cc1ncsc1-c1ccc(CNC(=O)[C@@H]2C[C@@H](O)CN2C(=O)[C@@H](NC(=O)CC(C)C)C(C)(C)C)cc1]

(2S,4R)-1-((S)-3,3-dimethyl-2-(3-methylbutanamido)butanoyl)-4-hydroxy-N-(4-(4-methylthiazol-5-yl)benzyl)pyrrolidine-2-carboxamide Example 19

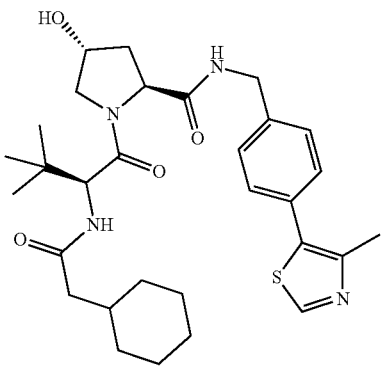 [SMILES: Cc1ncsc1-c1ccc(CNC(=O)[C@@H]2C[C@@H](O)CN2C(=O)[C@@H](NC(=O)CC2CCCCC2)C(C)(C)C)cc1]

(2S,4R)-1-((S)-2-(2-cyclohexylacetamido)-3,3-dimethylbutanoyl)-4-hydroxy-N-(4-(4-methylthiazol-5-yl)benzyl)pyrrolidine-2-carboxamide Example 20

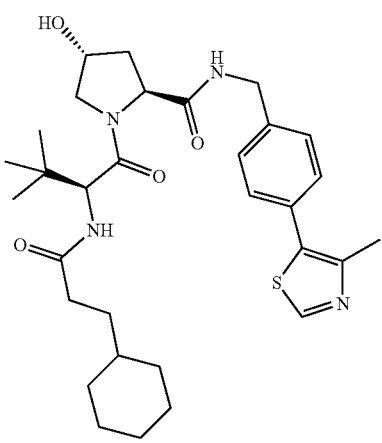 [SMILES: Cc1ncsc1-c1ccc(CNC(=O)[C@@H]2C[C@@H](O)CN2C(=O)[C@@H](NC(=O)CCC2CCCCC2)C(C)(C)C)cc1]

(2S,4R)-1-((S)-2-(3-cyclohexylpropanamido)-3,3-dimethylbutanoyl)-4-hydroxy-N-(4-(4-methylthiazol-5-yl)benzyl)pyrrolidine-2-carboxamide Example 21

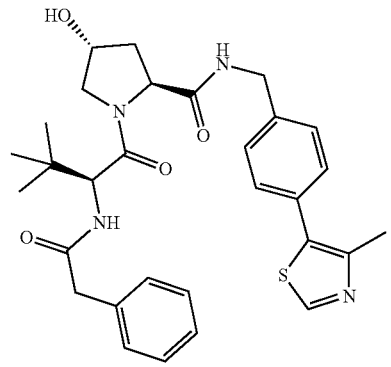 [SMILES: Cc1ncsc1-c1ccc(CNC(=O)[C@@H]2C[C@@H](O)CN2C(=O)[C@@H](NC(=O)Cc2ccccc2)C(C)(C)C)cc1]

(2S,4R)-1-((S)-3,3-dimethyl-2-(2-phenylacetamido)butanoyl)-4-hydroxy-N-(4-(4-methylthiazol-5-yl)benzyl)pyrrolidine-2-carboxamide Example 22

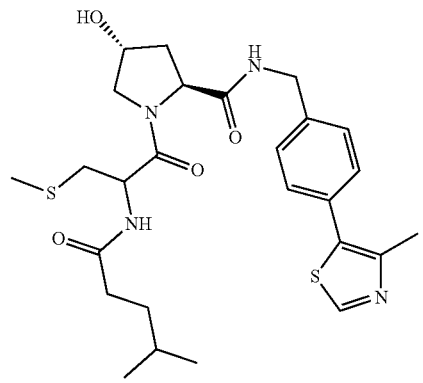

(2S,4R)-4-hydroxy-1-((R)-2-(4-methylpentanamido)-3-(methylthio)propanoyl)-N-(4-(4-methylthiazol-5-yl)benzyl)pyrrolidine-2-carboxamide Example 23

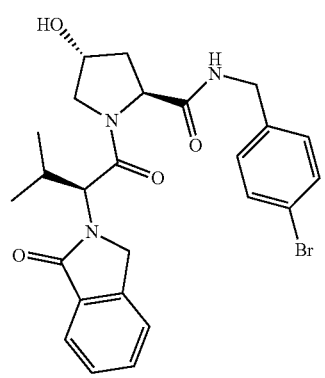 [SMILES: CC(C)[C@@H](C(=O)N1C[C@H](O)C[C@H]1C(=O)NCc1ccc(Br)cc1)N1Cc2ccccc2C1=O]

187

(2S,4R)—N-(4-bromobenzyl)-4-hydroxy-1-((S)-3-methyl-2-(1-oxoisoindolin-2-yl)butanoyl)pyrrolidine-2-carboxamide Example 24

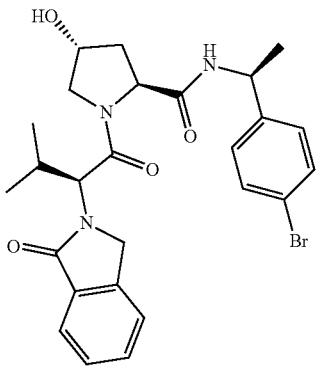 [SMILES: CC(C)[C@@H](C(=O)N1C[C@H](O)C[C@H]1C(=O)N[C@@H](C)c1ccc(Br)cc1)N1Cc2ccccc2C1=O]

(2S,4R)—N—((S)-1-(4-bromophenyl)ethyl)-4-hydroxy-1-((S)-3-methyl-2-(1-oxoisoindolin-2-yl)butanoyl)pyrrolidine-2-carboxamide Example 25

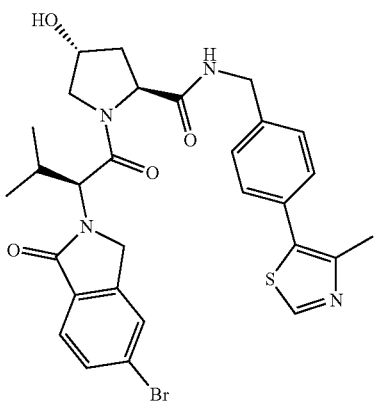 [SMILES: Cc1ncsc1-c1ccc(CNC(=O)[C@@H]2C[C@@H](O)CN2C(=O)[C@H](C(C)C)N2Cc3cc(Br)ccc3C2=O)cc1]

(2S,4R)-1-((S)-2-(5-bromo-1-oxoisoindolin-2-yl)-3-methylbutanoyl)-4-hydroxy-N-(4-(4-methylthiazol-5-yl)benzyl)pyrrolidine-2-carboxamide Example 26

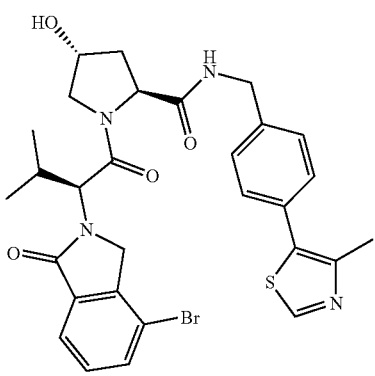 [SMILES: Cc1ncsc1-c1ccc(CNC(=O)[C@@H]2C[C@@H](O)CN2C(=O)[C@H](C(C)C)N2Cc3c(Br)cccc3C2=O)cc1]

188

(2S,4R)-1-((S)-2-(4-bromo-1-oxoisoindolin-2-yl)-3-methylbutanoyl)-4-hydroxy-N-(4-(4-methylthiazol-5-yl)benzyl)pyrrolidine-2-carboxamide Example 27

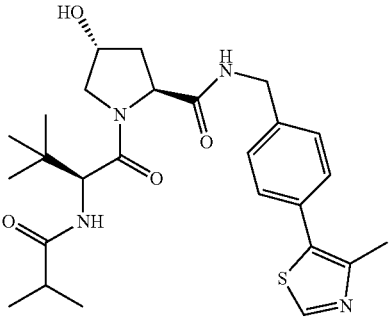 [SMILES: Cc1ncsc1-c1ccc(CNC(=O)[C@@H]2C[C@@H](O)CN2C(=O)[C@@H](NC(=O)C(C)C)C(C)(C)C)cc1]

(2S,4R)-4-hydroxy-1-((S)-2-isobutyramido-3,3-dimethylbutanoyl)-N-(4-(4-methylthiazol-5-yl)benzyl)pyrrolidine-2-carboxamide Example 28

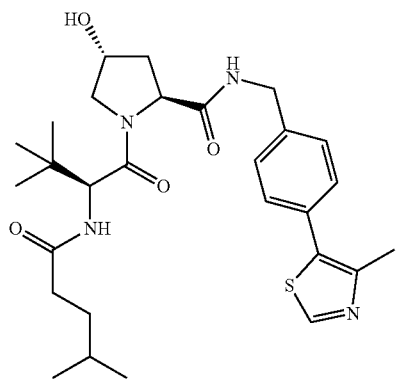 [SMILES: Cc1ncsc1-c1ccc(CNC(=O)[C@@H]2C[C@@H](O)CN2C(=O)[C@@H](NC(=O)CCC(C)C)C(C)(C)C)cc1]

(2S,4R)-1-((S)-3,3-dimethyl-2-(4-methylpentanamido)butanoyl)-4-hydroxy-N-(4-(4-methylthiazol-5-yl)benzyl)pyrrolidine-2-carboxamide Example 29

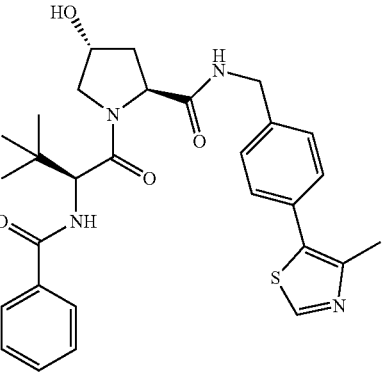

189

(2S,4R)-1-((S)-2-benzamido-3,3-dimethylbutanoyl)-4-hydroxy-N-(4-(4-methylthiazol-5-yl)benzyl)pyrrolidine-2-carboxamide Example 30

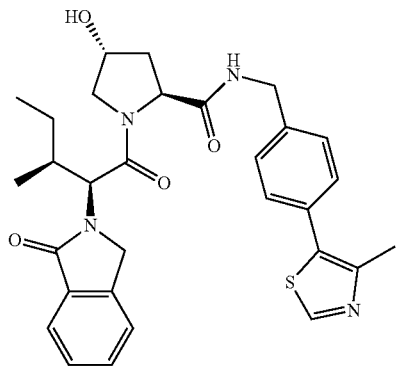 [SMILES: CC[C@H](C)[C@@H](C(=O)N1C[C@H](O)C[C@H]1C(=O)NCc1ccc(-c2scnc2C)cc1)N1Cc2ccccc2C1=O]

(2S,4R)-4-hydroxy-1-((2S,3S)-3-methyl-2-(1-oxoisoindolin-2-yl)pentanoyl)-N-(4-(4-methylthiazol-5-yl)benzyl)pyrrolidine-2-carboxamide Example 31

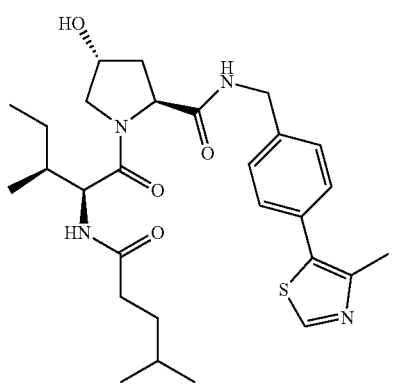 [SMILES: CC[C@H](C)[C@H](NC(=O)CCC(C)C)C(=O)N1C[C@H](O)C[C@H]1C(=O)NCc1ccc(-c2scnc2C)cc1]

(2S,4R)-4-hydroxy-1-((2S,3S)-3-methyl-2-(4-methylpentanamido)pentanoyl)-N-(4-(4-methylthiazol-5-yl)benzyl)pyrrolidine-2-carboxamide Example 32

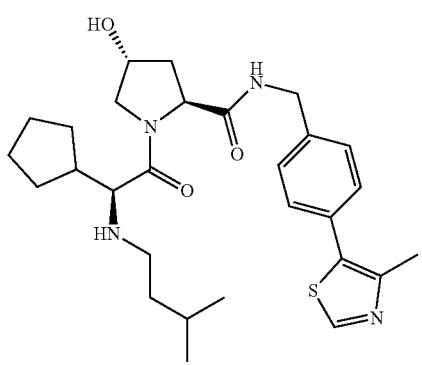 [SMILES: Cc1ncsc1-c1ccc(CNC(=O)[C@@H]2C[C@@H](O)CN2C(=O)[C@@H](NCCC(C)C)C2CCCC2)cc1]

190

(2S,4R)-1-((S)-2-cyclopentyl-2-(isopentylamino)acetyl)-4-hydroxy-N-(4-(4-methylthiazol-5-yl)benzyl)pyrrolidine-2-carboxamide Example 33

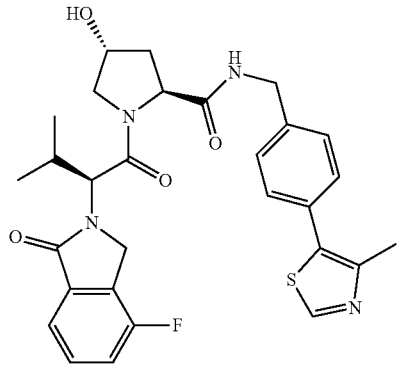 [SMILES: Cc1ncsc1-c1ccc(CNC(=O)[C@@H]2C[C@@H](O)CN2C(=O)[C@H](C(C)C)N2Cc3c(F)cccc3C2=O)cc1]

(2S,4R)-1-((S)-2-(4-fluoro-1-oxoisoindolin-2-yl)-3-methylbutanoyl)-4-hydroxy-N-(4-(4-methylthiazol-5-yl)benzyl)pyrrolidine-2-carboxamide Example 34

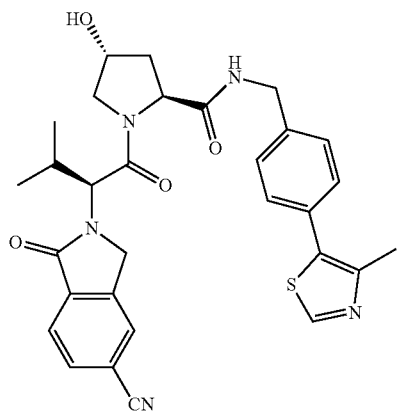

(2S,4R)-1-((S)-2-(5-cyano-1-oxoisoindolin-2-yl)-3-methylbutanoyl)-4-hydroxy-N-(4-(4-methylthiazol-5-yl)benzyl)pyrrolidine-2-carboxamide Example 35

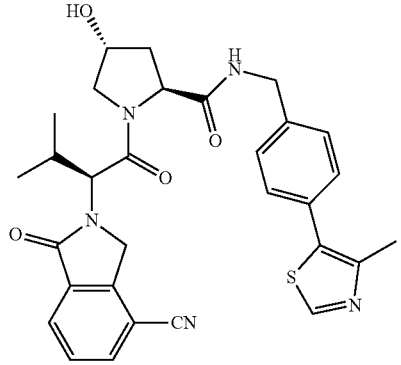 [SMILES: Cc1ncsc1-c1ccc(CNC(=O)[C@@H]2C[C@@H](O)CN2C(=O)[C@H](C(C)C)N2Cc3c(C#N)cccc3C2=O)cc1]

191

(2S,4R)-1-((S)-2-(4-cyano-1-oxoisoindolin-2-yl)-3-methylbutanoyl)-4-hydroxy-N-(4-(4-methylthiazol-5-yl)benzyl)pyrrolidine-2-carboxamide Example 36

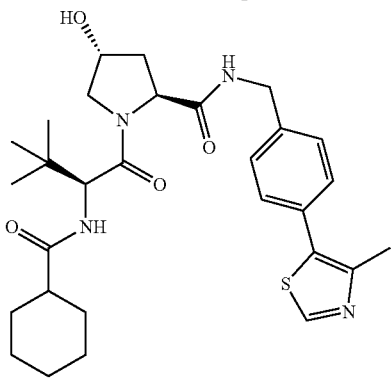 [SMILES: Cc1ncsc1-c1ccc(CNC(=O)[C@@H]2C[C@@H](O)CN2C(=O)[C@@H](NC(=O)C2CCCCC2)C(C)(C)C)cc1]

(2S,4R)-1-((S)-2-(cyclohexanecarboxamido)-3,3-dimethylbutanoyl)-4-hydroxy-N-(4-(4-methylthiazol-5-yl)benzyl)pyrrolidine-2-carboxamide Example 37

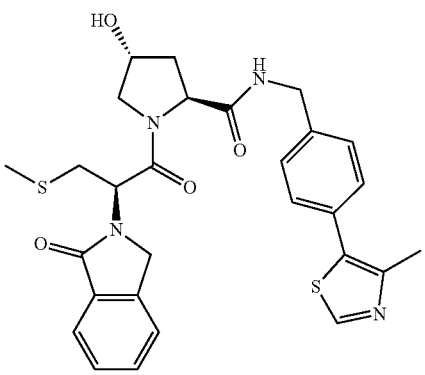

(2S,4R)-4-hydroxy-N-(4-(4-methylthiazol-5-yl)benzyl)-1-((R)-3-(methylthio)-2-(1-oxoisoindolin-2-yl)propanoyl)pyrrolidine-2-carboxamide Example 38

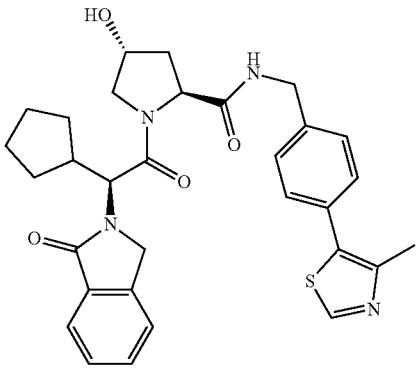 [SMILES: Cc1ncsc1-c1ccc(CNC(=O)[C@@H]2C[C@@H](O)CN2C(=O)[C@H](C2CCCC2)N2Cc3ccccc3C2=O)cc1]

192

(2S,4R)-1-((S)-2-cyclopentyl-2-(1-oxoisoindolin-2-yl)acetyl)-4-hydroxy-N-(4-(4-methylthiazol-5-yl)benzyl)pyrrolidine-2-carboxamide Example 39

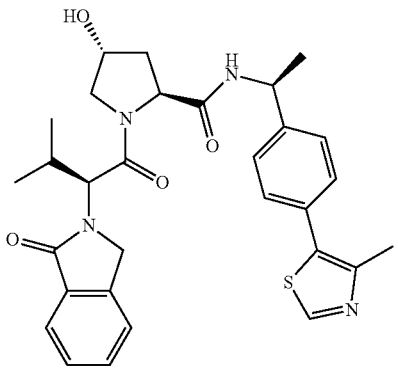 [SMILES: Cc1ncsc1-c1ccc([C@H](C)NC(=O)[C@@H]2C[C@@H](O)CN2C(=O)[C@H](C(C)C)N2Cc3ccccc3C2=O)cc1]

(2S,4R)-4-hydroxy-N-[(1S)-1-[4-(4-methyl-1,3-thiazol-5-yl)phenyl]ethyl]-1-[(2 S)-3-methyl-2-(1-oxo-2,3-dihydro-1H-isoindol-2-yl)butanoyl]pyrrolidine-2-carboxamide Example 40

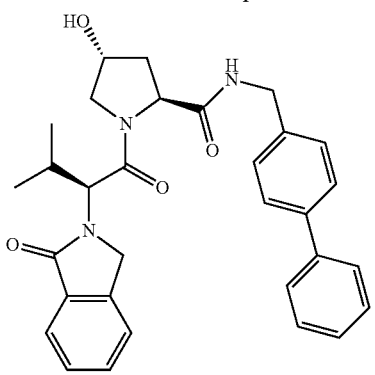

(2S,4R)—N-(biphenyl-4-ylmethyl)-4-hydroxy-1-((S)-3-methyl-2-(1-oxoisoindolin-2-yl)butanoyl)pyrrolidine-2-carboxamide Example 41

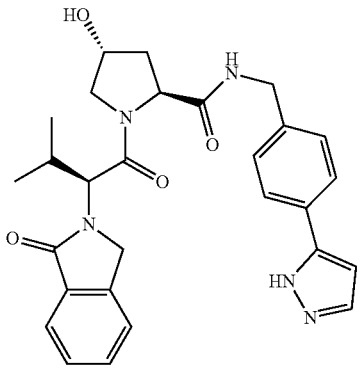 [SMILES: CC(C)[C@@H](C(=O)N1C[C@H](O)C[C@H]1C(=O)NCc1ccc(-c2ccn[nH]2)cc1)N1Cc2ccccc2C1=O]

(2S,4R)—N-(4-(1H-pyrazol-5-yl)benzyl)-4-hydroxy-1-((S)-3-methyl-2-(1-oxoisoindolin-2-yl)butanoyl)pyrrolidine-2-carboxamide Example 42

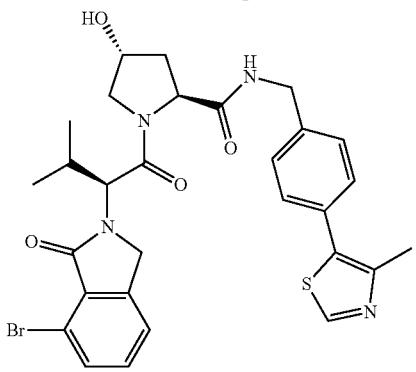 [SMILES: Cc1ncsc1-c1ccc(CNC(=O)[C@@H]2C[C@@H](O)CN2C(=O)[C@H](C(C)C)N2Cc3cccc(Br)c3C2=O)cc1]

(2S,4R)-1-((S)-2-(7-bromo-1-oxoisoindolin-2-yl)-3-methylbutanoyl)-4-hydroxy-N-(4-(4-methylthiazol-5-yl)benzyl)pyrrolidine-2-carboxamide Example 43

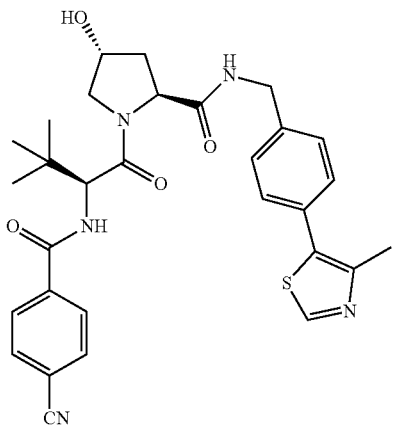 [SMILES: Cc1ncsc1-c1ccc(CNC(=O)[C@@H]2C[C@@H](O)CN2C(=O)[C@@H](NC(=O)c2ccc(C#N)cc2)C(C)(C)C)cc1]

(2S,4R)-1-((S)-2-(4-cyanobenzamido)-3,3-dimethylbutanoyl)-4-hydroxy-N-(4-(4-methylthiazol-5-yl)benzyl)pyrrolidine-2-carboxamide Example 44

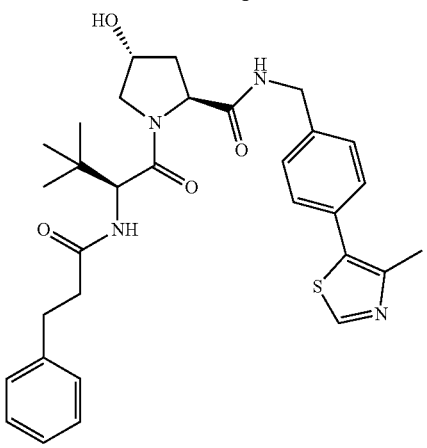

(2S,4R)-1-((S)-3,3-dimethyl-2-(3-phenylpropanamido)butanoyl)-4-hydroxy-N-(4-(4-methylthiazol-5-yl)benzyl)pyrrolidine-2-carboxamide Example 45

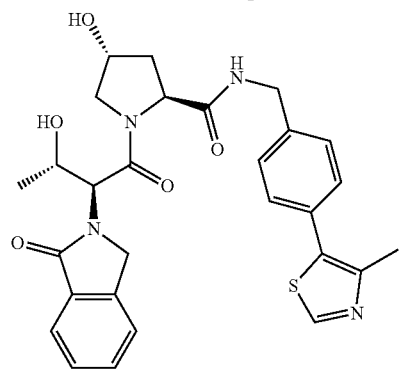 [SMILES: Cc1ncsc1-c1ccc(CNC(=O)[C@@H]2C[C@@H](O)CN2C(=O)[C@H]([C@H](C)O)N2Cc3ccccc3C2=O)cc1]

(2S,4R)-4-hydroxy-1-((2S,3S)-3-hydroxy-2-(1-oxoisoindolin-2-yl)butanoyl)-N-(4-(4-methylthiazol-5-yl)benzyl)pyrrolidine-2-carboxamide Example 46

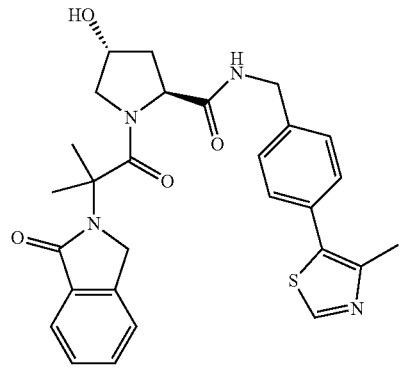 [SMILES: Cc1ncsc1-c1ccc(CNC(=O)[C@@H]2C[C@@H](O)CN2C(=O)C(C)(C)N2Cc3ccccc3C2=O)cc1]

(2S,4R)-4-hydroxy-1-(2-methyl-2-(1-oxoisoindolin-2-yl)propanoyl)-N-(4-(4-methylthiazol-5-yl)benzyl)pyrrolidine-2-carboxamide Example 47

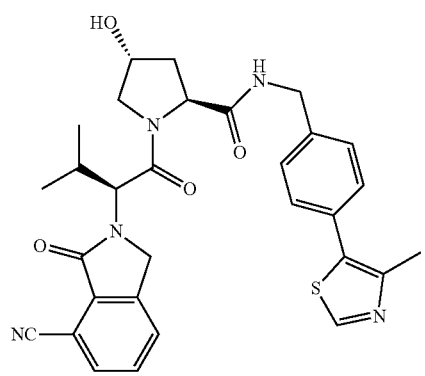 [SMILES: Cc1ncsc1-c1ccc(CNC(=O)[C@@H]2C[C@@H](O)CN2C(=O)[C@H](C(C)C)N2Cc3cccc(C#N)c3C2=O)cc1]

(2S,4R)-1-((S)-2-(7-cyano-1-oxoisoindolin-2-yl)-3-methylbutanoyl)-4-hydroxy-N-(4-(4-methylthiazol-5-yl)benzyl)pyrrolidine-2-carboxamide Example 48

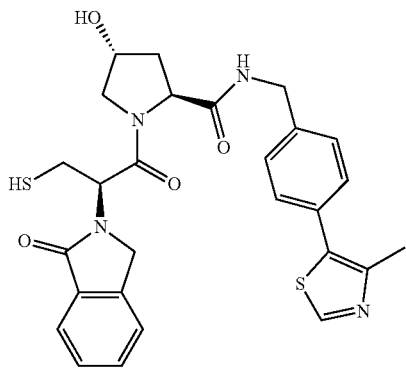 [SMILES: Cc1ncsc1-c1ccc(CNC(=O)[C@@H]2C[C@@H](O)CN2C(=O)[C@H](CS)N2Cc3ccccc3C2=O)cc1]

(2S,4R)-4-hydroxy-1-((R)-3-mercapto-2-(1-oxoisoindolin-2-yl)propanoyl)-N-(4-(4-methylthiazol-5-yl)benzyl)pyrrolidine-2-carboxamide Example 49

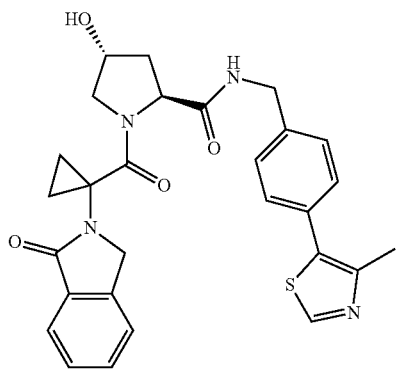 [SMILES: Cc1ncsc1-c1ccc(CNC(=O)[C@@H]2C[C@@H](O)CN2C(=O)C2(N3Cc4ccccc4C3=O)CC2)cc1]

(2S,4R)-4-hydroxy-N-(4-(4-methylthiazol-5-yl)benzyl)-1-(1-(1-oxoisoindolin-2-yl)cyclopropanecarbonyl)pyrrolidine-2-carboxamide Example 50

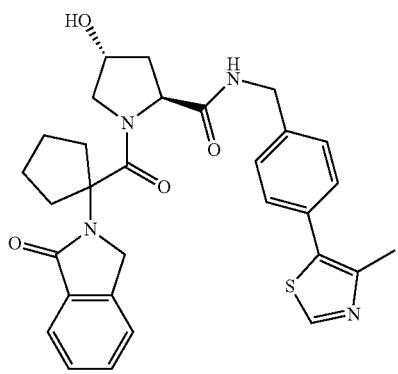 [SMILES: Cc1ncsc1-c1ccc(CNC(=O)[C@@H]2C[C@@H](O)CN2C(=O)C2(N3Cc4ccccc4C3=O)CCCC2)cc1]

(2S,4R)-4-hydroxy-N-(4-(4-methylthiazol-5-yl)benzyl)-1-(1-(1-oxoisoindolin-2-yl)cyclopentanecarbonyl)pyrrolidine-2-carboxamide Example 51

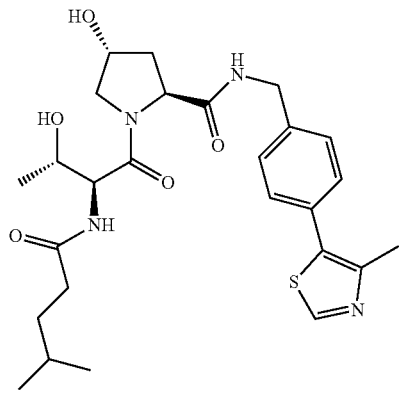 [SMILES: Cc1ncsc1-c1ccc(CNC(=O)[C@@H]2C[C@@H](O)CN2C(=O)[C@@H](NC(=O)CCC(C)C)[C@H](C)O)cc1]

(2S,4R)-4-hydroxy-1-((2S,3S)-3-hydroxy-2-(4-methylpentanamido)butanoyl)-N-(4-(4-methylthiazol-5-yl)benzyl)pyrrolidine-2-carboxamide Example 52

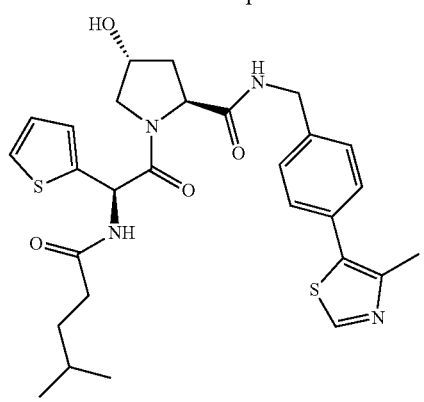

(2S,4R)-4-hydroxy-1-((R)-2-(4-methylpentanamido)-2-(thiophen-2-yl)acetyl)-N-(4-(4-methylthiazol-5-yl)benzyl)pyrrolidine-2-carboxamide Example 53

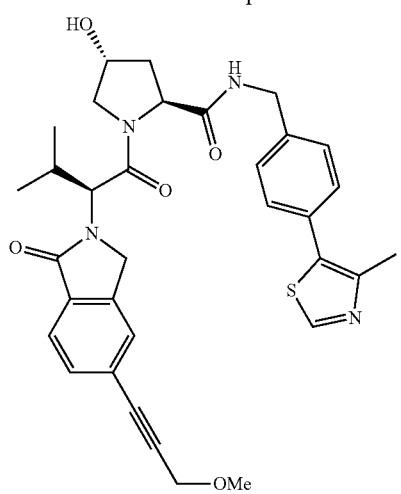

197

(2S,4R)-4-hydroxy-1-((S)-2-(5-(3-methoxyprop-1-ynyl)-1-oxoisoindolin-2-yl)-3-methylbutanoyl)-N-(4-(4-methylthiazol-5-yl)benzyl)pyrrolidine-2-carboxamide Example 54

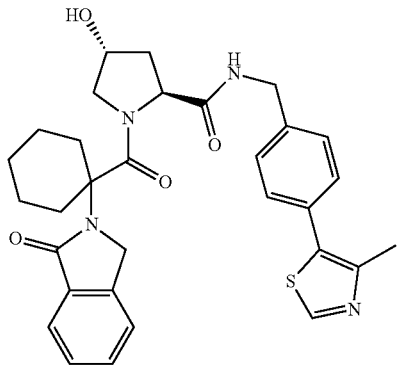 [SMILES: Cc1ncsc1-c1ccc(CNC(=O)[C@@H]2C[C@@H](O)CN2C(=O)C2(N3Cc4ccccc4C3=O)CCCCC2)cc1]

(2S,4R)-4-hydroxy-N-(4-(4-methylthiazol-5-yl)benzyl)-1-(1-(1-oxoisoindolin-2-yl)cyclohexanecarbonyl)pyrrolidine-2-carboxamide Example 55

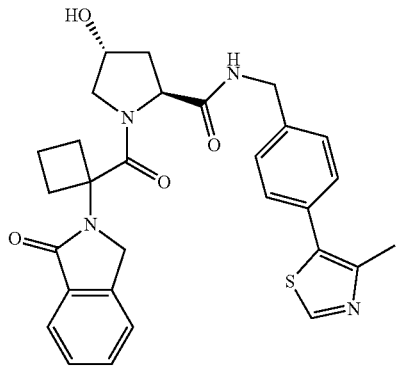 [SMILES: Cc1ncsc1-c1ccc(CNC(=O)[C@@H]2C[C@@H](O)CN2C(=O)C2(N3Cc4ccccc4C3=O)CCC2)cc1]

(2S,4R)-4-hydroxy-N-(4-(4-methylthiazol-5-yl)benzyl)-1-(1-(1-oxoisoindolin-2-yl)cyclobutanecarbonyl)pyrrolidine-2-carboxamide Example 56

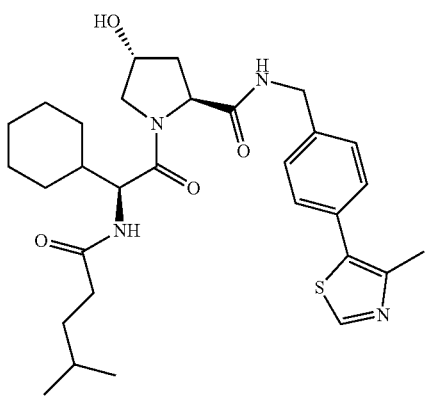 [SMILES: Cc1ncsc1-c1ccc(CNC(=O)[C@@H]2C[C@@H](O)CN2C(=O)[C@@H](NC(=O)CCC(C)C)C2CCCCC2)cc1]

198

(2S,4R)-1-((S)-2-cyclohexyl-2-(4-methylpentanamido)acetyl)-4-hydroxy-N-(4-(4-methylthiazol-5-yl)benzyl)pyrrolidine-2-carboxamide Example 57

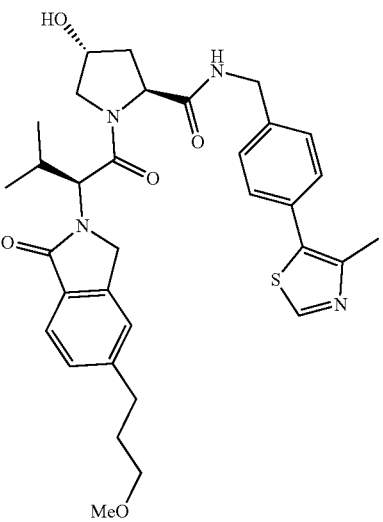 [SMILES: COCCCc1ccc2c(c1)CN([C@H](C(=O)N1C[C@H](O)C[C@H]1C(=O)NCc1ccc(-c3scnc3C)cc1)C(C)C)C2=O]

(2S,4R)-4-hydroxy-1-((S)-2-(5-(3-methoxypropyl)-1-oxoisoindolin-2-yl)-3-methylbutanoyl)-N-(4-(4-methylthiazol-5-yl)benzyl)pyrrolidine-2-carboxamide Example 58

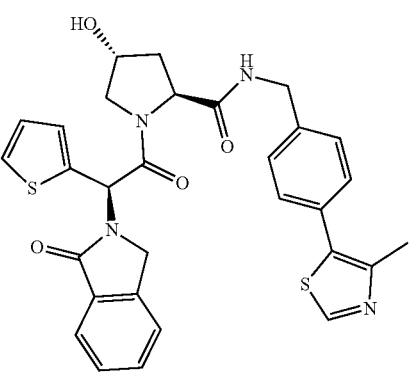 [SMILES: Cc1ncsc1-c1ccc(CNC(=O)[C@@H]2C[C@@H](O)CN2C(=O)[C@H](c2cccs2)N2Cc3ccccc3C2=O)cc1]

199

(2S,4R)-4-hydroxy-N-(4-(4-methylthiazol-5-yl)benzyl)-1-((R)-2-(1-oxoisoindolin-2-yl)-2-(thiophen-2-yl)acetyl)pyrrolidine-2-carboxamide Example 59

200

(S)-1-((S)-3-methyl-2-(1-oxoisoindolin-2-yl)butanoyl)-N-(4-(4-methylthiazol-5-yl)benzyl)-4-oxopyrrolidine-2-carboxamide Example 62

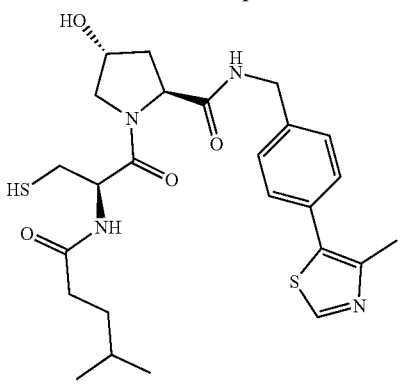

(2S,4R)-4-hydroxy-1-((R)-3-mercapto-2-(4-methylpentanamido)propanoyl)-N-(4-(4-methylthiazol-5-yl)benzyl)pyrrolidine-2-carboxamide Example 60

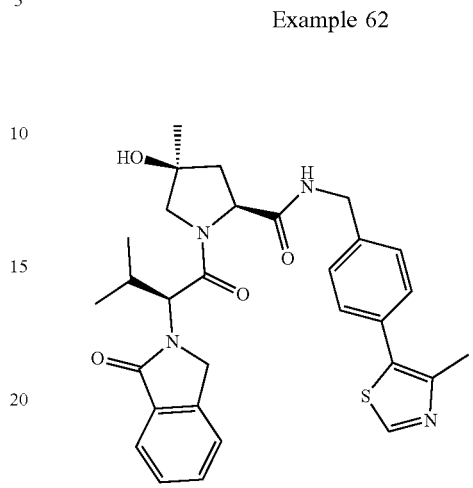

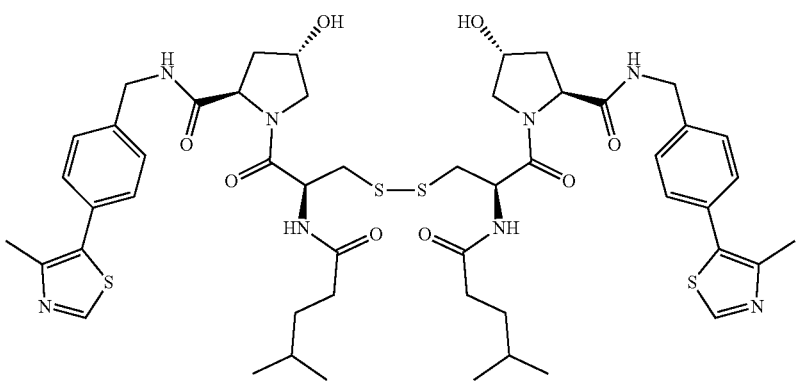

(2S,4R)-4-hydroxy-1-((R)-3-(((S)-3-((2R,4S)-4-hydroxy-2-(4-(4-methylthiazol-5-yl)benzylcarbamoyl)pyrrolidin-1-yl)-2-(4-methylpentanamido)-3-oxopropyl)disulfanyl)-2-(4-methylpentanamido)propanoyl)-N-(4-(4-methylthiazol-5-yl)benzyl)pyrrolidine-2-carboxamide Example 61

(2S,4S)-4-hydroxy-4-methyl-1-((S)-3-methyl-2-(1-oxoisoindolin-2-yl)butanoyl)-N-(4-(4-methylthiazol-5-yl)benzyl)pyrrolidine-2-carboxamide Example 63

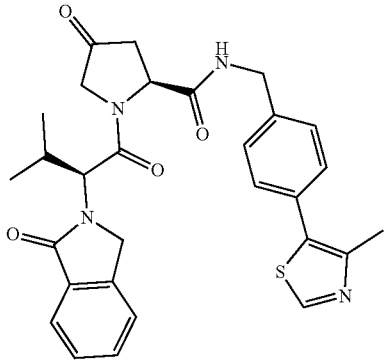 [SMILES: Cc1ncsc1-c1ccc(CNC(=O)[C@@H]2CC(=O)CN2C(=O)[C@H](C(C)C)N2Cc3ccccc3C2=O)cc1]

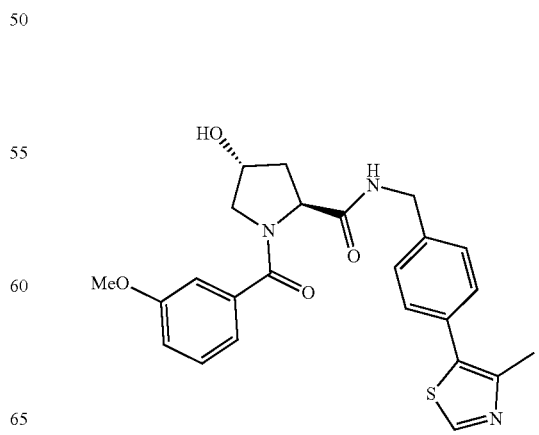

201

(2S,4R)-4-hydroxy-1-(3-methoxybenzoyl)-N-(4-(4-methylthiazol-5-yl)benzyl)pyrrolidine-2-carboxamide Example 64

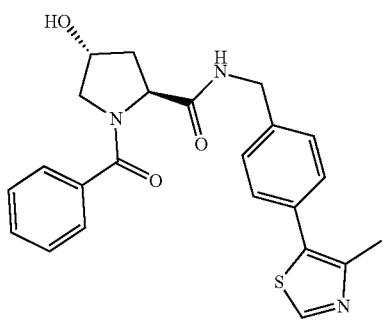 [SMILES: Cc1ncsc1-c1ccc(CNC(=O)[C@@H]2C[C@@H](O)CN2C(=O)c2ccccc2)cc1]

(2S,4R)-1-benzoyl-4-hydroxy-N-(4-(4-methylthiazol-5-yl)benzyl)pyrrolidine-2-carboxamide Example 65

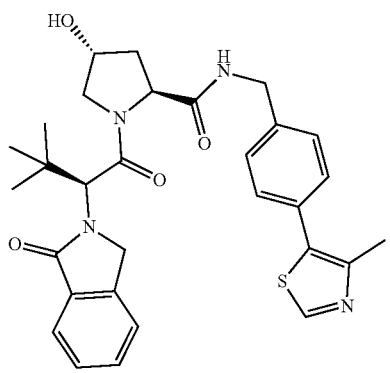 [SMILES: Cc1ncsc1-c1ccc(CNC(=O)[C@@H]2C[C@@H](O)CN2C(=O)[C@@H](N2Cc3ccccc3C2=O)C(C)(C)C)cc1]

(2S,4R)-1-((S)-3,3-dimethyl-2-(1-oxoisoindolin-2-yl)butanoyl)-4-hydroxy-N-(4-(4-methylthiazol-5-yl)benzyl)pyrrolidine-2-carboxamide Example 66

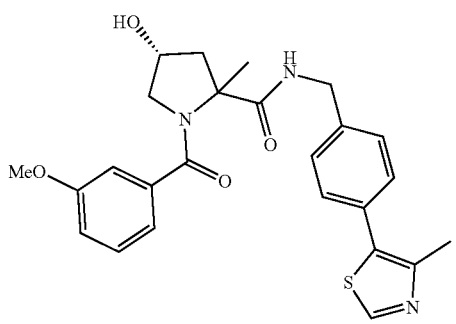 [SMILES: COc1cccc(C(=O)N2C[C@H](O)CC2(C)C(=O)NCc2ccc(-c3scnc3C)cc2)c1]

202

(4R)-4-hydroxy-1-(3-methoxybenzoyl)-2-methyl-N-(4-(4-methylthiazol-5-yl)benzyl)pyrrolidine-2-carboxamide Example 67

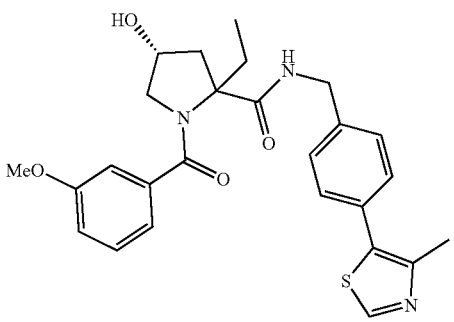 [SMILES: CCC1(C(=O)NCc2ccc(-c3scnc3C)cc2)C[C@@H](O)CN1C(=O)c1cccc(OC)c1]

(4R)-2-ethyl-4-hydroxy-1-(3-methoxybenzoyl)-N-(4-(4-methylthiazol-5-yl)benzyl)pyrrolidine-2-carboxamide Example 68

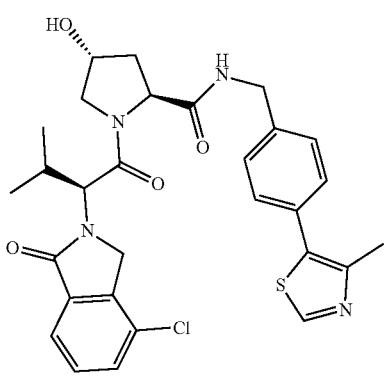 [SMILES: Cc1ncsc1-c1ccc(CNC(=O)[C@@H]2C[C@@H](O)CN2C(=O)[C@H](C(C)C)N2Cc3c(Cl)cccc3C2=O)cc1]

((2S,4R)-1-((S)-2-(4-chloro-1-oxoisoindolin-2-yl)-3-methylbutanoyl)-4-hydroxy-N-(4-(4-methylthiazol-5-yl)benzyl)pyrrolidine-2-carboxamide Example 69

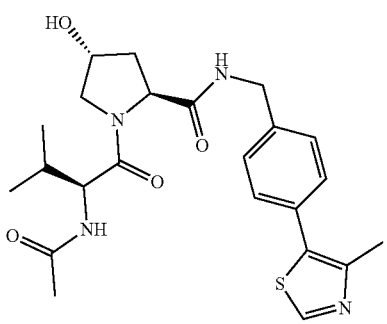 [SMILES: CC(=O)N[C@H](C(=O)N1C[C@H](O)C[C@H]1C(=O)NCc1ccc(-c2scnc2C)cc1)C(C)C]

203

(2S,4R)-1-((S)-2-acetamido-3-methylbutanoyl)-4-hydroxy-N-(4-(4-methylthiazol-5-yl)benzyl)pyrrolidine-2-carboxamide Example 70

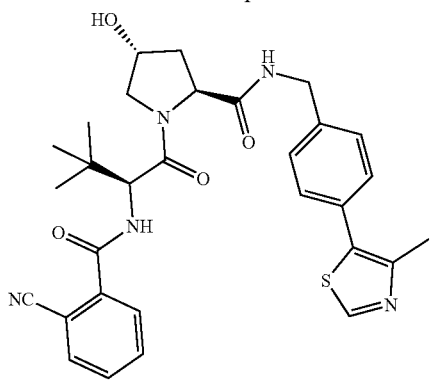

(2S,4R)-1-((S)-2-(2-cyanobenzamido)-3,3-dimethylbutanoyl)-4-hydroxy-N-(4-(4-methylthiazol-5-yl)benzyl)pyrrolidine-2-carboxamide Example 71

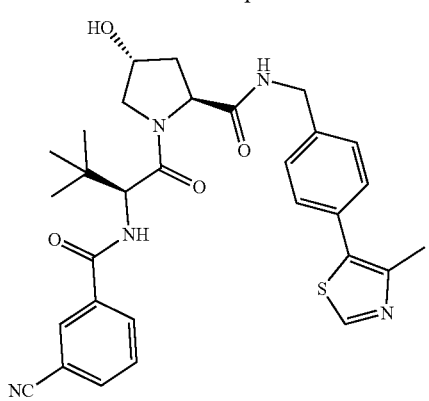

(2S,4R)-1-((S)-2-(3-cyanobenzamido)-3,3-dimethylbutanoyl)-4-hydroxy-N-(4-(4-methylthiazol-5-yl)benzyl)pyrrolidine-2-carboxamide Example 72

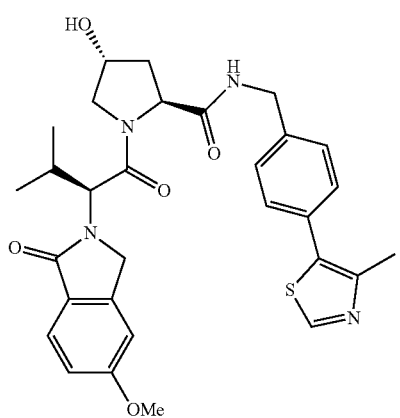 [SMILES: COc1ccc2c(c1)CN([C@H](C(=O)N1C[C@H](O)C[C@H]1C(=O)NCc1ccc(-c3scnc3C)cc1)C(C)C)C2=O]

204

(2S,4R)-4-hydroxy-1-((S)-2-(5-methoxy-1-oxoisoindolin-2-yl)-3-methylbutanoyl)-N-(4-(4-methylthiazol-5-yl)benzyl)pyrrolidine-2-carboxamide Example 73

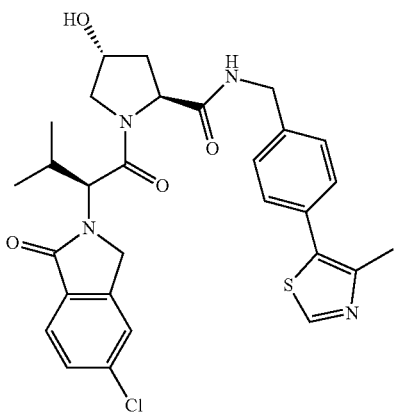

(2S,4R)-1-((S)-2-(5-chloro-1-oxoisoindolin-2-yl)-3-methylbutanoyl)-4-hydroxy-N-(4-(4-methylthiazol-5-yl)benzyl)pyrrolidine-2-carboxamide Example 74

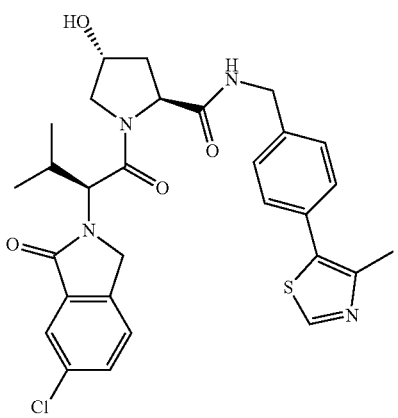 [SMILES: Cc1ncsc1-c1ccc(CNC(=O)[C@@H]2C[C@@H](O)CN2C(=O)[C@H](C(C)C)N2Cc3ccc(Cl)cc3C2=O)cc1]

205

(2S,4R)-1-((S)-2-(6-chloro-1-oxoisoindolin-2-yl)-3-methylbutanoyl)-4-hydroxy-N-(4-(4-methylthiazol-5-yl)benzyl)pyrrolidine-2-carboxamide Example 75

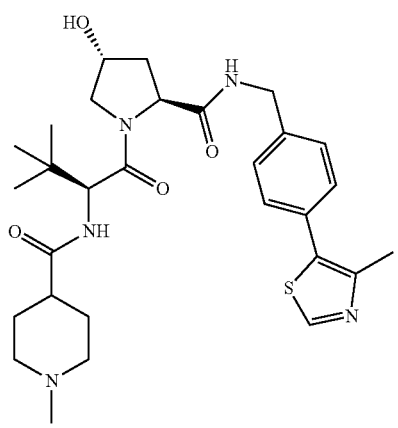 [SMILES: Cc1ncsc1-c1ccc(CNC(=O)[C@@H]2C[C@@H](O)CN2C(=O)[C@@H](NC(=O)C2CCN(C)CC2)C(C)(C)C)cc1]

N—((S)-1-((2S,4R)-4-hydroxy-2-(4-(4-methylthiazol-5-yl)benzylcarbamoyl)pyrrolidin-1-yl)-3,3-dimethyl-1-oxobutan-2-yl)-1-methylpiperidine-4-carboxamide Example 76

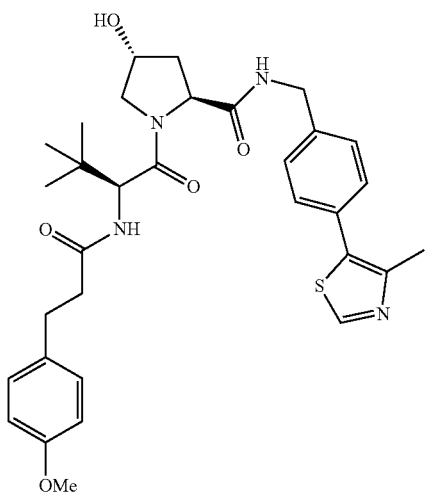 [SMILES: COc1ccc(CCC(=O)N[C@H](C(=O)N2C[C@H](O)C[C@H]2C(=O)NCc2ccc(-c3scnc3C)cc2)C(C)(C)C)cc1]

206

(2S,4R)-4-hydroxy-1-((S)-2-(3-(4-methoxyphenyl)propanamido)-3,3-dimethylbutanoyl)-N-(4-(4-methylthiazol-5-yl)benzyl)pyrrolidine-2-carboxamide Example 77

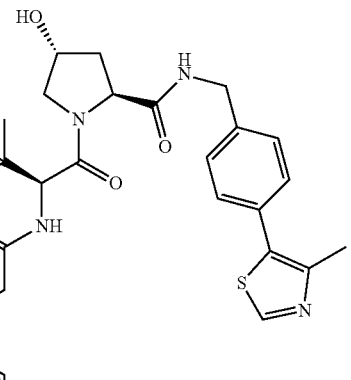

(2S,4R)-4-hydroxy-1-((S)-2-(3-(3-methoxyphenyl)propanamido)-3,3-dimethylbutanoyl)-N-(4-(4-methylthiazol-5-yl)benzyl)pyrrolidine-2-carboxamide Example 78

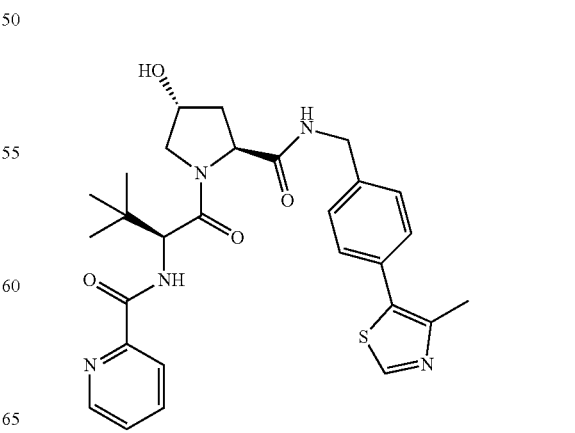

207

N—((S)-1-((2S,4R)-4-hydroxy-2-(4-(4-methylthi-azol-5-yl)benzylcarbamoyl)pyrrolidin-1-yl)-3,3-dimethyl-1-oxobutan-2-yl)picolinamide Example 79

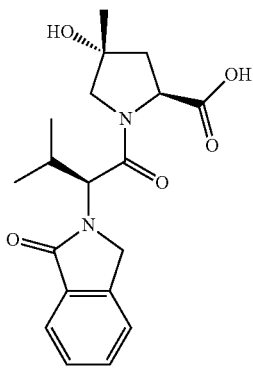 [SMILES: CC(C)[C@@H](C(=O)N1C[C@](C)(O)C[C@H]1C(=O)O)N1Cc2ccccc2C1=O]

(2S,4R)-4-hydroxy-4-methyl-1-[(2S)-3-methyl-2-(1-oxo-2,3-dihydro-1H-isoindol-2-yl)butanoyl]pyrrolidine-2-carboxylic acid Example 80

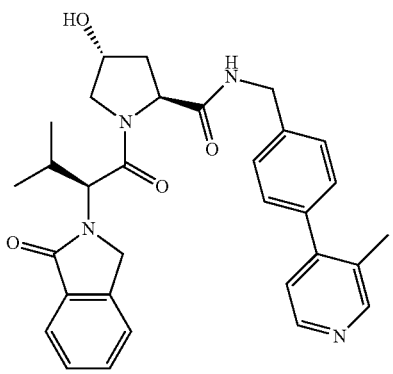 [SMILES: Cc1cnccc1-c1ccc(CNC(=O)[C@@H]2C[C@@H](O)CN2C(=O)[C@H](C(C)C)N2Cc3ccccc3C2=O)cc1]

(2S,4R)-4-hydroxy-1-((S)-3-methyl-2-(1-oxoisoindolin-2-yl)butanoyl)-N-(4-(3-methylpyridin-4-yl)benzyl)pyrrolidine-2-carboxamide Example 81

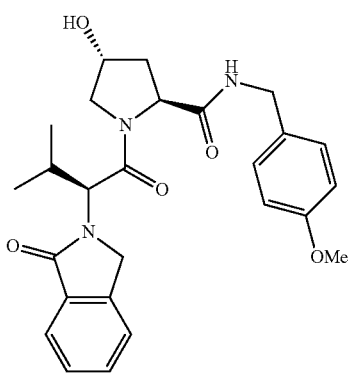 [SMILES: COc1ccc(CNC(=O)[C@@H]2C[C@@H](O)CN2C(=O)[C@H](C(C)C)N2Cc3ccccc3C2=O)cc1]

208

(2S,4R)-4-hydroxy-N-(4-methoxybenzyl)-1-((S)-3-methyl-2-(1-oxoisoindolin-2-yl)butanoyl)pyrrolidine-2-carboxamide Example 82

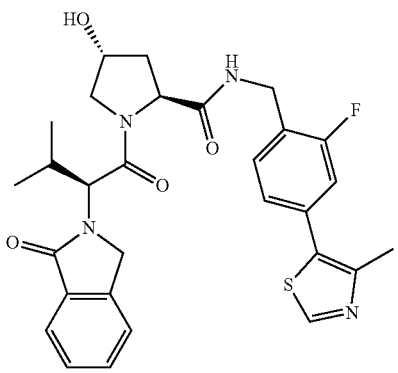 [SMILES: Cc1ncsc1-c1ccc(CNC(=O)[C@@H]2C[C@@H](O)CN2C(=O)[C@H](C(C)C)N2Cc3ccccc3C2=O)c(F)c1]

(2S,4R)—N-(2-fluoro-4-(4-methylthiazol-5-yl)benzyl)-4-hydroxy-1-((S)-3-methyl-2-(1-oxoisoindolin-2-yl)butanoyl)pyrrolidine-2-carboxamide Example 83

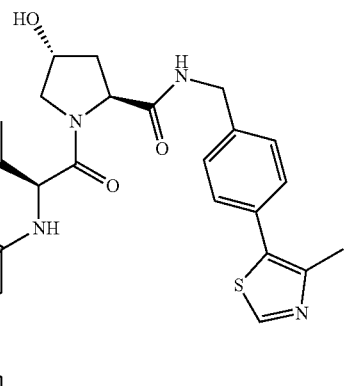

209

(2S,4R)-4-hydroxy-1-((S)-2-(3-(2-methoxyphenyl)
propanamido)-3,3-dimethylbutanoyl)-N-(4-(4-meth-
ylthiazol-5-yl)benzyl)pyrrolidine-2-carboxamide Example 84

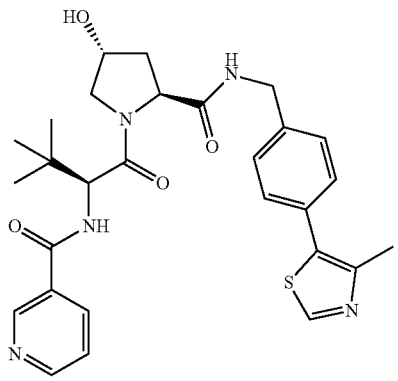 [SMILES: Cc1ncsc1-c1ccc(CNC(=O)[C@@H]2C[C@@H](O)CN2C(=O)[C@@H](NC(=O)c2cccnc2)C(C)(C)C)cc1]

N—((S)-1-(((2S,4R)-4-hydroxy-2-(4-(4-methylthi-
azol-5-yl)benzylcarbamoyl)pyrrolidin-1-yl)-3,3-
dimethyl-1-oxobutan-2-yl)nicotinamide Example 85

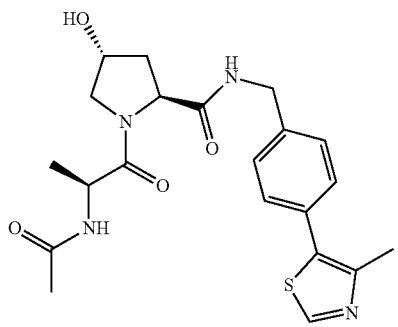 [SMILES: CC(=O)N[C@@H](C)C(=O)N1C[C@H](O)C[C@H]1C(=O)NCc1ccc(-c2scnc2C)cc1]

(2S,4R)-1-((S)-2-acetamidopropanoyl)-4-hydroxy-
N-(4-(4-methylthiazol-5-yl)benzyl)pyrrolidine-2-
carboxamide Example 86

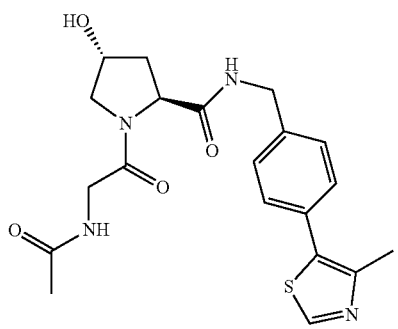 [SMILES: CC(=O)NCC(=O)N1C[C@H](O)C[C@H]1C(=O)NCc1ccc(-c2scnc2C)cc1]

210

(2S,4R)-1-(2-acetamidoacetyl)-4-hydroxy-N-(4-(4-
methylthiazol-5-yl)benzyl)pyrrolidine-2-carboxam-
ide Example 87

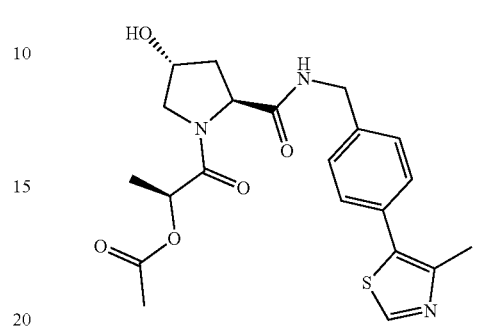

(S)-1-((2S,4R)-4-hydroxy-2-(4-(4-methylthiazol-5-
yl)benzylcarbamoyl)pyrrolidin-1-yl)-1-oxopropan-2-
yl acetate Example 88

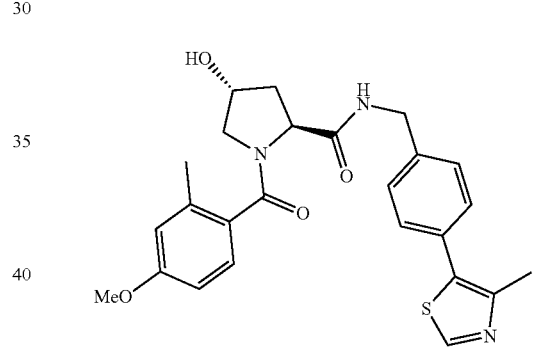

(2S,4R)-4-hydroxy-1-(4-methoxy-2-methylbenzoyl)-
N-(4-(4-methylthiazol-5-yl)benzyl)pyrrolidine-2-
carboxamide Example 89

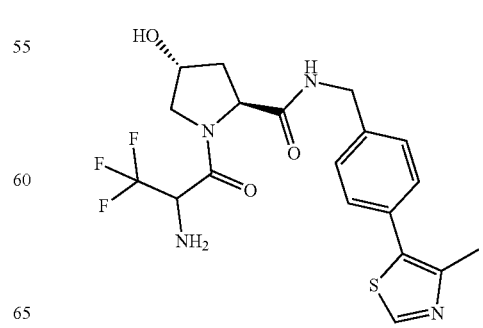

211

(2S,4R)-1-(2-amino-3,3,3-trifluoropropanoyl)-4-hydroxy-N-(4-(4-methylthiazol-5-yl)benzyl)pyrrolidine-2-carboxamide Example 90

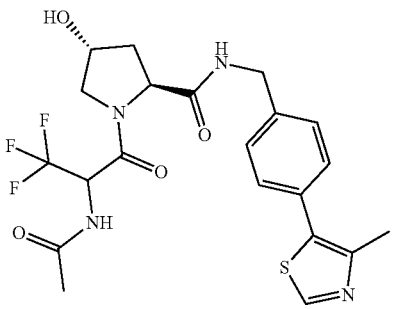 [SMILES: CC(=O)NC(C(=O)N1C[C@H](O)C[C@H]1C(=O)NCc1ccc(-c2scnc2C)cc1)C(F)(F)F]

(2S,4R)-1-(2-acetamido-3,3,3-trifluoropropanoyl)-4-hydroxy-N-(4-(4-methylthiazol-5-yl)benzyl)pyrrolidine-2-carboxamide Example 91

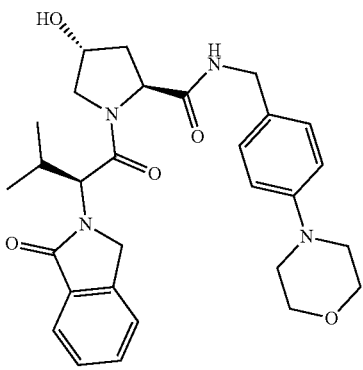 [SMILES: CC(C)[C@@H](C(=O)N1C[C@H](O)C[C@H]1C(=O)NCc1ccc(N2CCOCC2)cc1)N1Cc2ccccc2C1=O]

(2S,4R)-4-hydroxy-1-((S)-3-methyl-2-(1-oxoisoindolin-2-yl)butanoyl)-N-(4-morpholinobenzyl)pyrrolidine-2-carboxamide Example 92

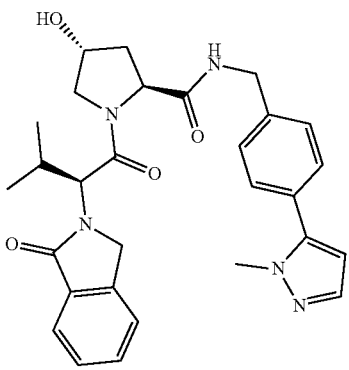

212

(2S,4R)-4-hydroxy-N-(4-(1-methyl-1H-pyrazol-5-yl)benzyl)-1-((S)-3-methyl-2-(1-oxoisoindolin-2-yl)butanoyl)pyrrolidine-2-carboxamide Example 93

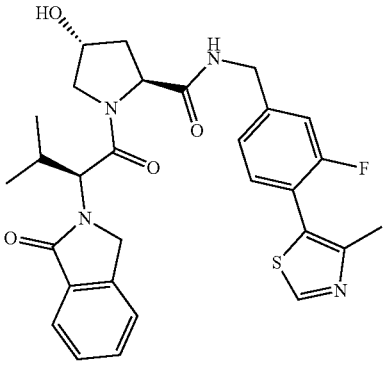 [SMILES: Cc1ncsc1-c1ccc(CNC(=O)[C@@H]2C[C@@H](O)CN2C(=O)[C@H](C(C)C)N2Cc3ccccc3C2=O)cc1F]

(2S,4R)—N-(3-fluoro-4-(4-methylthiazol-5-yl)benzyl)-4-hydroxy-1-((S)-3-methyl-2-(1-oxoisoindolin-2-yl)butanoyl)pyrrolidine-2-carboxamide Example 94

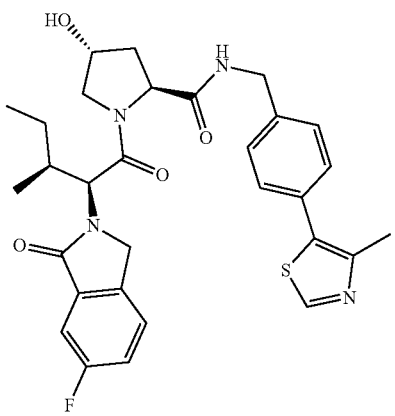 [SMILES: CC[C@H](C)[C@@H](C(=O)N1C[C@H](O)C[C@H]1C(=O)NCc1ccc(-c2scnc2C)cc1)N1Cc2ccc(F)cc2C1=O]

(2S,4R)-1-((2S,3S)-2-(6-fluoro-1-oxoisoindolin-2-yl)-3-methylpentanoyl)-4-hydroxy-N-(4-(4-methylthiazol-5-yl)benzyl)pyrrolidine-2-carboxamide Example 95

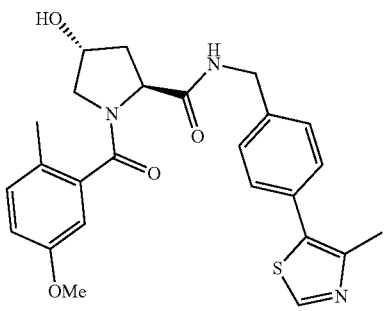 [SMILES: COc1ccc(C)c(C(=O)N2C[C@H](O)C[C@H]2C(=O)NCc2ccc(-c3scnc3C)cc2)c1]

213

(2S,4R)-4-hydroxy-1-(5-methoxy-2-methylbenzoyl)-N-(4-(4-methylthiazol-5-yl)benzyl)pyrrolidine-2-carboxamide Example 96

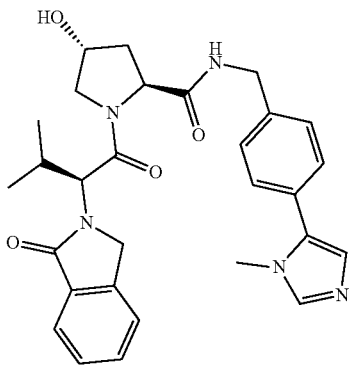 [SMILES: CC(C)[C@@H](C(=O)N1C[C@H](O)C[C@H]1C(=O)NCc1ccc(-c2cncn2C)cc1)N1Cc2ccccc2C1=O]

(2S,4R)-4-hydroxy-N-(4-(1-methyl-1H-imidazol-5-yl)benzyl)-1-((S)-3-methyl-2-(1-oxoisoindolin-2-yl)butanoyl)pyrrolidine-2-carboxamide Example 97

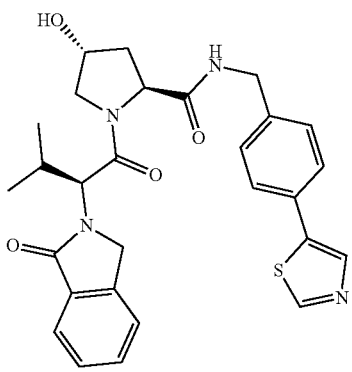 [SMILES: CC(C)[C@@H](C(=O)N1C[C@H](O)C[C@H]1C(=O)NCc1ccc(-c2cncs2)cc1)N1Cc2ccccc2C1=O]

(2S,4R)-4-hydroxy-1-((S)-3-methyl-2-(1-oxoisoindolin-2-yl)butanoyl)-N-(4-(thiazol-5-yl)benzyl)pyrrolidine-2-carboxamide; s Example 98

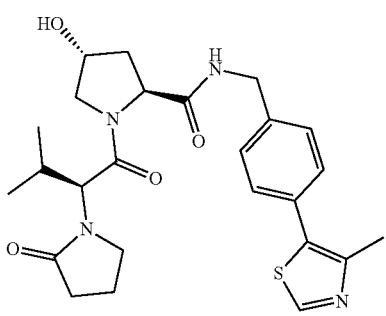 [SMILES: Cc1ncsc1-c1ccc(CNC(=O)[C@@H]2C[C@@H](O)CN2C(=O)[C@H](C(C)C)N2CCCC2=O)cc1]

214

(2S,4R)-4-hydroxy-1-((S)-3-methyl-2-(2-oxopyrrolidin-1-yl)butanoyl)-N-(4-(4-methylthiazol-5-yl)benzyl)pyrrolidine-2-carboxamide Example 99

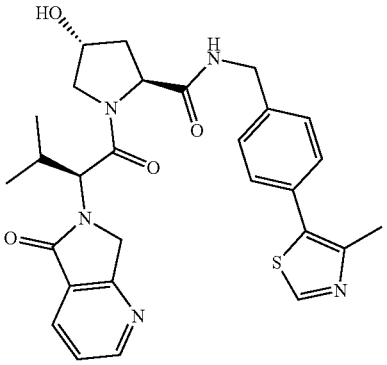 [SMILES: Cc1ncsc1-c1ccc(CNC(=O)[C@@H]2C[C@@H](O)CN2C(=O)[C@H](C(C)C)N2Cc3ncccc3C2=O)cc1]

(2S,4R)-4-hydroxy-1-((S)-3-methyl-2-(5-oxo-5H-pyrrolo[3,4-b]pyridin-6(7H)-yl)butanoyl)-N-(4-(4-methylthiazol-5-yl)benzyl)pyrrolidine-2-carboxamide Example 100

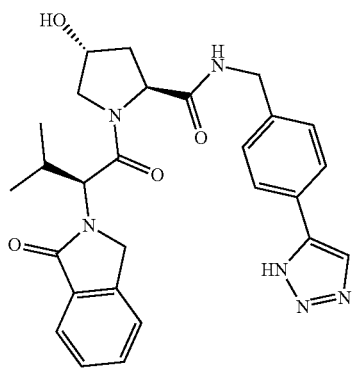 [SMILES: CC(C)[C@@H](C(=O)N1C[C@H](O)C[C@H]1C(=O)NCc1ccc(-c2cnn[nH]2)cc1)N1Cc2ccccc2C1=O]

(2S,4R)—N-(4-(1H-1,2,3-triazol-5-yl)benzyl)-4-hydroxy-1-((S)-3-methyl-2-(1-oxoisoindolin-2-yl)butanoyl)pyrrolidine-2-carboxamide Example 101

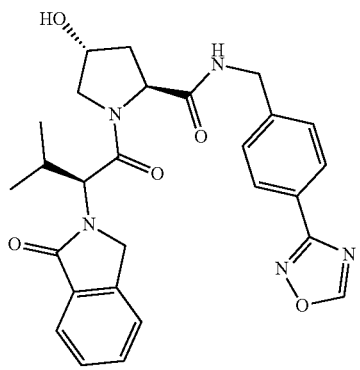 [SMILES: CC(C)[C@@H](C(=O)N1C[C@H](O)C[C@H]1C(=O)NCc1ccc(-c2ncon2)cc1)N1Cc2ccccc2C1=O]

215

(2S,4R)—N-(4-(1,2,4-oxadiazol-3-yl)benzyl)-4-hydroxy-1-((S)-3-methyl-2-(1-oxoisoindolin-2-yl)butanoyl)pyrrolidine-2-carboxamide Example 102

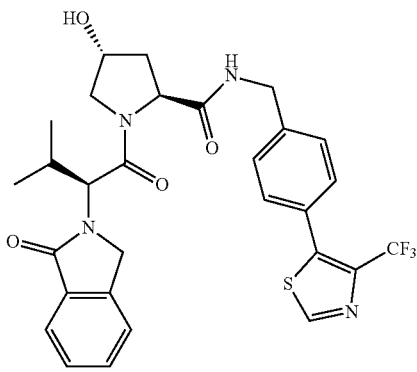 [SMILES: CC(C)[C@@H](C(=O)N1C[C@H](O)C[C@H]1C(=O)NCc1ccc(-c2scnc2C(F)(F)F)cc1)N1Cc2ccccc2C1=O]

(2S,4R)-4-hydroxy-1-((S)-3-methyl-2-(1-oxoisoindolin-2-yl)butanoyl)-N-(4-(4-(trifluoromethyl)thiazol-5-yl)benzyl)pyrrolidine-2-carboxamide Example 103

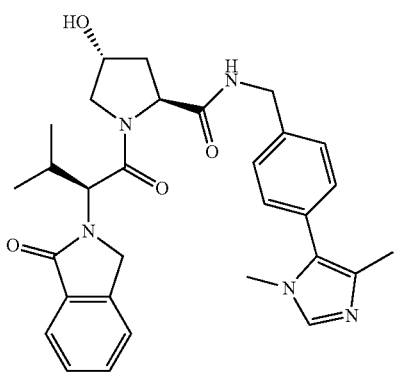 [SMILES: Cc1ncn(C)c1-c1ccc(CNC(=O)[C@@H]2C[C@@H](O)CN2C(=O)[C@H](C(C)C)N2Cc3ccccc3C2=O)cc1]

(2S,4R)—N-(4-(1,4-dimethyl-1H-imidazol-5-yl)benzyl)-4-hydroxy-1-((S)-3-methyl-2-(1-oxoisoindolin-2-yl)butanoyl)pyrrolidine-2-carboxamide Example 104

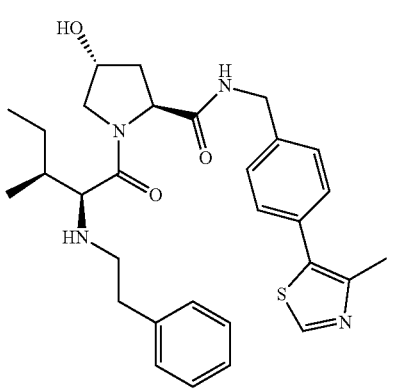 [SMILES: CC[C@H](C)[C@H](NCCc1ccccc1)C(=O)N1C[C@H](O)C[C@H]1C(=O)NCc1ccc(-c2scnc2C)cc1]

216

(2S,4R)-4-hydroxy-1-((2S,3S)-3-methyl-2-(phenethylamino)pentanoyl)-N-(4-(4-methylthiazol-5-yl)benzyl)pyrrolidine-2-carboxamide Example 105

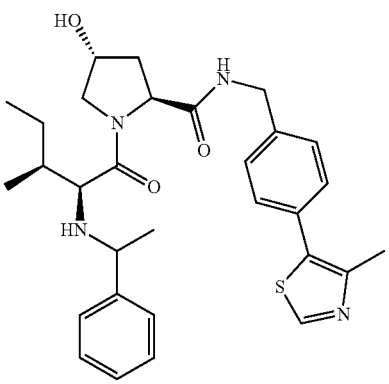 [SMILES: CC[C@H](C)[C@H](NC(C)c1ccccc1)C(=O)N1C[C@H](O)C[C@H]1C(=O)NCc1ccc(-c2scnc2C)cc1]

(2S,4R)-4-hydroxy-1-((2S,3S)-3-methyl-2-(1-phenylethylamino)pentanoyl)-N-(4-(4-methylthiazol-5-yl)benzyl)pyrrolidine-2-carboxamide Example 106

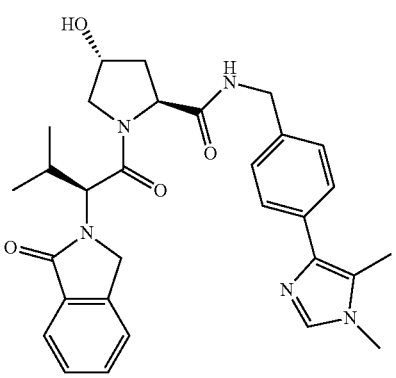 [SMILES: Cc1c(-c2ccc(CNC(=O)[C@@H]3C[C@@H](O)CN3C(=O)[C@H](C(C)C)N3Cc4ccccc4C3=O)cc2)ncn1C]

(2S,4R)—N-(4-(1,5-dimethyl-1H-imidazol-4-yl)benzyl)-4-hydroxy-1-((S)-3-methyl-2-(1-oxoisoindolin-2-yl)butanoyl)pyrrolidine-2-carboxamide Example 107

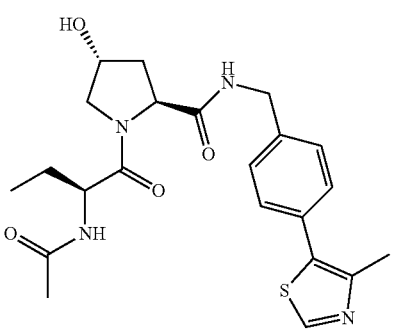 [SMILES: CC[C@H](NC(C)=O)C(=O)N1C[C@H](O)C[C@H]1C(=O)NCc1ccc(-c2scnc2C)cc1]

217

(2S,4R)-1-((S)-2-acetamidobutanoyl)-4-hydroxy-N-
(4-(4-methylthiazol-5-yl)benzyl)pyrrolidine-2-car-
boxamide Example 108

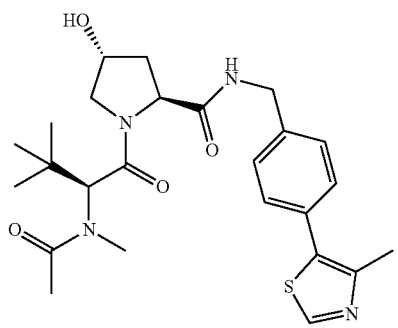 [SMILES: CC(=O)N(C)[C@H](C(=O)N1C[C@H](O)C[C@H]1C(=O)NCc1ccc(-c2scnc2C)cc1)C(C)(C)C]

(2S,4R)-1-((S)-3,3-dimethyl-2-(N-methylacetamido)
butanoyl)-4-hydroxy-N-(4-(4-methylthiazol-5-yl)
benzyl)pyrrolidine-2-carboxamide Example 109

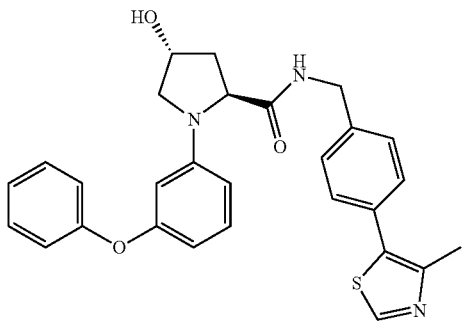 [SMILES: Cc1ncsc1-c1ccc(CNC(=O)[C@@H]2C[C@@H](O)CN2c2cccc(Oc3ccccc3)c2)cc1]

(2S,4R)-4-hydroxy-N-(4-(4-methylthiazol-5-yl)ben-
zyl)-1-(3-phenoxyphenyl)pyrrolidine-2-carboxamide Example 110

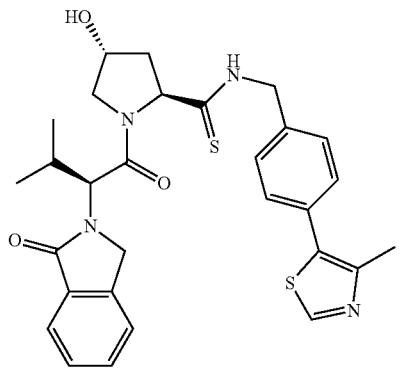 [SMILES: Cc1ncsc1-c1ccc(CNC(=S)[C@@H]2C[C@@H](O)CN2C(=O)[C@H](C(C)C)N2Cc3ccccc3C2=O)cc1]

218

(2S,4R)-4-hydroxy-1-((S)-3-methyl-2-(1-oxoisoin-
dolin-2-yl)butanoyl)-N-(4-(4-methylthiazol-5-yl)
benzyl)pyrrolidine-2-carbothioamide Example 111

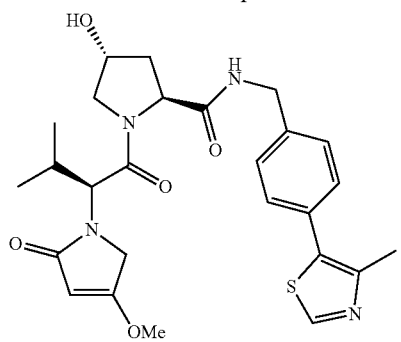

(2S,4R)-4-hydroxy-1-((S)-2-(4-methoxy-2-oxo-2,5-
dihydro-1H-pyrrol-1-yl)-3-methylbutanoyl)-N-(4-(4-
methylthiazol-5-yl)benzyl)pyrrolidine-2-carboxam-
ide Example 112

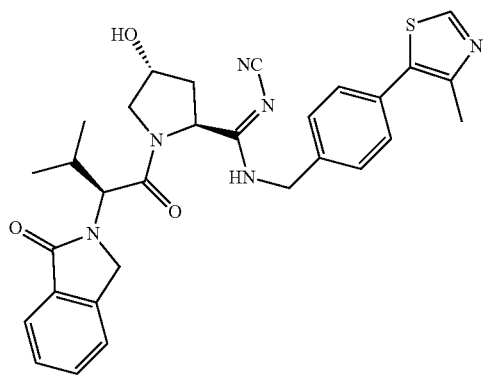 [SMILES: Cc1ncsc1-c1ccc(CN/C(=N/C#N)[C@@H]2C[C@@H](O)CN2C(=O)[C@H](C(C)C)N2Cc3ccccc3C2=O)cc1]

(2S,4R,E)-N'-cyano-4-hydroxy-1-((S)-3-methyl-2-
(1-oxoisoindolin-2-yl)butanoyl)-N-(4-(4-methylthi-
azol-5-yl)benzyl)pyrrolidine-2-carboximidamide Example 113

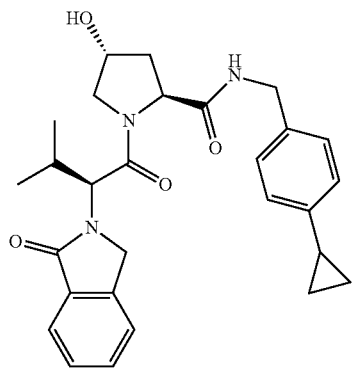 [SMILES: CC(C)[C@@H](C(=O)N1C[C@H](O)C[C@H]1C(=O)NCc1ccc(C2CC2)cc1)N1Cc2ccccc2C1=O]

(2S,4R)—N-(4-cyclopropylbenzyl)-4-hydroxy-1-((S)-3-methyl-2-(1-oxoisoindolin-2-yl)butanoyl)pyrrolidine-2-carboxamide Example 114

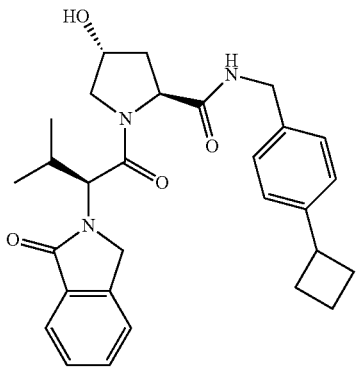 [SMILES: CC(C)[C@@H](C(=O)N1C[C@H](O)C[C@H]1C(=O)NCc1ccc(C2CCC2)cc1)N1Cc2ccccc2C1=O]

(2S,4R)—N-(4-cyclobutylbenzyl)-4-hydroxy-1-((S)-3-methyl-2-(1-oxoisoindolin-2-yl)butanoyl)pyrrolidine-2-carboxamide Example 115

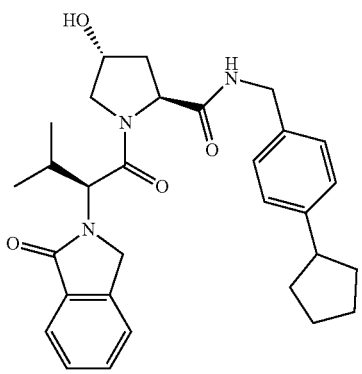 [SMILES: CC(C)[C@@H](C(=O)N1C[C@H](O)C[C@H]1C(=O)NCc1ccc(C2CCCC2)cc1)N1Cc2ccccc2C1=O]

(2S,4R)—N-(4-cyclopentylbenzyl)-4-hydroxy-1-((S)-3-methyl-2-(1-oxoisoindolin-2-yl)butanoyl)pyrrolidine-2-carboxamide Example 116

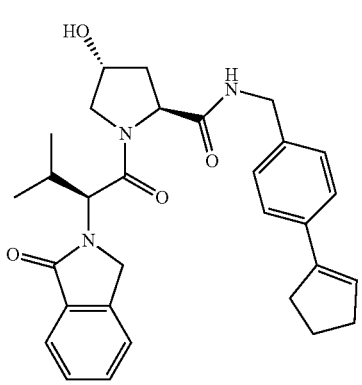 [SMILES: CC(C)[C@@H](C(=O)N1C[C@H](O)C[C@H]1C(=O)NCc1ccc(C2=CCCC2)cc1)N1Cc2ccccc2C1=O]

(2S,4R)—N-(4-cyclopentenylbenzyl)-4-hydroxy-1-((S)-3-methyl-2-(1-oxoisoindolin-2-yl)butanoyl)pyrrolidine-2-carboxamide Example 117

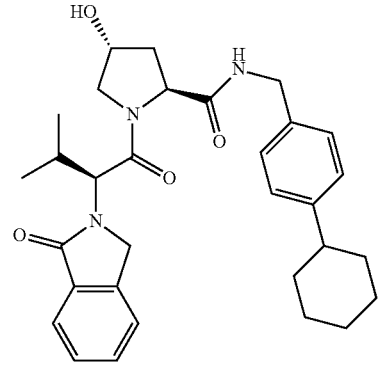 [SMILES: CC(C)[C@@H](C(=O)N1C[C@H](O)C[C@H]1C(=O)NCc1ccc(C2CCCCC2)cc1)N1Cc2ccccc2C1=O]

(2S,4R)—N-(4-cyclohexylbenzyl)-4-hydroxy-1-((S)-3-methyl-2-(1-oxoisoindolin-2-yl)butanoyl)pyrrolidine-2-carboxamide Example 118

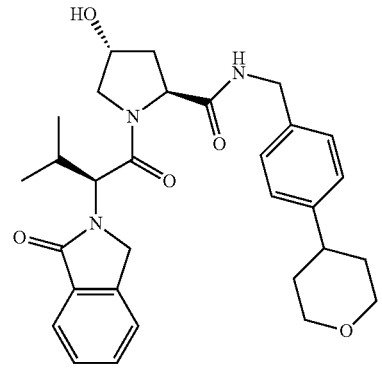 [SMILES: CC(C)[C@@H](C(=O)N1C[C@H](O)C[C@H]1C(=O)NCc1ccc(C2CCOCC2)cc1)N1Cc2ccccc2C1=O]

(2S,4R)-4-hydroxy-1-((S)-3-methyl-2-(1-oxoisoindolin-2-yl)butanoyl)-N-(4-(tetrahydro-2H-pyran-4-yl)benzyl)pyrrolidine-2-carboxamide Example 119

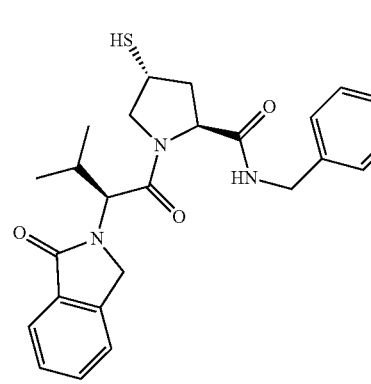

221

(2S,4R)-4-mercapto-1-((S)-3-methyl-2-(1-oxoisoin-
dolin-2-yl)butanoyl)-N-(4-(4-methylthiazol-5-yl)
benzyl)pyrrolidine-2-carboxamide Example 120

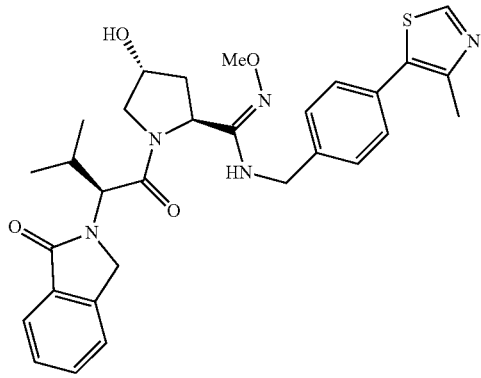 [SMILES: CO/N=C(/NCc1ccc(-c2scnc2C)cc1)[C@@H]1C[C@@H](O)CN1C(=O)[C@H](C(C)C)N1Cc2ccccc2C1=O]

(2S,4R,E)-4-hydroxy-N'-methoxy-1-((S)-3-methyl-
2-(1-oxoisoindolin-2-yl)butanoyl)-N-(4-(4-methyl-
thiazol-5-yl)benzyl)pyrrolidine-2-carboximidamide Example 121

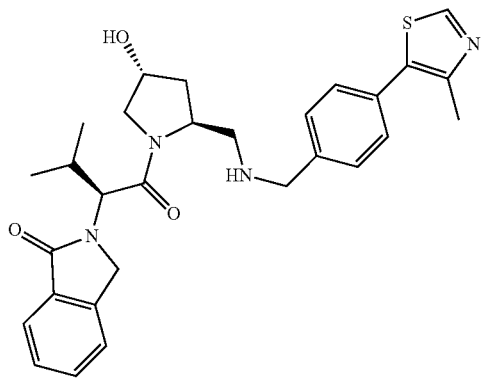 [SMILES: Cc1ncsc1-c1ccc(CNC[C@@H]2C[C@@H](O)CN2C(=O)[C@H](C(C)C)N2Cc3ccccc3C2=O)cc1]

2-((S)-1-((2S,4R)-4-hydroxy-2-((4-(4-methylthiazol-
5-yl)benzylamino)methyl)pyrrolidin-1-yl)-3-methyl-
1-oxobutan-2-yl)isoindolin-1-one Example 122

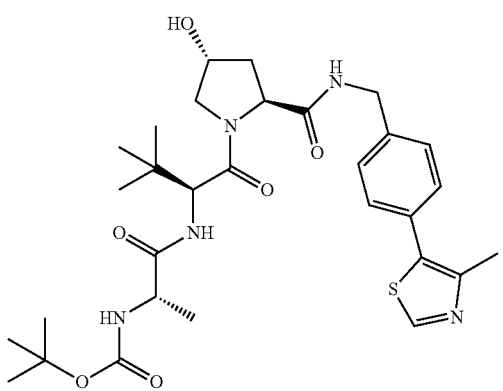 [SMILES: Cc1ncsc1-c1ccc(CNC(=O)[C@@H]2C[C@@H](O)CN2C(=O)[C@@H](NC(=O)[C@H](C)NC(=O)OC(C)(C)C)C(C)(C)C)cc1]

222 tert-butyl (S)-1-((S)-1-((2S,4R)-4-hydroxy-2-(4-(4-
methylthiazol-5-yl)benzylcarbamoyl)pyrrolidin-1-
yl)-3,3-dimethyl-1-oxobutan-2-ylamino)-1-oxopro-
pan-2-ylcarbamate Example 123

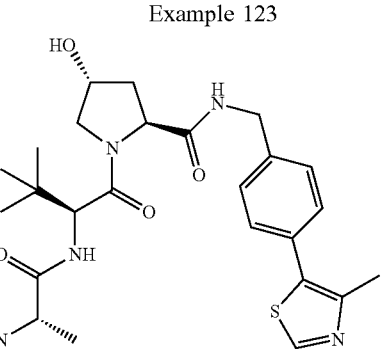

(2S,4R)-1-((S)-2-((S)-2-aminopropanamido)-3,3-
dimethylbutanoyl)-4-hydroxy-N-(4-(4-methylthi-
azol-5-yl)benzyl)pyrrolidine-2-carboxamide Example 124

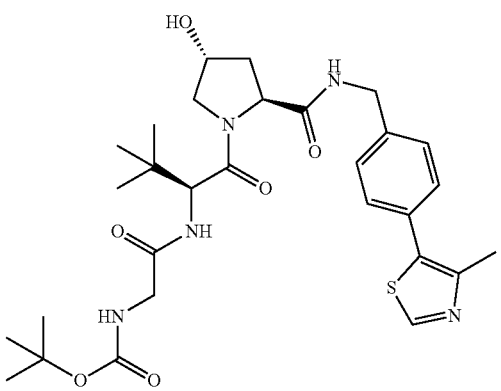 [SMILES: Cc1ncsc1-c1ccc(CNC(=O)[C@@H]2C[C@@H](O)CN2C(=O)[C@@H](NC(=O)CNC(=O)OC(C)(C)C)C(C)(C)C)cc1]

tert-butyl 2-((S)-1-((2S,4R)-4-hydroxy-2-(4-(4-
methylthiazol-5-yl)benzylcarbamoyl)pyrrolidin-1-
yl)-3,3-dimethyl-1-oxobutan-2-ylamino)-2-oxoethyl-
carbamate Example 125

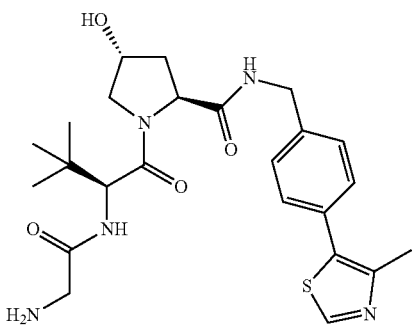 [SMILES: Cc1ncsc1-c1ccc(CNC(=O)[C@@H]2C[C@@H](O)CN2C(=O)[C@@H](NC(=O)CN)C(C)(C)C)cc1]

223

(2S,4R)-1-((S)-2-(2-aminoacetamido)-3,3-dimethylbutanoyl)-4-hydroxy-N-(4-(4-methylthiazol-5-yl)benzyl)pyrrolidine-2-carboxamide Example 126

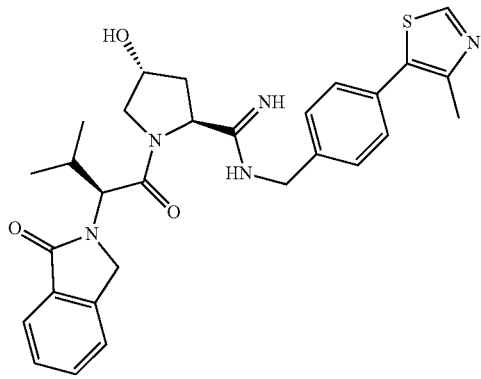 [SMILES: Cc1ncsc1-c1ccc(CNC(=N)[C@@H]2C[C@@H](O)CN2C(=O)[C@H](C(C)C)N2Cc3ccccc3C2=O)cc1]

(2S,4R)-4-hydroxy-1-((S)-3-methyl-2-(1-oxoisoindolin-2-yl)butanoyl)-N-(4-(4-methylthiazol-5-yl)benzyl)pyrrolidine-2-carboximidamide Example 127

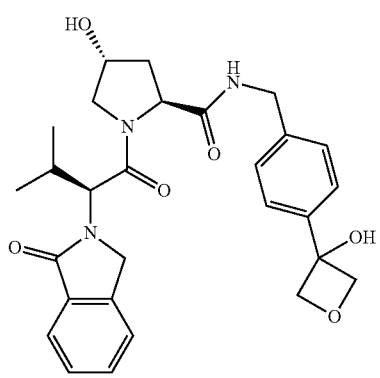 [SMILES: CC(C)[C@@H](C(=O)N1C[C@H](O)C[C@H]1C(=O)NCc1ccc(C2(O)COC2)cc1)N1Cc2ccccc2C1=O]

(2S,4R)-4-hydroxy-N-(4-(3-hydroxyoxetan-3-yl)benzyl)-1-((S)-3-methyl-2-(1-oxoisoindolin-2-yl)butanoyl)pyrrolidine-2-carboxamide Example 128

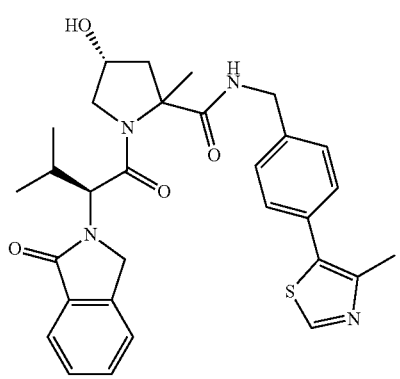 [SMILES: Cc1ncsc1-c1ccc(CNC(=O)C2(C)C[C@@H](O)CN2C(=O)[C@H](C(C)C)N2Cc3ccccc3C2=O)cc1]

224

((4R)-4-hydroxy-2-methyl-1-((S)-3-methyl-2-(1-oxoisoindolin-2-yl)butanoyl)-N-(4-(4-methylthiazol-5-yl)benzyl)pyrrolidine-2-carboxamide Isomer A Example 129

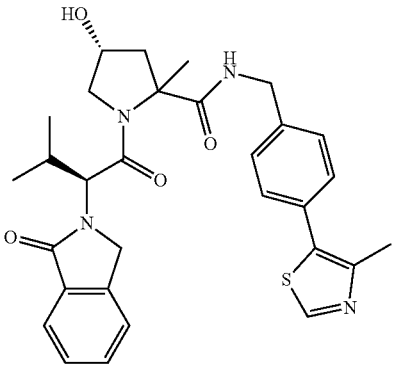 [SMILES: Cc1ncsc1-c1ccc(CNC(=O)C2(C)C[C@@H](O)CN2C(=O)[C@H](C(C)C)N2Cc3ccccc3C2=O)cc1]

((4R)-4-hydroxy-2-methyl-1-((S)-3-methyl-2-(1-oxoisoindolin-2-yl)butanoyl)-N-(4-(4-methylthiazol-5-yl)benzyl)pyrrolidine-2-carboxamide Isomer B Example 130

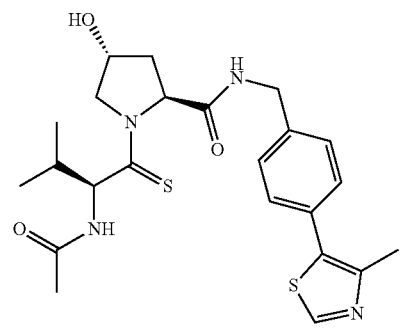 [SMILES: CC(=O)N[C@H](C(=S)N1C[C@H](O)C[C@H]1C(=O)NCc1ccc(-c2scnc2C)cc1)C(C)C]

(2S,4R)-1-((S)-2-acetamido-3-methylbutanethioyl)-4-hydroxy-N-(4-(4-methylthiazol-5-yl)benzyl)pyrrolidine-2-carboxamide Example 131

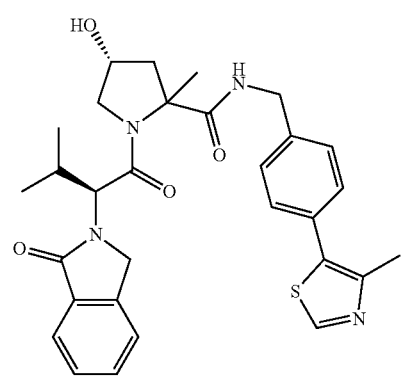 [SMILES: Cc1ncsc1-c1ccc(CNC(=O)C2(C)C[C@@H](O)CN2C(=O)[C@H](C(C)C)N2Cc3ccccc3C2=O)cc1]

((4R)-4-hydroxy-2-methyl-1-((S)-3-methyl-2-(1-oxoisoindolin-2-yl)butanoyl)-N-(4-(4-methylthiazol-5-yl)benzyl)pyrrolidine-2-carboxamide Isomer C Example 132

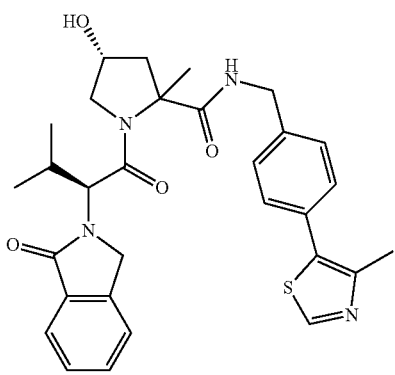 [SMILES: Cc1ncsc1-c1ccc(CNC(=O)C2(C)C[C@@H](O)CN2C(=O)[C@H](C(C)C)N2Cc3ccccc3C2=O)cc1]

((4R)-4-hydroxy-2-methyl-1-((S)-3-methyl-2-(1-oxoisoindolin-2-yl)butanoyl)-N-(4-(4-methylthiazol-5-yl)benzyl)pyrrolidine-2-carboxamide Isomer D Example 133

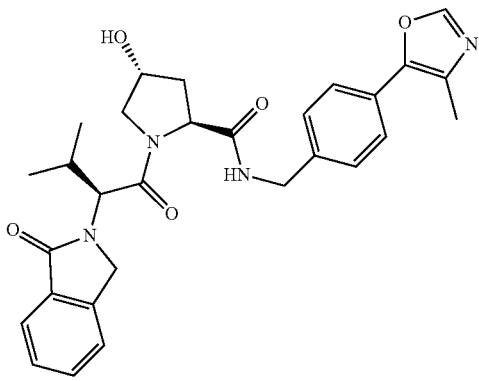 [SMILES: Cc1ncoc1-c1ccc(CNC(=O)[C@@H]2C[C@@H](O)CN2C(=O)[C@H](C(C)C)N2Cc3ccccc3C2=O)cc1]

(2S,4R)-4-hydroxy-1-((S)-3-methyl-2-(1-oxoisoindolin-2-yl)butanoyl)-N-(4-(4-methyloxazol-5-yl)benzyl)pyrrolidine-2-carboxamide Example 134

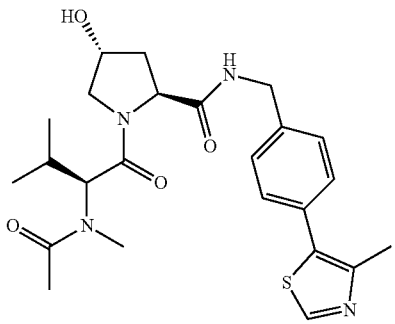 [SMILES: CC(=O)N(C)[C@H](C(=O)N1C[C@H](O)C[C@H]1C(=O)NCc1ccc(-c2scnc2C)cc1)C(C)C]

(2S,4R)-4-hydroxy-1-((S)-3-methyl-2-(N-methylacetamido)butanoyl)-N-(4-(4-methylthiazol-5-yl)benzyl)pyrrolidine-2-carboxamide Example 135

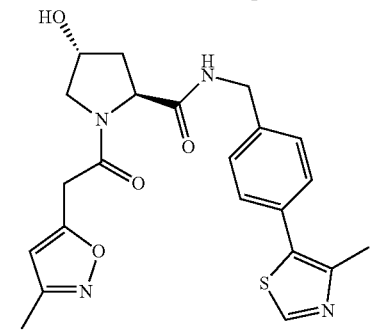

(2S,4R)-4-hydroxy-1-(2-(3-methylisoxazol-5-yl)acetyl)-N-(4-(4-methylthiazol-5-yl)benzyl)pyrrolidine-2-carboxamide Example 136

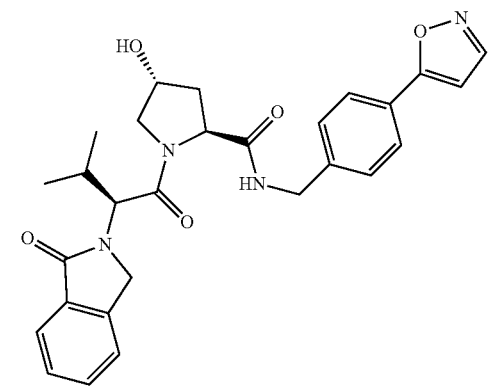 [SMILES: CC(C)[C@@H](C(=O)N1C[C@H](O)C[C@H]1C(=O)NCc1ccc(-c2ccno2)cc1)N1Cc2ccccc2C1=O]

(2S,4R)-4-hydroxy-N-(4-(isoxazol-5-yl)benzyl)-1-((S)-3-methyl-2-(1-oxoisoindolin-2-yl)butanoyl)pyrrolidine-2-carboxamide Example 137

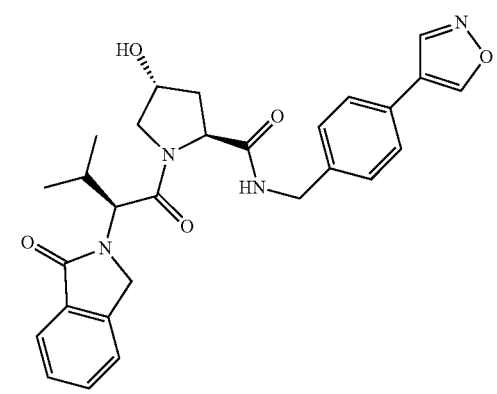 [SMILES: CC(C)[C@@H](C(=O)N1C[C@H](O)C[C@H]1C(=O)NCc1ccc(-c2cnoc2)cc1)N1Cc2ccccc2C1=O]

227

(2S,4R)-4-hydroxy-N-(4-(isoxazol-4-yl)benzyl)-1-((S)-3-methyl-2-(1-oxoisoindolin-2-yl)butanoyl)pyrrolidine-2-carboxamide Example 138

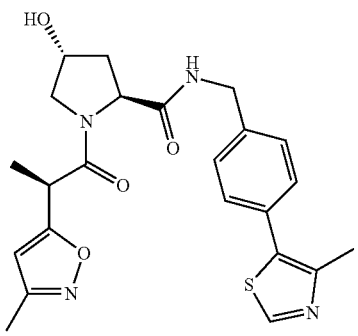

(2S,4R)-4-hydroxy-1-((R)-2-(3-methylisoxazol-5-yl)propanoyl)-N-(4-(4-methylthiazol-5-yl)benzyl)pyrrolidine-2-carboxamide Example 139

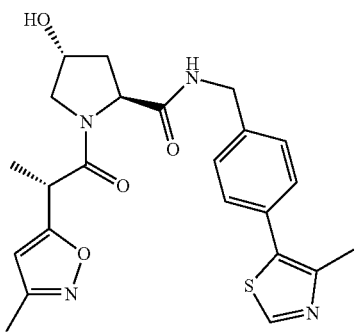

(2S,4R)-4-hydroxy-1-((S)-2-(3-methylisoxazol-5-yl)propanoyl)-N-(4-(4-methylthiazol-5-yl)benzyl)pyrrolidine-2-carboxamide Example 140

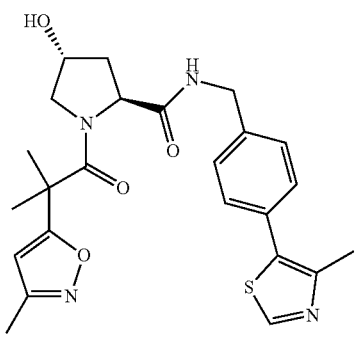

228

(2S,4R)-4-hydroxy-1-(2-methyl-2-(3-methylisoxazol-5-yl)propanoyl)-N-(4-(4-methylthiazol-5-yl)benzyl)pyrrolidine-2-carboxamide Example 141

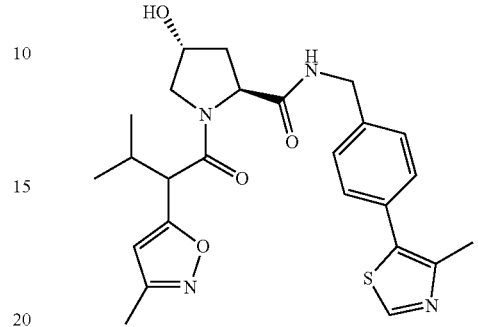

(2S,4R)-4-hydroxy-1-(3-methyl-2-(3-methylisoxazol-5-yl)butanoyl)-N-(4-(4-methylthiazol-5-yl)benzyl)pyrrolidine-2-carboxamide Example 142

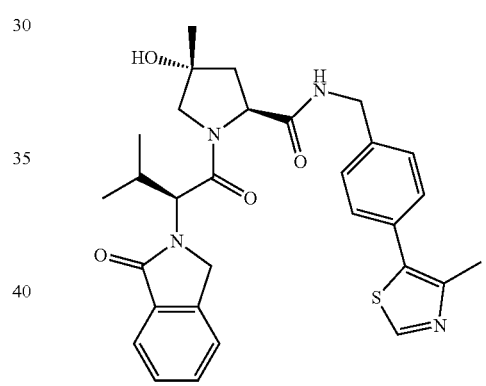

(2S,4R)-4-hydroxy-4-methyl-1-((S)-3-methyl-2-(1-oxoisoindolin-2-yl)butanoyl)-N-(4-(4-methylthiazol-5-yl)benzyl)pyrrolidine-2-carboxamide Example 143

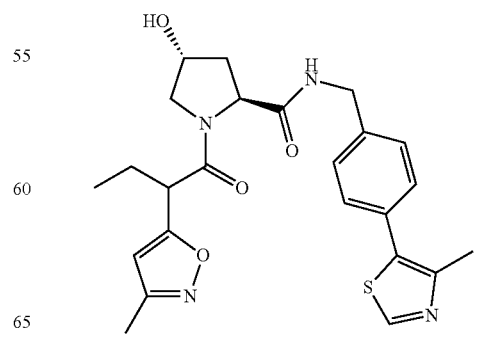

229

(2S,4R)-4-hydroxy-1-(2-(3-methylisoxazol-5-yl)
butanoyl)-N-(4-(4-methylthiazol-5-yl)benzyl)pyrro-
lidine-2-carboxamide Example 144

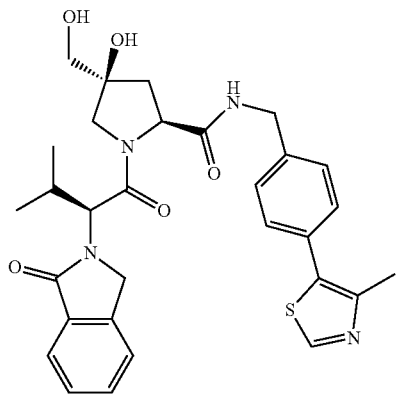 [SMILES: Cc1ncsc1-c1ccc(CNC(=O)[C@@H]2C[C@@](O)(CO)CN2C(=O)[C@H](C(C)C)N2Cc3ccccc3C2=O)cc1]

(2S,4S)-4-hydroxy-4-(hydroxymethyl)-1-((S)-3-
methyl-2-(1-oxoisoindolin-2-yl)butanoyl)-N-(4-(4-
methylthiazol-5-yl)benzyl)pyrrolidine-2-carboxam-
ide Example 145

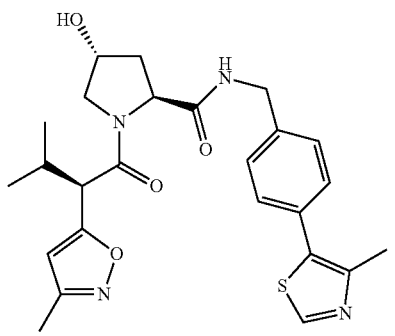 [SMILES: Cc1cc([C@H](C(=O)N2C[C@H](O)C[C@H]2C(=O)NCc2ccc(-c3scnc3C)cc2)C(C)C)on1]

(2S,4R)-4-hydroxy-1-((R)-3-methyl-2-(3-methyl-
isoxazol-5-yl)butanoyl)-N-(4-(4-methylthiazol-5-yl)
benzyl)pyrrolidine-2-carboxamide Example 146

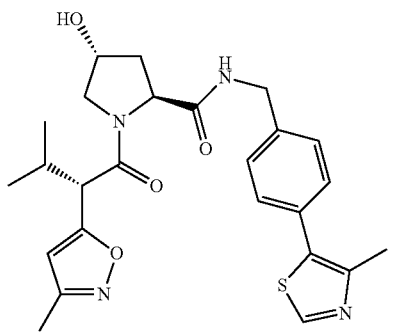 [SMILES: Cc1cc([C@@H](C(=O)N2C[C@H](O)C[C@H]2C(=O)NCc2ccc(-c3scnc3C)cc2)C(C)C)on1]

230

(2S,4R)-4-hydroxy-1-((S)-3-methyl-2-(3-methyl-
isoxazol-5-yl)butanoyl)-N-(4-(4-methylthiazol-5-yl)
benzyl)pyrrolidine-2-carboxamide Example 147

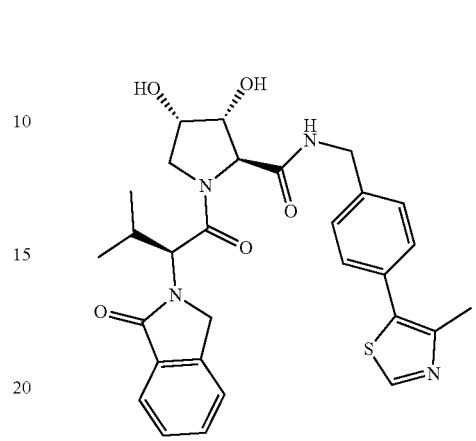

(2S,3R,4S)-3,4-dihydroxy-1-((S)-3-methyl-2-(1-
oxoisoindolin-2-yl)butanoyl)-N-(4-(4-methylthiazol-
5-yl)benzyl)pyrrolidine-2-carboxamide Example 148

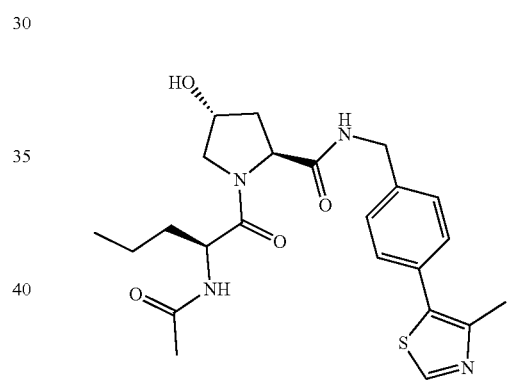

(2S,4R)-1-((S)-2-acetamidopentanoyl)-4-hydroxy-N-
(4-(4-methylthiazol-5-yl)benzyl)pyrrolidine-2-car-
boxamide Example 149

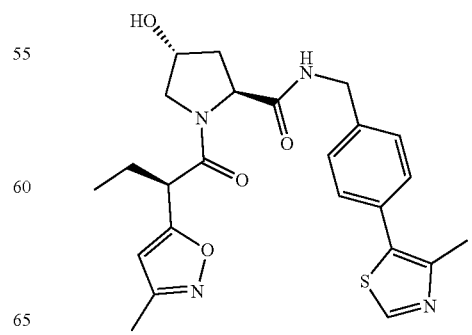

231

(2S,4R)-4-hydroxy-1-((R)-2-(3-methylisoxazol-5-yl)
butanoyl)-N-(4-(4-methylthiazol-5-yl)benzyl)pyrro-
lidine-2-carboxamide Example 150

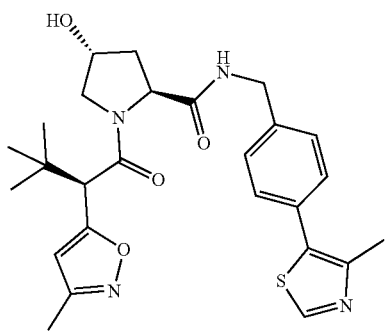 [SMILES: Cc1cc([C@H](C(=O)N2C[C@H](O)C[C@H]2C(=O)NCc2ccc(-c3scnc3C)cc2)C(C)(C)C)on1]

(2S,4R)-1-((R)-3,3-dimethyl-2-(3-methylisoxazol-5-
yl)butanoyl)-4-hydroxy-N-(4-(4-methylthiazol-5-yl)
benzyl)pyrrolidine-2-carboxamide Example 151

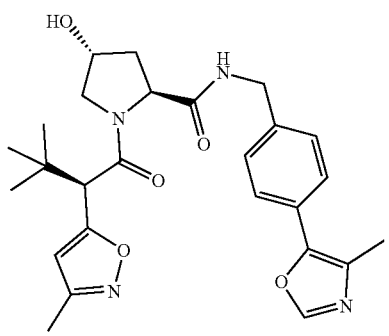 [SMILES: Cc1cc([C@H](C(=O)N2C[C@H](O)C[C@H]2C(=O)NCc2ccc(-c3ocnc3C)cc2)C(C)(C)C)on1]

(2S,4R)-1-((R)-3,3-dimethyl-2-(3-methylisoxazol-5-
yl)butanoyl)-4-hydroxy-N-(4-(4-methyloxazol-5-yl)
benzyl)pyrrolidine-2-carboxamide Example 152

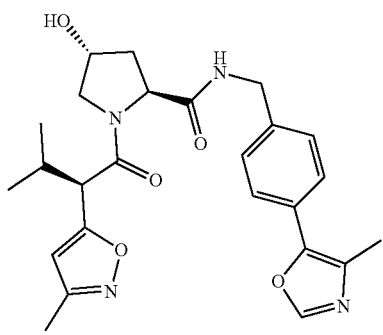 [SMILES: Cc1cc([C@H](C(=O)N2C[C@H](O)C[C@H]2C(=O)NCc2ccc(-c3ocnc3C)cc2)C(C)C)on1]

232

(2S,4R)-4-hydroxy-1-((R)-3-methyl-2-(3-methyl-
isoxazol-5-yl)butanoyl)-N-(4-(4-methyloxazol-5-yl)
benzyl)pyrrolidine-2-carboxamide Example 153

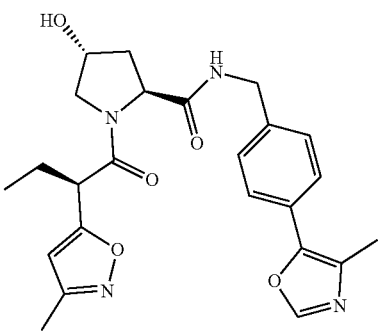 [SMILES: CC[C@@H](C(=O)N1C[C@H](O)C[C@H]1C(=O)NCc1ccc(-c2ocnc2C)cc1)c1cc(C)no1]

(2S,4R)-4-hydroxy-1-((R)-2-(3-methylisoxazol-5-yl)
butanoyl)-N-(4-(4-methyloxazol-5-yl)benzyl)pyrroli-
dine-2-carboxamide Example 154

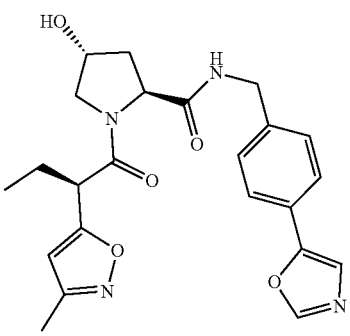 [SMILES: CC[C@@H](C(=O)N1C[C@H](O)C[C@H]1C(=O)NCc1ccc(-c2cnco2)cc1)c1cc(C)no1]

(2S,4R)-4-hydroxy-1-((R)-2-(3-methylisoxazol-5-yl)
butanoyl)-N-(4-(oxazol-5-yl)benzyl)pyrrolidine-2-
carboxamide Example 155

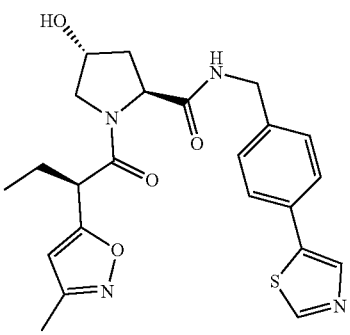 [SMILES: CC[C@@H](C(=O)N1C[C@H](O)C[C@H]1C(=O)NCc1ccc(-c2cncs2)cc1)c1cc(C)no1]

233

(2S,4R)-4-hydroxy-1-((R)-2-(3-methylisoxazol-5-yl)butanoyl)-N-(4-(thiazol-5-yl)benzyl)pyrrolidine-2-carboxamide Example 156

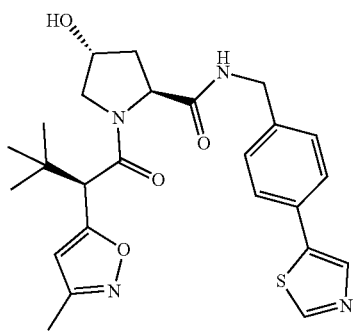 [SMILES: Cc1cc([C@H](C(=O)N2C[C@H](O)C[C@H]2C(=O)NCc2ccc(-c3cncs3)cc2)C(C)(C)C)on1]

(2S,4R)-1-((R)-3,3-dimethyl-2-(3-methylisoxazol-5-yl)butanoyl)-4-hydroxy-N-(4-(thiazol-5-yl)benzyl)pyrrolidine-2-carboxamide Example 157

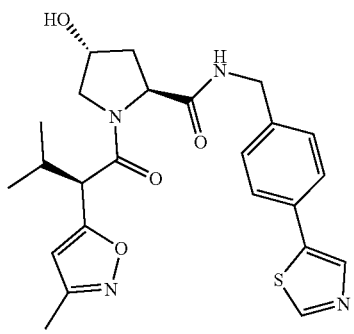

(2S,4R)-4-hydroxy-1-((R)-3-methyl-2-(3-methyl-isoxazol-5-yl)butanoyl)-N-(4-(thiazol-5-yl)benzyl)pyrrolidine-2-carboxamide Example 158

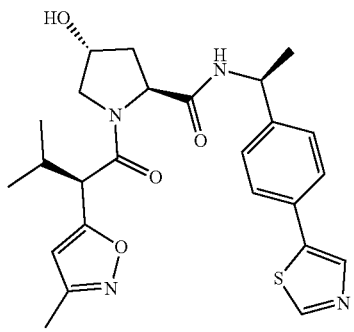

234

(2S,4R)-4-hydroxy-1-((R)-3-methyl-2-(3-methyl-isoxazol-5-yl)butanoyl)-N—((S)-1-(4-(thiazol-5-yl)phenyl)ethyl)pyrrolidine-2-carboxamide Example 159

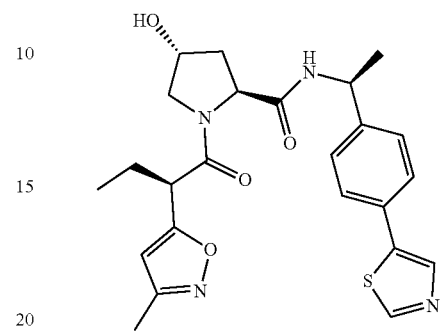

(2S,4R)-4-hydroxy-1-((R)-2-(3-methylisoxazol-5-yl)butanoyl)-N—((S)-1-(4-(thiazol-5-yl)phenyl)ethyl)pyrrolidine-2-carboxamide Example 160

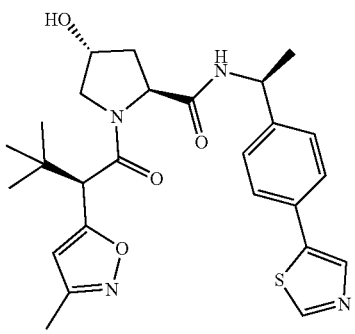 [SMILES: Cc1cc([C@H](C(=O)N2C[C@H](O)C[C@H]2C(=O)N[C@@H](C)c2ccc(-c3cncs3)cc2)C(C)(C)C)on1]

(2S,4R)-1-((R)-3,3-dimethyl-2-(3-methylisoxazol-5-yl)butanoyl)-4-hydroxy-N—((S)-1-(4-(thiazol-5-yl)phenyl)ethyl)pyrrolidine-2-carboxamide Example 161

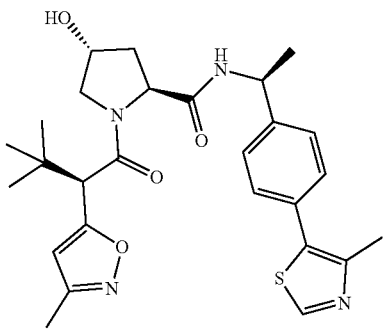 [SMILES: Cc1cc([C@H](C(=O)N2C[C@H](O)C[C@H]2C(=O)N[C@@H](C)c2ccc(-c3scnc3C)cc2)C(C)(C)C)on1]

(2S,4R)-1-((R)-3,3-dimethyl-2-(3-methylisoxazol-5-yl)butanoyl)-4-hydroxy-N—((S)-1-(4-(4-methylthiazol-5-yl)phenyl)ethyl)pyrrolidine-2-carboxamide Example 162

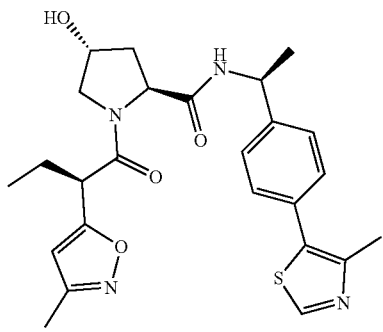

(2S,4R)-4-hydroxy-1-((R)-2-(3-methylisoxazol-5-yl)butanoyl)-N—((S)-1-(4-(4-methylthiazol-5-yl)phenyl)ethyl)pyrrolidine-2-carboxamide Example 163

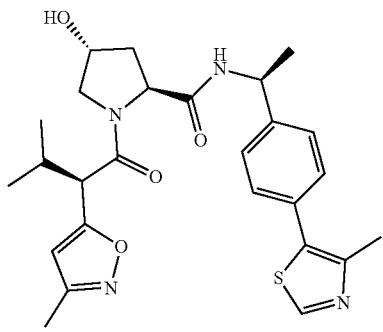 [SMILES: Cc1cc([C@H](C(=O)N2C[C@H](O)C[C@H]2C(=O)N[C@@H](C)c2ccc(-c3scnc3C)cc2)C(C)C)on1]

(2S,4R)-4-hydroxy-1-((R)-3-methyl-2-(3-methylisoxazol-5-yl)butanoyl)-N—((S)-1-(4-(4-methylthiazol-5-yl)phenyl)ethyl)pyrrolidine-2-carboxamide Example 164

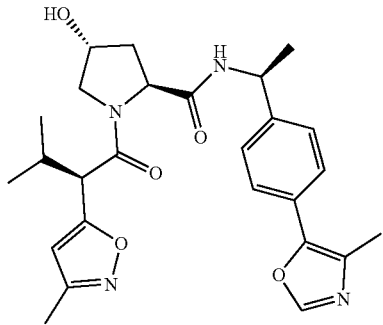 [SMILES: Cc1cc([C@H](C(=O)N2C[C@H](O)C[C@H]2C(=O)N[C@@H](C)c2ccc(-c3ocnc3C)cc2)C(C)C)on1]

(2S,4R)-4-hydroxy-1-((R)-3-methyl-2-(3-methylisoxazol-5-yl)butanoyl)-N—((S)-1-(4-(4-methyloxazol-5-yl)phenyl)ethyl)pyrrolidine-2-carboxamide Example 165

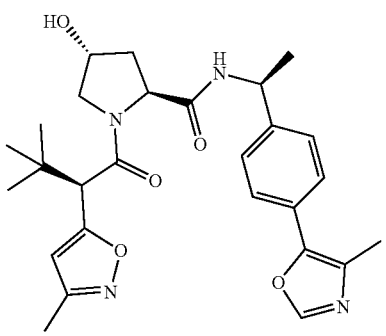 [SMILES: Cc1cc([C@H](C(=O)N2C[C@H](O)C[C@H]2C(=O)N[C@@H](C)c2ccc(-c3ocnc3C)cc2)C(C)(C)C)on1]

(2S,4R)-1-((R)-3,3-dimethyl-2-(3-methylisoxazol-5-yl)butanoyl)-4-hydroxy-N—((S)-1-(4-(4-methyloxazol-5-yl)phenyl)ethyl)pyrrolidine-2-carboxamide Example 166

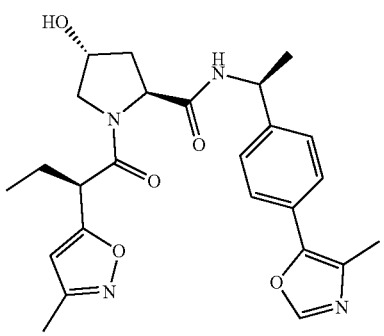 [SMILES: CC[C@@H](C(=O)N1C[C@H](O)C[C@H]1C(=O)N[C@@H](C)c1ccc(-c2ocnc2C)cc1)c1cc(C)no1]

(2S,4R)-4-hydroxy-1-((R)-2-(3-methylisoxazol-5-yl)butanoyl)-N—((S)-1-(4-(4-methyloxazol-5-yl)phenyl)ethyl)pyrrolidine-2-carboxamide Example 167

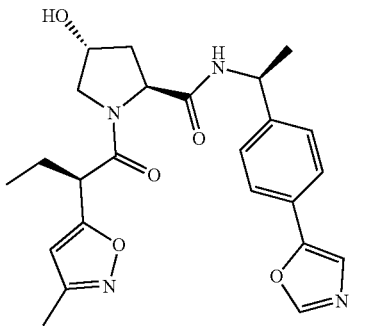 [SMILES: CC[C@@H](C(=O)N1C[C@H](O)C[C@H]1C(=O)N[C@@H](C)c1ccc(-c2cnco2)cc1)c1cc(C)no1]

237

(2S,4R)-4-hydroxy-1-((R)-2-(3-methylisoxazol-5-yl)butanoyl)-N—((S)-1-(4-(oxazol-5-yl)phenyl)ethyl)pyrrolidine-2-carboxamide Example 168

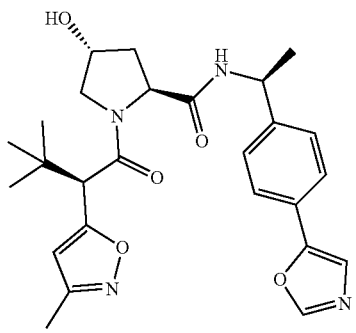

(2S,4R)-1-((R)-3,3-dimethyl-2-(3-methylisoxazol-5-yl)butanoyl)-4-hydroxy-N—(S)-1-(4-(oxazol-5-yl)phenyl)ethyl)pyrrolidine-2-carboxamide Example 169

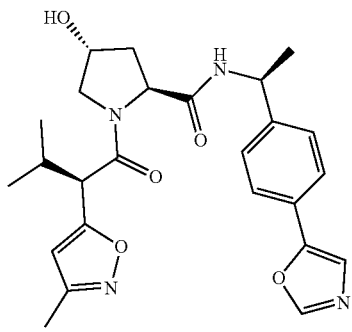 [SMILES: Cc1cc([C@H](C(=O)N2C[C@H](O)C[C@H]2C(=O)N[C@@H](C)c2ccc(-c3cnco3)cc2)C(C)(C)C)on1]

(2S,4R)-4-hydroxy-1-((R)-3-methyl-2-(3-methylisoxazol-5-yl)butanoyl)-N—((S)-1-(4-(oxazol-5-yl)phenyl)ethyl)pyrrolidine-2-carboxamide Example 170

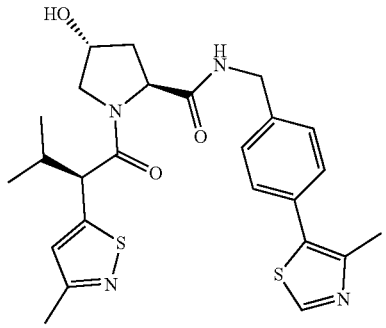 [SMILES: Cc1cc([C@H](C(=O)N2C[C@H](O)C[C@H]2C(=O)NCc2ccc(-c3scnc3C)cc2)C(C)C)sn1]

238

(2S,4R)-4-hydroxy-1-((S)-3-methyl-2-(3-methylisothiazol-5-yl)butanoyl)-N-(4-(4-methylthiazol-5-yl)benzyl)pyrrolidine-2-carboxamide Example 171

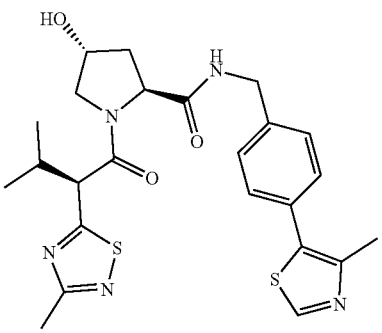 [SMILES: Cc1noc([C@H](C(=O)N2C[C@H](O)C[C@H]2C(=O)NCc2ccc(-c3scnc3C)cc2)C(C)C)n1]

(2S,4R)-4-hydroxy-1-((S)-3-methyl-2-(3-methyl-1,2,4-thiadiazol-5-yl)butanoyl)-N-(4-(4-methylthiazol-5-yl)benzyl)pyrrolidine-2-carboxamide Example 172

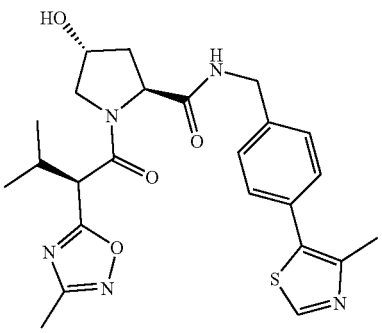

(2S,4R)-4-hydroxy-1-((R)-3-methyl-2-(3-methyl-1,2,4-oxadiazol-5-yl)butanoyl)-N-(4-(4-methylthiazol-5-yl)benzyl)pyrrolidine-2-carboxamide Example 173

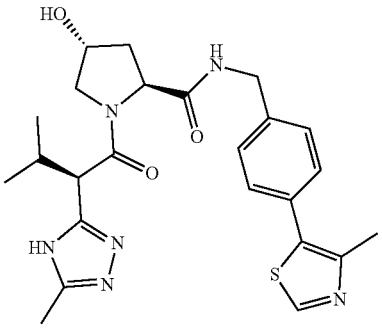 [SMILES: Cc1nnc([C@H](C(=O)N2C[C@H](O)C[C@H]2C(=O)NCc2ccc(-c3scnc3C)cc2)C(C)C)[nH]1]

(2S,4R)-4-hydroxy-1-((R)-3-methyl-2-(5-methyl-4H-1,2,4-triazol-3-yl)butanoyl)-N-(4-(4-methylthiazol-5-yl)benzyl)pyrrolidine-2-carboxamide Example 174

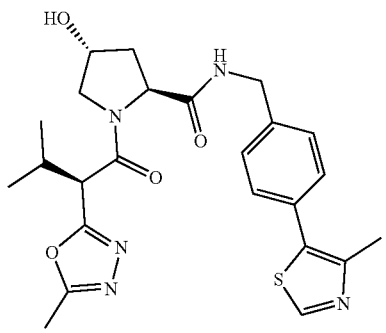 [SMILES: Cc1nnc([C@H](C(=O)N2C[C@H](O)C[C@H]2C(=O)NCc2ccc(-c3scnc3C)cc2)C(C)C)o1]

(2S,4R)-4-hydroxy-1-((R)-3-methyl-2-(5-methyl-1,3,4-oxadiazol-2-yl)butanoyl)-N-(4-(4-methylthiazol-5-yl)benzyl)pyrrolidine-2-carboxamide Example 175

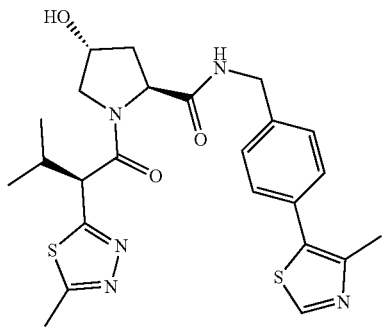 [SMILES: Cc1nnc([C@H](C(=O)N2C[C@H](O)C[C@H]2C(=O)NCc2ccc(-c3scnc3C)cc2)C(C)C)s1]

(2S,4R)-4-hydroxy-1-((S)-3-methyl-2-(5-methyl-1,3,4-thiadiazol-2-yl)butanoyl)-N-(4-(4-methylthiazol-5-yl)benzyl)pyrrolidine-2-carboxamide Example 176

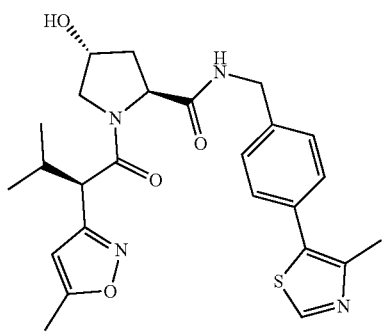 [SMILES: Cc1cc([C@H](C(=O)N2C[C@H](O)C[C@H]2C(=O)NCc2ccc(-c3scnc3C)cc2)C(C)C)no1]

(2S,4R)-4-hydroxy-1-((R)-3-methyl-2-(5-methylisoxazol-3-yl)butanoyl)-N-(4-(4-methylthiazol-5-yl)benzyl)pyrrolidine-2-carboxamide Example 177

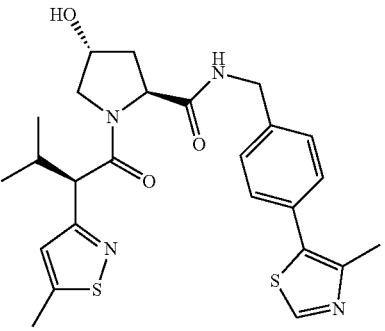 [SMILES: Cc1cc([C@H](C(=O)N2C[C@H](O)C[C@H]2C(=O)NCc2ccc(-c3scnc3C)cc2)C(C)C)ns1]

(2S,4R)-4-hydroxy-1-((R)-3-methyl-2-(5-methylisothiazol-3-yl)butanoyl)-N-(4-(4-methylthiazol-5-yl)benzyl)pyrrolidine-2-carboxamide Example 178

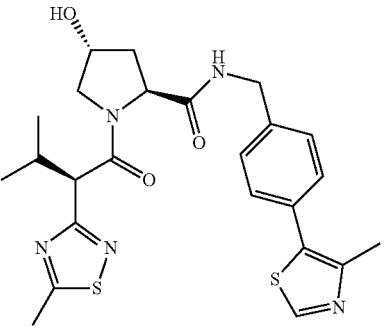 [SMILES: Cc1nc([C@H](C(=O)N2C[C@H](O)C[C@H]2C(=O)NCc2ccc(-c3scnc3C)cc2)C(C)C)ns1]

(2S,4R)-4-hydroxy-1-((R)-3-methyl-2-(5-methyl-1,2,4-thiadiazol-3-yl)butanoyl)-N-(4-(4-methylthiazol-5-yl)benzyl)pyrrolidine-2-carboxamide Example 179

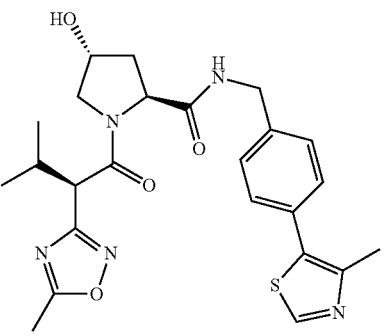 [SMILES: Cc1nc([C@H](C(=O)N2C[C@H](O)C[C@H]2C(=O)NCc2ccc(-c3scnc3C)cc2)C(C)C)no1]

241

(2S,4R)-4-hydroxy-1-((R)-3-methyl-2-(5-methyl-1,2,4-oxadiazol-3-yl)butanoyl)-N-(4-(4-methylthiazol-5-yl)benzyl)pyrrolidine-2-carboxamide Example 180

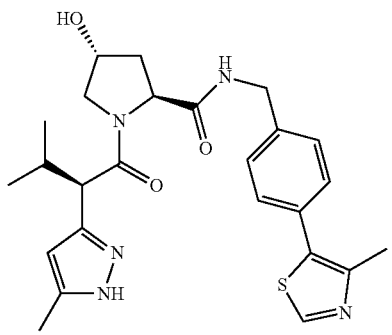 [SMILES: Cc1cc([C@H](C(=O)N2C[C@H](O)C[C@H]2C(=O)NCc2ccc(-c3scnc3C)cc2)C(C)C)n[nH]1]

(2S,4R)-4-hydroxy-1-((R)-3-methyl-2-(5-methyl-1H-pyrazol-3-yl)butanoyl)-N-(4-(4-methylthiazol-5-yl)benzyl)pyrrolidine-2-carboxamide Example 181

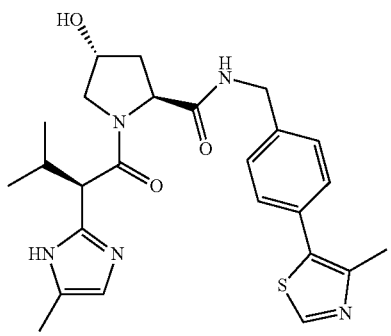 [SMILES: Cc1cnc([C@H](C(=O)N2C[C@H](O)C[C@H]2C(=O)NCc2ccc(-c3scnc3C)cc2)C(C)C)[nH]1]

(2S,4R)-4-hydroxy-1-((R)-3-methyl-2-(5-methyl-1H-imidazol-2-yl)butanoyl)-N-(4-(4-methylthiazol-5-yl)benzyl)pyrrolidine-2-carboxamide Example 182

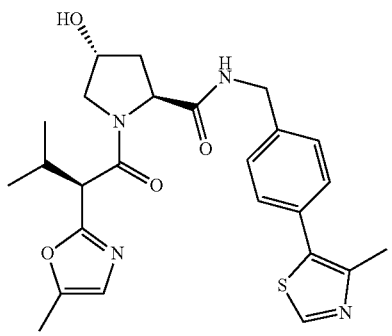 [SMILES: Cc1cnc([C@H](C(=O)N2C[C@H](O)C[C@H]2C(=O)NCc2ccc(-c3scnc3C)cc2)C(C)C)o1]

242

(2S,4R)-4-hydroxy-1-((R)-3-methyl-2-(5-methyloxazol-2-yl)butanoyl)-N-(4-(4-methylthiazol-5-yl)benzyl)pyrrolidine-2-carboxamide Example 183

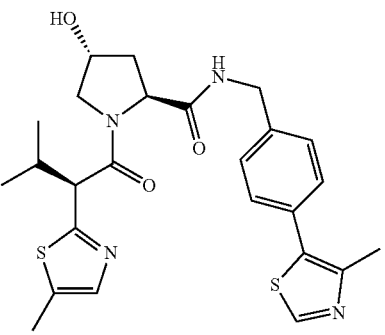 [SMILES: Cc1cnc([C@H](C(=O)N2C[C@H](O)C[C@H]2C(=O)NCc2ccc(-c3scnc3C)cc2)C(C)C)s1]

(2S,4R)-4-hydroxy-1-((S)-3-methyl-2-(5-methylthiazol-2-yl)butanoyl)-N-(4-(4-methylthiazol-5-yl)benzyl)pyrrolidine-2-carboxamide Example 184

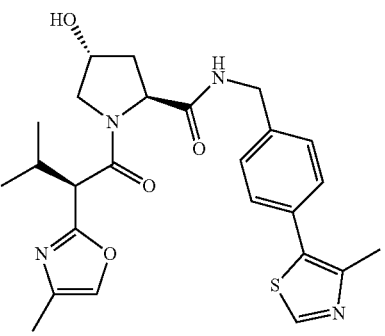 [SMILES: Cc1coc([C@H](C(=O)N2C[C@H](O)C[C@H]2C(=O)NCc2ccc(-c3scnc3C)cc2)C(C)C)n1]

(2S,4R)-4-hydroxy-1-((R)-3-methyl-2-(4-methyloxazol-2-yl)butanoyl)-N-(4-(4-methylthiazol-5-yl)benzyl)pyrrolidine-2-carboxamide Example 185

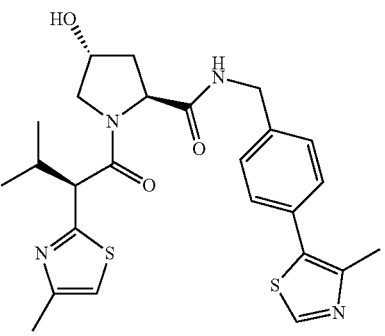 [SMILES: Cc1csc([C@H](C(=O)N2C[C@H](O)C[C@H]2C(=O)NCc2ccc(-c3scnc3C)cc2)C(C)C)n1]

243

(2S,4R)-4-hydroxy-1-((S)-3-methyl-2-(4-methylthi-
azol-2-yl)butanoyl)-N-(4-(4-methylthiazol-5-yl)ben-
zyl)pyrrolidine-2-carboxamide Example 186

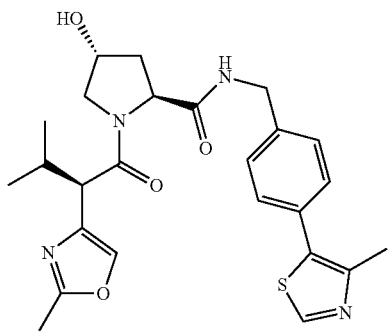 [SMILES: Cc1nc([C@H](C(=O)N2C[C@H](O)C[C@H]2C(=O)NCc2ccc(-c3scnc3C)cc2)C(C)C)co1]

(2S,4R)-4-hydroxy-1-((R)-3-methyl-2-(2-methyloxa-
zol-4-yl)butanoyl)-N-(4-(4-methylthiazol-5-yl)ben-
zyl)pyrrolidine-2-carboxamide Example 187

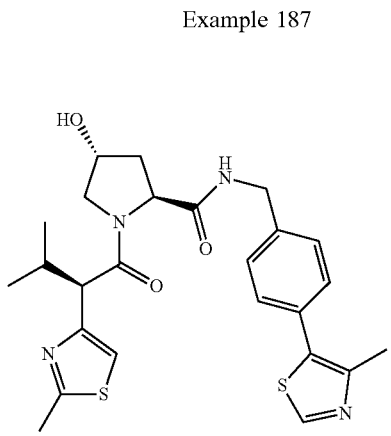

(2S,4R)-4-hydroxy-1-((R)-3-methyl-2-(2-methylthi-
azol-4-yl)butanoyl)-N-(4-(4-methylthiazol-5-yl)ben-
zyl)pyrrolidine-2-carboxamide Example 188

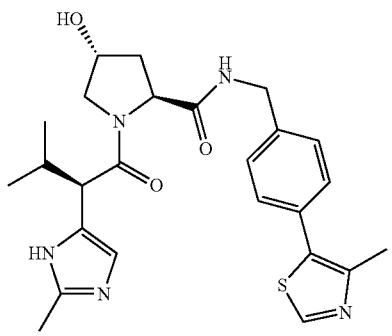 [SMILES: Cc1ncc([C@H](C(=O)N2C[C@H](O)C[C@H]2C(=O)NCc2ccc(-c3scnc3C)cc2)C(C)C)[nH]1]

244

(2S,4R)-4-hydroxy-1-((R)-3-methyl-2-(2-methyl-
1H-imidazol-5-yl)butanoyl)-N-(4-(4-methylthiazol-
5-yl)benzyl)pyrrolidine-2-carboxamide Example 189

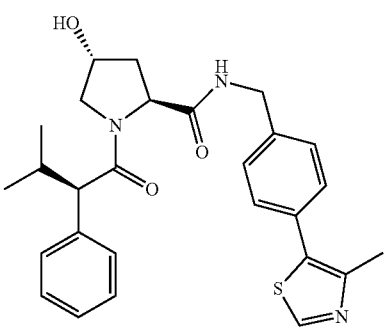

(2S,4R)-4-hydroxy-1-((R)-3-methyl-2-phenylbu-
tanoyl)-N-(4-(4-methylthiazol-5-yl)benzyl)pyrroli-
dine-2-carboxamide Example 190

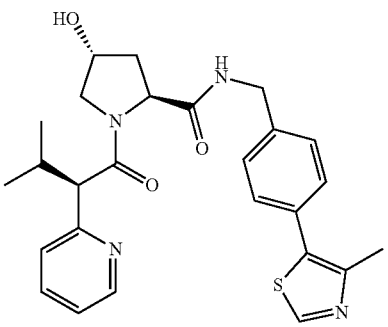 [SMILES: Cc1ncsc1-c1ccc(CNC(=O)[C@@H]2C[C@@H](O)CN2C(=O)[C@@H](c2ccccn2)C(C)C)cc1]

(2S,4R)-4-hydroxy-1-((R)-3-methyl-2-(pyridin-2-yl)
butanoyl)-N-(4-(4-methylthiazol-5-yl)benzyl)pyrro-
lidine-2-carboxamide Example 191

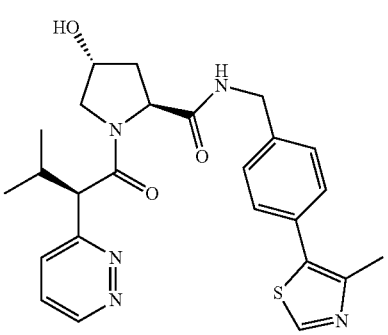 [SMILES: Cc1ncsc1-c1ccc(CNC(=O)[C@@H]2C[C@@H](O)CN2C(=O)[C@@H](c2cccnc2)C(C)C)cc1]

245

(2S,4R)-4-hydroxy-1-((R)-3-methyl-2-(pyridazin-3-yl)butanoyl)-N-(4-(4-methylthiazol-5-yl)benzyl)pyrrolidine-2-carboxamide Example 192

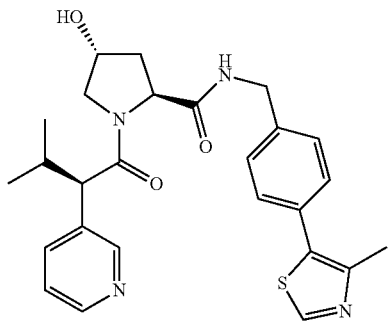

(2S,4R)-4-hydroxy-1-((R)-3-methyl-2-(pyridin-3-yl)butanoyl)-N-(4-(4-methylthiazol-5-yl)benzyl)pyrrolidine-2-carboxamide Example 193

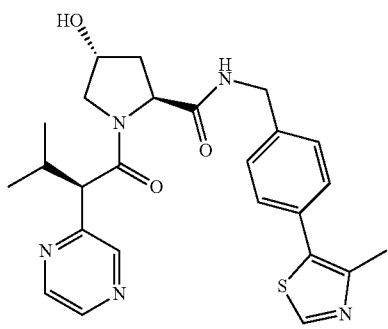 [SMILES: Cc1ncsc1-c1ccc(CNC(=O)[C@@H]2C[C@@H](O)CN2C(=O)[C@@H](c2cnccn2)C(C)C)cc1]

(2S,4R)-4-hydroxy-1-((R)-3-methyl-2-(pyrazin-2-yl)butanoyl)-N-(4-(4-methylthiazol-5-yl)benzyl)pyrrolidine-2-carboxamide Example 194

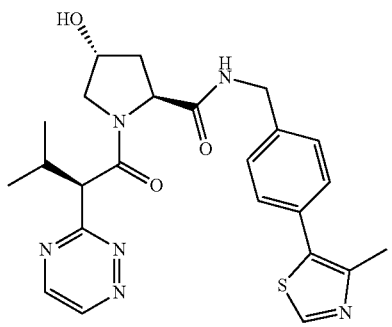

246

(2S,4R)-4-hydroxy-1-((R)-3-methyl-2-(pyrazin-2-yl)butanoyl)-N-(4-(4-methylthiazol-5-yl)benzyl)pyrrolidine-2-carboxamide Example 195

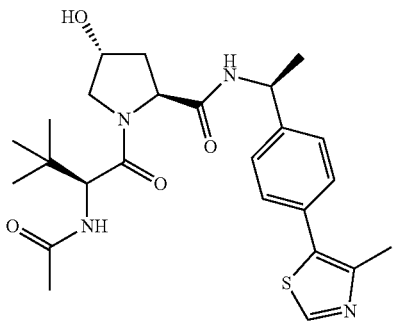 [SMILES: CC(=O)N[C@H](C(=O)N1C[C@H](O)C[C@H]1C(=O)N[C@@H](C)c1ccc(-c2scnc2C)cc1)C(C)(C)C]

(2S,4R)-1-[(2S)-2-acetamido-3,3-dimethylbutanoyl]-4-hydroxy-N-[(1S)-1-[4-(4-methyl-1,3-thiazol-5-yl)phenyl]ethyl]pyrrolidine-2-carboxamide Example 196

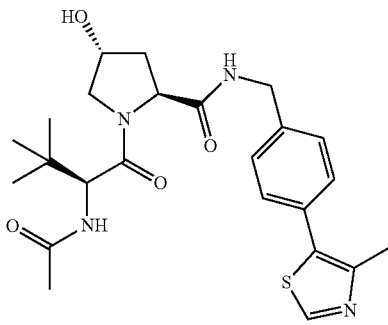

(2S,4R)-1-[(2S)-2-acetamido-3,3-dimethylbutanoyl]-4-hydroxy-N-({4-[4-(hydroxymethyl)-1,3-thiazol-5-yl]phenyl}methyl)pyrrolidine-2-carboxamide Example 197

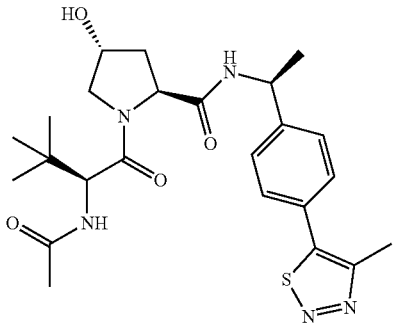 [SMILES: CC(=O)N[C@H](C(=O)N1C[C@H](O)C[C@H]1C(=O)N[C@@H](C)c1ccc(-c2snnc2C)cc1)C(C)(C)C]

247

(2S,4R)-1-[(2S)-2-acetamido-3,3-dimethylbutanoyl]-4-hydroxy-N-[(1S)-1-[4-(4-methyl-1,2,3-thiadiazol-5-yl)phenyl]ethyl]pyrrolidine-2-carboxamide Example 198

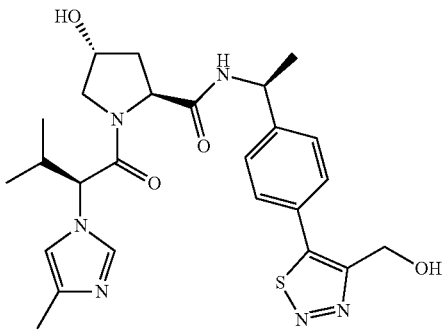 [SMILES: Cc1cn([C@H](C(=O)N2C[C@H](O)C[C@H]2C(=O)N[C@@H](C)c2ccc(-c3snnc3CO)cc2)C(C)C)cn1]

2S,4R)-4-hydroxy-N-[(1S)-1-{4-[4-(hydroxymethyl)-1,2,3-thiadiazol-5-yl]phenyl}ethyl]-1-[(2S)-3-methyl-2-(4-methyl-1H-imidazol-1-yl)butanoyl]pyrrolidine-2-carboxamide Example 199

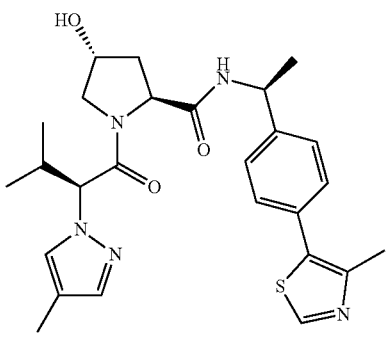 [SMILES: Cc1cnn([C@H](C(=O)N2C[C@H](O)C[C@H]2C(=O)N[C@@H](C)c2ccc(-c3scnc3C)cc2)C(C)C)c1]

(2S,4R)-4-hydroxy-N-[(1S)-1-[4-(4-methyl-1,3-thiazol-5-yl)phenyl]ethyl]-1-[(2 S)-3-methyl-2-(4-methyl-1H-pyrazol-1-yl)butanoyl]pyrrolidine-2-carboxamide Example 200

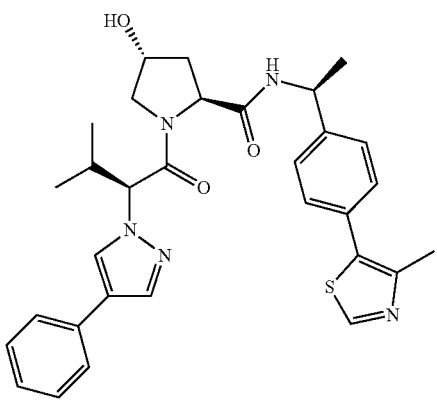 [SMILES: Cc1ncsc1-c1ccc([C@H](C)NC(=O)[C@@H]2C[C@@H](O)CN2C(=O)[C@H](C(C)C)n2cc(-c3ccccc3)cn2)cc1]

248

(2S,4R)-4-hydroxy-N-[(1S)-1-[4-(4-methyl-1,3-thiazol-5-yl)phenyl]ethyl]-1-[(2 S)-3-methyl-2-(4-phenyl-1H-pyrazol-1-yl)butanoyl]pyrrolidine-2-carboxamide Example 201

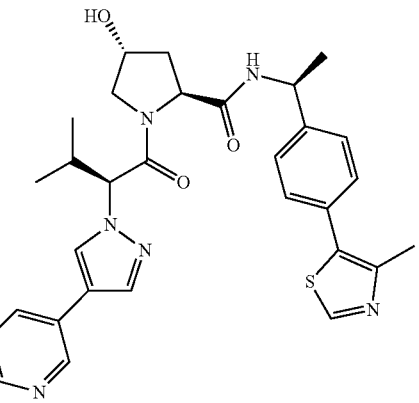

(2S,4R)-4-hydroxy-N-[(1S)-1-[4-(4-methyl-1,3-thiazol-5-yl)phenyl]ethyl]-1-[(2 S)-3-methyl-2-[4-(pyridin-3-yl)-1H-pyrazol-1-yl]butanoyl]pyrrolidine-2-carboxamide Example 202

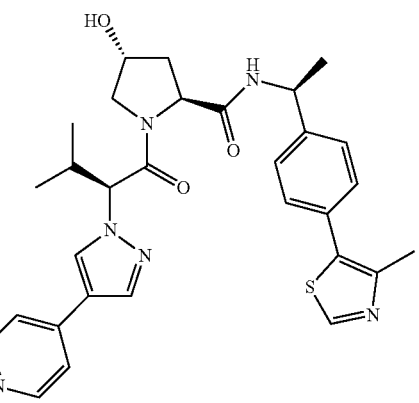

249

(2S,4R)-4-hydroxy-N-[(1S)-1-[4-(4-methyl-1,3-thi-
azol-5-yl)phenyl]ethyl]-1-[(2 S)-3-methyl-2-[4-
(pyridin-3-yl)-1H-pyrazol-1-yl]butanoyl]pyrrolidine-
2-carboxamide Example 203

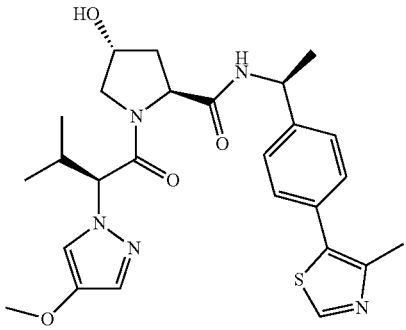

(2S,4R)-4-hydroxy-1-[(2S)-2-(4-methoxy-1H-pyra-
zol-1-yl)-3-methylbutanoyl]-N-[(1S)-1-[4-(4-methyl-
1,3-thiazol-5-yl)phenyl]ethyl]pyrrolidine-2-carbox-
amide Example 204

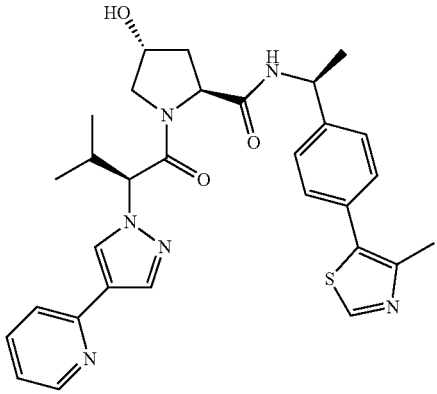 [SMILES: Cc1ncsc1-c1ccc([C@H](C)NC(=O)[C@@H]2C[C@@H](O)CN2C(=O)[C@H](C(C)C)n2cc(-c3ccccn3)cn2)cc1]

(2S,4R)-4-hydroxy-N-[(1S)-1-[4-(4-methyl-1,3-thi-
azol-5-yl)phenyl]ethyl]-1-[(2 S)-3-methyl-2-[4-
(pyridin-2-yl)-1H-pyrazol-1-yl]butanoyl]pyrrolidine-
2-carboxamide Example 205

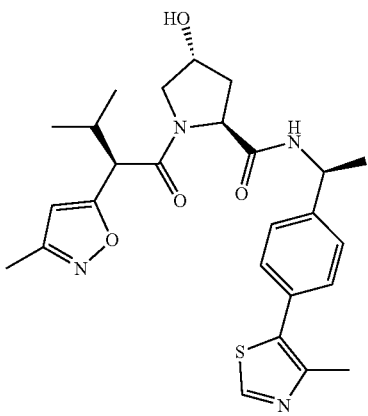 [SMILES: Cc1cc([C@H](C(=O)N2C[C@H](O)C[C@H]2C(=O)N[C@@H](C)c2ccc(-c3scnc3C)cc2)C(C)C)on1]

250

(2S,4R)-4-hydroxy-N-[(1S)-1-[4-(4-methyl-1,3-thi-
azol-5-yl)phenyl]ethyl]-1-[(2R)-3-methyl-2-(3-
methyl-1,2-oxazol-5-yl)butanoyl]pyrrolidine-2-car-
boxamide Example 206

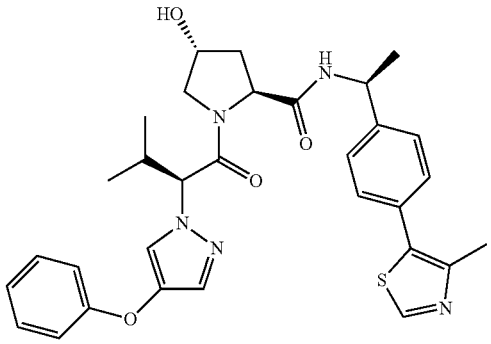 [SMILES: Cc1ncsc1-c1ccc([C@H](C)NC(=O)[C@@H]2C[C@@H](O)CN2C(=O)[C@H](C(C)C)n2cc(Oc3ccccc3)cn2)cc1]

(2S,4R)-4-hydroxy-N-[(1S)-1-[4-(4-methyl-1,3-thi-
azol-5-yl)phenyl]ethyl]-1-[(2 S)-3-methyl-2-(4-phe-
noxy-1H-pyrazol-1-yl)butanoyl]pyrrolidine-2-car-
boxamide Example 207

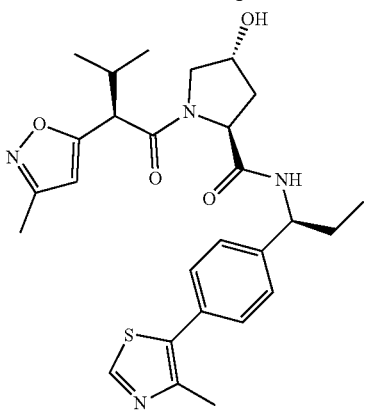

(2S,4R)-4-hydroxy-N-[(1S)-1-[4-(4-methyl-1,3-thi-
azol-5-yl)phenyl]propyl]-1-((2R)-3-methyl-2-(3-
methyl-1,2-oxazol-5-yl)butanoyl]pyrrolidine-2-car-
boxamide Example 208

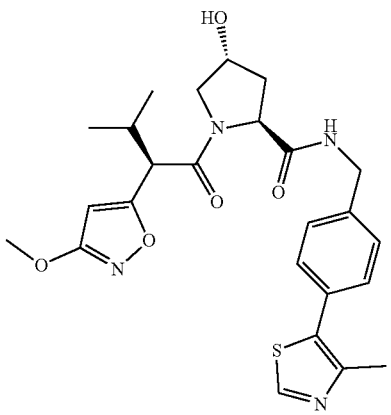

(2S,4R)-4-hydroxy-1-[(2R)-2-(3-methoxy-1,2-oxa-zol-5-yl)-3-methylbutanoyl]-N-{[4-(4-methyl-1,3-thiazol-5-yl)phenyl]methyl}pyrrolidine-2-carboxamide
Examplery Methods for PROTAC Synthesis
Amide Coupling Route: An examplery PROTAC synthesis approach for ULMs with free amine group
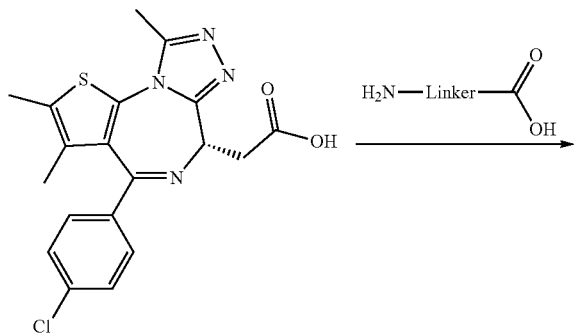
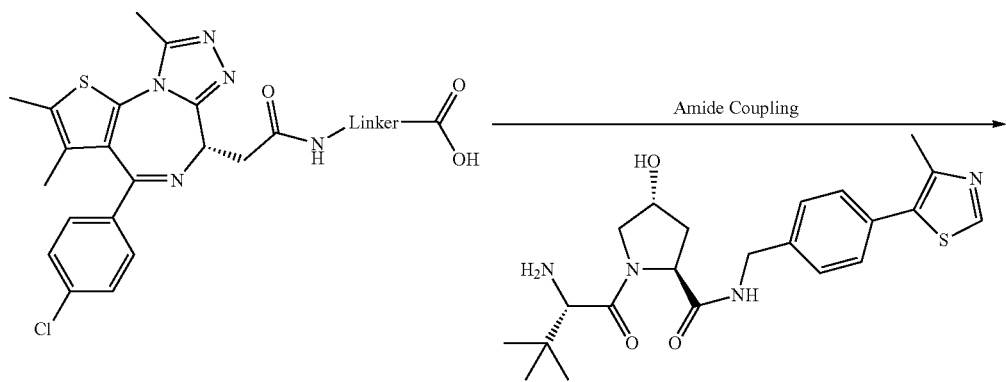
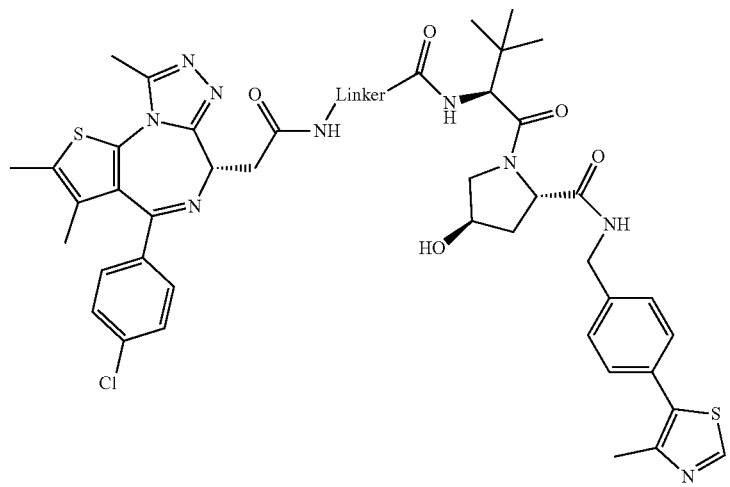

Mitsonobu Route: An examplery PROTAC synthesis route for ULMs with free hydroxyl group
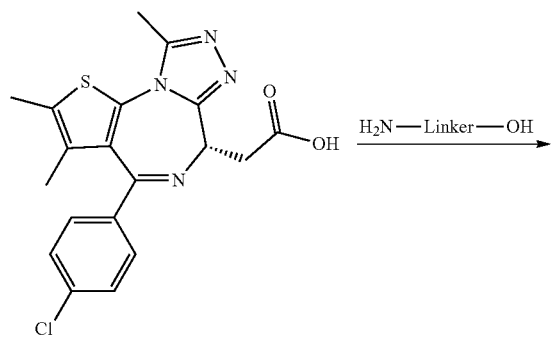
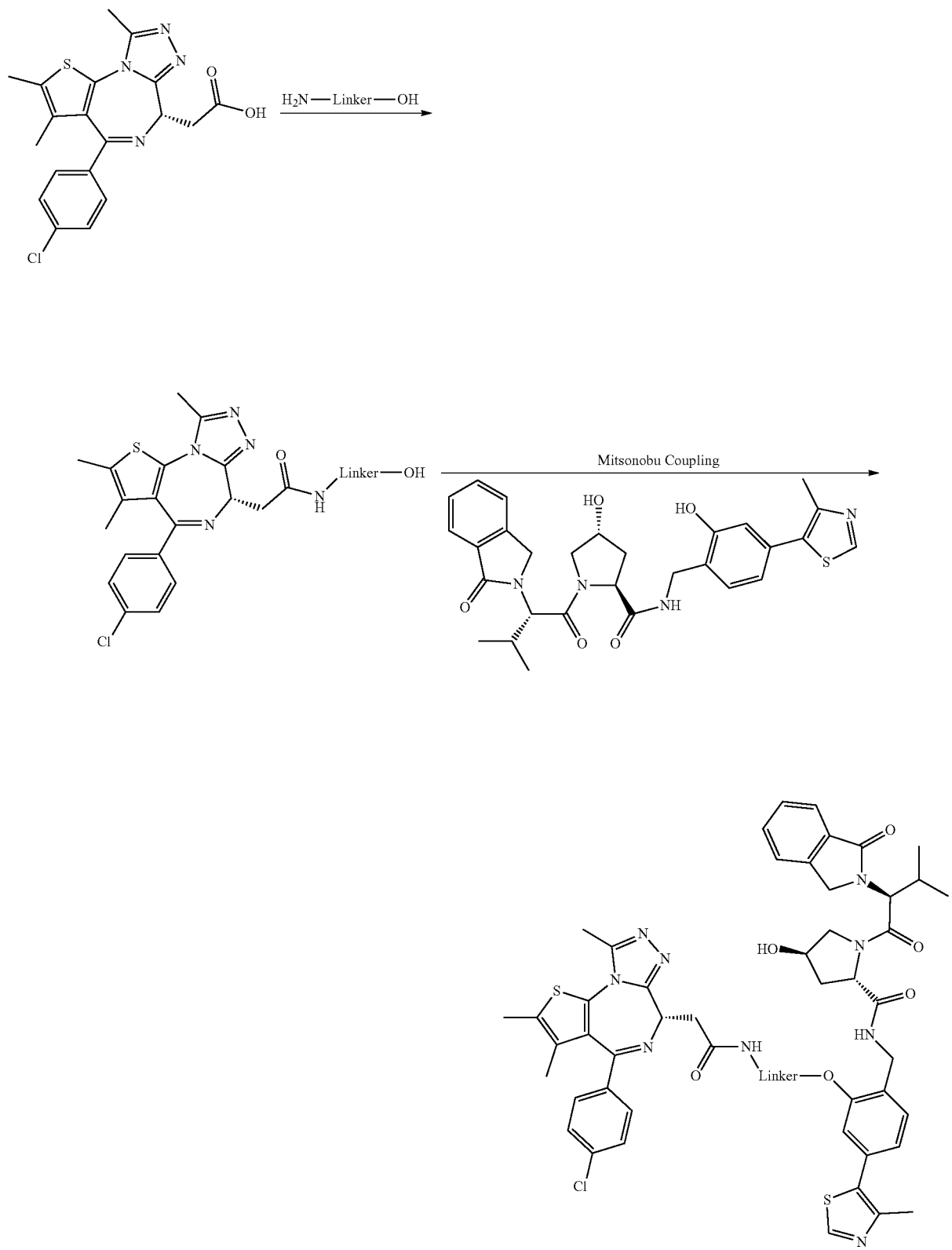

Suzuki Route: An examplery PROTAC synthesis route with halogen containing ULMs

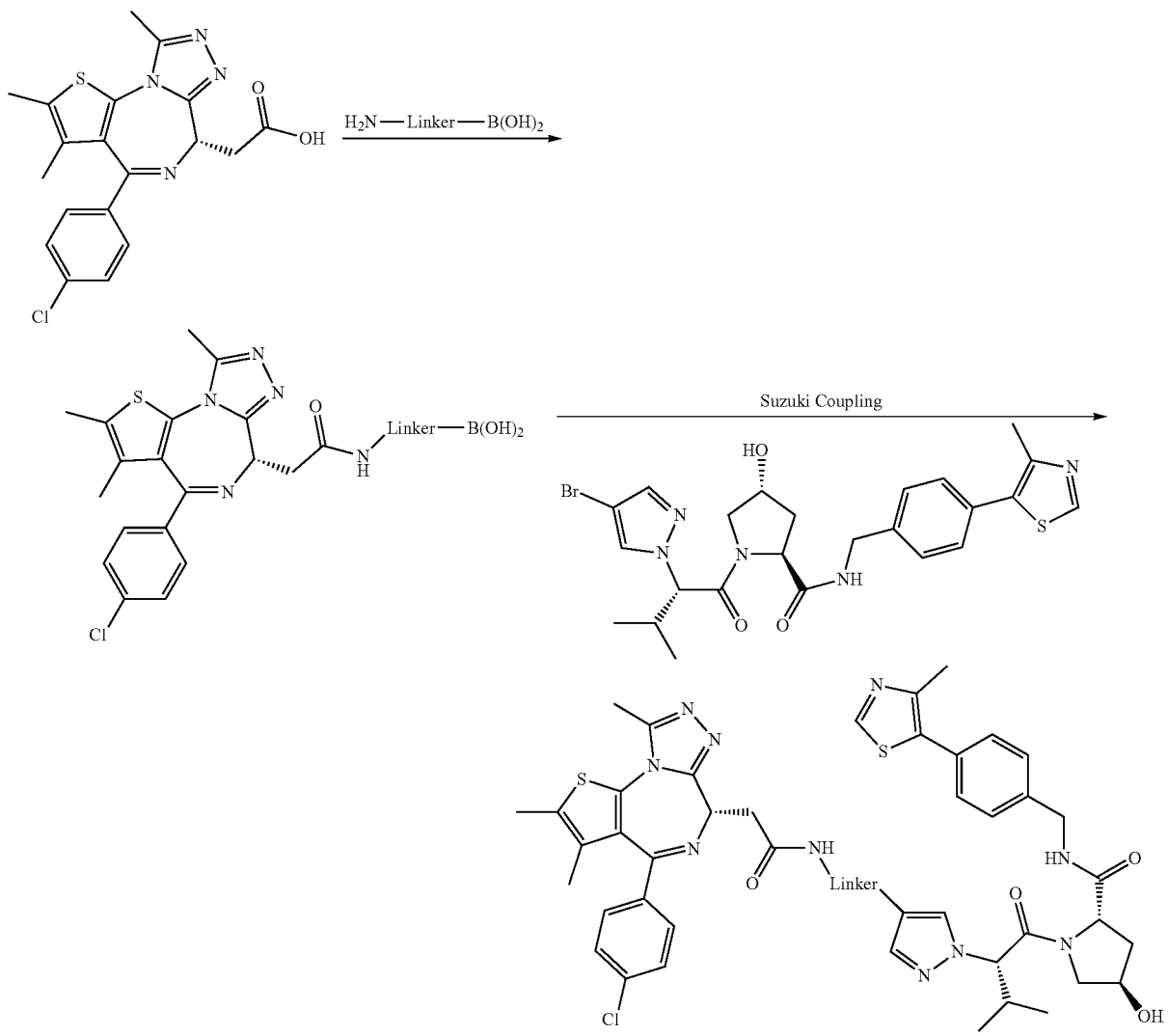

Using the above mentioned approaches and various other approaches very well documented in the literature, the following exemplary PROTAC compounds were prepared. (Table 3 and Table 4). The exemplary compounds in Table 3 and 4 were also assayed for their ability to effectuate the degration of BRD4 and AR. Thus, in certain embodiments, the description provides the compounds, including compositions comprising effective amount of a compound or a derivative, analog, or a prodrug of the same, in combination with at least one of a pharmaceutically acceptable carrier, another active agent, including a second PROTAC molecule as described herein or a combination thereof. In additional embodiments, the disclosure provides a method of treating a disease or condition in a subject in need thereof, comprising administering a composition comprising an effective amount of a compound listed below, wherein the composition is effective for treating or ameliorating a symptom of the disease or condition.

Cell Based Assays:
1. Fluorescence Polarization Assay

Ability of VHL ligands to compete for the HIF 1a binding site on VCB was determined through a fluorescence polarization competition assay as described in Buckley et al. JACS, 2012, 134, 4465-4468, WO 2013/106643, and US 2014-0356322, which are incorporated herein by reference in their entirety for all purposes.

2. Androgen Receptor ELISA Assay.

Compounds have been evaluated in this assay in LNCaP and/or VCaP cells utilizing similar protocols. The protocols used with VCaP cells are described below. The androgen receptor ELISA assay was performed using PathScan AR ELISA (Cell Signaling Catalog #128501 according to the following assay steps:

VCaP cells are seeded at 30,000 cells/well at a volume of 200 µL/well in VCaP assay medium [Phenol red free RPMI (Gibco Cat #11835-030); 5% Charcoal Stripped (Dextran treated) FBS (Omega Scientific, Cat #FB-04); Pen/Strep Life Technologies (Gibco Cat #: 10378-016); 0. 1 nM R1881 (Sigma, Cat #R0908) is added upon the start of the assay, not during initial plating of the cells) in Corning 3904 plates. The cells are grown for a minimum of 3 days.

First, cells are dosed with compounds diluted in 0.1% DMSO—use a polypropylene plate according to the following protocol: (1)(i) make 1000× stock plate in DMSO; (ii) 20 mM stock diluted 1/6.7 with DMSO (5 µL+28.3 µL DMSO)

=3 mM into row H; (iii) perform serial dilutions in ½ log doses (10 µL of PROTAC+20 µL DMSO) from row H towards row B. Reserve row A for DMSO; (iv) 7 doses total (final concentration in this 1000× plate will be 3 mM, 1 mM, 333 µM, 111 µM, etc). (2)(i) Make 10× stock plate in media; (ii) transfer 2.5 µL of the 1000× stock to a new 10× stock plate (use 12 channel pipet, start at A (DMSO control) work thru H. When 247.5 µL of media is added to this plate, it will serve as a 10× stock; (iii) make media+1 nM R1881 for making 10× stock plate; (iv) add 247.5 µL of media with 1 nM R1881 to each well of the 10× stock plate, mix.

Then 22 µL of 10× stock is added to cells and incubated for 24 h. 1× Cell Signaling Cell lysis buffer is made (Catalogue #9803; comes with the kit)—prepare for 50 µL/well. Keep on ice. Media is aspirated, and 50 µL 1× cell lysis buffer/well is added. The cells are placed on ice for 10 minutes. The solution is mixed and transferred to PCR plate, and centrifuged at 4 C for 10 minutes at 4000 rpm.

5 µL is transferred to fresh plate (use immediately or freeze −80 C); 115 µL ELISA Dilutant is added (0.15 ug/ml-0.075 ug/ml; comes with the PathScan ELISA).

Add 100 µL/well AR Elisa; cover and shake, 37 C for 2 hrs; dump, tap, wash 4× 200 µL ELISA wash buffer; add 100 µL/well mouse AR detection Ab; cover and shake, 37 C for 1 hr; dump, tap, wash 4× 200 µL ELISA wash buffer; add 100 µL/well anti-mouse—HRP conjugated Ab (comes with the kit); cover and shake, 37 C for 30 min; allow TMB reagent to come to RT; dump, tap, wash 4× 200 µL Elisa wash buffer; tap; add 100 µL TMB, shake 5 min—while watching color. Add the stop reagent when light blue color develops. Add 100 µL Stop solution; shake and read at 450 nM.

Progression of prostate cancer in patients treated with anti-androgen therapy usually involves one of several mechanisms of enhanced Androgen Receptor (AR) signaling, including increased intratumoral androgen synthesis, increased AR expression and AR mutations. PROTACs (PROteolysis TArgeting Chimera), which uses bi-functional molecules that simultaneously bind a target of choice and an E3 ligase, cause ubiquitination via induced proximity and degradation of the targeted, pathological protein. As opposed to traditional target inhibition, which is a competitive process, degradation is a progressive process. As such, it is less susceptible to increases in endogenous ligand, target expression, or mutations in the target. Thus this technology seems ideal for addressing the mechanisms of AR resistance in patients with prostate cancer.

AR PROTACs degrade AR in LNCaP and VCaP cells, with nM to pM potency, and had a >85% reduction in AR concentration ($D_{max}$). Degradation was rapid, with 50% of AR lost within 15 minutes and maximal degradation observed by 4 hours. The duration of AR knockdown was long-lasting, with no recovery of AR observed over several days. The degradation process in cells was specific, as PROTACs with an inactive epimer for E3 ligase binding did not degrade AR. AR PROTACs induced rapid apoptosis and cell death in VCaP cells. In LNCap and VCaP cell systems, AR PROTACs were anti-proliferative under conditions in which enzalutamide was inactive, such as increasing concentrations of the AR agonist R1881 and cells containing the $AR^{F876L}$ mutation. AR PROTACs typically had $t_{1/2}$ values of several hours and bioavailability of >50% after ip or sc injection. In mice, AR PROTACs have shown in vivo activity, including involution of seminal vesicles, reduction of AR protein levels in the prostate, and regression of VCaP tumors.

The results presented in Table 3 were generated using the androgen receptor ELISA Assay described above, where compound potencies were characterized in highest percentage of Androgen Receptor degradation ($D_{max}$) observed.

BDR4 Receptor ELISA Assay (Table 4)

22RV-1 cells were seeded at 30,000 cells/well at a volume of 75 µL/well in RPMI+10% FBS media in 96-well plates and grown overnight at 37 C. Cells were dosed with compounds at 4× concentration diluted in 0.4% DMSO; compounds were serially diluted 1:3 for 8-point dose curve. 25 ul of compound was added to cells for a final concentration starting at 300 nM-0.3 nM in 0.1% DMSO and incubated for 18 hrs. Media was aspirated, cells washed 1× with PBS and aspirated. Cells were lysed in 50 ul RIPA buffer (50 mM Tris pH8, 150 mM NaCl, 1% Tx-100, 0.1% SDS, 0.5% sodium deoxycholate) supplemented with protease and phosphatase inhibitors. Plates were incubated on ice for 15 minutes then centrifuged at 4° C. for 10 min at 4000 rpm. Added 50 ul of cleared lysate from 96-well assay plate into 96-well c-myc ELISA plate (Novex, Life Technologies Catalog #KH02041). Reconstituted c-myc standard with standard diluent buffer; standard curve range 333 pg/ml-0 pg/ml, diluted 1:2 for 8-point dose curve. The rest of the assay was performed following the protocol from the c-myc ELISA kit. Data was analyzed and plotted using GraphPad Prism software.

Surface Plasmon Resonance Assay

The surface plasmon resonance (SPR) experiments were conducted on a Biacore3000 (GE Healthcare). His-tagged VHL protein was immobilized on a carboxymethylated dextran surface with nitriloacetic acid (NTA), taking advantage of NTA/$Ni^{2+}$ chelation. The prepared surface was allowed to equilibrate over three hours in running buffer (Ambion 1×PBS buffer @ pH 7/4, 0.005% Tween, 2% DMSO).

All compounds were prepared in 100% DMSO stock plates with a top concentration of 5 mM in a 3× serial dilution. Compounds were transferred from the stock plate to the assay plate and diluted into running buffer containing no DMSO. All compounds were run as a six-concentration series with a final assay top concentration of 100 uM. Data analysis was performed in Scrubber 2 (BioLogic software, Campbell, Australia). Blanks were subtracted and data was corrected for DMSO using a standard DMSO curve. All reported KD values represent an average of at least N=2 and were obtained by fitting to a minimum of five concentrations using a 1:1 fitting algorithm.

The following (Table 1) demonstrates the VHL inhibition data (i.e., $IC_{50}$, µM) of each example at various DMSO concentrations (i.e., 0.25% in DMSO, 1% in DMSO, and 10% in DMSO) in the fluorescence polarization (FP) assay.

TABLE 1

VHL inhibition data (i.e., $IC_{50}$, µM) in fluorescence polarization (FP) assay.

| | VHL FP Assay $IC_{50}$ (uM) at various concentrations of test compounds in DMSO | | |
|---|---|---|---|
| Example No. | 0.25% in DMSO | 1% in DMSO | 10% in DMSO |
| 1 | 2.38 | 2.28 | |
| 2 | 2.86 | 0.732 | 0.533 |
| 3 | 2.54 | 0.696 | 1.48 |
| 4 | 3.34 | 1.22 | 1.94 |
| 5 | 7.72 | 0.799 | 1.58 |
| 6 | 6.37 | 0.697 | 1.48 |
| 7 | | 7.51 | 8.52 |
| 8 | 3.04 | 0.619 | 1.33 |

TABLE 1-continued

VHL inhibition data (i.e., IC$_{50}$, µM) in fluorescence polarization (FP) assay.

| Example No. | VHL FP Assay IC$_{50}$ (uM) at various concentrations of test compounds in DMSO | | |
|---|---|---|---|
| | 0.25% in DMSO | 1% in DMSO | 10% in DMSO |
| 9 | 1.28 | 0.309 | 0.498 |
| 10 | | ~6.73 | 295 |
| 11 | 1.56 | 0.542 | 0.0163 |
| 12 | 9.34 | 2.08 | 4.86 |
| 13 | 3.37 | 1.34 | 2.94 |
| 14 | 7.15 | 4.63 | 13.3 |
| 15 | 1.22 | 24.5 | 81.9 |
| 16 | 2.95 | 0.265 | 1.8 |
| 17 | 2.2 | 0.317 | 1.07 |
| 18 | 5.5 | 0.855 | 2.72 |
| 19 | 3.77 | 0.937 | 1.65 |
| 20 | 4.96 | 1.05 | 1.15 |
| 21 | 5.69 | 0.392 | 1.49 |
| 22 | | 6.25 | 8.29 |
| 23 | 1.14 | 2.51 | 6.04 |
| 24 | 1.39 | 8.65 | 28.0 |
| 25 | 2.38 | 1.33 | 1.67 |
| 26 | 2.94 | 0.941 | 0.441 |
| 27 | ~1.569 | 3.04 | 8.31 |
| 28 | 4.47 | 2.21 | 3.6 |
| 29 | 2.42 | 0.905 | 1.85 |
| 30 | 2.27 | 0.572 | 0.859 |
| 31 | 3.22 | 1.28 | 2.11 |
| 32 | 2.22 | 1.15 | 3.36 |
| 33 | 1.94 | 0.539 | 1.08 |
| 34 | 2.12 | 0.66 | 1.18 |
| 35 | 2.05 | 0.509 | 1.3 |
| 36 | 6.54 | 3.55 | 5.48 |
| 37 | 1.9 | 20.6 | 7.41 |
| 38 | 2.19 | 0.758 | 1.09 |
| 39 | 0.958 | 0.699 | 1.63 |
| 40 | 17.5 | 2.36 | 3.92 |
| 41 | 7.28 | 1.19 | 3.05 |
| 42 | | 4.95 | 15.7 |
| 43 | | 0.906 | 1.2 |
| 44 | | 0.385 | 0.465 |
| 45 | | ~32 | 472 |
| 46 | | 19410 | 5103 |
| 47 | | 0.178 | 0.339 |
| 48 | | 3.77 | 4.7 |
| 49 | | | 244 |
| 50 | | | 235 |
| 51 | | 56.6 | 1518 |
| 52 | | 2.48 | 3.73 |
| 53 | | 0.474 | 1.03 |
| 54 | | 0.834 | 1.21 |
| 55 | | 115 | 461 |
| 56 | | 0.878 | 1.48 |
| 57 | | 0.717 | 1.41 |
| 58 | | 32.6 | 26.2 |
| 59 | | 1.42 | 3.69 |
| 60 | | 1.45 | 0.293 |
| 61 | | Not Active | Not Active |
| 62 | | Not Active | Not Active |
| 63 | | 58.4 | 53.0 |
| 64 | | 16.8 | 30.5 |
| 65 | | 0.631 | 0.578 |
| 66 | | Not Active | Not Active |
| 67 | | Not Active | Not Active |
| 68 | | 0.972 | 0.668 |
| 69 | | 1.43 | 4.28 |
| 70 | | 2.02 | 1.2 |
| 71 | | 1.62 | 1.38 |
| 72 | | 0.86 | 1.03 |
| 73 | | 1.33 | 1.19 |
| 74 | | 0.45 | 0.264 |
| 75 | | 13.7 | 9.29 |
| 76 | | 0.169 | |
| 77 | | 0.55 | 0.349 |
| 78 | | 1.03 | 0.81 |
| 79 | | >100 | >100 |
| 80 | | 22.4 | 38.9 |
| 81 | | >49 | 371 |
| 82 | | 1.64 | 1.58 |
| 83 | | 0.626 | 0.32 |
| 84 | | 1.24 | 1.46 |
| 85 | | 28.9 | 21.2 |
| 86 | | 151 | 225 |
| 87 | | 384 | 263 |
| 88 | | 20.4 | 39.2 |
| 89 | | 60.6 | 139 |
| 90 | | 45.2 | 47.9 |
| 91 | | >100 | |
| 92 | | 1.65 | |
| 93 | | 1.2 | |
| 94 | | 0.566 | |
| 95 | | 23.4 | |
| 96 | | 35.4 | |
| 97 | | 1.45 | |
| 98 | | 4.15 | |
| 99 | | 0.418 | |
| 100 | | 9.77 | |
| 101 | | 4.39 | |
| 102 | | 7.75 | |
| 103 | | 33.8 | |
| 104 | | >10 | |
| 105 | | 37.7 | |
| 106 | | 14.2 | |
| 107 | | 64.6 | |
| 108 | | 33.5 | |
| 109 | | 6.67 | |
| 110 | | 21.6 | |
| 111 | | 0.859 | |
| 112 | | >100 | |
| 113 | | >10 | |
| 114 | | 47.3 | |
| 115 | | 15.8 | |
| 116 | | 3.9 | |
| 117 | | 15.5 | |
| 118 | | 330 | |
| 119 | | Not Active | |
| 120 | | 15.5 | |
| 121 | | >100 | |
| 122 | | 2.18 | |
| 123 | | 4.23 | |
| 124 | | 1.11 | |
| 125 | | 1.64 | |
| 126 | | 79.5 | 112 |
| 127 | | | 406 |
| 128 | | >100 | |
| 129 | | 19.3 | |
| 130 | | 3.89 | |
| 131 | | Not Active | |
| 132 | | 1.69 | |
| 133 | | 1.64 | |
| 134 | | 12.7 | |
| 135 | | 19.2 | |
| 136 | | 5.59 | |
| 137 | | 13.1 | |
| 138 | | 2.38 | |
| 139 | | 65.4 | |
| 140 | | 157 | |
| 141 | | 0.0709 | |
| 142 | | 134 | |
| 143 | | 0.964 | |
| 144 | | Not active | |
| 145 | | 0.1 | |
| 146 | | 17 | |
| 147 | | 12.4 | |
| 148 | | 6.2 | |

Table 2 illustrates VHL inhibition data (i.e., Kd, µM) of examples contained herein in a surface plasmon resonance (SPR) assay.

TABLE 2

SPR measured VHL affinity for exemplary ULMs.

| Example # | SPR Kd (uM) |
|---|---|
| 3 | 0.12 |
| 145 | 0.01 |
| 205 | 0.33 |

TABLE 2-continued

SPR measured VHL affinity for exemplary ULMs.

| Example # | SPR Kd (uM) |
|---|---|
| 207 | 0.24 |
| 208 | 13.0 |

Degradation Data for Exemplary PROTAC Compounds of the Invention

Table 3 provides functional (degradation Dmax) data for AR PROTACs that encompass VHL ligands and analogs described herein. Dmax: + (Dmax≤25%); ++ (26%≤Dmax≤50%); +++ (51%≤Dmax≤70%); ++++ (71%≤Dmax).

TABLE 3

Degradation data for exemplary AR PROTACs

| Examplery ULM | Structure | Dmax |
|---|---|---|
| 202 | 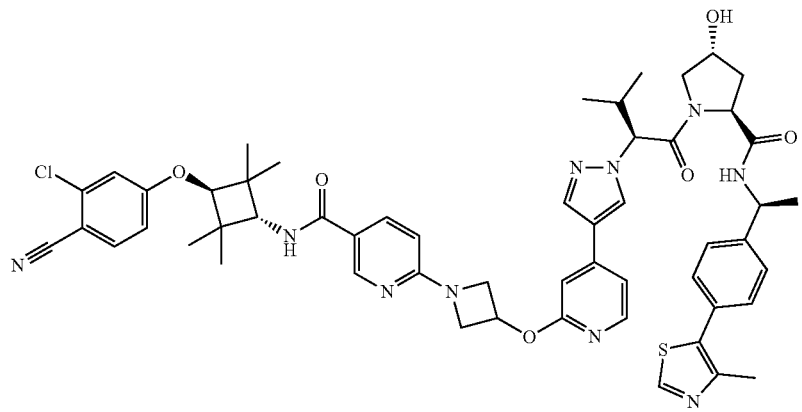 [SMILES: Cc1ncsc1-c1ccc([C@H](C)NC(=O)[C@@H]2C[C@@H](O)CN2C(=O)[C@H](C(C)C)n2cc(-c3ccnc(OC4CN(c5ccc(C(=O)N[C@H]6C(C)(C)[C@H](Oc7ccc(C#N)c(Cl)c7)C6(C)C)cn5)C4)c3)cn2)cc1] | +++ |
| 202 | 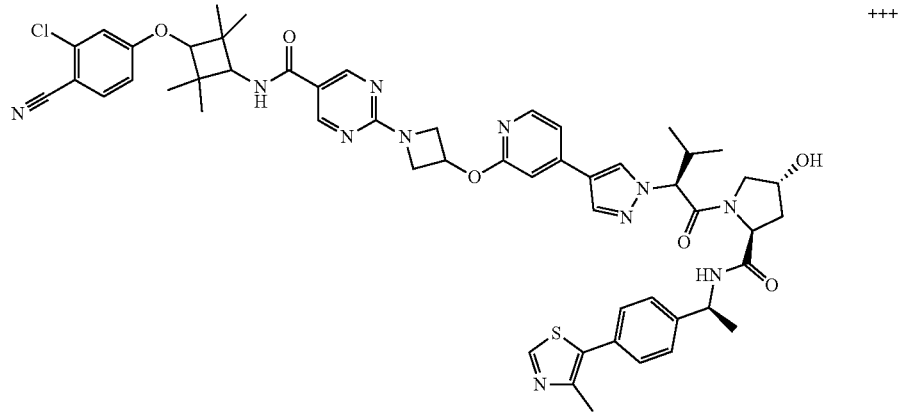 | +++ |

TABLE 3-continued

Degradation data for exemplary AR PROTACs

| Examplery ULM | Structure | Dmax |
|---|---|---|
| 203 | | +++ |
| 203 | | ++ |
| 202 | 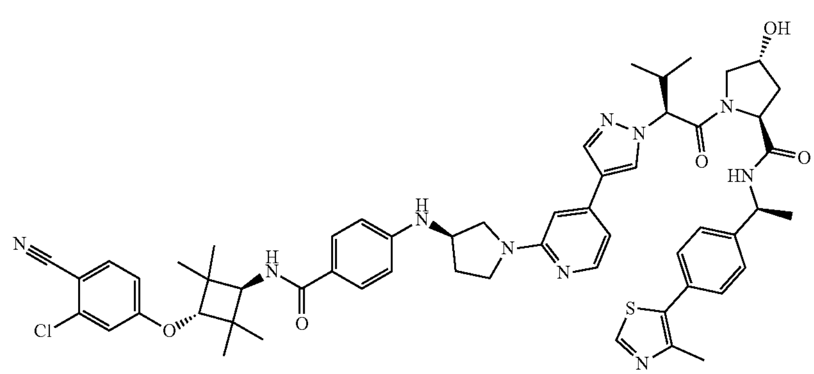 [SMILES: Cc1ncsc1-c1ccc([C@H](C)NC(=O)[C@@H]2C[C@@H](O)CN2C(=O)[C@H](C(C)C)n2cc(-c3ccnc(N4CC[C@@H](Nc5ccc(C(=O)N[C@H]6C(C)(C)[C@H](Oc7ccc(C#N)c(Cl)c7)C6(C)C)cc5)C4)c3)cn2)cc1] | ++ |

Table 4 provides functional (cMyc Imax) data for BRD4 PROTACs that encompass VHL ligands and analogs described herein. cMyc Imax: + (Imax≤25%); ++ (26%≤Imax≤50%); +++ (51%≤Imax≤70%); ++++ (71%≤Imax).

TABLE 4

Degradation readout data for exemplary Brd4 PROTACs

| Examplery ULM | Structure | cMyc Imax |
|---|---|---|
| 202 | | ++++ |
| 202 | | ++++ |
| 202 | | +++ |
| 202 | | ++++ |

TABLE 4-continued

Degradation readout data for exemplary Brd4 PROTACs

| Examplery ULM | Structure | cMyc Imax |
|---|---|---|
| 200 | 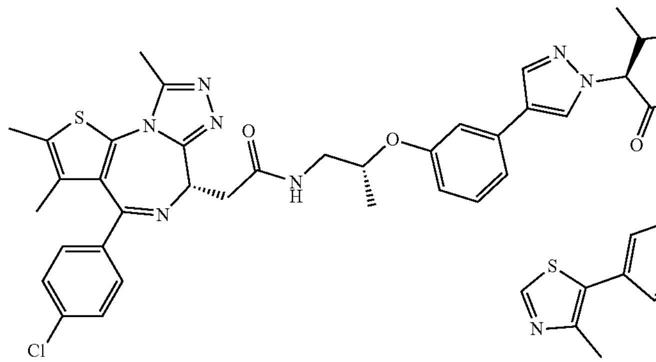 | ++++ |

The description, including examples and experimental data demonstrate the effectiveness and broad applicability of the bifunctional PROTAC compounds described herein to target any protein of interest for degradation. As presented herein, PROTAC-mediated protein degradation provides a mechanism to target the "undruggable" pathological proteins, which might not have been viable targets by traditional approaches.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the invention described herein. Such equivalents are intended to be encompassed by the following claims. It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

What is claimed is:

1. A compound that has the chemical structure PTM-L-ULM, wherein:
   (a) the L is a chemical linker group that is covalently bound to the PTM and the ULM, wherein the chemical linker group is represented by the formula $-(A)_q-$, q is an integer from 1 to 40;
   each A is independently $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$=$CR^{L2}$, C≡C, $SiR^{L1}R^{L2}$, $P(O)R^{L1}$, $P(O)OR^{L1}$, $NR^{L3}C$(=NCN)$NR^{L4}$, $NR^{L3}C$(=NCN), $NR^{L3}C$(=$CNO_2$)$NR^{L4}$, $C_{3-11}$cycloalkyl optionally substituted with 1-6 $R^{L1}$ and/or $R^{L2}$ groups, $C_{3-11}$heteocyclyl optionally substituted with 1-6 $R^{L1}$ and/or $R^{L2}$ groups, aryl optionally substituted with 1-6 $R^{L1}$ and/or $R^{L2}$ groups, or heteroaryl optionally substituted with 1-6 $R^{L1}$ and/or $R^{L2}$ groups, wherein $R^{L1}$ or $R^{L2}$, each independently, can be linked to other A groups to form a cycloalkyl moiety or a heterocyclyl moiety, each of which can be further substituted with 1-4 $R^{L5}$ groups; and
   each $R^{L1}$, $R^{L2}$, $R^{L3}$, $R^{L4}$ and $R^{L5}$ is independently, H, halogen, $C_{1-8}$alkyl, $OC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, $OC_{3-8}$cycloalkyl, $NHC_{3-8}$cycloalkyl, $N(C_{3-8}$cycloalkyl$)_2$, $N(C_{3-8}$cycloalkyl)($C_{1-8}$alkyl), OH, $NH_2$, CC—$C_{1-8}$alkyl, CCH, CH=$CH(C_{1-8}$alkyl), $C(C_{1-8}$alkyl)=$CH(C_{1-8}$alkyl), $C(C_{1-8}$alkyl)=$C(C_{1-8}$alkyl$)_2$, $COC_{1-8}$alkyl, $CO_2H$, CN, $CF_3$, $CHF_2$, $CH_2F$, $NO_2$, $CONHC_{1-8}$alkyl, $CON(C_{1-8}$alkyl$)_2$, $N(C_{1-8}$alkyl$)CONH(C_{1-8}$alkyl), $N(C_{1-8}$alkyl$)CON(C_{1-8}$alkyl$)_2$, $NHCONH(C_{1-8}$alkyl), $NHCON(C_{1-8}$alkyl$)_2$, or $NHCONH_2$;
   (b) the ULM is a Von Hippel-Lindau E3 ubiquitin ligase binding moiety that has the chemical structure:

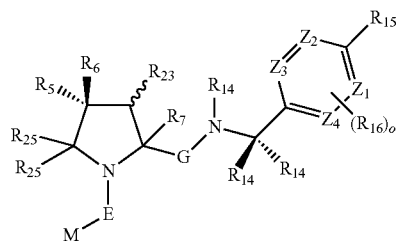

wherein:
one of $R_5$ and $R_6$ is —OH or —SH, and the other is H, or $R_5$, and $R_6$, and the carbon atom to which they are attached form a carbonyl;
$R_7$ is H or optionally substituted alkyl;
E is C=O;
G is C=O;

M is optionally substituted aryl, optionally substituted heteroaryl, optionally substituted heterocyclic, or

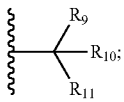

each $R_9$ and $R_{10}$ is independently H, optionally substituted alkyl, optionally substituted cycloalkyl, optionally substituted hydroxyalkyl, optionally substituted alkylthio, optionally substituted heteroaryl, or haloalkyl; or $R_9$, $R_{10}$, and the carbon atom to which they are attached form an optionally substituted cycloalkyl;

$R_{11}$ is optionally substituted heterocyclic, optionally substituted alkoxy, optionally substituted heteroaryl, optionally substituted aryl, or

$R_{12}$ is H or optionally substituted alkyl;

$R_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, optionally substituted (oxoalkyl)carbamate, or optionally substituted aralkyl;

each $R_{14}$ is independently H, haloalkyl, optionally substituted cycloalkyl, optionally substituted alkyl, or optionally substituted heterocycloalkyl, wherein one $R_{14}$ is haloalkyl, optionally substituted cycloalkyl, optionally substituted alkyl, or optionally substituted heterocycloalkyl;

$R_{15}$ is H, optionally substituted heteroaryl, haloalkyl, optionally substituted aryl, optionally substituted alkoxy, or optionally substituted heterocyclyl;

each $R_{16}$ is independently halogen, optionally substituted alkyl, optionally substituted haloalkyl, CN, or optionally substituted haloalkoxy;

each $R_{25}$ is independently H or optionally substituted alkyl; or both $R_{25}$ groups can be taken together to form an oxo or optionally substituted cycloalkyl group;

$R_{23}$ is H or OH;

$Z_1$, $Z_2$, $Z_3$, and $Z_4$ are independently C or N; and o is 0, 1, 2, 3, or 4, wherein the chemical linker group (L) is covalently attached to the ULM via M, $R_9$, $R_{10}$, $R_{11}$, $R_{15}$, or $R_{16}$; and (c) the PTM is a small molecule protein binding moiety that binds an intracellular target protein or an intracellular target polypeptide sufficiently to facilitate target protein or target polypeptide ubiquitination when coupled to the ULM, wherein the PTM is a moiety that binds to androgen receptor or estrogen receptor, or a pharmaceutically acceptable salt, or stereoisomer thereof.

2. The compound of claim 1, wherein the $R_{15}$ is selected from the group consisting of:

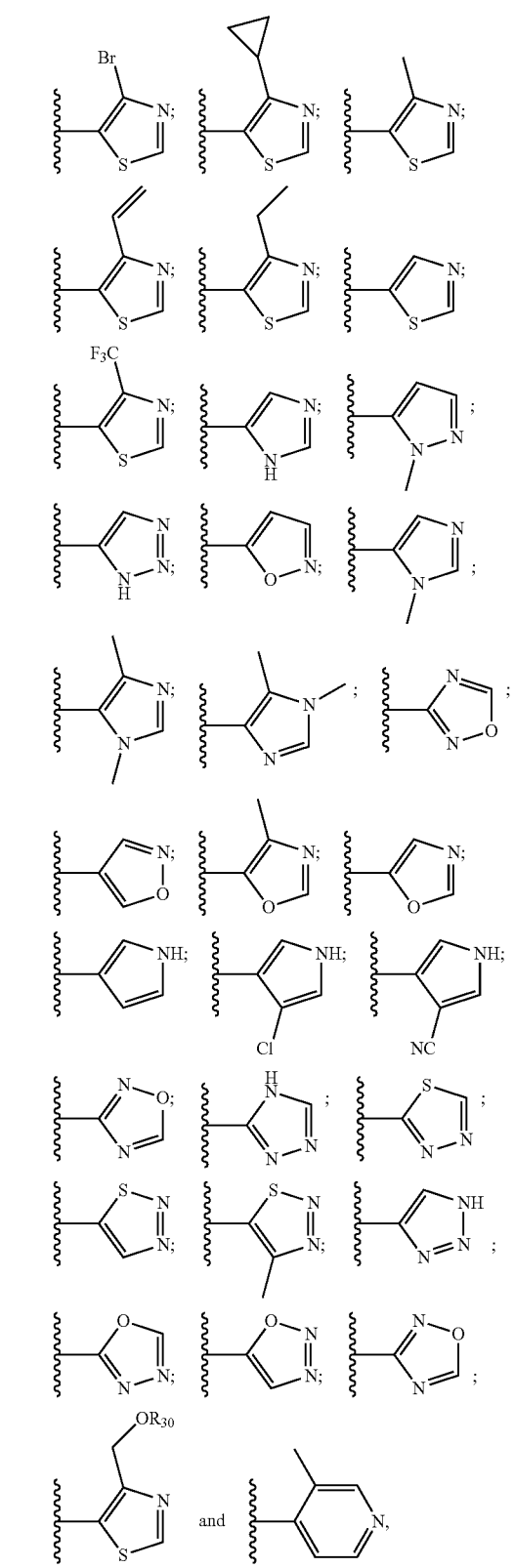

wherein $R_{30}$ is H or an optionally substituted alkyl.

3. The compound of claim 1, wherein:
M is

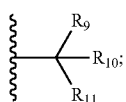

$R_{11}$ is

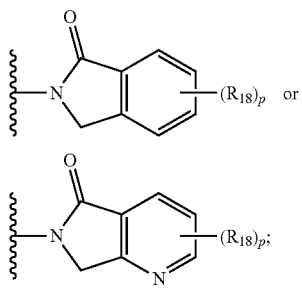

$R_{18}$ is independently halogen, optionally substituted alkoxy, cyano, optionally substituted alkyl, haloalkyl, or haloalkoxy; and p is 0, 1, 2, 3, or 4.

4. The compound of claim 3, wherein the $R_{11}$ is selected from the group consisting of:

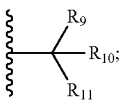

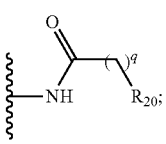

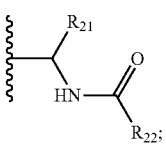

-continued

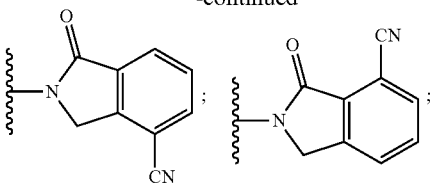

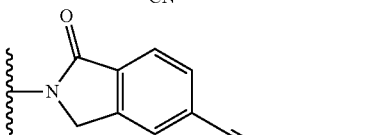

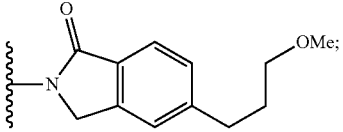

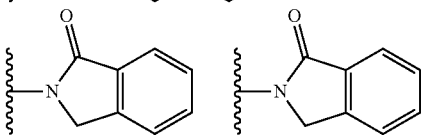

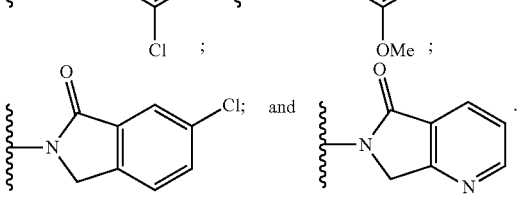

5. The compound of claim 1, wherein:
M is $R_{11}$ is optionally substituted heteroaryl or heterocyclic, or q of the ULM is 1 or 2;

$R_{20}$ is H, optionally substituted alkyl, optionally substituted cycloalkyl, optionally substituted aryl, or $R_{21}$ is H or optionally substituted alkyl; and
$R_{22}$ is H, optionally substituted alkyl, optionally substituted alkoxy, or haloalkyl.

6. The compound of claim 1, wherein:
M is

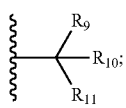

$R_{11}$ is an optionally substituted heterocycle, an optionally substituted heteroaryl, an optionally substituted aryl, or

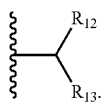

$R_{12}$ is H or optionally substituted alkyl;
$R_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, optionally substituted (oxoalkyl)carbamate, or optionally substituted aralkyl.

7. The compound of claim 6, wherein $R_{11}$ is selected from the group consisting of:

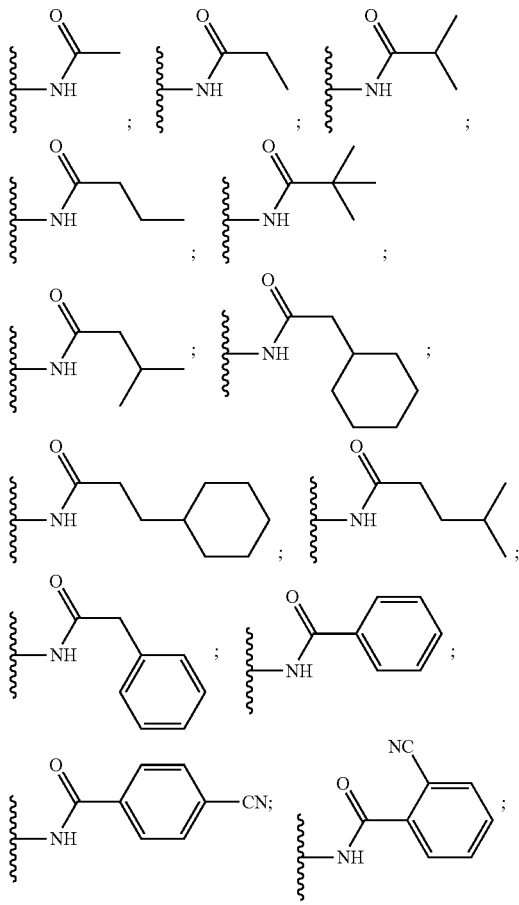

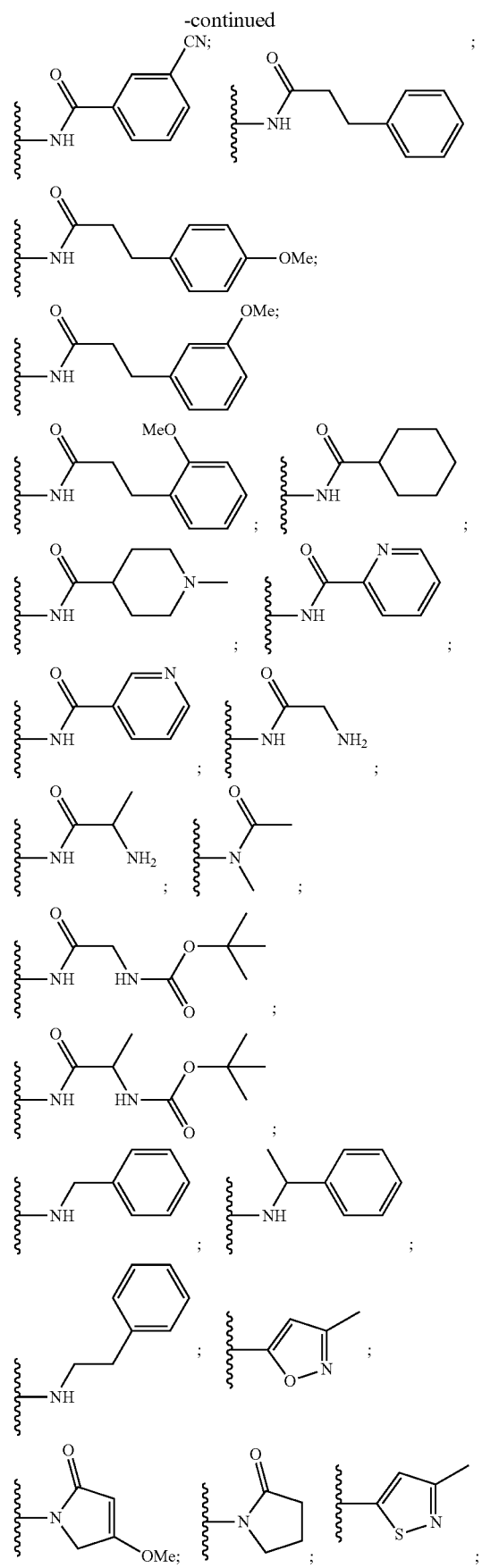

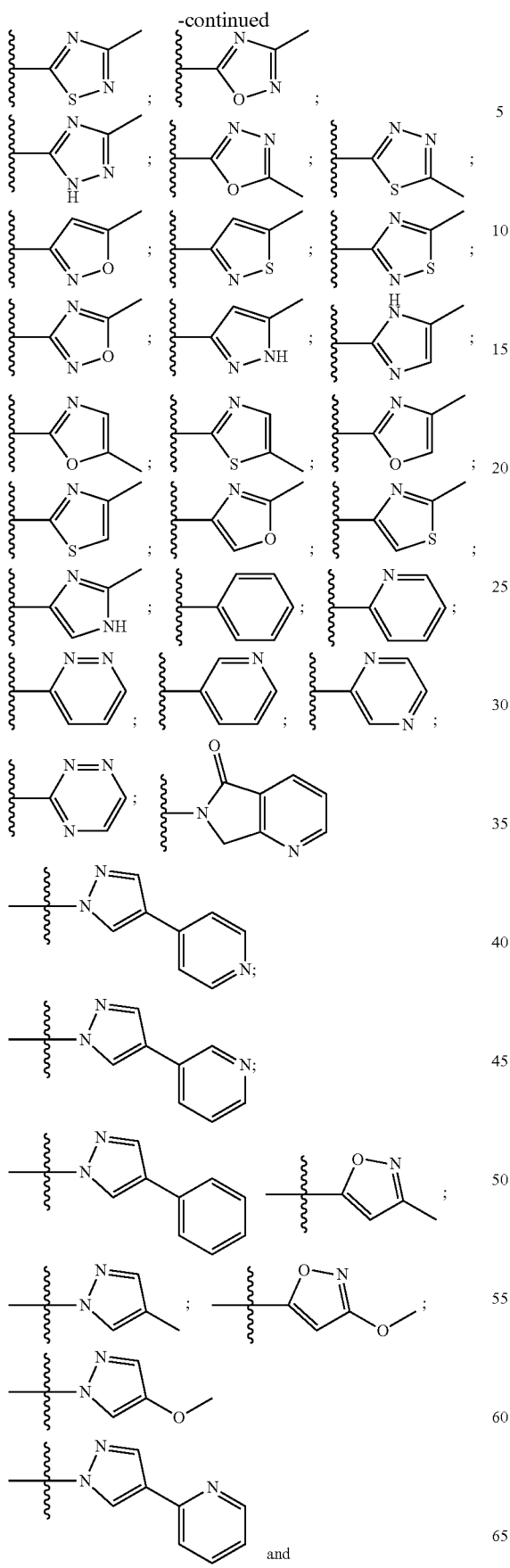

and

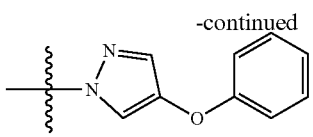

8. The compound of claim 1, wherein the ULM is a group according to the chemical structure:

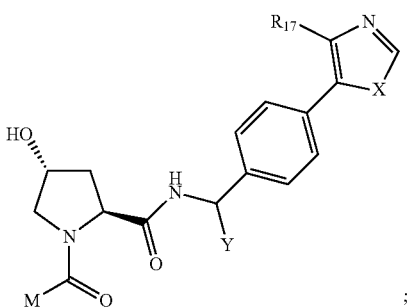

wherein:
X is O or S;
Y is methyl or ethyl;
R$_{17}$ is H, methyl, ethyl, hydoxymethyl, or cyclopropyl;
M is optionally substituted heteroaryl, optionally substituted aryl, or

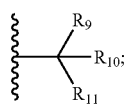

R$_9$ is H;
R$_{10}$ is H, optionally substituted alkyl, optionally substituted haloalkyl, optionally substituted heteroaryl, optionally substituted aryl, optionally substituted hydroxyalkyl, optionally substituted thioalkyl, or cycloalkyl;
R$_{11}$ is optionally substituted heteroaromatic, optionally substituted heterocyclic, optionally substituted aryl, or

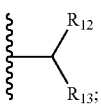

R$_{12}$ is H or optionally substituted alkyl; and
R$_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, optionally substituted (oxoalkyl)carbamate, or optionally substituted aralkyl,
or a pharmaceutically acceptable salt, or stereoisomer thereof.

9. The compound of claim 1, wherein the ULM has the chemical structure:

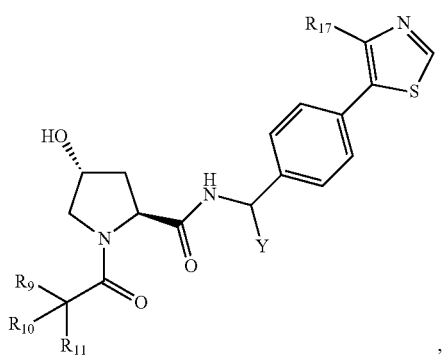

wherein:
Y is methyl or ethyl;
$R_9$ is H;
$R_{10}$ is isopropyl, tert-butyl, sec-butyl, cyclopentyl, or cyclohexyl;
$R_{11}$ is optionally substituted amide, optionally substituted isoindolinone, optionally substituted isooxazole, or optionally substituted heterocycles; and
$R_{17}$ is H, methyl, ethyl, hydroxymethyl, or cyclopropyl.

10. The compound of claim 1, wherein the ULM is selected from the group consisting of:

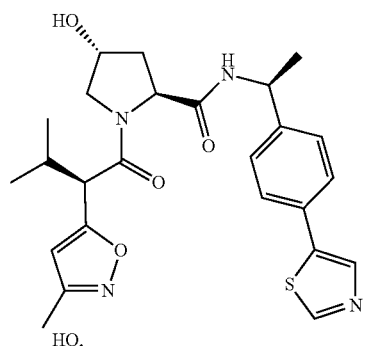

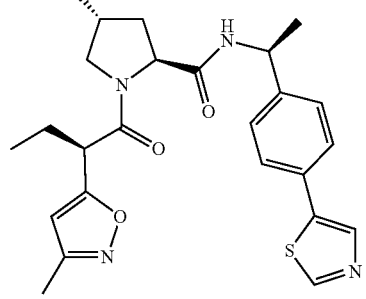

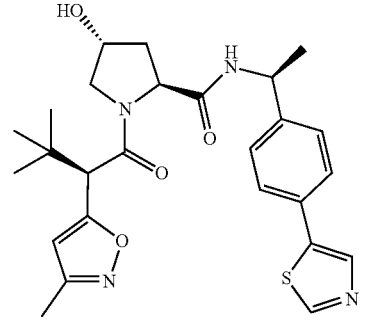

-continued

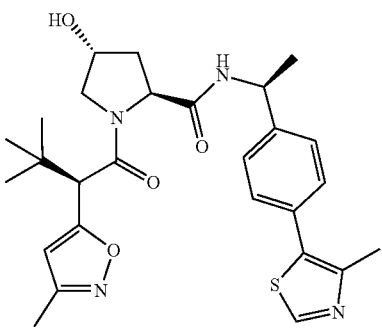

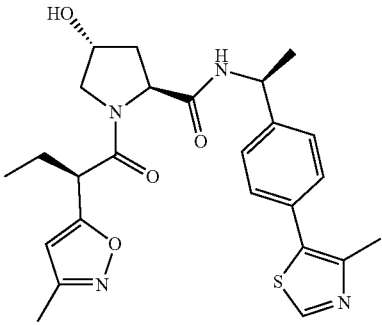

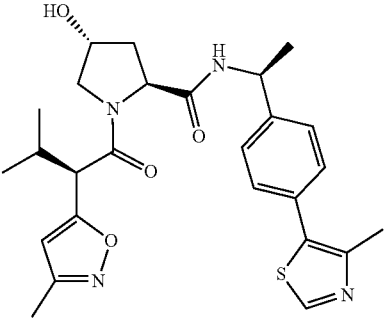

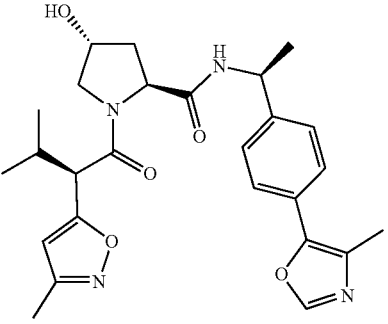

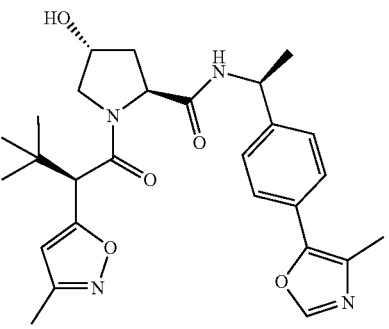

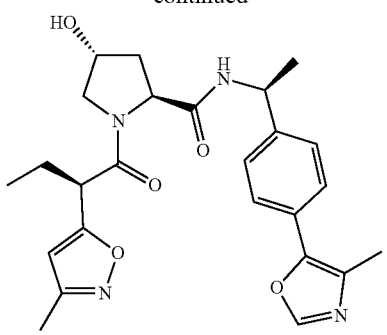
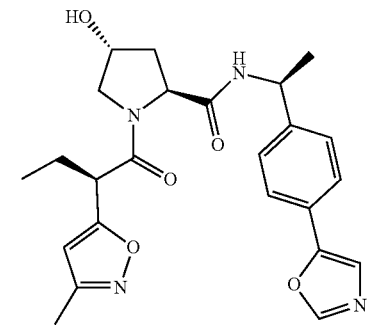
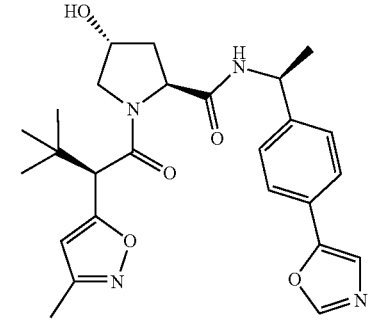
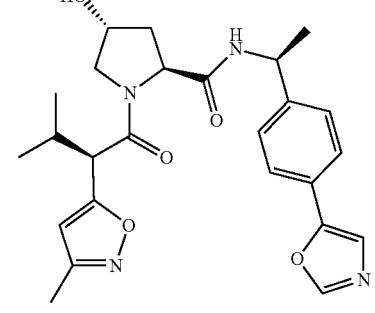
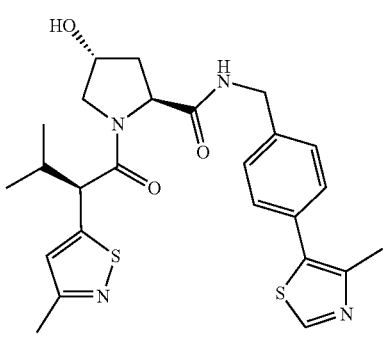
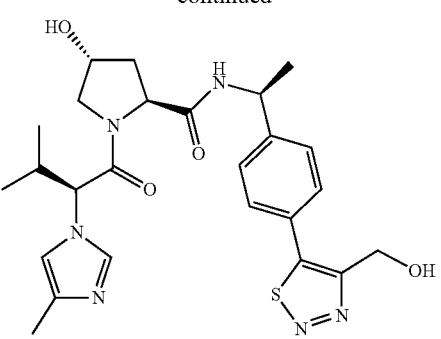
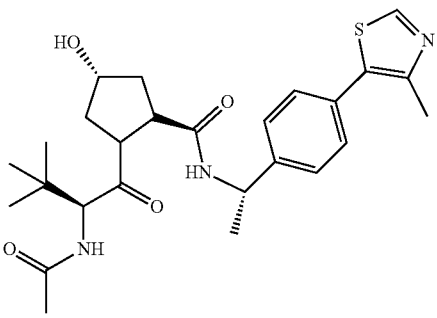
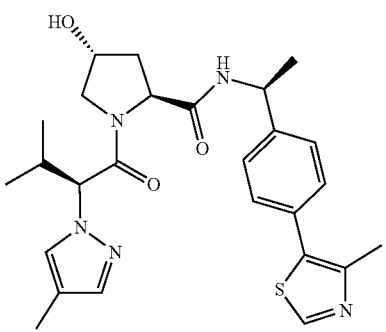
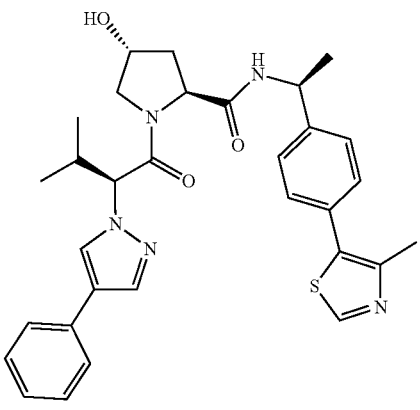

281
-continued

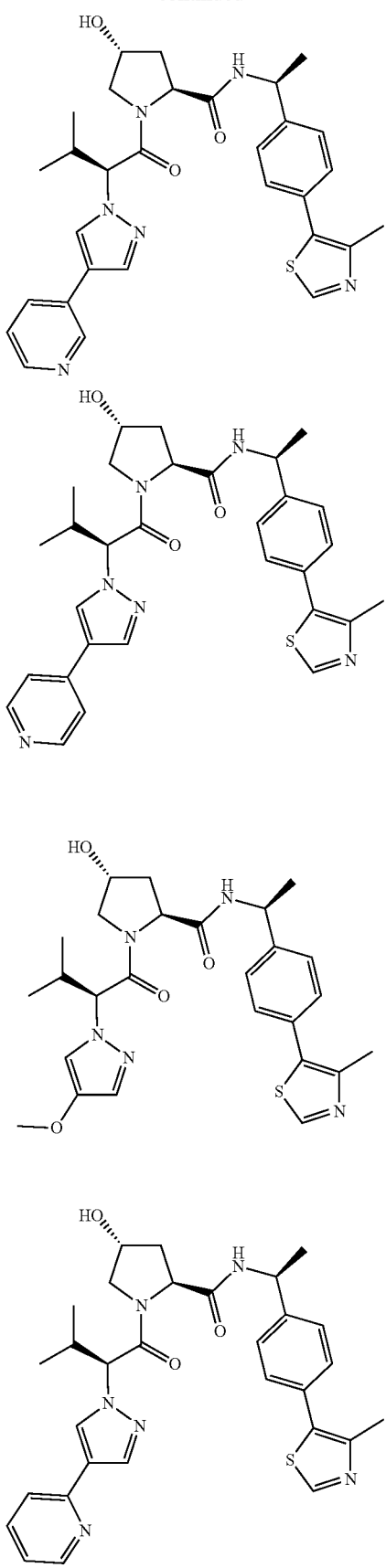

282
-continued

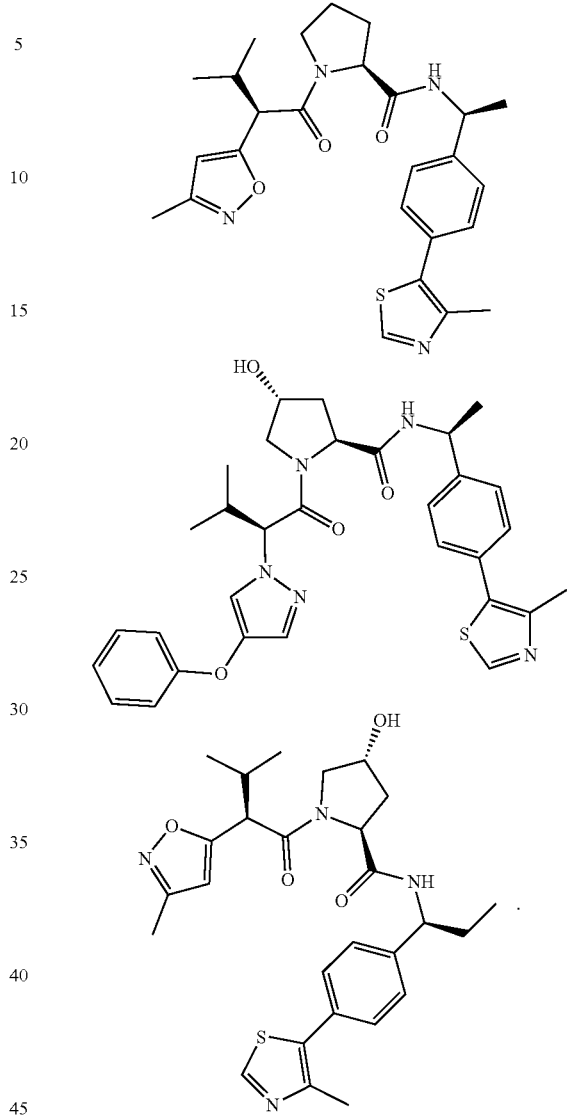

11. The compound of claim 1, wherein q is an integer from 1 to 20.

12. The compound of claim 1, wherein the chemical linker group is an optionally substituted polyethylene group that has from 2 to 20 ethylene glycol units.

13. The compound of claim 12, wherein said polyethylene glycol group contains between 2 and 10 ethylene glycol units.

14. A pharmaceutical composition comprising an effective amount of a compound according to claim 1 in combination with a pharmaceutically acceptable carrier, additive or excipient.

15. The pharmaceutical composition of claim 14, further comprising an additional bioactive agent that is an anticancer agent.

16. The pharmaceutical composition of claim 15, wherein said anticancer agent is selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(But)-Leu-Arg-Pro-Azgly-NH$_2$ acetate [C$_{59}$H$_{84}$N$_{18}$O$_{14}$—(C$_2$H$_4$O$_2$)x where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevac, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa, and combinations thereof.

17. A compound of the structure:

wherein:
PTM is a small molecule protein binding moiety that binds an intracellular target protein or an intracellular target polypeptide sufficiently to facilitate target protein or target polypeptide ubiquitination, wherein the PTM is a moiety that binds to androgen receptor or estrogen receptor;
L is a chemical linker group that is covalently bound to the PTM and the ULM, wherein the chemical linker group is represented by the formula -(A)$_q$-,
q is an integer from 1 to 40;
each A is independently CR$^{L1}$R$^{L2}$, O, S, SO, SO$_2$, NR$^{L3}$, SO$_2$NR$^{L3}$, SONR$^{L3}$, CONR$^{L3}$, NR$^{L3}$CONR$^{L4}$, NR$^{L3}$SO$_2$NR$^{L4}$, CO, CR$^{L1}$=CR$^{L2}$, C≡C, C$_{3-11}$cycloalkyl optionally substituted with 1-6 R$^{L1}$ and/or R$^{L2}$ groups, C$_{3-11}$heteocyclyl optionally substituted with 1-6 R$^{L1}$ and/or R$^{L2}$ groups, aryl optionally substituted with 1-6 R$^{L1}$ and/or R$^{L2}$ groups, or heteroaryl optionally substituted with 1-6 R$^{L1}$ and/or R$^{L2}$ groups, wherein R$^{L1}$ or R$^{L2}$, each independently, can be linked to other A groups to form a cycloalkyl moiety or a heterocyclyl moiety, each of which can be further substituted with 1-4 R$^{L5}$ groups; and
each R$^{L1}$, R$^{L2}$, R$^{L3}$, R$^{L4}$ and R$^{L5}$ is independently, H, halogen, C$_{1-8}$alkyl, OC$_{1-8}$alkyl, NHC$_{1-8}$alkyl, N(C$_{1-8}$alkyl)$_2$, C$_{3-11}$cycloalkyl, aryl, heteroaryl, C$_{3-11}$heterocyclyl, OC$_{3-8}$cycloalkyl, NHC$_{3-8}$cycloalkyl, N(C$_{3-8}$cycloalkyl)$_2$, N(C$_{3-8}$cycloalkyl)(C$_{1-8}$alkyl), OH, NH$_2$ CC—C$_{1-8}$alkyl, CCH, CH=CH(C$_{1-8}$alkyl), C(C$_{1-8}$alkyl)=CH(C$_{1-8}$alkyl), C(C$_{1-8}$alkyl)=C(C$_{1-8}$alkyl)$_2$, COC$_{1-8}$alkyl, CO$_2$H, CN, CF$_3$, CHF$_2$, CH$_2$F, NO$_2$, CONHC$_{1-8}$alkyl, CON(C$_{1-8}$alkyl)$_2$, N(C$_{1-8}$alkyl)CONH(C$_{1-8}$alkyl), N(C$_{1-8}$alkyl)CON(C$_{1-8}$alkyl)$_2$, NHCONH(C$_{1-8}$alkyl), NHCON(C$_{1-8}$alkyl)$_2$, and NHCONH$_2$;

X is O, N, or S;

Y is methyl or ethyl;

R$_{17}$ is H, methyl, ethyl, hydoxymethyl, or cyclopropyl;

M is optionally substituted heteroaryl, optionally substituted aryl, or

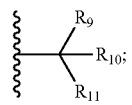

R$_9$ is H;

R$_{10}$ is H, optionally substituted alkyl, optionally substituted haloalkyl, optionally substituted heteroaryl, optionally substituted aryl, optionally substituted hydroxyalkyl, optionally substituted alkylthio, or cycloalkyl;

R$_{11}$ is selected from the group:

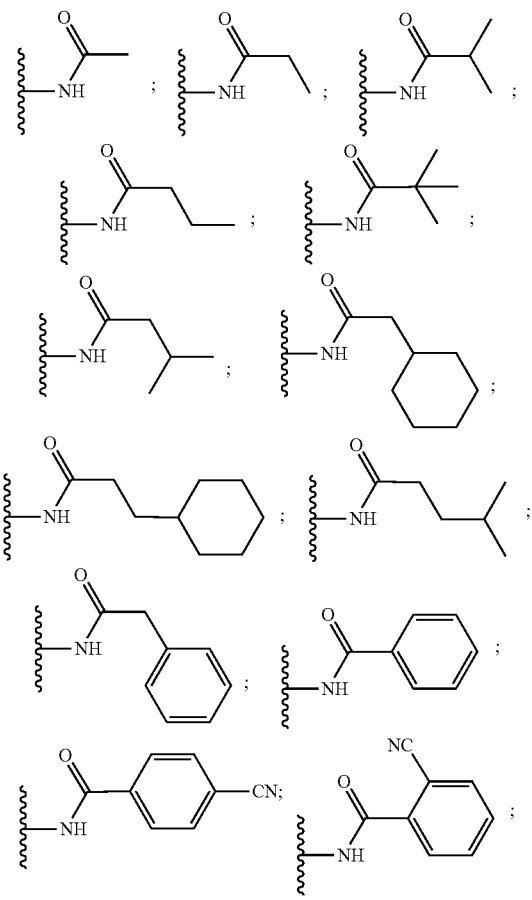

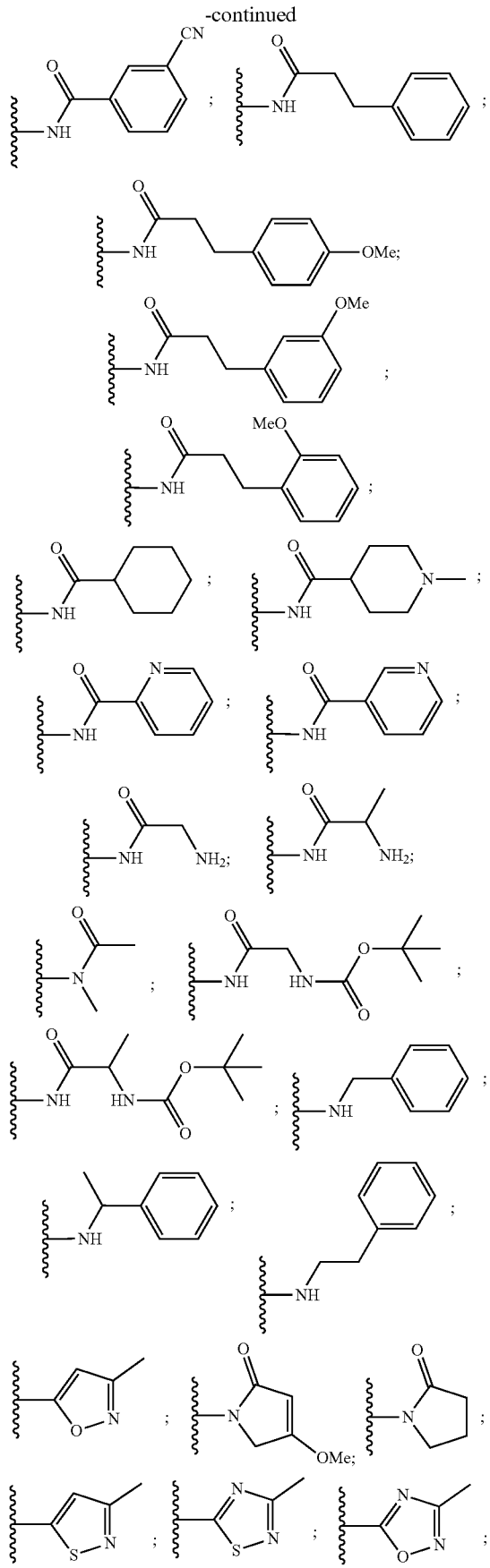

287
-continued
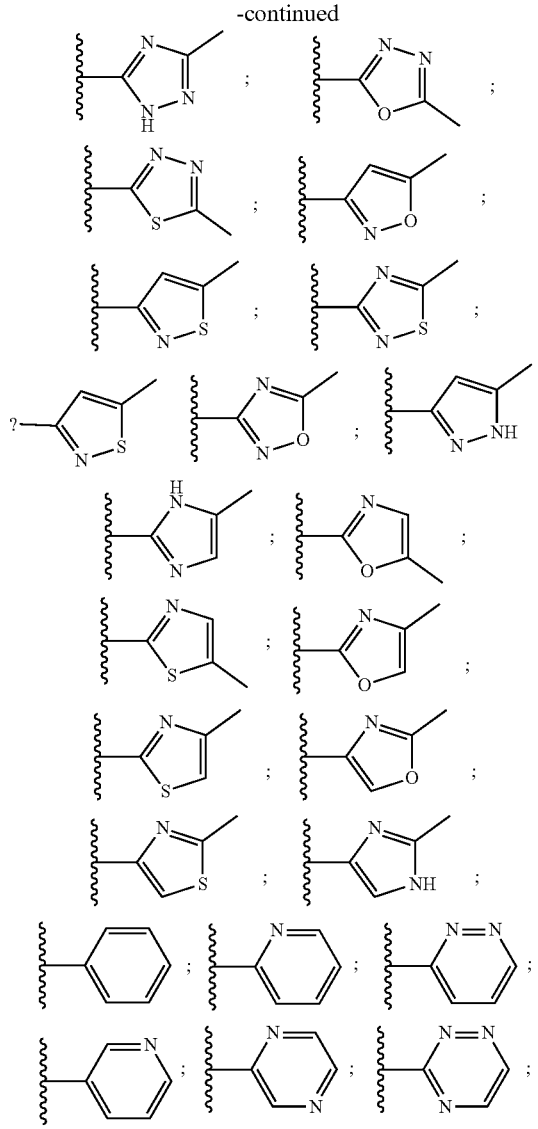
288
-continued
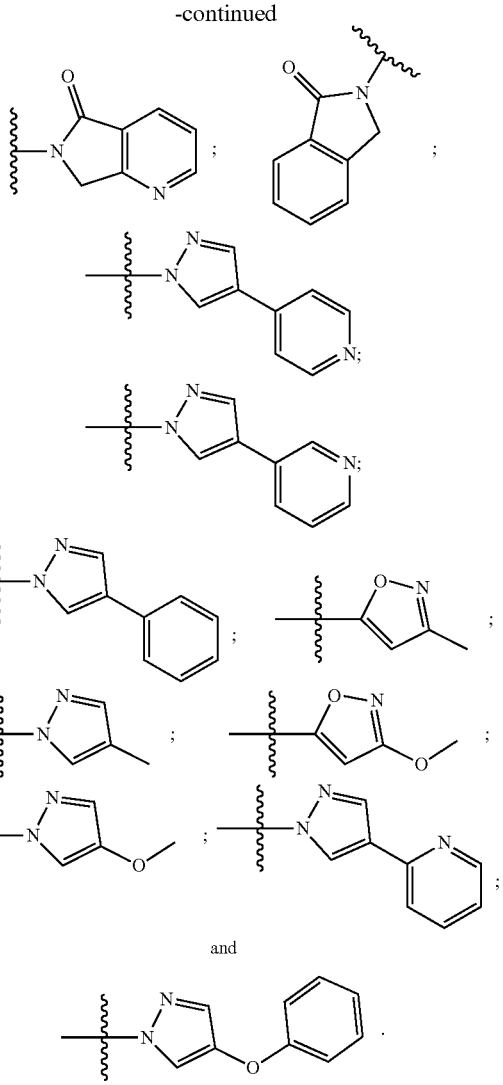
and
* * * * *

UNITED STATES PATENT AND TRADEMARK OFFICE
CERTIFICATE OF CORRECTION

PATENT NO. : 11,512,083 B2
APPLICATION NO. : 16/905641
DATED : November 29, 2022
INVENTOR(S) : Andrew P. Crew Page 1 of 1

It is certified that error appears in the above-identified patent and that said Letters Patent is hereby corrected as shown below:

In the Claims

Claim 1, Column 268, Line 55, change 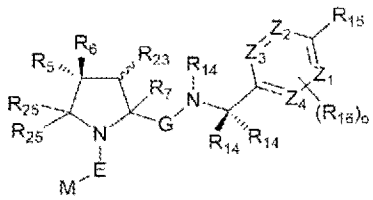 to 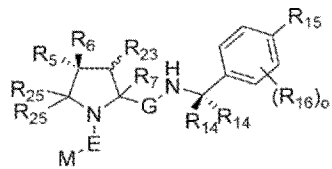

Claim 1, Column 269, Line 25; Claim 6, Column 273, Line 16; and Claim 8, Column 276, Line 50, change 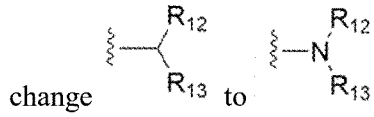

Claim 9, Column 277, Line 24, change heterocycles to heterocycle

Signed and Sealed this
Twenty-fifth Day of April, 2023

Katherine Kelly Vidal
*Director of the United States Patent and Trademark Office*